US009187539B2

(12) United States Patent
Popel et al.

(10) Patent No.: US 9,187,539 B2
(45) Date of Patent: Nov. 17, 2015

(54) COMPOSITIONS HAVING ANTIANGIOGENIC ACTIVITY AND USES THEREOF

(71) Applicant: The Johns Hopkins University, Baltimore, MD (US)

(72) Inventors: Aleksander S. Popel, Lutherville, MD (US); Emmanouil D. Karagiannis, Cambridge, MA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/975,168

(22) Filed: Aug. 23, 2013

(65) Prior Publication Data

US 2014/0045757 A1 Feb. 13, 2014

Related U.S. Application Data

(62) Division of application No. 13/369,240, filed on Feb. 8, 2012, now Pat. No. 8,557,772, which is a division of application No. 11/992,001, filed as application No. PCT/US2006/035580 on Sep. 12, 2006, now abandoned.

(60) Provisional application No. 60/716,341, filed on Sep. 12, 2005.

(51) Int. Cl.
*A61K 38/10* (2006.01)
*C07K 14/47* (2006.01)
*C07K 17/00* (2006.01)
*C07K 9/00* (2006.01)
*C07K 14/475* (2006.01)
*C07K 14/78* (2006.01)
*C12N 9/64* (2006.01)

(52) U.S. Cl.
CPC .............. *C07K 14/47* (2013.01); *C07K 14/472* (2013.01); *C07K 14/475* (2013.01); *C07K 14/78* (2013.01); *C12N 9/6421* (2013.01); *C12N 9/6489* (2013.01)

(58) Field of Classification Search
CPC .......... C07K 14/47; C07K 17/00; C07K 9/00; A61K 38/10
USPC ................................. 530/326; 514/13.3, 21.4
See application file for complete search history.

(56) References Cited

U.S. PATENT DOCUMENTS

| | | | |
|---|---|---|---|
| 2002/0147132 A1* | 10/2002 | Fujisawa et al. ................... | 514/2 |
| 2003/0100510 A1 | 5/2003 | Hudson et al. | |
| 2003/0109690 A1 | 6/2003 | Ruben et al. | |
| 2004/0057925 A1 | 3/2004 | Pelus et al. | |
| 2004/0086501 A1* | 5/2004 | Wetzel ......................... | 424/94.63 |
| 2004/0091473 A1 | 5/2004 | DuBose et al. | |
| 2004/0143094 A1 | 7/2004 | Donda et al. | |
| 2014/0271804 A1* | 9/2014 | Perricone ....................... | 424/450 |

FOREIGN PATENT DOCUMENTS

DE 102005035864 2/2007

OTHER PUBLICATIONS

Properdin precursor from NCBI Accession No. NP_001138724, pp. 1-3. Accessed Oct. 19, 2014.*
Fibulin-6 from NCBI Accession No. CAC37630, pp. 1-5. Accessed Oct. 19, 2014.*
Water from www.biology-online.org/dictionary/Water, pp. 1-3. Accessed Apr. 24, 2014.*
Beremdsem. HJC, "A Glimpse of the Holy Grail?", Science, 1998, 282: pp. 642-643.
Bradley, CM, et al., "Limits of Coorperativity in a Structurally Modular Protein: Response of the Notch Ankyrin Domain to Analogous Alanine Substitutions in Each Repeat", J. Mol. Biol., 2002, 324: pp. 373-386.
Iruela-Arispe et al., "Inhibition of angiogenesis by thrombospondin-1 is mediated by 2 independent regions within the type 1 repeats" Circulation, 1999, vol. 100. pp. 1423-1431.
Ngo, JT, et al., "Computational Complexity, Protein Structure Prediction, and the Levintal Paradox", The Protein Folding Problem and Tertiary Structure Prediction, K. Merc Jr. and S. Le Grand Edition, 1994, pp. 491-495.
Rudinger, J, "Characteristics of the amino acids as components of a peptide hormone sequence", Peptide Hormones, JA Parsons Edition, University Park Press, Jun. 1976, pp. 1-7.
Schinzel, R., et al., "The Phosphate Recognition Site of *Escherichia coli* Maltodextrin Phosphorylase", FEBS, Jul. 1991, 286(1,2): pp. 125-128.
"Designing Custom Peptides", SIGMA Genosys, Accessed Dec. 2004, pp. 1-2.
Voet, D, et al., Biochemistry, Second Edition, John Wiley & Sons, Inc., 1995, pp. 235-241.

* cited by examiner

*Primary Examiner* — Julie Ha
(74) *Attorney, Agent, or Firm* — Mintz Levin Cohn Ferris Glovsky and Popeo, P.C.; Peter F. Corless; Richard B. Emmons

(57) ABSTRACT

Compositions and methods that are useful for modulating blood vessel formation, as well as methods that provide for the systematic and efficient identification of angiogenesis modulators are described. As discussed in more detail below, a systematic computational methodology based on bioinformatics was used to identify novel peptide modulators of angiogenesis that have been characterized in vitro and/or in vivo.

8 Claims, 56 Drawing Sheets

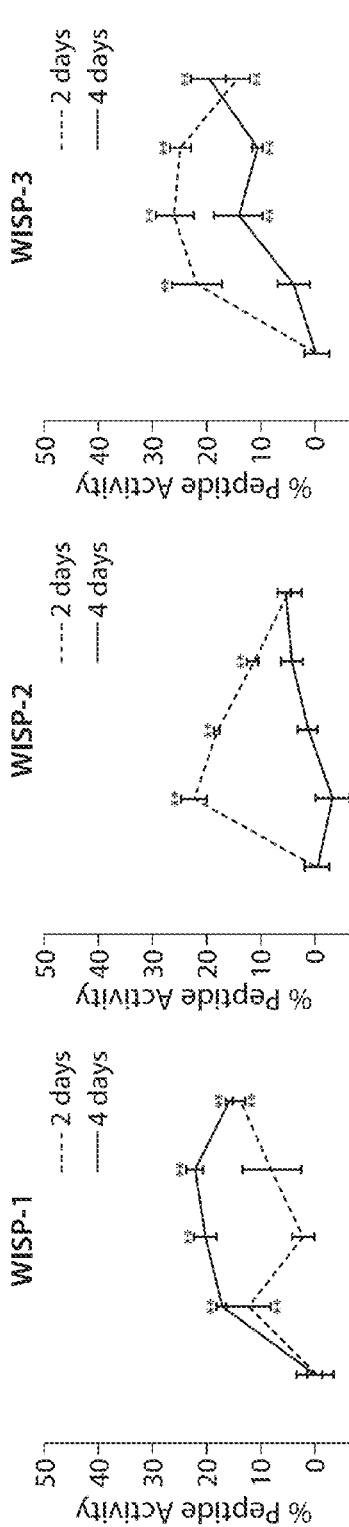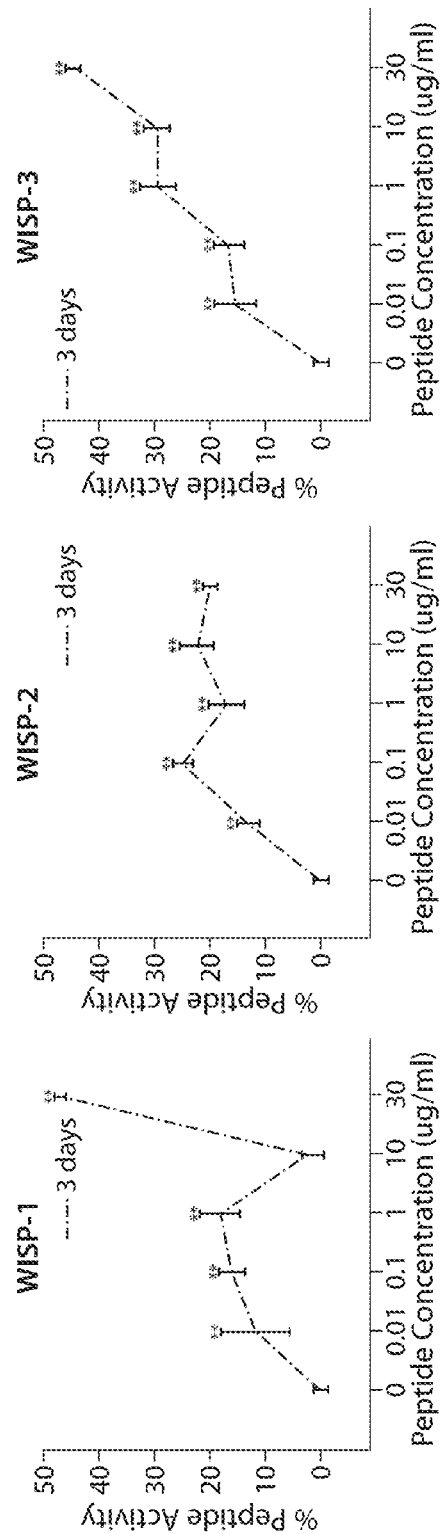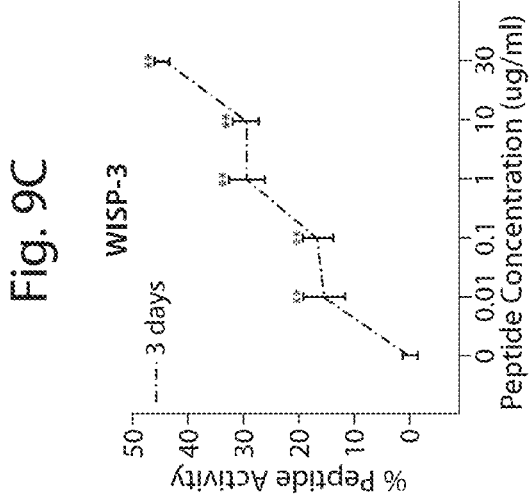

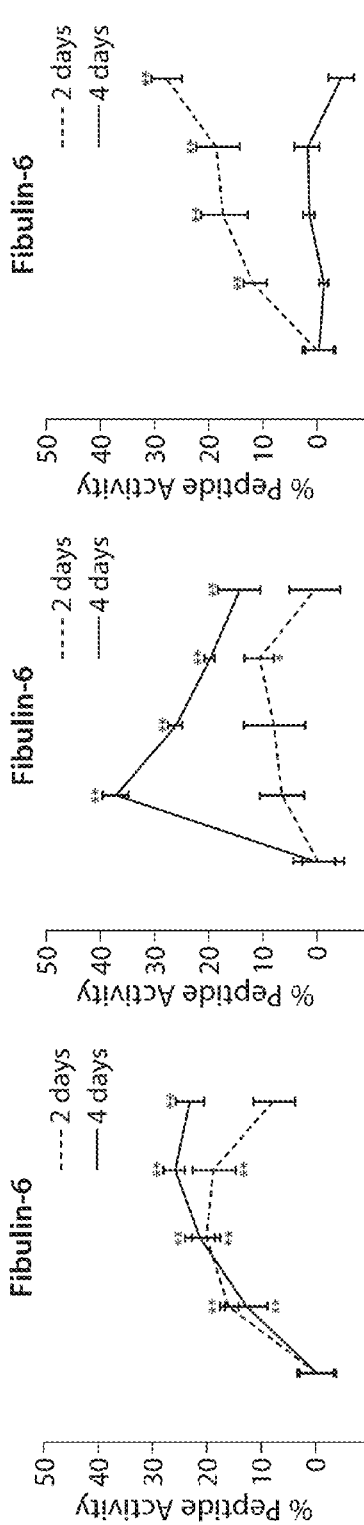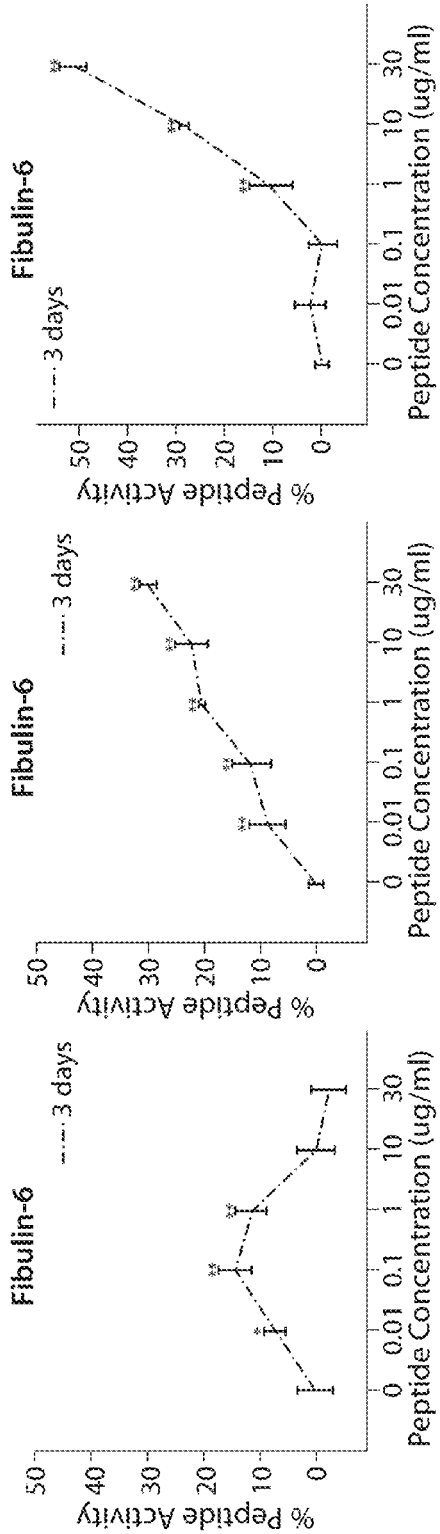
Fig. 12A  Fig. 12B  Fig. 12C
Fig. 12D  Fig. 12E  Fig. 12F

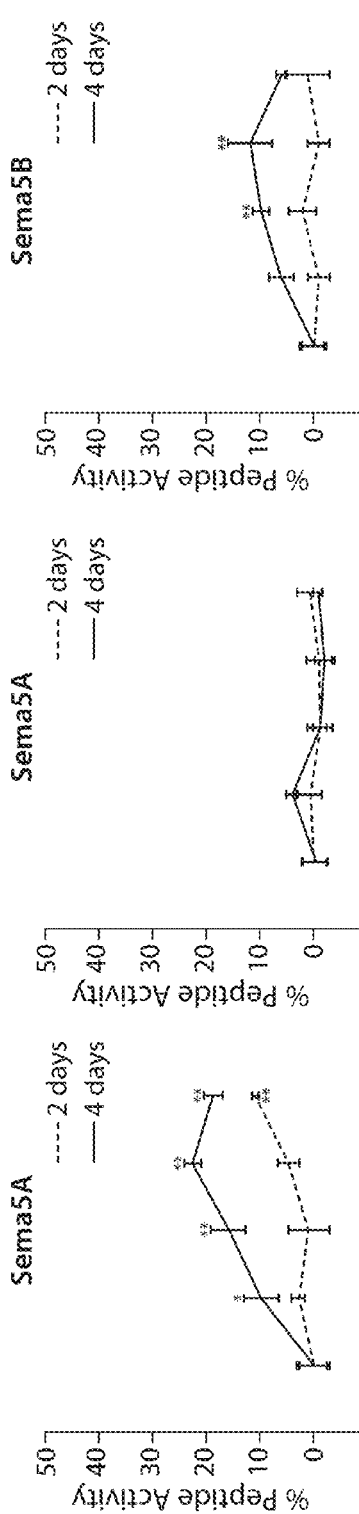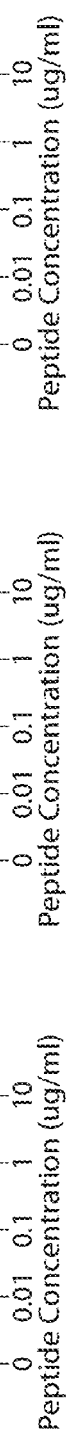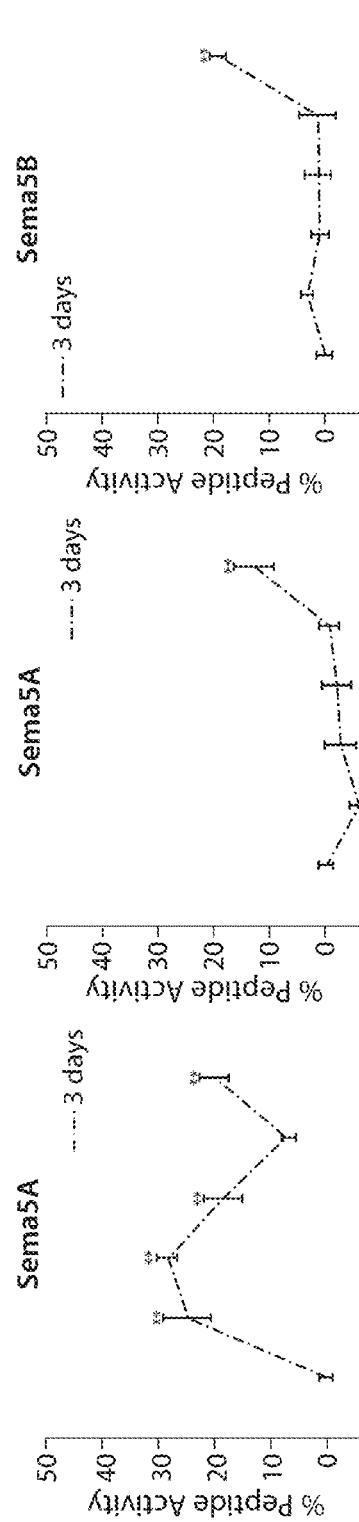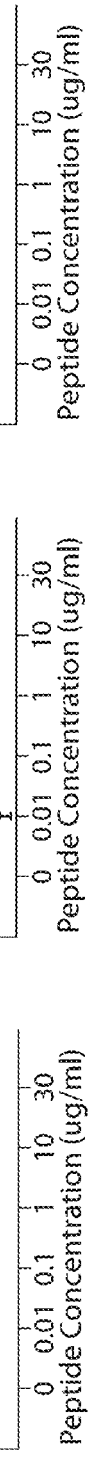
Fig. 24A  Fig. 24B  Fig. 24C
Fig. 24D  Fig. 24E  Fig. 24F

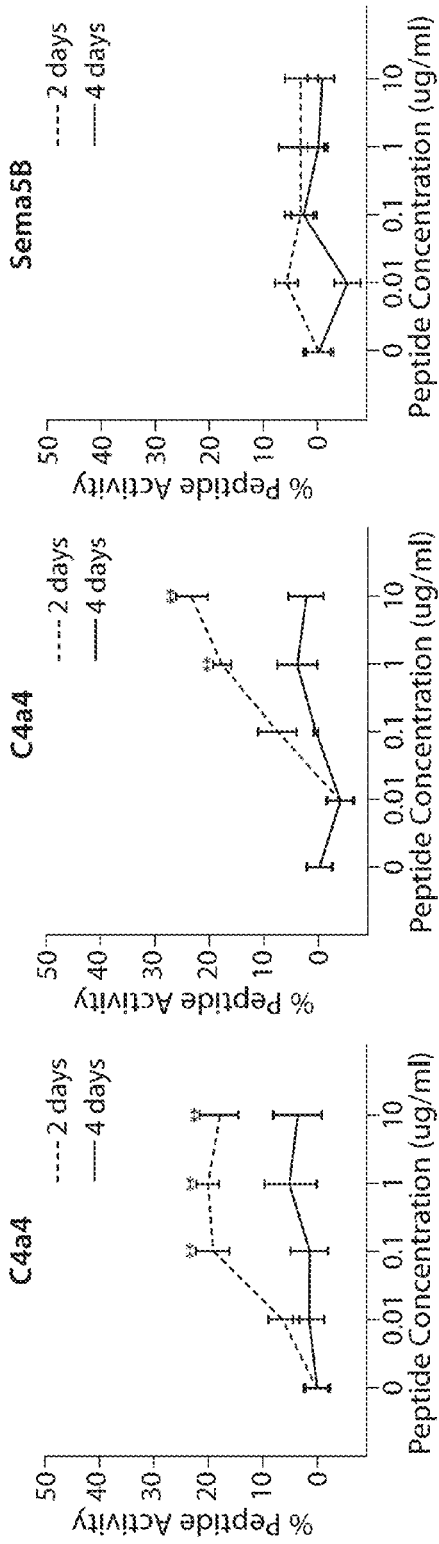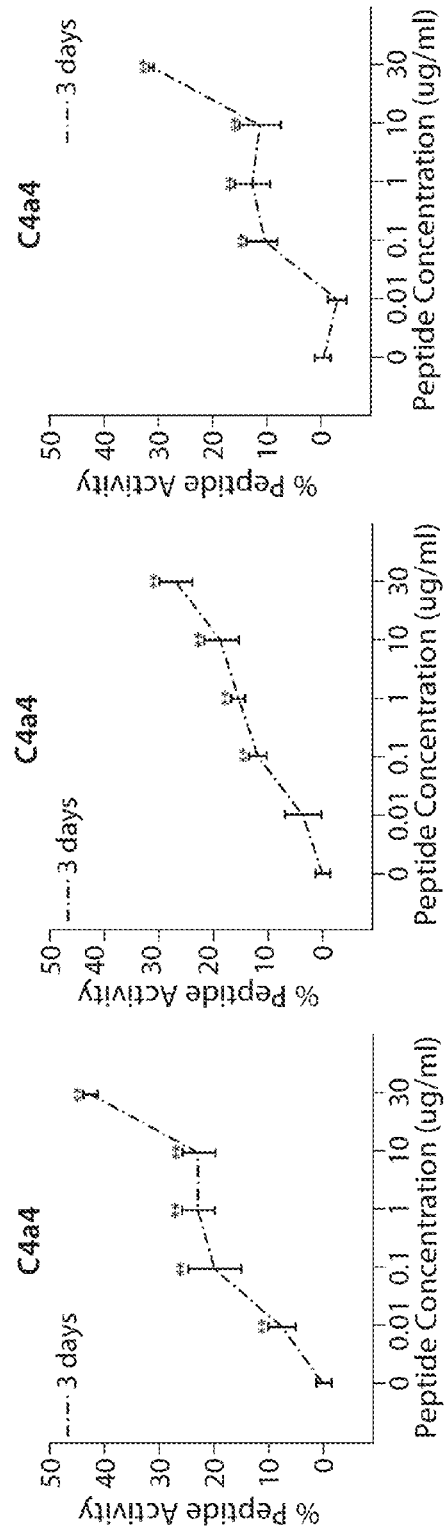
Fig. 35A, Fig. 35B, Fig. 35C, Fig. 35D, Fig. 35E, Fig. 35F

```
                              10
ADAMTS-01/1-20     G P W G D C S R T C G G G V Q Y T M R -
ADAMTS-02/1-18     G P W S Q C S V T C G N G T Q E R - - -
ADAMTS-03/1-18     G P W S E C S V T C G E G T E V R - - -
ADAMTS-04(a)/1-15  G P W G D C S R T C G G G V - - - - - -
ADAMTS-04(b)/1-20  G P W G D C S R T C G G G V Q F S S R -
ADAMTS-05/1-18     G P W L A C S R T C D T G W H T R - - -
ADAMTS-06(a)/1-15  Q P W S E C S A T C A G G V - - - - - -
ADAMTS-06(b)/1-18  Q P W S E C S A T C A G G V Q R Q - - -
ADAMTS-07(a)/1-18  G P W G Q C S G P C G G G V Q R R - - -
ADAMTS-07(b)/1-15  G P W T K C T V T C G R G V - - - - - -
ADAMTS-08(a)/1-15  G P W G E C S R T C G G G V - - - - - -
ADAMTS-08(b)/1-20  G P W G E C S R T C G G G V Q F S H R -
ADAMTS-09(a)/1-16  - - W S S C S V T C G Q G R A T R - - -
ADAMTS-09(b)/1-18  G P W G A C S S T C A G G S Q R R - - -
ADAMTS-10/1-20     T P W G D C S R T C G G G V S S S S R -
ADAMTS-12(a)/1-16  - - W D L C S T S C G G G F Q K R - - -
ADAMTS-12(b)/1-15  S P W S H C S R T C G A G V - - - - - -
ADAMTS-13/1-16     - - W M E C S V S C G D G I Q R R - - -
ADAMTS-14/1-16     - - W S Q C S A T C G E G I Q Q R - - -
ADAMTS-151-18      S A W S P C S K S C G R G F Q R R - - -
ADAMTS-16(a)/1-18  S P W S Q C T A S C G G G V Q T R - - -
ADAMTS-16(b)/1-19  S P W S Q C T A S C G G G V Q T R S - -
ADAMTS-18(a)/1-17  - P W Q Q C T V T C G G G V Q T R - - -
ADAMTS-18(b)/1-18  - P W Q Q C T V T C G G G V Q T R S - -
ADAMTS-18(c)/1-18  G P W S Q C S K T C G R G V R K R - - -
ADAMTS-18(d)/1-20  S K W S E C S R T C G G G V K F Q E R -
ADAMTS-19/1-17     - - W S K C S I T C G K G M Q S R V - -
ADAMTS-20(a)/1-18  N S W N E C S V I C G S G V Q Q R - - -
ADAMTS-20(b)/1-19  G P W G Q C S S S C S G G L Q H R A - -
ADAMTS-20(c)/1-16  - - W S K C S V T C G I G I M K R - - - -
```

Fig. 41

SEQUENCE LISTING

<160> NUMBER OF SEQ ID NOS: 190

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Cys His Gly His Gly Val Cys Asn Ser Asn Lys Asn
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Gln Cys His Gly Arg Gly Val Cys Asn Asn Arg Lys Asn
1               5                   10

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Pro Trp Gly Asp Cys Ser Arg Thr Cys Gly Gly Gly Val Gln Tyr
1               5                   10                  15

Thr Met Arg

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Pro Trp Ser Gln Cys Ser Val Thr Cys Gly Asn Gly Thr Gln Glu
1               5                   10                  15

Arg

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Pro Trp Ser Glu Cys Ser Val Thr Cys Gly Glu Gly Thr Glu Val
1               5                   10                  15

Arg

```
<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Pro Trp Gly Asp Cys Ser Arg Thr Cys Gly Gly Gly Val
1               5                   10

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Pro Trp Gly Asp Cys Ser Arg Thr Cys Gly Gly Gly Val Gln Phe
1               5                   10                  15

Ser Ser Arg

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Pro Trp Leu Ala Cys Ser Arg Thr Cys Asp Thr Gly Trp His Thr
1               5                   10                  15

Arg

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Pro Trp Ser Glu Cys Ser Ala Thr Cys Ala Gly Gly Val
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Pro Trp Ser Glu Cys Ser Ala Thr Cys Ala Gly Gly Val Gln Arg
1               5                   10                  15

Gln

<210> SEQ ID NO 11
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 11

Gly Pro Trp Gly Gln Cys Ser Gly Pro Cys Gly Gly Val Gln Arg
1               5                   10                  15

Arg

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Pro Trp Thr Lys Cys Thr Val Thr Cys Gly Arg Gly Val
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Pro Trp Gly Glu Cys Ser Arg Thr Cys Gly Gly Val
1               5                   10

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Pro Trp Gly Glu Cys Ser Arg Thr Cys Gly Gly Val Gln Phe
1               5                   10                  15

Ser His Arg

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Ser Ser Cys Ser Val Thr Cys Gly Gln Gly Arg Ala Thr Arg
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 16

Gly Pro Trp Gly Ala Cys Ser Ser Thr Cys Ala Gly Gly Ser Gln Arg
1               5                   10                  15

Arg

<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Pro Phe Gly Thr Cys Ser Arg Thr Cys Gly Gly Gly Ile Lys Thr
1               5                   10                  15

Ala Ile Arg

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Pro Trp Gly Asp Cys Ser Arg Thr Cys Gly Gly Gly Val Ser Ser
1               5                   10                  15

Ser Ser Arg

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Asp Leu Cys Ser Thr Ser Cys Gly Gly Gly Phe Gln Lys Arg
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Pro Trp Ser His Cys Ser Arg Thr Cys Gly Ala Gly Val
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Met Glu Cys Ser Val Ser Cys Gly Asp Gly Ile Gln Arg Arg
```

```
<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Ser Gln Cys Ser Ala Thr Cys Gly Glu Gly Ile Gln Gln Arg
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ala Trp Ser Pro Cys Ser Lys Ser Cys Gly Arg Gly Phe Gln Arg
1               5                   10                  15

Arg

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Pro Trp Ser Gln Cys Thr Ala Ser Cys Gly Gly Gly Val Gln Thr
1               5                   10                  15

Arg

<210> SEQ ID NO 25
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Pro Trp Ser Gln Cys Thr Ala Ser Cys Gly Gly Gly Val Gln Thr
1               5                   10                  15

Arg Ser

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Pro Trp Gln Gln Cys Thr Val Thr Cys Gly Gly Gly Val Gln Thr Arg
1               5                   10                  15
```

```
<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Pro Trp Gln Gln Cys Thr Val Thr Cys Gly Gly Gly Val Gln Thr Arg
1               5                   10                  15

Ser

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Pro Trp Ser Gln Cys Ser Lys Thr Cys Gly Arg Gly Val Arg Lys
1               5                   10                  15

Arg

<210> SEQ ID NO 29
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Lys Trp Ser Glu Cys Ser Arg Thr Cys Gly Gly Gly Val Lys Phe
1               5                   10                  15

Gln Glu Arg

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Ser Lys Cys Ser Ile Thr Cys Gly Lys Gly Met Gln Ser Arg Val
1               5                   10                  15

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Asn Ser Trp Asn Glu Cys Ser Val Thr Cys Gly Ser Gly Val Gln Gln
1               5                   10                  15

Arg

<210> SEQ ID NO 32
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Pro Trp Gly Gln Cys Ser Ser Cys Ser Gly Gly Leu Gln His
1               5                   10                  15

Arg Ala

<210> SEQ ID NO 33
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Ser Lys Cys Ser Val Thr Cys Gly Ile Gly Ile Met Lys Arg
1               5                   10                  15

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Tyr Ser Ser Cys Ser Arg Thr Cys Gly Gly Gly Ile Glu Ser Ala
1               5                   10                  15

Thr Arg

<210> SEQ ID NO 35
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ser Pro Trp Ser Val Cys Ser Ser Thr Cys Gly Glu Gly Trp Gln Thr
1               5                   10                  15

Arg Thr Arg

<210> SEQ ID NO 36
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ser Pro Trp Ser Val Cys Ser Leu Thr Cys Gly Gln Gly Leu Gln Val
1               5                   10                  15

Arg Thr Arg

<210> SEQ ID NO 37
<211> LENGTH: 19
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ser Pro Trp Ser Leu Cys Ser Phe Thr Cys Gly Arg Gly Gln Arg Thr
1               5                   10                  15

Arg Thr Arg

<210> SEQ ID NO 38
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Thr Gln Trp Thr Ser Cys Ser Lys Thr Cys Asn Ser Gly Thr Gln Ser
1               5                   10                  15

Arg His Arg

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ser Pro Trp Ser Lys Cys Ser Ala Ala Cys Gly Gln Thr Gly Val Gln
1               5                   10                  15

Thr Arg Thr Arg
            20

<210> SEQ ID NO 40
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Pro Trp Gly Pro Cys Ser Gly Ser Cys Gly Pro Gly Arg Arg Leu
1               5                   10                  15

Arg Arg Arg

<210> SEQ ID NO 41
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Glu Trp Ser Ala Cys Ser Lys Thr Cys Gly Met Gly Ile Ser Thr
1               5                   10                  15

Arg Val
```

-continued

```
<210> SEQ ID NO 42
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Thr Ser Trp Ser Gln Cys Ser Lys Thr Cys Gly Thr Gly Ile Ser Thr
1               5                   10                  15

Arg Val

<210> SEQ ID NO 43
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ala Trp Arg Ala Cys Ser Val Thr Cys Gly Lys Gly Ile Gln Lys
1               5                   10                  15

Arg Ser Arg

<210> SEQ ID NO 44
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Pro Trp Gly Thr Cys Ser Glu Ser Cys Gly Lys Gly Thr Gln Thr
1               5                   10                  15

Arg Ala Arg

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ser Trp Ser Ala Cys Ser Val Ser Cys Gly Gly Gly Ala Arg Gln
1               5                   10                  15

Arg Thr Arg

<210> SEQ ID NO 46
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Glu Trp Thr Ala Cys Ser Lys Ser Cys Gly Met Gly Phe Ser Thr
1               5                   10                  15

Arg Val
```

```
<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Gln Trp Ser Pro Cys Ser Arg Thr Cys Gly Gly Val Ser Phe
1               5                   10                  15

Arg Glu Arg

<210> SEQ ID NO 48
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Pro Trp Ala Pro Cys Ser Ala Ser Cys Gly Gly Gly Ser Gln Ser
1               5                   10                  15

Arg Ser

<210> SEQ ID NO 49
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Pro Trp Glu Pro Cys Ser Val Thr Cys Ser Lys Gly Thr Arg Thr
1               5                   10                  15

Arg Arg Arg

<210> SEQ ID NO 50
<211> LENGTH: 79
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Tyr Asn Ser Thr Gly Val Asp Tyr Arg Gly Thr Val Ser Val Thr
1               5                   10                  15

Lys Ser Gly Arg Gln Cys Gln Pro Trp Asn Ser Gln Tyr Pro His Thr
                20                  25                  30

His Thr Phe Thr Ala Leu Arg Phe Pro Glu Leu Asn Gly Gly His Ser
            35                  40                  45

Tyr Cys Arg Asn Pro Gly Asn Gln Lys Glu Ala Pro Trp Cys Phe Thr
        50                  55                  60

Leu Asp Glu Asn Phe Lys Ser Asp Leu Cys Asp Ile Pro Ala Cys
65                  70                  75

<210> SEQ ID NO 51
<211> LENGTH: 82
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 51

Asn His Lys Cys Tyr Asn Ser Thr Gly Val Asp Tyr Arg Gly Thr Val
1               5                   10                  15

Ser Val Thr Lys Ser Gly Arg Gln Cys Gln Pro Trp Asn Ser Gln Tyr
            20                  25                  30

Pro His Thr His Thr Phe Thr Ala Leu Arg Phe Pro Glu Leu Asn Gly
        35                  40                  45

Gly His Ser Tyr Cys Arg Asn Pro Gly Asn Gln Lys Glu Ala Pro Trp
    50                  55                  60

Cys Phe Thr Leu Asp Glu Asn Phe Lys Ser Asp Leu Cys Asp Ile Pro
65                  70                  75                  80

Ala Cys

<210> SEQ ID NO 52
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Lys Cys Tyr Asn Ser Thr Gly Val Asp Tyr Arg Gly Thr Val Ser
1               5                   10                  15

Val Thr Lys Ser Gly Arg Gln Cys Gln Pro Trp Asn Ser Gln Tyr Pro
            20                  25                  30

His Thr His Thr Phe Thr Ala Leu Arg Phe Pro Glu Leu Asn Gly Gly
        35                  40                  45

His Ser Tyr Cys Arg Asn Pro Gly Asn Gln Lys Glu Ala Pro Trp Cys
    50                  55                  60

Phe Thr Leu Asp Glu Asn Phe Lys Ser Asp Leu Cys Asp Ile
65                  70                  75

<210> SEQ ID NO 53
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

His Lys Cys Tyr Asn Ser Thr Gly Val Asp Tyr Arg Gly Thr Val Ser
1               5                   10                  15

Val Thr Lys Ser Gly Arg Gln Cys Gln Pro Trp Asn Ser Gln Tyr Pro
            20                  25                  30

His Thr His Thr Phe Thr Ala Leu Arg Phe Pro Glu Leu Asn Gly Gly
        35                  40                  45

His Ser Tyr Cys Arg Asn Pro Gly Asn Gln Lys Glu Ala Pro Trp Cys
    50                  55                  60

Phe Thr Leu Asp Glu Asn Phe Lys Ser Asp Leu Cys Asp Ile Pro Ala
65                  70                  75                  80

Cys

<210> SEQ ID NO 54
```

```
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Cys Tyr Asn Ser Thr Gly Val Asp Tyr Arg Gly Thr Val Ser Val
1               5                   10                  15

Thr Lys Ser Gly Arg Gln Cys Gln Pro Trp Asn Ser Gln Tyr Pro His
            20                  25                  30

Thr His Thr Phe Thr Ala Leu Arg Phe Pro Glu Leu Asn Gly Gly His
        35                  40                  45

Ser Tyr Cys Arg Asn Pro Gly Asn Gln Lys Glu Ala Pro Trp Cys Phe
    50                  55                  60

Thr Leu Asp Glu Asn Phe Lys Ser Asp Leu Cys Asp Ile Pro Ala Cys
65                  70                  75                  80

Asp

<210> SEQ ID NO 55
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Cys Tyr Asn Gly Ser Gly Met Asp Tyr Arg Gly Thr Ala Ser Thr
1               5                   10                  15

Thr Lys Ser Gly His Gln Cys Gln Pro Trp Ala Leu Gln His Pro His
            20                  25                  30

Ser His His Leu Ser Ser Thr Asp Phe Pro Glu Leu Gly Gly Gly His
        35                  40                  45

Ala Tyr Cys Arg Asn Pro Gly Gly Gln Met Glu Gly Pro Trp Cys Phe
    50                  55                  60

Thr Gln Asn Lys Asn Val Arg Met Glu Leu Cys Asp Val Pro Ser Cys
65                  70                  75                  80

Ser

<210> SEQ ID NO 56
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Gln Cys Tyr Asn Gly Ser Gly Met Asp Tyr Arg Gly Thr Ala Ser
1               5                   10                  15

Thr Thr Lys Ser Gly His Gln Cys Gln Pro Trp Ala Leu Gln His Pro
            20                  25                  30

His Ser His His Leu Ser Ser Thr Asp Phe Pro Glu Leu Gly Gly Gly
        35                  40                  45

His Ala Tyr Cys Arg Asn Pro Gly Gly Gln Met Glu Gly Pro Trp Cys
    50                  55                  60

Phe Thr Gln Asn Lys Asn Val Arg Met Glu Leu Cys Asp Val
65                  70                  75
```

<210> SEQ ID NO 57
<211> LENGTH: 81
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

His Gln Cys Tyr Asn Gly Ser Gly Met Asp Tyr Arg Gly Thr Ala Ser
1               5                   10                  15

Thr Thr Lys Ser Gly His Gln Cys Gln Pro Trp Ala Leu Gln His Pro
            20                  25                  30

His Ser His His Leu Ser Ser Thr Asp Phe Pro Glu Leu Gly Gly Gly
        35                  40                  45

His Ala Tyr Cys Arg Asn Pro Gly Gly Gln Met Glu Gly Pro Trp Cys
    50                  55                  60

Phe Thr Gln Asn Lys Asn Val Arg Met Glu Leu Cys Asp Val Pro Ser
65                  70                  75                  80

Cys

<210> SEQ ID NO 58
<211> LENGTH: 82
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

His Gln Cys Tyr Asn Gly Ser Gly Met Asp Tyr Arg Gly Thr Ala Ser
1               5                   10                  15

Thr Thr Lys Ser Gly His Gln Cys Gln Pro Trp Ala Leu Gln His Pro
            20                  25                  30

His Ser His His Leu Ser Ser Thr Asp Phe Pro Glu Leu Gly Gly Gly
        35                  40                  45

His Ala Tyr Cys Arg Asn Pro Gly Gly Gln Met Glu Gly Pro Trp Cys
    50                  55                  60

Phe Thr Gln Asn Lys Asn Val Arg Met Glu Leu Cys Asp Val Pro Ser
65                  70                  75                  80

Cys Ser

<210> SEQ ID NO 59
<211> LENGTH: 80
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Gln Cys Tyr Asn Gly Ser Gly Met Asp Tyr Arg Gly Thr Ala Ser Thr
1               5                   10                  15

Thr Lys Ser Gly His Gln Cys Gln Pro Trp Ala Leu Gln His Pro His
            20                  25                  30

Ser His His Leu Ser Ser Thr Asp Phe Pro Glu Leu Gly Gly Gly His
        35                  40                  45

Ala Tyr Cys Arg Asn Pro Gly Gly Gln Met Glu Gly Pro Trp Cys Phe
    50                  55                  60

Thr Gln Asn Lys Asn Val Arg Met Glu Leu Cys Asp Val Pro Ser Cys
 65                  70                  75                  80

<210> SEQ ID NO 60
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Pro Trp Glu Arg Cys Thr Ala Gln Cys Gly Gly Gly Ile Gln Ala
  1               5                  10                  15

Arg Arg Arg

<210> SEQ ID NO 61
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Pro Trp Thr Lys Cys Ser Ala Thr Cys Gly Gly Gly His Tyr Met
  1               5                  10                  15

Arg Thr Arg

<210> SEQ ID NO 62
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Ser Trp Ser Pro Cys Ser Ala Ser Cys Gly Gly Gly His Tyr Gln
  1               5                  10                  15

Arg Thr Arg

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Pro Trp Glu Asp Cys Ser Val Ser Cys Gly Gly Gly Glu Gln Leu
  1               5                  10                  15

Arg Ser Arg

<210> SEQ ID NO 64
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Gln Pro Trp Ser Gln Cys Ser Ala Thr Cys Gly Asp Gly Val Arg Glu
1               5                   10                  15

Arg Arg Arg

<210> SEQ ID NO 65
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Pro Trp Ser Pro Cys Ser Gly Asn Cys Ser Thr Gly Lys Gln Gln
1               5                   10                  15

Arg Thr Arg

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Thr Arg Cys Ser Ser Ser Cys Gly Arg Gly Val Ser Val Arg Ser
1               5                   10                  15

Arg

<210> SEQ ID NO 67
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Pro Trp Ser Ser Cys Ser Val Thr Cys Gly Val Gly Asn Ile Thr
1               5                   10                  15

Arg Ile Arg

<210> SEQ ID NO 68
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Pro Trp Ser Ala Cys Thr Val Thr Cys Ala Gly Gly Ile Arg Glu
1               5                   10                  15

Arg Thr Arg

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69
```

```
Ser Pro Trp Ser Gln Cys Ser Val Arg Cys Gly Arg Gly Gln Arg Ser
1               5                   10                  15

Arg Gln Val Arg
            20

<210> SEQ ID NO 70
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Thr Glu Trp Ser Val Cys Asn Ser Arg Cys Gly Arg Gly Tyr Gln Lys
1               5                   10                  15

Arg Thr Arg

<210> SEQ ID NO 71
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Glu Trp Ser Ala Cys Asn Val Arg Cys Gly Arg Gly Trp Gln Lys
1               5                   10                  15

Arg Ser Arg

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Asp Glu Cys Ser Ala Thr Cys Gly Met Gly Met Lys Lys Arg His
1               5                   10                  15

Arg

<210> SEQ ID NO 73
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ser Glu Trp Ser Asp Cys Ser Val Thr Cys Gly Lys Gly Met Arg Thr
1               5                   10                  15

Arg Gln Arg

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 74

Ser Pro Trp Ser Pro Cys Ser Thr Ser Cys Gly Leu Gly Val Ser Thr
1               5                   10                  15

Arg Ile

<210> SEQ ID NO 75
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Thr Ala Trp Gly Pro Cys Ser Thr Thr Cys Gly Leu Gly Met Ala Thr
1               5                   10                  15

Arg Val

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Lys Trp Thr Pro Cys Ser Arg Thr Cys Gly Met Gly Ile Ser Asn
1               5                   10                  15

Arg Val

<210> SEQ ID NO 77
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Asn Glu Arg Ala His Gly Gln Asp Leu Gly Thr Ala Gly Ser Cys Leu
1               5                   10                  15

Arg Lys Phe Ser Thr Met Pro Phe Leu Phe Cys Asn Ile Asn Asn Val
            20                  25                  30

Cys Asn Phe Ala Ser Arg Asn Asp Tyr Ser Tyr Trp Leu Ser Thr Pro
        35                  40                  45

Glu Pro Met Pro Met Ser Met Ala Pro Ile Thr Gly Glu Asn Ile Arg
    50                  55                  60

Pro Phe Ile Ser Arg Cys Ala Val Cys Glu Ala Pro Ala Met
65                  70                  75

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Arg Lys Phe Ser Thr Met Pro Phe Leu Phe Cys Asn Ile Asn Asn
1               5                   10                  15
```

```
Val Cys Asn Phe
            20

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Cys Asn Ile Asn Asn Val Cys Asn Phe Ala Ser Arg Asn Asp Tyr
1               5                   10                  15

Ser Tyr Trp Leu
            20

<210> SEQ ID NO 80
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ala Pro Phe Ile Glu Cys His Gly Arg Gly Thr Cys Asn Tyr Tyr
1               5                   10                  15

Ala Asn Ala

<210> SEQ ID NO 81
<211> LENGTH: 77
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gln Glu Lys Ala His Asn Gln Asp Leu Gly Leu Ala Gly Ser Cys Leu
1               5                   10                  15

Ala Arg Phe Ser Thr Met Pro Phe Leu Tyr Cys Asn Pro Gly Asp Val
            20                  25                  30

Cys Tyr Tyr Ala Ser Arg Asn Asp Lys Ser Tyr Trp Leu Ser Thr Thr
        35                  40                  45

Ala Pro Leu Pro Met Met Pro Val Ala Glu Asp Glu Ile Lys Pro Tyr
    50                  55                  60

Ile Ser Arg Cys Ser Val Cys Glu Ala Pro Ala Ile Ala
65                  70                  75

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Tyr Cys Asn Pro Gly Asp Val Cys Tyr Tyr Ala Ser Arg Asn Asp Lys
1               5                   10                  15

Ser Tyr Trp Leu
            20
```

<210> SEQ ID NO 83
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Thr Pro Phe Ile Glu Cys Asn Gly Gly Arg Gly Thr Cys His Tyr
1               5                   10                  15

Tyr Ala Asn

<210> SEQ ID NO 84
<211> LENGTH: 77
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gln Glu Lys Ala His Asn Gln Asp Leu Gly Leu Ala Gly Ser Cys Leu
1               5                   10                  15

Pro Val Phe Ser Thr Leu Pro Phe Ala Tyr Cys Asn Ile His Gln Val
                20                  25                  30

Cys His Tyr Ala Gln Arg Asn Asp Arg Ser Tyr Trp Leu Ala Ser Ala
            35                  40                  45

Ala Pro Leu Pro Met Met Pro Leu Ser Glu Glu Ala Ile Arg Pro Tyr
    50                  55                  60

Val Ser Arg Cys Ala Val Cys Glu Ala Pro Ala Gln Ala
65                  70                  75

<210> SEQ ID NO 85
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Leu Pro Val Phe Ser Thr Leu Pro Phe Ala Tyr Cys Asn Ile His Gln
1               5                   10                  15

Val Cys His Tyr
            20

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Cys Asn Ile His Gln Val Cys His Tyr Ala Gln Arg Asn Asp Arg
1               5                   10                  15

Ser Tyr Trp Leu
            20

<210> SEQ ID NO 87

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Ala Pro Phe Leu Glu Cys Gln Gly Arg Gln Gly Thr Cys His Phe
1               5                   10                  15

Phe Ala Asn

<210> SEQ ID NO 88
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asn Lys Arg Ala His Gly Gln Asp Leu Gly Thr Ala Gly Ser Cys Leu
1               5                   10                  15

Arg Arg Phe Ser Thr Met Pro Phe Met Phe Cys Asn Ile Asn Asn Val
                20                  25                  30

Cys Asn Phe Ala Ser Arg Asn Asp Tyr Ser Tyr Trp Leu Ser Thr Pro
            35                  40                  45

Glu Pro Met Pro Met Ser Met Gln Pro Leu Lys Gly Gln Ser Ile Gln
    50                  55                  60

Pro Phe Ile Ser Arg Cys Ala Val Cys Glu Ala Pro Ala Val
65                  70                  75

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Arg Arg Phe Ser Thr Met Pro Phe Met Phe Cys Asn Ile Asn Asn
1               5                   10                  15

Val Cys Asn Phe
            20

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Cys Asn Ile Asn Asn Val Cys Asn Phe Ala Ser Arg Asn Asp Tyr
1               5                   10                  15

Ser Tyr Trp Leu
            20

<210> SEQ ID NO 91
<211> LENGTH: 19
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 91

Ser Ala Pro Phe Ile Glu Cys His Gly Arg Gly Thr Cys Asn Tyr Tyr
1               5                   10                  15

Ala Asn Ser

<210> SEQ ID NO 92
<211> LENGTH: 77
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Glu Lys Ala His Asn Gln Asp Leu Gly Phe Ala Gly Ser Cys Leu
1               5                   10                  15

Pro Arg Phe Ser Thr Met Pro Phe Ile Tyr Cys Asn Ile Asn Glu Val
            20                  25                  30

Cys His Tyr Ala Arg Arg Asn Asp Lys Ser Tyr Trp Leu Ser Thr Thr
        35                  40                  45

Ala Pro Ile Pro Met Met Pro Val Ser Gln Thr Gln Ile Pro Gln Tyr
    50                  55                  60

Ile Ser Arg Cys Ser Val Cys Glu Ala Pro Ser Gln Ala
65                  70                  75

<210> SEQ ID NO 93
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Tyr Cys Asn Ile Asn Glu Val Cys His Tyr Ala Arg Arg Asn Asp Lys
1               5                   10                  15

Ser Tyr Trp Leu
            20

<210> SEQ ID NO 94
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Thr Pro Phe Ile Glu Cys Ser Gly Ala Arg Gly Thr Cys His Tyr
1               5                   10                  15

Phe Ala Asn

<210> SEQ ID NO 95
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 95

Asn Gly Lys Glu Ile Cys Leu Asp Pro Glu Ala Pro Phe Leu Lys Lys
1               5                   10                  15

Val Ile Gln Lys Ile Leu Asp
            20

<210> SEQ ID NO 96
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Cys Val Cys Leu Gln Thr Thr Gln Gly Val His Pro Lys Met Ile
1               5                   10                  15

Ser Asn Leu Gln Val Phe Ala Ile Gly Pro Gln Cys Ser Lys Val Glu
            20                  25                  30

Val Val Ala Ser Leu Lys Asn Gly Lys Glu Ile Cys Leu Asp Pro Glu
        35                  40                  45

Ala Pro Phe Leu Lys Lys Val Ile
    50                  55

<210> SEQ ID NO 97
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Cys Leu Gln Thr Thr Gln Gly Val His Pro Lys Met Ile Ser Asn Leu
1               5                   10                  15

Gln Val Phe Ala Ile Gly Pro Gln Cys Ser Lys Val Glu Val Val Ala
            20                  25                  30

Ser Leu Lys Asn Gly Lys Glu Ile Cys Leu Asp Pro Glu Ala Pro Phe
        35                  40                  45

Leu Lys Lys Val Ile Gln Lys Ile Leu
    50                  55

<210> SEQ ID NO 98
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asn Gly Lys Gln Val Cys Leu Asp Pro Glu Ala Pro Phe Leu Lys Lys
1               5                   10                  15

Val Ile Gln Lys Ile Leu Asp Ser
            20

<210> SEQ ID NO 99
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 99

Leu Arg Cys Thr Cys Leu Arg Val Thr Leu Arg Val Asn Pro Lys Thr
1               5                   10                  15

Ile Gly Lys Leu Gln Val Phe Pro Ala Gly Pro Gln Cys Ser Lys Val
            20                  25                  30

Glu Val Ala Ser Leu Lys Asn Gly Lys Gln Val Cys Leu Asp Pro
        35                  40                  45

Glu Ala Pro Phe Leu Lys Lys Val Ile Gln Lys Ile
    50                  55                  60

<210> SEQ ID NO 100
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Cys Thr Cys Leu Arg Val Thr Leu Arg Val Asn Pro Lys Thr Ile
1               5                   10                  15

Gly Lys Leu Gln Val Phe Pro Ala Gly Pro Gln Cys Ser Lys Val Glu
            20                  25                  30

Val Val Ala Ser Leu Lys Asn Gly Lys Gln Val Cys Leu Asp Pro Glu
        35                  40                  45

Ala Pro Phe Leu Lys Lys Val Ile
    50                  55

<210> SEQ ID NO 101
<211> LENGTH: 57
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Leu Arg Val Thr Leu Arg Val Asn Pro Lys Thr Ile Gly Lys Leu
1               5                   10                  15

Gln Val Phe Pro Ala Gly Pro Gln Cys Ser Lys Val Glu Val Val Ala
            20                  25                  30

Ser Leu Lys Asn Gly Lys Gln Val Cys Leu Asp Pro Glu Ala Pro Phe
        35                  40                  45

Leu Lys Lys Val Ile Gln Lys Ile Leu
    50                  55

<210> SEQ ID NO 102
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Asn Gly Arg Lys Ala Cys Leu Asn Pro Ala Ser Pro Ile Val Lys Lys
1               5                   10                  15

Ile Ile Glu Lys Met Leu Asn Ser
            20

<210> SEQ ID NO 103
<211> LENGTH: 56
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Arg Cys Gln Cys Leu Gln Thr Leu Gln Gly Ile His Pro Lys Asn Ile
1               5                   10                  15

Gln Ser Val Asn Val Lys Ser Pro Gly Pro His Cys Ala Gln Thr Glu
            20                  25                  30

Val Ile Ala Thr Leu Lys Asn Gly Arg Lys Ala Cys Leu Asn Pro Ala
        35                  40                  45

Ser Pro Ile Val Lys Lys Ile Ile
    50                  55

<210> SEQ ID NO 104
<211> LENGTH: 58
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Gln Cys Leu Gln Thr Leu Gln Gly Ile His Pro Lys Asn Ile Gln Ser
1               5                   10                  15

Val Asn Val Lys Ser Pro Gly Pro His Cys Ala Gln Thr Glu Val Ile
            20                  25                  30

Ala Thr Leu Lys Asn Gly Arg Lys Ala Cys Leu Asn Pro Ala Ser Pro
        35                  40                  45

Ile Val Lys Lys Ile Ile Glu Lys Met Leu
    50                  55

<210> SEQ ID NO 105
<211> LENGTH: 56
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Arg Cys Gln Cys Leu Gln Thr Leu Gln Gly Ile His Leu Lys Asn Ile
1               5                   10                  15

Gln Ser Val Lys Val Lys Ser Pro Gly Pro His Cys Ala Gln Thr Glu
            20                  25                  30

Val Ile Ala Thr Leu Lys Asn Gly Gln Lys Ala Cys Leu Asn Pro Ala
        35                  40                  45

Ser Pro Met Val Lys Lys Ile Ile
    50                  55

<210> SEQ ID NO 106
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

```
Asn Gly Lys Lys Ala Cys Leu Asn Pro Ala Ser Pro Met Val Gln Lys
1               5                   10                  15

Ile Ile Glu Lys Ile Leu
            20
```

<210> SEQ ID NO 107
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Gln Cys Leu Gln Thr Leu Gln Gly Ile His Leu Lys Asn Ile Gln Ser
1               5                   10                  15

Val Asn Val Arg Ser Pro Gly Pro His Cys Ala Gln Thr Glu Val Ile
            20                  25                  30

Ala Thr Leu Lys Asn Gly Lys Lys Ala Cys Leu Asn Pro Ala Ser Pro
        35                  40                  45

Met Val Gln Lys Ile Ile Glu Lys Ile Leu
    50                  55
```

<210> SEQ ID NO 108
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Arg Cys Gln Cys Leu Gln Thr Leu Gln Gly Ile His Leu Lys Asn Ile
1               5                   10                  15

Gln Ser Val Asn Val Arg Ser Pro Gly Pro His Cys Ala Gln Thr Glu
            20                  25                  30

Val Ile Ala Thr Leu Lys Asn Gly Lys Lys Ala Cys Leu Asn Pro Ala
        35                  40                  45

Ser Pro Met Val Gln Lys Ile Ile
    50                  55
```

<210> SEQ ID NO 109
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Gln Cys Ile Lys Thr Tyr Ser Lys Pro Phe His Pro Lys Phe Ile Lys
1               5                   10                  15

Glu Leu Arg Val Ile Glu Ser Gly Pro His Cys Ala Asn Thr Glu Ile
            20                  25                  30

Ile Val Lys Leu Ser Asp Gly Arg Glu Leu Cys Leu Asp Pro Lys Glu
        35                  40                  45

Asn Trp Val Gln Arg Val Val Glu Lys Phe Leu Lys
    50                  55                  60
```

<210> SEQ ID NO 110
<211> LENGTH: 23
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 110

Asp Gly Arg Glu Leu Cys Leu Asp Pro Lys Glu Asn Trp Val Gln Arg
1               5                   10                  15

Val Val Glu Lys Phe Leu Lys
            20

<210> SEQ ID NO 111
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Cys Thr Cys Ile Ser Ile Ser Asn Gln Pro Val Asn Pro Arg Ser
1               5                   10                  15

Leu Glu Lys Leu Glu Ile Ile Pro Ala Ser Gln Phe Cys Pro Arg Val
            20                  25                  30

Glu Ile Ile Ala Thr Met Lys Lys Lys Gly Glu Lys Arg Cys Leu Asn
        35                  40                  45

Pro Glu Ser Lys Ala Ile Lys Asn Leu Leu
        50                  55

<210> SEQ ID NO 112
<211> LENGTH: 60
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Cys Ile Ser Thr Asn Gln Gly Thr Ile His Leu Gln Ser Leu Lys
1               5                   10                  15

Asp Leu Lys Gln Phe Ala Pro Ser Pro Ser Cys Glu Lys Ile Glu Ile
            20                  25                  30

Ile Ala Thr Leu Lys Asn Gly Val Gln Thr Cys Leu Asn Pro Asp Ser
        35                  40                  45

Ala Asp Val Lys Glu Leu Ile Lys Lys Trp Glu Lys
        50                  55                  60

<210> SEQ ID NO 113
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Cys Val Lys Thr Thr Ser Gln Val Arg Pro Arg His Ile Thr Ser Leu
1               5                   10                  15

Glu Val Ile Lys Ala Gly Pro His Cys Pro Thr Ala Gln Leu Ile Ala
            20                  25                  30

Thr Leu Lys Asn Gly Arg Lys Ile Cys Leu Asp Leu Gln Ala Pro Leu
        35                  40                  45
```

Tyr Lys Lys Ile Ile Lys Lys Leu Leu Glu
        50                  55

<210> SEQ ID NO 114
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asp Gly Arg Lys Ile Cys Leu Asp Pro Asp Ala Pro Arg Ile Lys Lys
1               5                   10                  15

Ile Val Gln Lys Lys Leu
            20

<210> SEQ ID NO 115
<211> LENGTH: 56
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Cys Met Cys Ile Lys Thr Thr Ser Gly Ile His Pro Lys Asn Ile
1               5                   10                  15

Gln Ser Leu Glu Val Ile Gly Lys Gly Thr His Cys Asn Gln Val Glu
            20                  25                  30

Val Ile Ala Thr Leu Lys Asp Gly Arg Lys Ile Cys Leu Asp Pro Asp
        35                  40                  45

Ala Pro Arg Ile Lys Lys Ile Val
    50                  55

<210> SEQ ID NO 116
<211> LENGTH: 58
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Met Cys Ile Lys Thr Thr Ser Gly Ile His Pro Lys Asn Ile Gln Ser
1               5                   10                  15

Leu Glu Val Ile Gly Lys Gly Thr His Cys Asn Gln Val Glu Val Ile
            20                  25                  30

Ala Thr Leu Lys Asp Gly Arg Lys Ile Cys Leu Asp Pro Asp Ala Pro
        35                  40                  45

Arg Ile Lys Lys Ile Val Gln Lys Lys Leu
    50                  55

<210> SEQ ID NO 117
<211> LENGTH: 82
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Cys Met Phe Gly Asn Gly Lys Gly Tyr Arg Gly Lys Lys Ala Thr
1               5                   10                  15

Thr Val Thr Gly Thr Pro Cys Gln Glu Trp Ala Ala Gln Glu Pro His
            20                  25                  30

Arg His Ser Thr Phe Ile Pro Gly Thr Asn Lys Trp Ala Gly Leu Glu
        35                  40                  45

Lys Asn Tyr Cys Arg Asn Pro Asp Gly Asp Ile Asn Gly Pro Trp Cys
 50                  55                  60

Tyr Thr Met Asn Pro Arg Lys Leu Phe Asp Tyr Cys Asp Ile Pro Leu
 65                  70                  75                  80

Cys Ala

<210> SEQ ID NO 118
<211> LENGTH: 83
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gln Asp Cys Met Phe Gly Asn Gly Lys Gly Tyr Arg Gly Lys Lys Ala
 1               5                  10                  15

Thr Thr Val Thr Gly Thr Pro Cys Gln Glu Trp Ala Ala Gln Glu Pro
            20                  25                  30

His Arg His Ser Thr Phe Ile Pro Gly Thr Asn Lys Trp Ala Gly Leu
        35                  40                  45

Glu Lys Asn Tyr Cys Arg Asn Pro Asp Gly Asp Ile Asn Gly Pro Trp
 50                  55                  60

Cys Tyr Thr Met Asn Pro Arg Lys Leu Phe Asp Tyr Cys Asp Ile Pro
 65                  70                  75                  80

Leu Cys Ala

<210> SEQ ID NO 119
<211> LENGTH: 78
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Asp Cys Met Phe Gly Asn Gly Lys Gly Tyr Arg Gly Lys Lys Ala Thr
 1               5                  10                  15

Thr Val Thr Gly Thr Pro Cys Gln Glu Trp Ala Ala Gln Glu Pro His
            20                  25                  30

Arg His Ser Thr Phe Ile Pro Gly Thr Asn Lys Trp Ala Gly Leu Glu
        35                  40                  45

Lys Asn Tyr Cys Arg Asn Pro Asp Gly Asp Ile Asn Gly Pro Trp Cys
 50                  55                  60

Tyr Thr Met Asn Pro Arg Lys Leu Phe Asp Tyr Cys Asp Ile
 65                  70                  75

<210> SEQ ID NO 120
<211> LENGTH: 80
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Cys Met Phe Gly Asn Gly Lys Gly Tyr Arg Gly Lys Lys Ala Thr Thr
1               5                   10                  15

Val Thr Gly Thr Pro Cys Gln Glu Trp Ala Ala Gln Glu Pro His Arg
            20                  25                  30

His Ser Thr Phe Ile Pro Gly Thr Asn Lys Trp Ala Gly Leu Glu Lys
        35                  40                  45

Asn Tyr Cys Arg Asn Pro Asp Gly Asp Ile Asn Gly Pro Trp Cys Tyr
    50                  55                  60

Thr Met Asn Pro Arg Lys Leu Phe Asp Tyr Cys Asp Ile Pro Leu Cys
65                  70                  75                  80

<210> SEQ ID NO 121
<211> LENGTH: 77
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ser Cys Tyr Asp Gly Arg Gly Leu Ser Tyr Arg Gly Leu Ala Arg Thr
1               5                   10                  15

Thr Leu Ser Gly Ala Pro Cys Gln Pro Trp Ala Ser Glu Ala Thr Tyr
            20                  25                  30

Arg Asn Val Thr Ala Glu Gln Ala Arg Asn Trp Gly Leu Gly Gly His
        35                  40                  45

Ala Phe Cys Arg Asn Pro Asp Asn Asp Ile Arg Pro Trp Cys Phe Val
    50                  55                  60

Leu Asn Arg Asp Arg Leu Ser Trp Glu Tyr Cys Asp Leu
65                  70                  75

<210> SEQ ID NO 122
<211> LENGTH: 82
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Lys Ala Ser Cys Tyr Asp Gly Arg Gly Leu Ser Tyr Arg Gly Leu Ala
1               5                   10                  15

Arg Thr Thr Leu Ser Gly Ala Pro Cys Gln Pro Trp Ala Ser Glu Ala
            20                  25                  30

Thr Tyr Arg Asn Val Thr Ala Glu Gln Ala Arg Asn Trp Gly Leu Gly
        35                  40                  45

Gly His Ala Phe Cys Arg Asn Pro Asp Asn Asp Ile Arg Pro Trp Cys
    50                  55                  60

Phe Val Leu Asn Arg Asp Arg Leu Ser Trp Glu Tyr Cys Asp Leu Ala
65                  70                  75                  80

Gln Cys

<210> SEQ ID NO 123
<211> LENGTH: 82
<212> TYPE: PRT
<213> ORGANISM: Artificial Sequence
<220> FEATURE:
<223> OTHER INFORMATION: Description of Artificial Sequence: Synthetic
      peptide

```
-continued

<400> SEQUENCE: 123

Ala Ser Cys Tyr Asp Gly Arg Gly Leu Ser Tyr Arg Gly Leu Ala Arg
1               5                   10                  15

Thr Thr Leu Ser Gly Ala Pro Cys Gln Pro Trp Ala Ser Glu Ala Thr
            20                  25                  30

Tyr Arg Asn Val Thr Ala Glu Gln Ala Arg Asn Trp Gly Leu Gly Gly
        35                  40                  45

His Ala Phe Cys Arg Asn Pro Asp Asn Asp Ile Arg Pro Trp Cys Phe
    50                  55                  60

Val Leu Asn Arg Asp Arg Leu Ser Trp Glu Tyr Cys Asp Leu Ala Gln
65                  70                  75                  80

Cys Gln

<210> SEQ ID NO 124
<211> LENGTH: 80
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Asn Cys Ile Ile Gly Lys Gly Arg Ser Tyr Lys Gly Thr Val Ser Ile
1               5                   10                  15

Thr Lys Ser Gly Ile Lys Cys Gln Pro Trp Ser Ser Met Ile Pro His
            20                  25                  30

Glu His Ser Phe Leu Pro Ser Ser Tyr Arg Gly Lys Asp Leu Gln Glu
        35                  40                  45

Asn Tyr Cys Arg Asn Pro Arg Gly Glu Glu Gly Gly Pro Trp Cys Phe
    50                  55                  60

Thr Ser Asn Pro Glu Val Arg Tyr Glu Val Cys Asp Ile Pro Gln Cys
65                  70                  75                  80

<210> SEQ ID NO 125
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Asn Cys Ile Ile Gly Lys Gly Arg Ser Tyr Lys Gly Thr Val Ser Ile
1               5                   10                  15

Thr Lys Ser Gly Ile Lys Cys Gln Pro Trp Ser Ser Met Ile Pro His
            20                  25                  30

Glu His Ser Phe Leu Pro Ser Ser Tyr Arg Gly Lys Asp Leu Gln Glu
        35                  40                  45

Asn Tyr Cys Arg Asn Pro Arg Gly Glu Glu Gly Gly Pro Trp Cys Phe
    50                  55                  60

Thr Ser Asn Pro Glu Val Arg Tyr Glu Val Cys Asp Ile Pro Gln Cys
65                  70                  75                  80

Ser

<210> SEQ ID NO 126
<211> LENGTH: 74
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 126

Glu Cys Ile Gln Gly Gln Gly Glu Gly Tyr Arg Gly Thr Val Asn Thr
1               5                   10                  15

Ile Trp Asn Gly Ile Pro Cys Gln Arg Trp Asp Ser Gln Tyr Pro His
            20                  25                  30

Glu His Asp Met Thr Pro Glu Asn Phe Lys Cys Lys Asp Leu Arg Glu
        35                  40                  45

Asn Tyr Cys Arg Asn Pro Asp Gly Ser Glu Ser Pro Trp Cys Phe Thr
    50                  55                  60

Thr Asp Pro Asn Ile Arg Val Gly Tyr Cys
65                  70

<210> SEQ ID NO 127
<211> LENGTH: 80
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Glu Cys Met Thr Cys Asn Gly Glu Ser Tyr Arg Gly Leu Met Asp His
1               5                   10                  15

Thr Glu Ser Gly Lys Ile Cys Gln Arg Trp Asp His Gln Thr Pro His
            20                  25                  30

Arg His Lys Phe Leu Pro Glu Arg Tyr Pro Asp Lys Gly Phe Asp Asp
        35                  40                  45

Asn Tyr Cys Arg Asn Pro Asp Gly Gln Pro Arg Pro Trp Cys Tyr Thr
    50                  55                  60

Leu Asp Pro His Thr Arg Trp Glu Tyr Cys Ala Ile Lys Thr Cys Ala
65                  70                  75                  80

<210> SEQ ID NO 128
<211> LENGTH: 80
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Glu Cys Ile Gln Gly Gln Gly Glu Gly Tyr Arg Gly Thr Val Asn Thr
1               5                   10                  15

Ile Trp Asn Gly Ile Pro Cys Gln Arg Trp Asp Ser Gln Tyr Pro His
            20                  25                  30

Glu His Asp Met Thr Pro Glu Asn Phe Lys Cys Lys Asp Leu Arg Glu
        35                  40                  45

Asn Tyr Cys Arg Asn Pro Asp Gly Ser Glu Ser Pro Trp Cys Phe Thr
    50                  55                  60

Thr Asp Pro Asn Ile Arg Val Gly Tyr Cys Ser Gln Ile Pro Asn Cys
65                  70                  75                  80

<210> SEQ ID NO 129
<211> LENGTH: 86
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 129

Asp Asp Cys Tyr Val Gly Asp Gly Tyr Ser Tyr Arg Gly Lys Met Asn
1               5                   10                  15

Arg Thr Val Asn Gln His Ala Cys Leu Tyr Trp Asn Ser His Leu Leu
            20                  25                  30

Leu Gln Glu Asn Tyr Asn Met Phe Met Glu Asp Ala Glu Thr His Gly
        35                  40                  45

Ile Gly Glu His Asn Phe Cys Arg Asn Pro Asp Ala Asp Glu Lys Pro
    50                  55                  60

Trp Cys Phe Ile Lys Val Thr Asn Asp Lys Val Lys Trp Glu Tyr Cys
65                  70                  75                  80

Asp Val Ser Ala Cys Ser
                85

<210> SEQ ID NO 130
<211> LENGTH: 85
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Asp Asp Cys Tyr Val Gly Asp Gly Tyr Ser Tyr Arg Gly Lys Met Asn
1               5                   10                  15

Arg Thr Val Asn Gln His Ala Cys Leu Tyr Trp Asn Ser His Leu Leu
            20                  25                  30

Leu Gln Glu Asn Tyr Asn Met Phe Met Glu Asp Ala Glu Thr His Gly
        35                  40                  45

Ile Gly Glu His Asn Phe Cys Arg Asn Pro Asp Ala Asp Glu Lys Pro
    50                  55                  60

Trp Cys Phe Ile Lys Val Thr Asn Asp Lys Val Lys Trp Glu Tyr Cys
65                  70                  75                  80

Asp Val Ser Ala Cys
                85

<210> SEQ ID NO 131
<211> LENGTH: 84
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Glu Cys Phe Thr Ala Asn Gly Ala Asp Tyr Arg Gly Thr Gln Asn Trp
1               5                   10                  15

Thr Ala Leu Gln Gly Gly Lys Pro Cys Leu Phe Trp Asn Glu Thr Phe
            20                  25                  30

Gln His Pro Tyr Asn Thr Leu Lys Tyr Pro Asn Gly Glu Gly Gly Leu
        35                  40                  45

Gly Glu His Asn Tyr Cys Arg Asn Pro Asp Gly Asp Val Ser Pro Trp
    50                  55                  60

Cys Tyr Val Ala Glu His Glu Asp Gly Val Tyr Trp Lys Tyr Cys Glu
65                  70                  75                  80

Ile Pro Ala Cys
```

<210> SEQ ID NO 132
<211> LENGTH: 85
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

```
Glu Cys Phe Thr Ala Asn Gly Ala Asp Tyr Arg Gly Thr Gln Asn Trp
1               5                   10                  15

Thr Ala Leu Gln Gly Gly Lys Pro Cys Leu Phe Trp Asn Glu Thr Phe
            20                  25                  30

Gln His Pro Tyr Asn Thr Leu Lys Tyr Pro Asn Gly Glu Gly Gly Leu
        35                  40                  45

Gly Glu His Asn Tyr Cys Arg Asn Pro Asp Gly Asp Val Ser Pro Trp
    50                  55                  60

Cys Tyr Val Ala Glu His Glu Asp Gly Val Tyr Trp Lys Tyr Cys Glu
65                  70                  75                  80

Ile Pro Ala Cys Gln
            85
```

<210> SEQ ID NO 133
<211> LENGTH: 85
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

```
Glu Cys Phe Gln Val Asn Gly Ala Asp Tyr Arg Gly His Gln Asn Arg
1               5                   10                  15

Thr Gly Pro Arg Gly Ala Gly Arg Pro Cys Leu Phe Trp Asp Gln Thr
            20                  25                  30

Gln Gln His Ser Tyr Ser Ser Ala Ser Asp Pro His Gly Arg Trp Gly
        35                  40                  45

Leu Gly Ala His Asn Phe Cys Arg Asn Pro Asp Gly Asp Val Gln Pro
    50                  55                  60

Trp Cys Tyr Val Ala Glu Thr Glu Glu Gly Ile Tyr Trp Arg Tyr Cys
65                  70                  75                  80

Asp Ile Pro Ser Cys
            85
```

<210> SEQ ID NO 134
<211> LENGTH: 86
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

```
Ser Glu Cys Phe Gln Val Asn Gly Ala Asp Tyr Arg Gly His Gln Asn
1               5                   10                  15

Arg Thr Gly Pro Arg Gly Ala Gly Arg Pro Cys Leu Phe Trp Asp Gln
            20                  25                  30

Thr Gln Gln His Ser Tyr Ser Ser Ala Ser Asp Pro His Gly Arg Trp
        35                  40                  45

Gly Leu Gly Ala His Asn Phe Cys Arg Asn Pro Asp Gly Asp Val Gln
```

```
                50                  55                  60
Pro Trp Cys Tyr Val Ala Glu Thr Glu Gly Ile Tyr Trp Arg Tyr
 65                  70                  75                  80

Cys Asp Ile Pro Ser Cys
                 85

<210> SEQ ID NO 135
<211> LENGTH: 76
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Glu Gln Arg Pro Gly Val Gln Glu Cys Tyr His Gly Asn Gly Gln
 1               5                  10                  15

Ser Tyr Arg Gly Thr Tyr Ser Thr Thr Val Thr Gly Arg Thr Cys Gln
                20                  25                  30

Ala Trp Ser Ser Met Thr Pro His Ser His Ser Arg Thr Pro Glu Tyr
            35                  40                  45

Tyr Pro Asn Ala Gly Leu Ile Met Asn Tyr Cys Arg Asn Pro Asp Ala
 50                  55                  60

Val Ala Ala Pro Tyr Cys Tyr Thr Arg Asp Pro Gly
 65                  70                  75

<210> SEQ ID NO 136
<211> LENGTH: 80
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Asp Cys Tyr Tyr His Tyr Gly Gln Ser Tyr Arg Gly Thr Tyr Ser
 1               5                  10                  15

Thr Thr Val Thr Gly Arg Thr Cys Gln Ala Trp Ser Ser Met Thr Pro
                20                  25                  30

His Gln His Ser Arg Thr Pro Glu Asn Tyr Pro Asn Ala Gly Leu Thr
            35                  40                  45

Arg Asn Tyr Cys Arg Asn Pro Asp Ala Glu Ile Arg Pro Trp Cys Tyr
 50                  55                  60

Thr Met Asp Pro Ser Val Arg Trp Glu Tyr Cys Asn Leu Thr Gln Cys
 65                  70                  75                  80

<210> SEQ ID NO 137
<211> LENGTH: 79
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gln Cys Tyr His Gly Asn Gly Gln Ser Tyr Arg Gly Thr Phe Ser Thr
 1               5                  10                  15

Thr Val Thr Gly Arg Thr Cys Gln Ser Trp Ser Ser Met Thr Pro His
                20                  25                  30

Arg His Gln Arg Thr Pro Glu Asn Tyr Pro Asn Asp Gly Leu Thr Met
            35                  40                  45
```

```
Asn Tyr Cys Arg Asn Pro Asp Ala Asp Thr Gly Pro Trp Cys Phe Thr
 50                  55                  60
Met Asp Pro Ser Ile Arg Trp Glu Tyr Cys Asn Leu Thr Arg Cys
 65                  70                  75
```

<210> SEQ ID NO 138
<211> LENGTH: 84
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
Glu Gln Asp Cys Met Phe Gly Asn Gly Lys Gly Tyr Arg Gly Lys Lys
1               5                   10                  15
Ala Thr Thr Val Thr Gly Thr Pro Cys Gln Glu Trp Ala Ala Gln Glu
                20                  25                  30
Pro His Arg His Ser Thr Phe Ile Pro Gly Thr Asn Lys Trp Ala Gly
                35                  40                  45
Leu Glu Lys Asn Tyr Cys Arg Asn Pro Asp Gly Asp Ile Asn Gly Pro
 50                  55                  60
Trp Cys Tyr Thr Met Asn Pro Arg Lys Leu Phe Asp Tyr Cys Asp Ile
 65                  70                  75                  80
Pro Leu Cys Ala
```

<210> SEQ ID NO 139
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
Glu Ala Ala Cys Val Trp Cys Asn Gly Glu Glu Tyr Arg Gly Ala Val
1               5                   10                  15
Asp Arg Thr Glu Ser Gly Arg Glu Cys Gln Arg Trp Asp Leu Gln His
                20                  25                  30
Pro His Gln His Pro Phe Glu Pro Gly Lys Phe Leu Asp Gln Gly Leu
                35                  40                  45
Asp Asp Asn Tyr Cys Arg Asn Pro Asp Gly Ser Glu Arg Pro Trp Cys
 50                  55                  60
Tyr Thr Thr Asp Pro Gln Ile Glu Arg Glu Phe Cys Asp Leu Pro Arg
 65                  70                  75                  80
Cys
```

<210> SEQ ID NO 140
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Gln Asp Cys Tyr His Gly Ala Gly Glu Gln Tyr Arg Gly Thr Val Ser
1               5                   10                  15
Lys Thr Arg Lys Gly Val Gln Cys Gln Arg Trp Ser Ala Glu Thr Pro
                20                  25                  30
```

His Lys Pro Gln Phe Thr Phe Thr Ser Glu Pro His Ala Gln Leu Glu
            35                  40                  45

Glu Asn Phe Cys Arg Asn Pro Asp Gly Asp Ser His Gly Pro Trp Cys
 50                  55                  60

Tyr Thr Met Asp Pro Arg Thr Pro Phe Asp Tyr Cys Ala Leu Arg Arg
 65                  70                  75                  80

Cys

<210> SEQ ID NO 141
<211> LENGTH: 82
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gln Asp Cys Tyr His Gly Ala Gly Glu Gln Tyr Arg Gly Thr Val Ser
 1               5                  10                  15

Lys Thr Arg Lys Gly Val Gln Cys Gln Arg Trp Ser Ala Glu Thr Pro
            20                  25                  30

His Lys Pro Gln Phe Thr Phe Thr Ser Glu Pro His Ala Gln Leu Glu
            35                  40                  45

Glu Asn Phe Cys Arg Asn Pro Asp Gly Asp Ser His Gly Pro Trp Cys
 50                  55                  60

Tyr Thr Met Asp Pro Arg Thr Pro Phe Asp Tyr Cys Ala Leu Arg Arg
 65                  70                  75                  80

Cys Ala

<210> SEQ ID NO 142
<211> LENGTH: 79
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Tyr His Gly Ala Gly Glu Gln Tyr Arg Gly Thr Val Ser Lys Thr
 1               5                  10                  15

Arg Lys Gly Val Gln Cys Gln Arg Trp Ser Ala Glu Thr Pro His Lys
            20                  25                  30

Pro Gln Phe Thr Phe Thr Ser Glu Pro His Ala Gln Leu Glu Glu Asn
            35                  40                  45

Phe Cys Arg Asn Pro Asp Gly Asp Ser His Gly Pro Trp Cys Tyr Thr
 50                  55                  60

Met Asp Pro Arg Thr Pro Phe Asp Tyr Cys Ala Leu Arg Arg Cys
 65                  70                  75

<210> SEQ ID NO 143
<211> LENGTH: 82
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Glu Gly Asn Cys Ala Glu Gly Leu Gly Thr Asn Tyr Arg Gly His Val
 1               5                  10                  15

Asn Ile Thr Arg Ser Gly Ile Glu Cys Gln Leu Trp Arg Ser Arg Tyr
            20                  25                  30

Pro His Lys Pro Glu Ile Asn Ser Thr Thr His Pro Gly Ala Asp Leu
        35                  40                  45

Gln Glu Asn Phe Cys Arg Asn Pro Asp Ser Ser Thr Thr Gly Pro Trp
50                  55                  60

Cys Tyr Thr Thr Asp Pro Thr Val Arg Arg Gln Glu Cys Ser Ile Pro
65                  70                  75                  80

Val Cys

<210> SEQ ID NO 144
<211> LENGTH: 81
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Asn Cys Ala Glu Gly Leu Gly Thr Asn Tyr Arg Gly His Val Asn
1               5                   10                  15

Ile Thr Arg Ser Gly Ile Glu Cys Gln Leu Trp Arg Ser Arg Tyr Pro
            20                  25                  30

His Lys Pro Glu Ile Asn Ser Thr Thr His Pro Gly Ala Asp Leu Gln
        35                  40                  45

Glu Asn Phe Cys Arg Asn Pro Asp Ser Ser Thr Thr Gly Pro Trp Cys
50                  55                  60

Tyr Thr Thr Asp Pro Thr Val Arg Arg Gln Glu Cys Ser Ile Pro Val
65                  70                  75                  80

Cys

<210> SEQ ID NO 145
<211> LENGTH: 77
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Asn Cys Ala Glu Gly Leu Gly Thr Asn Tyr Arg Gly His Val Asn Ile
1               5                   10                  15

Thr Arg Ser Gly Ile Glu Cys Gln Leu Trp Arg Ser Arg Tyr Pro His
            20                  25                  30

Lys Pro Glu Ile Asn Ser Thr Thr His Pro Gly Ala Asp Leu Gln Glu
        35                  40                  45

Asn Phe Cys Arg Asn Pro Asp Ser Ser Thr Thr Gly Pro Trp Cys Tyr
    50                  55                  60

Thr Thr Asp Pro Thr Val Arg Arg Gln Glu Cys Ser Ile
65                  70                  75

<210> SEQ ID NO 146
<211> LENGTH: 80
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

```
Asn Cys Ala Glu Gly Leu Gly Thr Asn Tyr Arg Gly His Val Asn Ile
1               5                   10                  15

Thr Arg Ser Gly Ile Glu Cys Gln Leu Trp Arg Ser Arg Tyr Pro His
            20                  25                  30

Lys Pro Glu Ile Asn Ser Thr Thr His Pro Gly Ala Asp Leu Gln Glu
            35                  40                  45

Asn Phe Cys Arg Asn Pro Asp Ser Ser Thr Gly Pro Trp Cys Tyr
50                  55                  60

Thr Thr Asp Pro Thr Val Arg Arg Gln Glu Cys Ser Ile Pro Val Cys
65                  70                  75                  80
```

<210> SEQ ID NO 147
<211> LENGTH: 80
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

```
Asp Cys Tyr Phe Gly Asn Gly Ser Ala Tyr Arg Gly Thr His Ser Leu
1               5                   10                  15

Thr Glu Ser Gly Ala Ser Cys Leu Pro Trp Asn Ser Met Ile Leu Ile
            20                  25                  30

Gly Lys Val Tyr Thr Ala Gln Asn Pro Ser Ala Gln Ala Leu Gly Leu
            35                  40                  45

Gly Lys His Asn Tyr Cys Arg Asn Pro Asp Gly Asp Ala Lys Pro Trp
50                  55                  60

Cys His Val Leu Lys Ser Arg Arg Leu Thr Trp Glu Tyr Cys Asp Val
65                  70                  75                  80
```

<210> SEQ ID NO 148
<211> LENGTH: 84
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

```
Ser Asp Cys Tyr Phe Gly Asn Gly Ser Ala Tyr Arg Gly Thr His Ser
1               5                   10                  15

Leu Thr Glu Ser Gly Ala Ser Cys Leu Pro Trp Asn Ser Met Ile Leu
            20                  25                  30

Ile Gly Lys Val Tyr Thr Ala Gln Asn Pro Ser Ala Gln Ala Leu Gly
            35                  40                  45

Leu Gly Lys His Asn Tyr Cys Arg Asn Pro Asp Gly Asp Ala Lys Pro
50                  55                  60

Trp Cys His Val Leu Lys Ser Arg Arg Leu Thr Trp Glu Tyr Cys Asp
65                  70                  75                  80

Val Pro Ser Cys
```

<210> SEQ ID NO 149
<211> LENGTH: 85
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Asp Cys Tyr Phe Gly Asn Gly Ser Ala Tyr Arg Gly Thr His Ser
1               5                   10                  15

Leu Thr Glu Ser Gly Ala Ser Cys Leu Pro Trp Asn Ser Met Ile Leu
            20                  25                  30

Ile Gly Lys Val Tyr Thr Ala Gln Asn Pro Ser Ala Gln Ala Leu Gly
        35                  40                  45

Leu Gly Lys His Asn Tyr Cys Arg Asn Pro Asp Gly Asp Ala Lys Pro
    50                  55                  60

Trp Cys His Val Leu Lys Ser Arg Arg Leu Thr Trp Glu Tyr Cys Asp
65                  70                  75                  80

Val Pro Ser Cys Ser
                85

<210> SEQ ID NO 150
<211> LENGTH: 83
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Asp Cys Tyr Phe Gly Asn Gly Ser Ala Tyr Arg Gly Thr His Ser Leu
1               5                   10                  15

Thr Glu Ser Gly Ala Ser Cys Leu Pro Trp Asn Ser Met Ile Leu Ile
            20                  25                  30

Gly Lys Val Tyr Thr Ala Gln Asn Pro Ser Ala Gln Ala Leu Gly Leu
        35                  40                  45

Gly Lys His Asn Tyr Cys Arg Asn Pro Asp Gly Asp Ala Lys Pro Trp
    50                  55                  60

Cys His Val Leu Lys Ser Arg Arg Leu Thr Trp Glu Tyr Cys Asp Val
65                  70                  75                  80

Pro Ser Cys

<210> SEQ ID NO 151
<211> LENGTH: 135
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
            20                  25                  30

Glu Glu Ala Tyr Ile Pro Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

```
Asp Leu Leu Lys Asp Leu Glu Glu Gly Ile Gln Thr Leu Met Gly Arg
        115                 120                 125

Leu Glu Asp Gly Ser Pro Arg
    130                 135

<210> SEQ ID NO 152
<211> LENGTH: 135
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Phe Pro Thr Ile Pro Leu Ser Arg Leu Phe Asp Asn Ala Met Leu
1               5                   10                  15

Arg Ala Arg Arg Leu Tyr Gln Leu Ala Tyr Asp Thr Tyr Gln Glu Phe
            20                  25                  30

Glu Glu Ala Tyr Ile Leu Lys Glu Gln Lys Tyr Ser Phe Leu Gln Asn
        35                  40                  45

Pro Gln Thr Ser Leu Cys Phe Ser Glu Ser Ile Pro Thr Pro Ser Asn
    50                  55                  60

Arg Ala Lys Thr Gln Gln Lys Ser Asn Leu Glu Leu Leu Arg Ile Ser
65                  70                  75                  80

Leu Leu Leu Ile Gln Ser Trp Leu Glu Pro Val Gln Leu Leu Arg Ser
                85                  90                  95

Val Phe Ala Asn Ser Leu Val Tyr Gly Ala Ser Asp Ser Asn Val Tyr
            100                 105                 110

Arg His Leu Lys Asp Leu Glu Glu Gly Ile Gln Thr Leu Met Trp Arg
        115                 120                 125

Leu Glu Asp Gly Ser Pro Arg
    130                 135

<210> SEQ ID NO 153
<211> LENGTH: 135
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Val Gln Thr Val Pro Leu Ser Arg Leu Phe Asp His Ala Met Leu
1               5                   10                  15

Gln Ala His Arg Ala His Gln Leu Ala Ile Asp Thr Tyr Gln Glu Phe
            20                  25                  30

Glu Glu Thr Tyr Ile Pro Lys Asp Gln Lys Tyr Ser Phe Leu His Asp
        35                  40                  45

Ser Gln Thr Ser Phe Cys Phe Ser Asp Ser Ile Pro Thr Pro Ser Asn
    50                  55                  60

Met Glu Glu Thr Gln Gln Lys Ser Asn Leu Glu Leu Leu Arg Ile Ser
65                  70                  75                  80

Leu Leu Leu Ile Glu Ser Trp Leu Glu Pro Val Arg Phe Leu Arg Ser
                85                  90                  95

Met Phe Ala Asn Asn Leu Val Tyr Asp Thr Ser Asp Ser Asp Asp Tyr
            100                 105                 110

His Leu Leu Lys Asp Leu Glu Glu Gly Ile Gln Thr Leu Met Gly Arg
        115                 120                 125
```

```
Leu Glu Asp Gly Ser Arg Arg
    130                 135

<210> SEQ ID NO 154
<211> LENGTH: 120
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Phe Pro Thr Ile Pro Leu Ser Arg Leu Phe Asp Asn Ala Ser Leu
1               5                   10                  15

Arg Ala His Arg Leu His Gln Leu Ala Phe Asp Thr Tyr Gln Glu Phe
            20                  25                  30

Asn Pro Gln Thr Ser Leu Cys Phe Ser Glu Ser Ile Pro Thr Pro Ser
        35                  40                  45

Met Arg Glu Glu Thr Gln Gln Lys Ser Asn Leu Glu Leu Leu Arg Ile
    50                  55                  60

Ser Leu Leu Leu Ile Gln Ser Trp Leu Glu Pro Val Gln Phe Leu Arg
65                  70                  75                  80

Ser Val Phe Ala Asn Ser Leu Val Tyr Gly Ala Ser Asp Ser Asn Val
                85                  90                  95

Tyr Asp Leu Leu Lys Asp Leu Glu Glu Gly Ile Gln Thr Leu Met Gly
            100                 105                 110

Arg Leu Glu Asp Gly Ser Pro Arg
        115                 120

<210> SEQ ID NO 155
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Cys Leu Trp Thr Asp Met Leu Ser Asn Phe Gly Tyr Pro Gly Tyr
1               5                   10                  15

Gln Ser Lys His Tyr Ala Cys Ile
            20

<210> SEQ ID NO 156
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Cys Leu Trp Thr Asp Trp Leu Leu Glu Arg Lys Leu Tyr Gly Tyr
1               5                   10                  15

Gln Ala Gln His Tyr Val Cys Met
            20

<210> SEQ ID NO 157
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 157

Lys Cys His Gly His Gly Val Cys Asn Ser
1               5                   10

<210> SEQ ID NO 158
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Asp Val Phe Asn Lys Asp Gly Lys Val Ile Leu Leu Ser Pro Gln
1               5                   10                  15

Ala Ile Cys Leu Pro Lys Glu Lys
            20

<210> SEQ ID NO 159
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Leu Cys Met Thr Lys Ser Asp Cys Tyr Gln Pro Ala Trp Tyr Ile His
1               5                   10                  15

Glu Gly Phe Tyr Asn Leu Ser Gly
            20

<210> SEQ ID NO 160
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Glu Cys Leu Trp Met Asp Trp Val Thr Glu Lys Asn Ile Asn Gly His
1               5                   10                  15

Gln Ala Lys Phe Phe Ala Cys Ile
            20

<210> SEQ ID NO 161
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
```

<400> SEQUENCE: 161

Trp Xaa Xaa Cys Xaa Xaa Xaa Cys Xaa Xaa Gly
1               5                   10

<210> SEQ ID NO 162
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Thr, Gly, Gln or Ala
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(4)
<223> OTHER INFORMATION: Ser, Thr, Gly, Glu, Asp, Arg or Ala
<220> FEATURE:
<221> NAME/KEY: MOD_RES
<222> LOCATION: (5)..(5)
<223> OTHER INFORMATION: Pro, Ala, Gln, Asp, Glu, Lys, Arg or Val
<220> FEATURE:
<221> NAME/KEY: MOD_RES
<222> LOCATION: (7)..(7)
<223> OTHER INFORMATION: Ser, Asn or Thr
<220> FEATURE:
<221> NAME/KEY: MOD_RES
<222> LOCATION: (8)..(8)
<223> OTHER INFORMATION: Val, Ala, Arg, Lys, Gly, Ser, Thr or Glu
<220> FEATURE:
<221> NAME/KEY: MOD_RES
<222> LOCATION: (9)..(9)
<223> OTHER INFORMATION: Thr, Ser, Arg or Asn
<220> FEATURE:
<221> NAME/KEY: MOD_RES
<222> LOCATION: (11)..(11)
<223> OTHER INFORMATION: Gly, Ser or Asn
<220> FEATURE:
<221> NAME/KEY: MOD_RES
<222> LOCATION: (12)..(12)
<223> OTHER INFORMATION: Gly, Lys, Arg, Met, Thr, Leu, Asp, Ser or Pro
<220> FEATURE:
<221> NAME/KEY: MOD_RES
<222> LOCATION: (14)..(14)
<223> OTHER INFORMATION: Val, Ile, Met, Thr, His, Ala, Glu, Phe, Lys,
      Arg, Ser, Gln, Trp or Tyr
<220> FEATURE:
<221> NAME/KEY: MOD_RES
<222> LOCATION: (15)..(15)
<223> OTHER INFORMATION: Gln, Ser, Arg, Lys, Tyr or Ala
<220> FEATURE:
<221> NAME/KEY: MOD_RES
<222> LOCATION: (16)..(16)
<223> OTHER INFORMATION: Thr, Phe, Lys, Gln, Ser, Leu, Glu, Met, Asn or
      Val
<220> FEATURE:
<221> NAME/KEY: MOD_RES
<222> LOCATION: (17)..(17)
<223> OTHER INFORMATION: Arg, Ser or Gln
<220> FEATURE:
<221> NAME/KEY: MOD_RES
<222> LOCATION: (18)..(18)
<223> OTHER INFORMATION: Ser, Thr, Val, Arg, His, Glu, Gln, Ala or Ile
<220> FEATURE:
<221> NAME/KEY: MOD_RES
<222> LOCATION: (19)..(19)
<223> OTHER INFORMATION: Arg or Val

<400> SEQUENCE: 162

```
Xaa Xaa Trp Xaa Xaa Cys Xaa Xaa Xaa Cys Xaa Xaa Gly Xaa Xaa Xaa
 1               5                  10                  15

Xaa Xaa Xaa Arg
            20

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(5)
<223> OTHER INFORMATION: Thr, Ser or Asn
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid

<400> SEQUENCE: 163

Trp Xaa Xaa Cys Xaa Xaa Xaa Cys Xaa Xaa Gly
 1               5                  10

<210> SEQ ID NO 164
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (12)..(14)
<223> OTHER INFORMATION: Variable amino acid
<220> FEATURE:
<221> NAME/KEY: MOD_RES
<222> LOCATION: (16)..(18)
<223> OTHER INFORMATION: Variable amino acid

<400> SEQUENCE: 164

Trp Xaa Xaa Cys Ser Xaa Xaa Cys Gly Xaa Gly Xaa Xaa Xaa Arg Xaa
 1               5                  10                  15

Xaa Xaa

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (12)..(14)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (17)..(17)
<223> OTHER INFORMATION: Arg or Val

<400> SEQUENCE: 165

Trp Xaa Xaa Cys Ser Xaa Xaa Cys Gly Xaa Gly Xaa Xaa Xaa Arg Xaa
1               5                   10                  15

Xaa

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (7)..(7)
<223> OTHER INFORMATION: Ser, Arg or Thr
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (12)..(14)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (17)..(17)
<223> OTHER INFORMATION: Arg or Val
<220> FEATURE:
<221> NAME/KEY: MOD_RES
<222> LOCATION: (18)..(18)
<223> OTHER INFORMATION: Variable amino acid

<400> SEQUENCE: 166

Trp Xaa Xaa Cys Ser Xaa Xaa Cys Gly Xaa Gly Xaa Xaa Xaa Arg Xaa
1               5                   10                  15
```

Xaa Xaa

<210> SEQ ID NO 167
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(5)
<223> OTHER INFORMATION: Thr, Ser or Asn
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (9)..(10)
<223> OTHER INFORMATION: Variable amino acid
<220> FEATURE:
<221> NAME/KEY: MOD_RES
<222> LOCATION: (12)..(16)
<223> OTHER INFORMATION: Variable amino acid
<220> FEATURE:
<221> NAME/KEY: MOD_RES
<222> LOCATION: (17)..(17)
<223> OTHER INFORMATION: Arg or Val

<400> SEQUENCE: 167

Trp Xaa Xaa Cys Xaa Xaa Xaa Cys Xaa Xaa Gly Xaa Xaa Xaa Xaa Xaa
1               5                   10                  15

Xaa

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(4)
<223> OTHER INFORMATION: Variable amino acid
<220> FEATURE:
<221> NAME/KEY: MOD_RES
<222> LOCATION: (6)..(8)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid

<400> SEQUENCE: 168

Pro Trp Xaa Xaa Cys Xaa Xaa Xaa Cys Xaa Xaa Gly
1               5                   10

<210> SEQ ID NO 169
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)

```
<223> OTHER INFORMATION: Ser, Gly or Gln
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)..(11)
<223> OTHER INFORMATION: Gly or Ser
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<221> NAME/KEY: MOD_RES
<222> LOCATION: (17)..(17)
<223> OTHER INFORMATION: Arg or Ser

<400> SEQUENCE: 169

Xaa Pro Trp Xaa Xaa Cys Xaa Xaa Xaa Cys Xaa Xaa Gly Xaa Xaa Xaa
1               5                   10                  15

Xaa

<210> SEQ ID NO 170
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (9)..(18)
<223> OTHER INFORMATION: Variable amino acid
<220> FEATURE:
<221> NAME/KEY: MOD_RES
<222> LOCATION: (20)..(20)
<223> OTHER INFORMATION: Variable amino acid

<400> SEQUENCE: 170

Gly Xaa Xaa Xaa Cys Leu Xaa Pro Xaa Xaa Xaa Xaa Xaa Xaa Xaa Xaa
1               5                   10                  15

Xaa Xaa Lys Xaa Leu
                20

<210> SEQ ID NO 171
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: Asn or Asp
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (4)..(4)
<223> OTHER INFORMATION: Lys, Glu or Gln
<220> FEATURE:
<221> NAME/KEY: MOD_RES
<222> LOCATION: (5)..(5)
<223> OTHER INFORMATION: Ala, Ile, Leu or Val
<220> FEATURE:
<221> NAME/KEY: MOD_RES
<222> LOCATION: (8)..(8)
<223> OTHER INFORMATION: Asp or Asn
<220> FEATURE:
<221> NAME/KEY: MOD_RES
<222> LOCATION: (10)..(10)
<223> OTHER INFORMATION: Ala, Glu, Asp or Lys
<220> FEATURE:
<221> NAME/KEY: MOD_RES
<222> LOCATION: (11)..(11)
<223> OTHER INFORMATION: Ala, Ser or Glu
<220> FEATURE:
<221> NAME/KEY: MOD_RES
<222> LOCATION: (13)..(13)
<223> OTHER INFORMATION: Phe, Ile, Met, Arg or Trp
<220> FEATURE:
<221> NAME/KEY: MOD_RES
<222> LOCATION: (14)..(14)
<223> OTHER INFORMATION: Val, Leu or Ile
<220> FEATURE:
<221> NAME/KEY: MOD_RES
<222> LOCATION: (15)..(15)
<223> OTHER INFORMATION: Lys or Gln
<220> FEATURE:
<221> NAME/KEY: MOD_RES
<222> LOCATION: (16)..(16)
<223> OTHER INFORMATION: Lys or Arg
<220> FEATURE:
<221> NAME/KEY: MOD_RES
<222> LOCATION: (17)..(17)
<223> OTHER INFORMATION: Ile or Val
<220> FEATURE:
<221> NAME/KEY: MOD_RES
<222> LOCATION: (18)..(18)
<223> OTHER INFORMATION: Ile or Val
<220> FEATURE:
<221> NAME/KEY: MOD_RES
<222> LOCATION: (19)..(19)
<223> OTHER INFORMATION: Glu or Gln
<220> FEATURE:
<221> NAME/KEY: MOD_RES
<222> LOCATION: (21)..(21)
<223> OTHER INFORMATION: Ile, Phe, Lys or Met

<400> SEQUENCE: 171

Xaa Gly Xaa Xaa Xaa Cys Leu Xaa Pro Xaa Xaa Pro Xaa Xaa Xaa Xaa
1               5                   10                  15

Xaa Xaa Xaa Lys Xaa Leu
            20

<210> SEQ ID NO 172
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

```
<223> OTHER INFORMATION: Asn, Asp or Lys
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (8)..(8)
<223> OTHER INFORMATION: Asp or Asn
<220> FEATURE:
<221> NAME/KEY: MOD_RES
<222> LOCATION: (9)..(9)
<223> OTHER INFORMATION: Pro or Leu
<220> FEATURE:
<221> NAME/KEY: MOD_RES
<222> LOCATION: (10)..(14)
<223> OTHER INFORMATION: Variable amino acid
<220> FEATURE:
<221> NAME/KEY: MOD_RES
<222> LOCATION: (15)..(15)
<223> OTHER INFORMATION: Lys or Gln
<220> FEATURE:
<221> NAME/KEY: MOD_RES
<222> LOCATION: (16)..(16)
<223> OTHER INFORMATION: Lys, Arg or Asn
<220> FEATURE:
<221> NAME/KEY: MOD_RES
<222> LOCATION: (17)..(17)
<223> OTHER INFORMATION: Ile, Val or Leu
<220> FEATURE:
<221> NAME/KEY: MOD_RES
<222> LOCATION: (18)..(18)
<223> OTHER INFORMATION: Ile, Val or Leu
<220> FEATURE:
<221> NAME/KEY: MOD_RES
<222> LOCATION: (19)..(24)
<223> OTHER INFORMATION: Variable amino acid

<400> SEQUENCE: 172

Xaa Gly Xaa Xaa Xaa Cys Leu Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 173
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asn or Asp
<220> FEATURE:
<221> NAME/KEY: MOD_RES
<222> LOCATION: (3)..(3)
<223> OTHER INFORMATION: Arg or Lys
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (8)..(8)
<223> OTHER INFORMATION: Asn or Asp
<220> FEATURE:
<221> NAME/KEY: MOD_RES
<222> LOCATION: (10)..(11)
<223> OTHER INFORMATION: Variable amino acid
<220> FEATURE:
<221> NAME/KEY: MOD_RES
<222> LOCATION: (12)..(12)
<223> OTHER INFORMATION: Pro or Asn
<220> FEATURE:
```

<221> NAME/KEY: MOD_RES
<222> LOCATION: (13)..(14)
<223> OTHER INFORMATION: Variable amino acid
<220> FEATURE:
<221> NAME/KEY: MOD_RES
<222> LOCATION: (15)..(15)
<223> OTHER INFORMATION: Lys or Gln
<220> FEATURE:
<221> NAME/KEY: MOD_RES
<222> LOCATION: (16)..(16)
<223> OTHER INFORMATION: Lys or Gln
<220> FEATURE:
<221> NAME/KEY: MOD_RES
<222> LOCATION: (17)..(17)
<223> OTHER INFORMATION: Ile or Val
<220> FEATURE:
<221> NAME/KEY: MOD_RES
<222> LOCATION: (18)..(18)
<223> OTHER INFORMATION: Ile or Val
<220> FEATURE:
<221> NAME/KEY: MOD_RES
<222> LOCATION: (19)..(19)
<223> OTHER INFORMATION: Glu or Gln
<220> FEATURE:
<221> NAME/KEY: MOD_RES
<222> LOCATION: (21)..(21)
<223> OTHER INFORMATION: Variable amino acid

<400> SEQUENCE: 173

Xaa Gly Xaa Xaa Xaa Cys Leu Xaa Pro Xaa Xaa Xaa Xaa Xaa Xaa
1               5                   10                  15

Xaa Xaa Xaa Lys Xaa Leu
            20

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Variable amino acid

<400> SEQUENCE: 174

Cys Asn Xaa Xaa Xaa Val Cys
1               5

<210> SEQ ID NO 175
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (8)..(12)
<223> OTHER INFORMATION: Variable amino acid

<400> SEQUENCE: 175

Pro Phe Xaa Glu Cys Xaa Gly Xaa Xaa Xaa Xaa Xaa Ala Asn
1               5                   10

```
<210> SEQ ID NO 176
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)..(11)
<223> OTHER INFORMATION: Variable amino acid
<220> FEATURE:
<221> NAME/KEY: MOD_RES
<222> LOCATION: (15)..(15)
<223> OTHER INFORMATION: Variable amino acid

<400> SEQUENCE: 176

Cys Asn Xaa Xaa Xaa Val Cys Xaa Xaa Ala Xaa Arg Asn Asp Xaa Ser
1               5                   10                  15

Tyr Trp Leu

<210> SEQ ID NO 177
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (7)..(7)
<223> OTHER INFORMATION: Variable amino acid
<220> FEATURE:
<221> NAME/KEY: MOD_RES
<222> LOCATION: (10)..(11)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid

<400> SEQUENCE: 177

Leu Xaa Xaa Phe Ser Thr Xaa Pro Phe Xaa Xaa Cys Asn Xaa Xaa Xaa
1               5                   10                  15

Val Cys

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ile or Leu
<220> FEATURE:
<221> NAME/KEY: MOD_RES
```

```
<222> LOCATION: (6)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (9)..(9)
<223> OTHER INFORMATION: Arg or Gly
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (11)..(11)
<223> OTHER INFORMATION: Tyr or Phe
<220> FEATURE:
<221> NAME/KEY: MOD_RES
<222> LOCATION: (12)..(12)
<223> OTHER INFORMATION: Tyr or Phe

<400> SEQUENCE: 178

Pro Phe Xaa Glu Cys Xaa Gly Xaa Xaa Xaa Xaa Xaa Ala Asn
1               5                   10

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (7)..(14)
<223> OTHER INFORMATION: Variable amino acid
<220> FEATURE:
<221> NAME/KEY: MOD_RES
<222> LOCATION: (16)..(16)
<223> OTHER INFORMATION: Variable amino acid
<220> FEATURE:
<221> NAME/KEY: MOD_RES
<222> LOCATION: (18)..(22)
<223> OTHER INFORMATION: Variable amino acid

<400> SEQUENCE: 179

Glu Cys Leu Trp Xaa Asp Xaa Xaa Xaa Xaa Xaa Xaa Xaa Gly Xaa
1               5                   10                  15

Tyr Xaa Xaa Xaa Xaa Xaa Cys
            20

<210> SEQ ID NO 180
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
```

```
<222> LOCATION: (7)..(9)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (14)..(20)
<223> OTHER INFORMATION: Variable amino acid

<400> SEQUENCE: 180

Xaa Xaa Trp Xaa Xaa Cys Xaa Xaa Xaa Cys Xaa Xaa Gly Xaa Xaa Xaa
1               5                   10                  15

Xaa Xaa Xaa Xaa
            20

<210> SEQ ID NO 181
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(7)
<223> OTHER INFORMATION: Thr, Ser or Asn
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (14)..(20)
<223> OTHER INFORMATION: Variable amino acid

<400> SEQUENCE: 181

Xaa Xaa Trp Xaa Xaa Cys Xaa Xaa Xaa Cys Xaa Xaa Gly Xaa Xaa Xaa
1               5                   10                  15

Xaa Xaa Xaa Xaa
            20

<210> SEQ ID NO 182
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (8)..(9)
```

<223> OTHER INFORMATION: Variable amino acid
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<221> NAME/KEY: MOD_RES
<222> LOCATION: (18)..(20)
<223> OTHER INFORMATION: Variable amino acid

<400> SEQUENCE: 182

Xaa Xaa Trp Xaa Xaa Cys Ser Xaa Xaa Cys Gly Xaa Gly Xaa Xaa Xaa
1               5                   10                  15

Arg Xaa Xaa Xaa
            20

<210> SEQ ID NO 183
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid
<220> FEATURE:
<221> NAME/KEY: MOD_RES
<222> LOCATION: (19)..(19)
<223> OTHER INFORMATION: Arg or Val
<220> FEATURE:
<221> NAME/KEY: MOD_RES
<222> LOCATION: (20)..(20)
<223> OTHER INFORMATION: Variable amino acid

<400> SEQUENCE: 183

Xaa Xaa Trp Xaa Xaa Cys Ser Xaa Xaa Cys Gly Xaa Gly Xaa Xaa Xaa
1               5                   10                  15

Arg Xaa Xaa Xaa
            20

<210> SEQ ID NO 184
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (9)..(9)
<223> OTHER INFORMATION: Ser, Arg or Thr
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<221> NAME/KEY: MOD_RES
<222> LOCATION: (18)..(18)
<223> OTHER INFORMATION: Variable amino acid
<220> FEATURE:
<221> NAME/KEY: MOD_RES
<222> LOCATION: (19)..(19)
<223> OTHER INFORMATION: Arg or Val
<220> FEATURE:
<221> NAME/KEY: MOD_RES
<222> LOCATION: (20)..(20)
<223> OTHER INFORMATION: Variable amino acid

<400> SEQUENCE: 184

Xaa Xaa Trp Xaa Xaa Cys Ser Xaa Xaa Cys Gly Xaa Gly Xaa Xaa Xaa
1               5                   10                  15

Arg Xaa Xaa Xaa
            20

<210> SEQ ID NO 185
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (14)..(20)
<223> OTHER INFORMATION: Variable amino acid

<400> SEQUENCE: 185

Xaa Pro Trp Xaa Xaa Cys Xaa Xaa Xaa Cys Xaa Xaa Gly Xaa Xaa Xaa
1               5                   10                  15
```

-continued

Xaa Xaa Xaa Xaa
            20

<210> SEQ ID NO 186
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Gly or Gln
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (11)..(11)
<223> OTHER INFORMATION: Gly or Ser
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (14)..(16)
<223> OTHER INFORMATION: Variable amino acid
<220> FEATURE:
<221> NAME/KEY: MOD_RES
<222> LOCATION: (17)..(17)
<223> OTHER INFORMATION: Arg or Ser
<220> FEATURE:
<221> NAME/KEY: MOD_RES
<222> LOCATION: (18)..(20)
<223> OTHER INFORMATION: Variable amino acid

<400> SEQUENCE: 186

Xaa Pro Trp Xaa Xaa Cys Xaa Xaa Xaa Cys Xaa Xaa Gly Xaa Xaa Xaa
1               5                   10                  15

Xaa Xaa Xaa Xaa
            20

<210> SEQ ID NO 187
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(7)
<223> OTHER INFORMATION: Thr, Ser or Asn
<220> FEATURE:
<221> NAME/KEY: MOD_RES
<222> LOCATION: (8)..(9)

```
<223> OTHER INFORMATION: Variable amino acid
<220> FEATURE:
<221> NAME/KEY: MOD_RES
<222> LOCATION: (11)..(12)
<223> OTHER INFORMATION: Variable amino acid
<220> FEATURE:
<221> NAME/KEY: MOD_RES
<222> LOCATION: (14)..(18)
<223> OTHER INFORMATION: Variable amino acid
<220> FEATURE:
<221> NAME/KEY: MOD_RES
<222> LOCATION: (19)..(19)
<223> OTHER INFORMATION: Arg or Val
<220> FEATURE:
<221> NAME/KEY: MOD_RES
<222> LOCATION: (20)..(20)
<223> OTHER INFORMATION: Variable amino acid

<400> SEQUENCE: 187

Xaa Xaa Trp Xaa Xaa Cys Xaa Xaa Xaa Cys Xaa Xaa Gly Xaa Xaa Xaa
1               5                   10                  15

Xaa Xaa Xaa Xaa
            20

<210> SEQ ID NO 188
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(5)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (10)..(19)
<223> OTHER INFORMATION: Variable amino acid
<220> FEATURE:
<221> NAME/KEY: MOD_RES
<222> LOCATION: (21)..(21)
<223> OTHER INFORMATION: Variable amino acid

<400> SEQUENCE: 188

Xaa Gly Xaa Xaa Xaa Cys Leu Xaa Pro Xaa Xaa Xaa Xaa Xaa Xaa Xaa
1               5                   10                  15

Xaa Xaa Xaa Lys Xaa Leu
            20

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid
```

```
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (10)..(14)
<223> OTHER INFORMATION: Variable amino acid

<400> SEQUENCE: 189

Xaa Xaa Pro Phe Xaa Glu Cys Xaa Gly Xaa Xaa Xaa Xaa Xaa Ala Asn
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (5)..(5)
<223> OTHER INFORMATION: Ile or Leu
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (11)..(11)
<223> OTHER INFORMATION: Arg or Gly
<220> FEATURE:
<221> NAME/KEY: MOD_RES
<222> LOCATION: (12)..(12)
<223> OTHER INFORMATION: Variable amino acid
<220> FEATURE:
<221> NAME/KEY: MOD_RES
<222> LOCATION: (13)..(13)
<223> OTHER INFORMATION: Tyr or Phe
<220> FEATURE:
<221> NAME/KEY: MOD_RES
<222> LOCATION: (14)..(14)
<223> OTHER INFORMATION: Tyr or Phe

<400> SEQUENCE: 190

Xaa Xaa Pro Phe Xaa Glu Cys Xaa Gly Xaa Xaa Xaa Xaa Xaa Ala Asn
1               5                   10                  15
```

COMPOSITIONS HAVING ANTIANGIOGENIC ACTIVITY AND USES THEREOF

CROSS-REFERENCE TO RELATED APPLICATIONS

This application is a divisional of U.S. application Ser. No. 13/369,240, filed Feb. 8, 2012, granted, which is a divisional of U.S. application Ser. No. 11/992,001, filed Apr. 2, 2009, which is the U.S. National Stage application of PCT/US2006/035580, filed Sep. 12, 2006, which claims the benefit of U.S. Provisional Application No. 60/716,341, filed Sep. 12, 2005. Each of these are hereby incorporated by reference in their entirety.

STATEMENT OF RIGHTS TO INVENTIONS MADE UNDER FEDERALLY SPONSORED RESEARCH

This work was supported by the following grant from the National Institutes of Health, Grant No.: HL79653. The government may have certain rights in the invention.

SEQUENCE LISTING

The instant application contains a Sequence Listing which has been submitted in ASCII format via EFS-Web and is hereby incorporated by reference in its entirety. Said ASCII copy, created on Aug. 23, 2013, is named 64756DIV2_71699_ST25.txt and is 110,592 bytes in size.

BACKGROUND OF THE INVENTION

Angiogenesis, the process of developing a novel vascular network from a pre-existing one, is tightly controlled by various endogenous regulators. These regulatory elements include both pro- and anti-angiogenic proteins that finely modulate the neovascular morphological and functional characteristics. Where the regulation of such processes is disrupted a variety of pathological conditions can ensue, including neoplasia, hematologic malignancies, rheumatoid arthritis, diabetic retinopathy, age-related macular degeneration, atherosclerosis, endometriosis, pathologic obesity, and ischemic heart and limb disease. An urgent need exists for angiogenesis modulators that can be used as therapeutics for these and other numerous angiogenesis related diseases and conditions. While some promising angiogenesis modulators have been identified, to date, the quest for the experimental identification of such agents has been an empirical time-consuming process. Improved angiogenesis modulators and methods for systematically identifying and assessing the biological activity of such agents are urgently required.

SUMMARY OF THE INVENTION

As described below, the present invention generally features angiogenesis modulators, related prophylactic and therapeutic methods, as well as screening methods for the identification of such agents.

In one aspect, the invention generally features an isolated peptide or analog thereof containing or consisting essentially of the amino acid sequence $W-X_2-C-X_3-C-X_2-G$ (SEQ ID NO: 161) that reduces blood vessel formation in a cell, tissue or organ. In various embodiments, the peptide contains at least 11, 12, 15, 20, 25, 30, 35, or more amino acids of a thrombospondin-1 domain or thrombospondin-2 domain.

In another aspect, the invention features an isolated peptide or analog thereof containing or consisting essentially of a 20 amino acid (AA) sequence having positions AA1-AA20 (SEQ ID NO: 162), wherein:

AA1 is X, S, T, G, Q, or A;
AA2 is X, P, E, S, A, Q, or K;
AA3 is W;
AA4 is X, S, T, G, E, D, R, or A;
AA5 is X, P, A, Q, D, E, K, R, or V;
AA6 is C;
AA7 is X, S, N, or T;
AA8 is X, V, A, R, K, G, S, T, or E;
AA9 is X, T, S, R, or N;
AA10 is C;
AA11 is X, G, S, or N;
AA12 is X, G, K, R, M, T, L, D, S, or P;
AA13 is G;
AA14 is X, V, I, M, T, H, A, E, F, K, R, S, Q, W, or Y;
AA15 is X, Q, S, R, K, Y, or A;
AA16 is X, T, F, K, Q, S, L, E, M, N, or V;
AA17 is X, R, S, or Q;
AA18 is X, S, T, V, R, H, E, Q, A, or I;
AA19 is X, R, or V; and
AA20 is R;

wherein X denotes a variable amino acid; W is tryptophan; C is cysteine, T is threonine, S is serine; N is asparagine; G is glycine; R is arginine; V is valine, P is proline, and Q is glutamine; and wherein the peptide reduces blood vessel formation in a cell, tissue or organ. In various embodiments, the peptide contains an amino acid sequence selected from the group consisting of:

(SEQ ID NO: 163)
$W-X_2-C-(T/S/N)-X_2-C-X_2-G;$ (SEQ ID NO: 164)
$W-X_2-C-S-X_2-C-G-X-G-X_3-R-X_3;$ (SEQ ID NO: 165)
$W-X_2-C-S-X_2-C-G-X_1-G-X_3-R-X_1-(R/V);$ (SEQ ID NO: 166)
$W-X_2-C-S-X-(S/R/T)-C-G-X-G-X_3-R-X-(R/V)-X;$ (SEQ ID NO: 167)
$W-X_2-C-(T/S/N)-X_2-C-X_2-G-X_5-(R/V);$ (SEQ ID NO: 168)
$P-W-X_2-C-X_3-C-X_2-G;$
and (SEQ ID NO: 169)
$(S/G/Q)-P-W-X_2-C-(T/S)-X_2-C-(G/S)-X_1-G-X_3-(R/S).$ In another aspect, the invention features an isolated peptide or analog thereof containing a thrombospondin-1 domain, wherein the peptide reduces blood vessel formation in a cell, tissue or organ and contains a sequence having at least 75%, 80%, 85%, 90%, 95% or 100% amino acid sequence identity to an amino acid sequence selected from peptides containing a TSP-1 domain listed in Table 1.

In yet another aspect, the invention features an isolated peptide or analog thereof containing a thrombospondin-1 domain, wherein the peptide contains a sequence having at least 75%, 80%, 85%, 90%, 95% or 100% amino acid sequence identity to an amino acid sequence selected from the group consisting of:

THSD-1:
QPWSQCSATCGDGVRERRR; (SEQ ID NO: 64)

THSD-3:
SPWSPCSGNCSTGKQQRTR; (SEQ ID NO: 65)

THSD-6:
WTRCSSSCGRGVSVRSR; (SEQ ID NO: 66)

CILP:
SPWSKCSAACGQTGVQTRTR; (SEQ ID NO: 39)

WISP-1:
SPWSPCSTSCGLGVSTRI; (SEQ ID NO: 74)

WISP-2:
TAWGPCSTTCGLGMATRV; (SEQ ID NO: 75)

WISP-3:
TKWTPCSRTCGMGISNRV; (SEQ ID NO: 76)

F-spondin:
SEWSDCSVTCGKGMRTRQR; (SEQ ID NO: 73)

F-spondin:
WDECSATCGMGMKKRHR; (SEQ ID NO: 72)

CTGF:
TEWSACSKTCGMGISTRV; (SEQ ID NO: 41)

fibulin-6:
ASWSACSVSCGGGARQRTR; (SEQ ID NO: 45)

fibulin-6:
QPWGTCSESCGKGTQTRAR; (SEQ ID NO: 44)

fibulin-6:
SAWRACSVTCGKGIQKRSR; (SEQ ID NO: 43)

CYR61:
TSWSQCSKTCGTGISTRV; (SEQ ID NO: 42)

NOVH:
TEWTACSKSCGMGFSTRV; (SEQ ID NO: 46)

UNC5-C:
TEWSVCNSRCGRGYQKRTR; (SEQ ID NO: 70)

UNC5-D:
TEWSACNVRCGRGWQKRSR; (SEQ ID NO: 71)

SCO-spondin:
GPWEDCSVSCGGGEQLRSR; (SEQ ID NO: 63)

Properdin:
GPWEPCSVTCSKGTRTRRR; (SEQ ID NO: 49)

C6:
TQWTSCSKTCNSGTQSRHR; (SEQ ID NO: 38)

ADAMTS-like-4:
SPWSQCSVRCGRGQRSRQVR; (SEQ ID NO: 69)

ADAMTS-4:
GPWGDCSRTCGGGVQFSSR; (SEQ ID NO: 7)

ADAMTS-8:
GPWGECSRTCGGGVQFSHR; (SEQ ID NO: 14)

ADAMTS-16:
SPWSQCTASCGGGVQTR; (SEQ ID NO: 24)

ADAMTS-18:
SKWSECSRTCGGGVKFQER; (SEQ ID NO: 29)

semaphorin 5A:
GPWERCTAQCGGGIQARRR; (SEQ ID NO: 60)

semaphorin 5A:
SPWTKCSATCGGGHYMRTR; (SEQ ID NO: 61)

semaphoring 5B:
TSWSPCSASCGGGHYQRTR; (SEQ ID NO: 62)

papilin:
GPWAPCSASCGGGSQSRS; (SEQ ID NO: 48)

papilin:
SQWSPCSRTCGGGVSFRER; (SEQ ID NO: 47)

ADAM-9:
KCHGHGVCNS; (SEQ ID NO: 157)
and

ADAM-12:
MQCHGRGVCNNRKN, (SEQ ID NO: 2)

wherein A is alanine; I is isoleucine; M is methionine; H is histidine; Y is tyrosine; K is lysine; W is tryptophan; C is cysteine, T is threonine, S is serine; N is asparagine; G is glycine; R is arginine; V is valine, P is proline, and Q is glutamine wherein the peptide reduces blood vessel formation in a cell, tissue or organ.

In another aspect, the invention features an isolated peptide or analog thereof containing the amino acid sequence $G-X_3-C-L-X-P-X_{10}-K-X-L$ (SEQ ID NO: 170), wherein the peptide reduces blood vessel formation in a cell, tissue or organ.

In another aspect, the invention features an isolated peptide or analog thereof containing a 22 amino acid sequence having positions AA1-AA22 (SEQ ID NO: 171), wherein:
AA1 is X, N or D;
AA2 is G;
AA3 is X, R or K;
AA4 is X, K, E, or Q;
AA5 is X, A, I, L, or V;
AA6 is C;
AA7 is L;
AA8 is X, D or N;
AA9 is P;
AA10 is X, A, E, D, or K;
AA11 is X, A, S, or E;
AA12 is P;
AA13 is X, F, I, M, R, or W;
AA14 is X, V, L, or I;
AA15 is X, K or Q;

AA16 is X, K or R;
AA17 is X, I or V;
AA18 is X, I or V;
AA19 is X, E or Q;
AA20 is K;
AA21 is X, I, F, K, or M; and
AA22 is L;
wherein X denotes a variable amino acid; A is alanine; I is isoleucine; F is phenylalanine; D is aspartic acid; M is methionine; H is histidine; Y is tyrosine; K is lysine; W is tryptophan; C is cysteine, T is threonine, S is serine; N is asparagine; G is glycine; R is arginine; V is valine, P is proline, and Q is glutamine; and wherein the peptide reduces blood vessel formation in a cell, tissue or organ. In various embodiments, the peptide contains an amino acid sequence selected from the group consisting of:

G-$X_3$-C-L-X-P-$X_{10}$-K-X-L;

(SEQ ID NO: 170)

(N/D/K)-G-$X_3$-C-L-(D/N)-(P/L)-$X_5$-(K/Q)-(K/R/N)-(I/V/L)-(I/V/L)-$X_6$;

(SEQ ID NO: 172)

and (N/D)-G-(R/K)-$X_2$-C-L-(N/D)-P-$X_2$-(P/N)-$X_2$-(K/Q)-(K/Q)-(I/V)-(I/V)-(E/Q)-K-X-L.

(SEQ ID NO: 173)

In another aspect, the invention features an isolated peptide or analog thereof containing at least a fragment of a C-X-C polypeptide, wherein the peptide contains a sequence that has at least 75%, 80%, 85%, 90%, 95% or 100% amino acid sequence identity to an amino acid sequence selected from a peptide that contains the C-X-C motif listed in Table 1.

In another aspect, the invention features an isolated peptide or analog thereof having at least 75%, 80%, 85%, 90%, 95% or 100% identity to an amino acid sequence selected from the group consisting of:

```
ENA-78:
                       (SEQ ID NO: 95)
NGKEICLDPEAPFLKKVIQKILD;

CXCL6:
                       (SEQ ID NO: 98)
NGKQVCLDPEAPFLKKVIQKILDS;

CXCL1:
                       (SEQ ID NO: 102)
NGRKACLNPASPIVKKIIEKMLNS;

Gro-γ:
                       (SEQ ID NO: 106)
NGKKACLNPASPMVQKIIEKIL;

Beta thromboglobulin/CXCL7:
                       (SEQ ID NO: 114)
DGRKICLDPDAPRIKKIVQKKL, Interleukin 8(IL-8)/CXCL8:
                       (SEQ ID NO: 110)
DGRELCLDPKENWVQRVVEKFLK,

GCP-2:
                       (SEQ ID NO: 98)
NGKQVCLDPEAPFLKKVIQKILDS,
``` wherein A is alanine; I is isoleucine; F is phenylalanine; D is aspartic acid; M is methionine; H is histidine; Y is tyrosine; K is lysine; W is tryptophan; C is cysteine, T is threonine, S is serine; N is asparagine; G is glycine; R is arginine; V is valine, P is proline, and Q is glutamine; and wherein the peptide reduces blood vessel formation in a tissue or organ. In one embodiment, the peptide contains at least a fragment of a C-X-C polypeptide.

In another aspect, the invention features an isolated peptide or analog thereof containing the amino acid sequence C-N-$X_3$-V-C (SEQ ID NO: 174) or P-F-X-E-C-X-G-$X_5$-A-N (SEQ ID NO: 175), wherein X denotes a variable amino acid; F is phenylalanine; C is cysteine, N is asparagine; G is glycine; V is valine, P is proline, and Q is glutamine wherein the peptide reduces blood vessel formation in a tissue or organ. In one embodiment, the peptide contains at least 5, 10, 25, 20, 25, 30, or 35 amino acids of a type IV collagen polypeptide.

In yet another aspect, the invention features an isolated peptide or analog thereof containing at least a fragment of a type IV collagen C4 domain, wherein the peptide reduces blood vessel formation in a tissue or organ and contains a sequence having at least 75%, 80%, 85%, 90%, 95% or 100% identity to an amino acid sequence selected from type IV collagen peptides listed in Table 1.

In yet another aspect, the invention features an isolated peptide or analog thereof containing one of the following amino acid sequences:
C-N-$X_3$-V-C-$X_2$-A-X-R-N-D-X-S-Y-W-L (SEQ ID NO: 176); or L-$X_2$-F-S-T-X-P-F-$X_2$-C-N-$X_3$-V-C (SEQ ID NO: 177), wherein the peptide reduces blood vessel formation in a cell, tissue or organ. In one embodiment, the sequence C-N-$X_3$-V-C (SEQ ID NO: 174) is 5' of the sequence C-N-$X_3$-V-C-$X_2$-A-X-R-N-D-X-S-Y-W-L (SEQ ID NO: 176). In another embodiment, the sequence C-N-$X_3$-V-C (SEQ ID NO: 174) is 3' of the amino acid sequence L-$X_2$-F-S-T-X-P-F-$X_2$-C-N-$X_3$-V-C (SEQ ID NO: 177).

In yet another aspect, the invention features an isolated peptide or analog thereof containing the amino acid sequence P-F-(I/L)-E-C-X-G-X-(R/G)-X-(Y/F)-(Y/F)-A-N (SEQ ID NO: 178), wherein the peptide reduces blood vessel formation in a cell, tissue or organ.

In yet another aspect, the invention features an isolated peptide or analog thereof having at least 75%, 80%, 85%, 90%, 95% or 100% amino acid sequence identity to an amino acid sequence selected from the group consisting of

```
Alpha 6 fibril of type 4 collagen:
                       (SEQ ID NO: 93)
YCNINEVCHYARRNDKSYWL;

Alpha 5 fibril of type 4 collagen:
                       (SEQ ID NO: 89)
LRRFSTMPFMFCNINNVCNF;

Alpha 4 fibril of type 4 collagen:
                       (SEQ ID NO: 87)
AAPFLECQGRQGTCHFFAN;

Alpha 4 fibril of type 4 collagen:
                       (SEQ ID NO: 85)
LPVFSTLPFAYCNIHQVCHY;
and Alpha 4 fibril of type 4 collagen:
                       (SEQ ID NO: 86)
YCNIHQVCHYAQRNDRSYWL,
``` wherein A is alanine; I is isoleucine; F is phenylalanine; D is aspartic acid; M is methionine; H is histidine; Y is tyrosine; K is lysine; W is tryptophan; C is cysteine, T is threonine, S is serine; N is asparagine; G is glycine; R is arginine; V is valine, P is proline, and Q is glutamine wherein the peptide reduces blood vessel formation in a tissue or organ.

In yet another aspect, the invention features an isolated peptide or analog thereof containing the amino acid sequence E-C-L-W-X-D-$X_8$-G-X-Y-$X_5$-C (SEQ ID NO: 179), wherein the peptide reduces blood vessel formation in a cell, tissue or organ. In various embodiments, the peptide contains or consists essentially of 23, 24, 25, 30, 35, or 40 amino acids of a TIMP polypeptide. In another embodiment, the peptide contains or consists essentially of an amino acid sequence having at least 75%, 80%, 85%, 90%, 95% or 100% amino acid sequence identity to ECLWTDMLSNFGYPGYQSKHYACI (SEQ ID NO: 155), wherein the peptide reduces blood vessel formation in a cell, tissue or organ.

In yet another aspect, the invention features an isolated peptide or analog thereof containing at least a fragment of a TIMP, wherein the peptide contains a sequence having at least 75%, 80%, 85%, 90%, 95% or 100% amino acid sequence identity to an amino acid sequence selected from TIMP peptides listed in Table 1, and wherein the peptide reduces blood vessel formation in a cell, tissue or organ.

In yet another aspect, the invention features an isolated polypeptide or analog thereof containing at least a fragment of an amino acid sequence selected from the group consisting of SEQ ID Nos. 1-156.

In yet another aspect, the invention features an isolated peptide or analog thereof containing or consisting essentially of an amino acid sequence having at least 75%, 80%, 85%, 90%, 95% or 100% identity to an amino acid sequence selected from the group consisting of SEQ ID Nos. 1-156. In other embodiments, the peptide has at least 90%, 95%, or 100% identity to an amino acid sequence selected from the group consisting of SEQ ID Nos. 1-156. In other embodiments, the peptide differs in at least 1, 2, 3 or 4 amino acids from the amino acid sequence of SEQ ID Nos. 1-156. In one embodiment, the isolated peptide or analog of any previous aspect consists of an amino acid sequence selected from the group consisting of SEQ ID Nos. 1-156. In other embodiments, the peptide contains at least one modification in an amino acid of SEQ ID Nos. 1-156 (e.g., a sequence alteration, modified amino acid, post-translational modification) that increases protease resistance, biodistribution, or therapeutic efficacy. In other embodiments, the peptide is cyclized or pegylated.

In yet another aspect, the invention features a peptide conjugate containing a peptide having an amino acid sequence selected from the group consisting of SEQ ID Nos. 1-156 conjugated to an agent that specifically binds a tumor marker or endothelial cell marker. In one embodiment, the agent (e.g., aptamer or an antibody) targets the peptide to a tumor or an endothelial cell. In other embodiments, the aptamer or antibody specifically binds fibronectin, tenascin-C, integrin, VEGF, prostate-specific membrane antigen, CD44, or tumor endothelial marker (TEM).

In yet another aspect, the invention features an isolated nucleic acid molecule encoding the peptide of any previous aspect.

In yet another aspect, the invention features an expression vector containing the nucleic acid molecule of any previous aspect, wherein the nucleic acid molecule is positioned for expression. In one embodiment, the vector further contains a promoter suitable for expressing the nucleic acid molecule in a mammalian cell.

In yet another aspect, the invention features a host cell containing the peptide of any previous aspect or a nucleic acid molecule encoding the peptide. In one embodiment, the cell is a prokaryotic or eukaryotic cell (e.g., a cell in vitro or in vivo). In another embodiment, the cell is a human cell.

In yet another aspect, the invention features a method of reducing blood vessel formation in a cell, tissue or organ, the method involving contacting an endothelial cell, or a tissue or organ containing an endothelial cell with an effective amount of a peptide of any one previous aspect, thereby reducing blood vessel formation in the tissue or organ.

In yet another aspect, the invention features a method of reducing endothelial cell proliferation, migration, survival, or stability in a tissue or organ, the method involving contacting a cell, tissue or organ containing an endothelial cell with an effective amount of a peptide of any one previous aspect, thereby reducing endothelial cell proliferation, migration, survival, or stability in the tissue or organ.

In yet another aspect, the invention features a method of increasing endothelial cell death in a tissue or organ, the method involving contacting a tissue or organ containing an endothelial cell with an effective amount of a peptide of any previous aspect or a peptide conjugate, thereby increasing endothelial cell death in the tissue or organ.

In various embodiments of any previous aspect, the cell, tissue or organ is selected from the group consisting of bladder, bone, brain, breast, cartilage, nervous tissue, esophagus, fallopian tube, heart, pancreas, intestines, gallbladder, kidney, liver, lung, ovaries, prostate, skeletal muscle, skin, spinal cord, spleen, stomach, testes, thymus, thyroid, trachea, urogenital tract, ureter, urethra, uterus, eye, blood cells, bone marrow, neoplastic tissue, an engineered tissue, and lymph vessels.

In yet another aspect, the invention features a method of reducing blood vessel formation in a tissue or organ the method involving: contacting the tissue, or organ with a vector encoding a polypeptide of SEQ ID Nos. 1-156; and expressing the polypeptide in a cell of the tissue or organ, thereby reducing blood vessel formation in the tissue or organ.

In one embodiment of any previous aspect, the tissue or organ is in vitro or in vivo. In another embodiment, the cell is a human cell, tissue, or organ. In yet another embodiment, the number or volume of blood vessels in the tissue or organ are reduced by at least 10% relative to a control condition. In yet another embodiment, the peptide acts on an endothelial cell (e.g., blood vascular endothelial cells, lymph vascular endothelial cells, endothelial cell lines, primary culture endothelial cells, endothelial cells derived from stem cells, bone marrow derived stem cells, cord blood derived cells, HUVEC, lymphatic endothelial cells, and endothelial progenitor cells).

In yet another aspect, the invention features a method for decreasing blood vessel formation in a subject in need thereof, the method involving administering an effective amount of a peptide of any previous aspect or a peptide conjugate to the subject thereby decreasing blood vessel formation.

In yet another aspect, the invention features a method of reducing endothelial cell proliferation, migration, survival, or stability in a subject in need thereof, the method involving administering an effective amount of a peptide of any one of claims 1-8 or a peptide conjugate to the subject thereby reducing endothelial cell proliferation, migration, survival, or stability in the tissue or organ.

In yet another aspect, the invention features a method of increasing endothelial cell death in a subject in need thereof, the method involving administering an effective amount of a peptide of any previous aspect or a peptide conjugate to the subject, thereby increasing endothelial cell death in the subject. In one embodiment, the subject has or is at risk of developing a disease or disorder characterized by excess or undesirable angiogenesis or vasculogenesis. In another embodiment, the method ameliorates or prevents a disease or disorder characterized by excess or undesirable angiogenesis or vasculogenesis. In still other embodiments of a previous aspect, the disease or disorder is an ocular disease selected from the group consisting of ischemic retinopathy, intraocular neovascularization, age-related macular degeneration, corneal neovascularization, retinal neovascularization, choroidal neovascularization, diabetic macular edema, diabetic retinal ischemia, diabetic retinal edema, proliferative diabetic retinopathy, retinopathy of prematurity; and persistent hyperplastic retinal syndrome. In still other embodiments of a previous aspect, wherein the disease or disorder is related to an undesirable immune response and is selected from the group consisting of scleroderma, psoriasis, rheumatoid arthritis, and Crohn's disease. In still other embodiments of a previous aspect, wherein the disease or disorder is a neoplasia (e.g., breast cancer, leukemia, lymphoma, solid tumor, small cell lung carcinoma, melanoma, and prostate cancer). In still other embodiments of a previous aspect the disease or disorder is an inflammatory disorder selected from the group consisting of asthma, osteoarthritis, chronic obstructive and pulmonary disease. In still other embodiments of a previous aspect, the disease or disorder is a viral or bacterial infection. In still other embodiments of a previous aspect, the excess angiogenesis is associated with a urogenital disorder selected from the group consisting of endometriosis, dysfunctional uterine bleeding, and follicular cysts. In still other embodiments, the excess angiogenesis is associated with a condition selected from the group consisting of Kaposi's sarcoma, plaque neovascularization, atherosclerosis, restenosis, coronary collaterals, cerebral collaterals, arteriovenous malformations, angiofibroma, wound granulation, transplant arteriopathy and atherosclerosis, vascular malformations, DiGeorge syndrome, hereditary hemorrhagic telangiectasia, cavernous hemangioma, cutaneous hemangioma, and lymphatic malformations. In still other embodiments of a previous aspect, the excess angiogenesis is associated with radiotherapy-induced injury and chemotherapy-induced injury. In still other embodiments of a previous aspect, the disease or disorder is obesity (e.g., reduces the survival or proliferation of an adipose cell or tissue). In still other embodiments, the method reduces angiogenesis or vasculogenesis or modulates blood vessel sprouting, endothelial cell proliferation, blood vessel remodeling, restenosis, or blood vessel differentiation.

In another aspect, the invention features a composition containing an effective amount of an isolated peptide of any previous aspect or a peptide conjugate in a pharmacologically acceptable excipient.

In yet another aspect, the invention features a pharmaceutical composition containing an effective amount of a nucleic acid molecule or portion thereof encoding a peptide of any previous aspect or a peptide conjugate in a pharmacologically acceptable excipient. In still other embodiments, the composition contains 2, 3, 4, 5, 10, 15, 20, 25, 50, 100, 125, 150 or more peptides of SEQ ID Nos. 1-156.

In yet another aspect, the invention features a method for identifying an amino acid sequence of interest, the method involving:

(a) identifying an initial polypeptide or fragment thereof having amino acid sequence identity to a reference sequence having a biological function of interest;

(b) generating a random sequence containing the amino acid composition of the initial polypeptide of interest and comparing the random sequence to the reference sequence to determine amino acid sequence identity, wherein said amino acid sequence identity determines a random sequence cut-off value;

(c) comparing the sequence identity of step a to the random sequence cut-off value of step b, wherein a sequence identity that is significantly greater (5%, 10%, 20%, 25%, 50%, 75%, or 100%) than the random sequence cut-off value identifies an amino acid sequence of interest. In one embodiment, the reference sequence is a thrombospondin containing protein, collagen, CXC chemokine, kringle containing protein, somatotropin, or TIMP polypeptide.

In yet another aspect, the invention features a method for identifying a peptide having angiogenic modulating activity, the method involving:

(a) identifying a polypeptide or fragment thereof having amino acid sequence identity to a reference sequence having angiogenic modulating activity;

(b) identifying a hydrophobic region within the polypeptide; and (c) comparing the amino acid sequence of the hydrophobic region with a corresponding amino acid sequence of a second organism to identify a region having at least 75%, 80%, 85%, 90%, 95% or 100% homology, thereby identifying a peptide having angiogenic modulating activity. In one embodiment, the peptide inhibits or enhances angiogenesis.

In yet another aspect, the invention features a kit containing an effective amount of a peptide selected from the group consisting of SEQ ID Nos. 1-156 and directions for using the peptide to treat a disease characterized by undesirable or excess angiogenesis.

In yet another aspect, the invention features a method for identifying an agent having angiogenic modulating activity, the method involving contacting a peptide selected from the group consisting of SEQ ID Nos. 1-156 with an agent; and identifying binding of the agent to the peptide, wherein an agent that specifically binds the peptide is identified as having angiogenic modulating activity. In one embodiment, the agent binds the peptide.

The invention provides agents that modulate angiogenesis. Other features and advantages of the invention will be apparent from the detailed description, and from the claims.

DEFINITIONS

By "thrombospondin containing protein" is meant a protein, analog, or fragment thereof comprising at least the amino acid motif $W-X_2-C-X_3-C-X_2-G$ (SEQ ID NO: 161), or having at least 85% amino acid sequence identity to a type 1 Thrombospondin conserved domain, and having angiogenesis modulating activity. Exemplary thrombospondin containing proteins include ADAMTS 1-18, BAI 1-3, C6, CILP, Fibulin-6, papilin, properdin, semaphorin 5A, semaphorin 5B, ADAM-9, and ADAM-12.

By "Tsp-1 domain" is meant a domain containing about 50 to 61 amino acids having homology to a domain of human thrombospondin comprising amino acids 361-412, 417-473, or 474-530 as described by Lawler and Hynes J. Cell Biol. 103:1635-1648, 1986. In particular, a Tsp-1 domain includes 57 amino acids, including two or three conserved tryptophan residues separated by two to four amino acids each; six conserved cysteine residues; and two highly conserved arginines and two glycines as described by Lawler and Hynes J. Cell Biol. 103:1635-1648, 1986, which is incorporated herein by reference in its entirety.

By "Tsp-2 domain" is meant a domain containing about 55 to 61 amino acids having homology to a domain of human thrombospondin comprising amino acids 531-571, 572-629, or 630 to 674 as described by Lawler and Hynes J. Cell Biol. 103:1635-1648, 1986. In particular, a Tsp-2 domain includes six conserved cysteine residues and has 20% to 35% pairwise identity over 46 residues as described by Lawler and Hynes J. Cell Biol. 103:1635-1648, 1986.

By "collagen" is meant a protein, analog, or fragment thereof comprising at least the amino acid motif C-N-$X_3$-V-C (SEQ ID NO: 174), or having at least 85% amino acid sequence identity to an al, 2, 4, 5, or 6 domain of collagen IV and having angiogenesis modulating activity.

By "C-X-C chemokine" is meant a polypeptide comprising at least the amino acid motif G-$X_3$-C-L-X-P-$X_{10}$-K-X-L (SEQ ID NO: 170), or having at least 85% amino acid sequence identity to a C-X-C chemokine comprising the C-X-C chemokine motif. Glu-Leu-Arg (ELR) and having angiogenesis modulating activity. Exemplary C-X-C chemokines include Gro-α/CXC1, Gro-β/CXCL2, Gro-γ/CXCL3, PF-4/CXCL4, ENA-78/CXCL5, GCP-2/CXCL6, THBG-β/CXCL7, IL-8/CXCL8, and IP-10/CXCL10.

By "kringle containing protein" is meant a polypeptide, analog, or fragment thereof comprising a kringle domain and having angiogenesis modulating activity. A kringle domain is a protein structure comprising ~80 amino acids with conserved triple disulfide bonds as defined by Varadi, A. (1984) *FEBS Lett.* 171, 131-136). Examplary kringle containing proteins include kininogen, AK-38 protein, lipoprotein and thrombin.

By "somatotropin" is meant a polypeptide, analog, or fragment thereof having at least 85% amino acid sequence identity to a member of the human prolactin/growth hormone family that includes a somatotropin domain. See, for example, Struman Proc Natl Acad Sci USA. 1999 Feb. 16; 96(4): 1246-1251. Examplary somatotoropins include Growth Hormone-1 (GH-1), Growth Hormone-2 (GH-2), somatoliberin and placental lactogen.

By "TIMP" is meant a polypeptide, analog, or fragment thereof comprising at least the motif E-C-L-W-X-D-$X_8$-G-X-Y-$X_5$-C (SEQ ID NO: 179) or having at least 85% amino acid sequence identity to the loop-6 domain of TIMP-2, and having angiogenesis modulating activity. Examplary TIMPs include TIMP3 and TIMP4.

By "blood vessel formation" is meant the dynamic process that includes one or more steps of blood vessel development and/or maturation, such as angiogenesis, vasculogenesis, formation of an immature blood vessel network, blood vessel remodeling, blood vessel stabilization, blood vessel maturation, blood vessel differentiation, or establishment of a functional blood vessel network.

By "angiogenesis" is meant the growth of new blood vessels originating from existing blood vessels. Angiogenesis can be assayed by measuring the total length of blood vessel segments per unit area, the functional vascular density (total length of perfused blood vessel per unit area), or the vessel volume density (total of blood vessel volume per unit volume of tissue).

By "vasculogenesis" is meant the development of new blood vessels originating from stem cells, angioblasts, or other precursor cells.

By "blood vessel stability" is meant the maintenance of a blood vessel network.

By "alteration" is meant a change in the sequence or in a modification (e.g., a post-translational modification) of a gene or polypeptide relative to an endogeneous wild-type reference sequence.

By "ameliorate" is meant decrease, suppress, attenuate, diminish, arrest, or stabilize the development or progression of a disease.

By "antibody" is meant any immunoglobulin polypeptide, or fragment thereof, having immunogen binding ability.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells.

By "disease" is meant any condition or disorder that damages or interferes with the normal function of a cell, tissue, or organ.

By "an effective amount" is meant the amount required to ameliorate the symptoms of a disease relative to an untreated patient. The effective amount of active compound(s) used to practice the present invention for therapeutic treatment of an angiogenesis-associated disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By "isolated nucleic acid molecule" is meant a nucleic acid (e.g., a DNA) that is free of the genes, which, in the naturally occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule which is transcribed from a DNA molecule, as well as a recombinant DNA which is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

"By "neoplasia" is meant a disease that is caused by or results in inappropriately high levels of cell division, inappropriately low levels of apoptosis, or both. Solid tumors, hematological disorders, and cancers are examples of neoplasias.

By "operably linked" is meant that a first polynucleotide is positioned adjacent to a second polynucleotide that directs transcription of the first polynucleotide when appropriate molecules (e.g., transcriptional activator proteins) are bound to the second polynucleotide.

By "peptide" is meant any fragment of a polypeptide. Typically peptide lengths vary between 5 and 1000 amino acids (e.g., 5, 10, 15, 20, 25, 50, 100, 200, 250, 500, 750, and 1000).

By "polypeptide" is meant any chain of amino acids, regardless of length or post-translational modification.

By "promoter" is meant a polynucleotide sufficient to direct transcription.

By "reduce" is meant a decrease in a parameter (e.g., blood vessel formation) as detected by standard art known methods, such as those described herein. As used herein, reduce includes a 10% change, preferably a 25% change, more preferably a 40% change, and even more preferably a 50% or greater change.

By "reference" is meant a standard or control condition.

By "subject" is meant a mammal, including, but not limited to, a human or non-human mammal, such as a bovine, equine, canine, ovine, or feline.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and even more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

"Sequence identity" or "identity" in the context of two nucleic acid or polypeptide sequences includes reference to the residues in the two sequences which are the same when aligned for maximum correspondence over a specified comparison window, and can take into consideration additions, deletions and substitutions. When percentage of sequence identity is used in reference to proteins it is recognized that residue positions which are not identical often differ by conservative amino acid substitutions, where amino acid residues are substituted for other amino acid residues with similar chemical properties (for example, charge or hydrophobicity) and therefore do not deleteriously change the functional properties of the molecule. Where sequences differ in conservative substitutions, the percent sequence identity may be adjusted upwards to correct for the conservative nature of the substitution. Sequences which differ by such conservative substitutions are said to have sequence similarity. Approaches for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers and Miller, *Computer Applic. Biol. Sci.*, 4: 11-17, 1988, for example, as implemented in the program PC/GENE (Intelligenetics, Mountain View, Calif., USA).

"Percentage of sequence identity" means the value determined by comparing two optimally aligned sequences over a comparison window, wherein the portion of the polynucleotide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" or "homologous" in their various grammatical forms in the context of polynucleotides means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 85%, 90%, and even more preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, for example, when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid, although such cross-reactivity is not required for two polypeptides to be deemed substantially identical.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

A "recombinant host" may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

The term "operably linked" is used to describe the connection between regulatory elements and a gene or its coding region. That is, gene expression is typically placed under the control of certain regulatory elements, including constitutive or inducible promoters, tissue-specific regulatory elements, and enhancers. Such a gene or coding region is said to be "operably linked to" or "operatively linked to" or "operably associated with" the regulatory elements, meaning that the gene or coding region is controlled or influenced by the regulatory element.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 5, 10, or 15 amino acids, preferably at least about 20 amino acids, more preferably at least about 25 amino acids, and even more preferably about 35 amino acids, about 50 amino acids, about 100 amino acids, or about 150 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides about 300 nucleotides or about 450 nucleotides or any integer thereabout or therebetween.

Methods of alignment of sequences for comparison are well-known in the art. Optimal alignment of sequences for comparison may be conducted by the local homology algorithm of Smith and Waterman, *Adv. Appl. Math.*, 2: 482, 1981; by the homology alignment algorithm of Needleman and Wunsch, *J. Mol. Biol.*, 48: 443, 1970; by the search for similarity method of Pearson and Lipman, *Proc. Natl. Acad. Sci. USA*, 8: 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, Gene, 73: 237-244, 1988; Corpet, et al., *Nucleic Acids Research*, 16:881-90, 1988; Huang, et al., *Computer Applications in the Biosciences*, 8:1-6, 1992; and Pearson, et al., *Methods in Molecular Biology*, 24:7-331, 1994. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York, 1995. New versions of the above programs or new programs altogether will undoubtedly become available in the future, and can be used with the present invention.

Unless otherwise stated, sequence identity/similarity values provided herein refer to the value obtained using the BLAST 2.0 suite of programs, or their successors, using default parameters (Altschul et al., *Nucleic Acids Res*, 2:3389-3402, 1997). It is to be understood that default settings of these parameters can be readily changed as needed in the future.

As those ordinary skilled in the art will understand, BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163, 1993) and XNU (Clayerie and States, *Comput. Chem.*, 17:191-1, 1993) low-complexity filters can be employed alone or in combination.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

A "tumor," as used herein, refers to all neoplastic cell growth and proliferation, whether malignant or benign, and all precancerous and cancerous cells and tissues.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

BRIEF DESCRIPTION OF THE DRAWINGS

FIG. 2A shows scores for proteins containing a CXC conserved domain. FIG. 2B shows scores for proteins that contain a collagen type IV domain. FIG. 2C shows scores for proteins that belong to the serpin family. FIG. 2D shows scores for Kringle containing proteins. FIG. 2E shows scores for proteins with a somatotropin hormone conserved domain. As in FIG. 1 the similarity between the query (vertically positioned domain) and the corresponding domains of various proteins (horizontally positioned domains) is calculated. Similarities scoring higher than 45% are shown in gray scale.

FIGS. 9A-9F are graphs showing the activity of WISP isoforms in an in vitro cell proliferation assay. FIGS. 9A and 9D show the activity of the WISP-1 derived peptide, SPWSPCSTSCGLGVSTRI (SEQ ID NO: 74). FIGS. 9B and 9E show the activity of the WISP-2 derived peptide, TAWGPCSTTCGLGMATRV (SEQ ID NO: 75). FIGS. 9C and 9F show the activity of the WISP-3 derived peptide TKWTPCSRTCGMGISNRV (SEQ ID NO: 76).

FIGS. 12A-12F are graphs showing the activity of three fragments of fibulin-6 in an in vitro cell proliferation assay. FIGS. 12A and 12D shows the activity profile for the ASWSACSVSCGGGARQRTR (SEQ ID NO: 45) fragment of fibulin-6; FIGS. 12B and 12E show the activity profile for QPWGTCSESCGKGTQTRAR (SEQ ID NO: 44) fragment of fibulin-6; FIGS. 12C and 12E show the activity profile of the SAWRACSVTCGKGIQKRSR (SEQ ID NO: 43) fragment of fibulin-6.

FIGS. 15A and 15C show the activity profile for UNC5-C TEWSVCNSRCGRGYQKRTR (SEQ ID NO: 70) fragment; FIGS. 15B and 15D show the activity profile for UNC5-D TEWSACNVRCGRGWQKRSR (SEQ ID NO: 71).

FIGS. 24A-24F are graphs showing the activity of Semaphorin 5A and 5B derived peptides in in vitro cell proliferation assays. FIGS. 24A,D show the activity profile for GPWERCTAQCGGGIQARRR (SEQ ID NO: 60) fragment of semaphorin 5A; FIGS. 24B,E show the activity profile for SPWTKCSATCGGGHYMRTR (SEQ ID NO: 61) fragment of semaphorin 5A; FIGS. 24C,F show the activity profile for TSWSPCSASCGGGHYQRTR (SEQ ID NO: 62) fragment of semaphorin 5B.

FIGS. 25A and 25C show activity for the first fragment GPWAPCSASCGGGSQSRS (SEQ ID NO: 48); FIGS. 25B and 25D show activity for the second fragment SPWTKCSATCGGGHYMRTR (SEQ ID NO: 61).

FIGS. 35A-35F are graphs showing the activity of the C4-alpha4 fragments in in vitro cell proliferation assays.

FIGS. 44B and 44C show novel motifs when shifting the abundant 7-mer downstream (B) or upstream (C) in the peptide sequences. (A) SEQ ID NOS 79, 90, 77, 78, 89, 88, 92, 93, 81, 82 & 84-86 are disclosed respectively in order of appearance. (B) SEQ ID NOS 77, 78, 89, 88, 92, 81, 94, & 85 are disclosed respectively in order of appearance. (C) SEQ ID NOS 79, 90, 77, 88, 92, 93, 81, 82, 85 & 86 are disclosed in order of appearance.

DETAILED DESCRIPTION OF THE INVENTION

Figure 1:
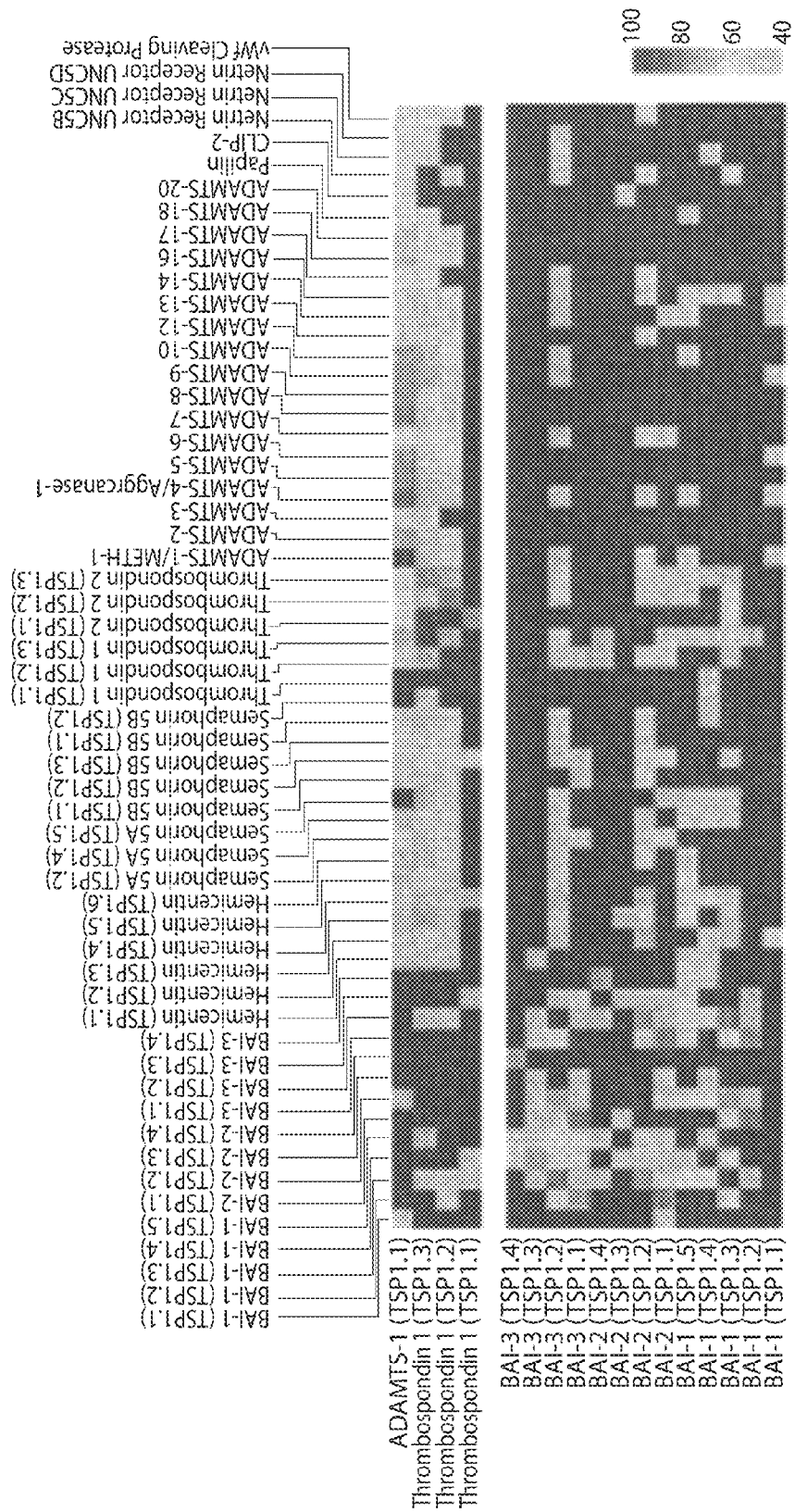
FIG. 1 shows a scaled similarity score (bits) for different type I thrombospondin (TSP1) conserved domains. The similarity between the query (vertically positioned domain) and the corresponding domains of various proteins (horizontally positioned domains) is calculated. Similarities scoring higher than 45% are color coded in gray scale as shown.

The invention generally features compositions and methods that are useful for modulating blood vessel formation, as well as methods that provide for the systematic and efficient identification of angiogenesis inhibitors. As described in more detail below, a systematic computational methodology based on bioinformatics was used to identify and classify novel putative endogenous inhibitors of angiogenesis. A list of proteins and protein fragments having anti-angiogenic or pro-apoptotic properties was compiled. Based on similarity to these known anti-angiogenic fragments and the existence of conserved domains within these sequences, novel putative angiogenic inhibitors were identified and classified. These novel angiogenic inhibitors include members of the ADAM, ADAMTS, CXC and semaphorin protein families, as well as coagulation factors, receptor tyrosine kinase-like orphan receptors and various kringle-containing proteins. Clustering of similarities among the hits allowed predictions to be made concerning the localization of the anti-angiogenic activity within the protein sequences. The powerful computational methods used provided for the efficient identification of novel anti-angiogenic proteins and fragments. The anti-angiogenic activity of a variety of these peptides has been characterized experimentally in vitro and/or in vivo.

Angiogenesis

Angiogenesis, which involves the growth or sprouting of new microvessels from pre-existing vasculature, and vasculogenesis, which involves de novo vascular growth, is essential to many physiological and pathological conditions, including embryogenesis, cancer, rheumatoid arthritis, diabetic retinopathy, obesity, atherosclerosis, ischemic heart and limb disease, and wound healing. Over 70 diseases have been identified as angiogenesis dependent (Carmeliet, *Nature*, 438:932-6, 2005). Under physiological conditions, the growth of new microvessels is tightly regulated and orchestrated by maintaining a balance between endogenous pro- and anti-angiogenic factors. Tipping the balance of this regulation may lead to either excessive neovascularization, as in cancer, age-related macular degeneration, and rheumatoid arthritis, or insufficient vascularization, as in ischemic heart and limb disease, ischemic brain, and neural degeneration.

Angiogenesis is a complex multistep process that involves interactions between endothelial cells (EC), pericytes, vascular smooth muscle cells, and stromal cells (e.g., stem cells and parenchymal cells). These interactions occur through secreted factors, such as vascular endothelial growth factor (VEGF), platelet-derived growth factor (PDGF), basic fibroblast growth factor (bFGF or FGF-2) and angiopoietins, as well as through cell-cell and cell-extracellular matrix (ECM) interactions. Endothelial cell-ECM interactions regulate numerous processes that are critical for angiogenesis, including endothelial cell migration, proliferation, differentiation and apoptosis. Angiogenic processes include network stabilization and remodeling that may involve the recruitment of stromal cells, as well as the pruning of some vessels. In many cases, angiogenesis occurs as a response to hypoxia. A transcription factor called hypoxia-inducible factor, HIM a, has been demonstrated to act as an oxygen sensor whose activity leads to upregulation of VEGF in parenchymal and stromal cells (Semenza, *Physiology (Bethesda)*, 19:176-82, 2004). VEGF is secreted as a homodimer in the form of several heparin-binding and non-heparin-binding splice-variant isoforms; it diffuses through the interstitial space and can bind to the endothelial cell receptors VEGFR1 and VEGFR2, as well as co-receptors such as Neuropilin-1, thus initiating a signal transduction cascade that leads to endothelial cell proliferation and migration. The production of endothelial cell matrix metalloproteinases, MMPs, increases as a result of endothelial cell activation; MMPs are necessary for selectively clipping the capillary basement membrane and the ECM, which constitute physical barriers to endothelial cell migration and capillary sprouting. MMPs and their associated molecules also play a crucial role in uncovering cryptic sites of the ECM proteins, a number of which have been identified as anti-angiogenic (Davis et al., *Anat Rec*, 268:252-75, 2002; Folkman, *Annu Rev Med*, 57:1-18, 2006; Rundhaug, *J Cell Mol Med*, 9:267-85, 2005; Schenk and Quaranta, *Trends Cell Biol*, 13:366-75, 2003), and in processing cell-surface receptors (Mott and Werb, *Curr Opin Cell Biol*, 16:558-64, 2004).

Diseases Associated with Undesirable Angiogenesis

Where the processes regulating angiogenesis are disrupted, pathology may result. Such pathology affects a wide variety of tissues and organ systems. Diseases characterized by excess or undesirable angiogenesis are susceptible to treatment with therapeutic agents described herein.

Excess angiogenesis in numerous organs is associated with cancer and metastasis, including neoplasia and hematologic malignancies.

Angiogenesis-related diseases and disorders are commonly observed in the eye where they may result in blindness. Such disease include, but are not limited to, age-related macular degeneration, choroidal neovascularization, persistent hyperplastic vitreous syndrome, diabetic retinopathy, and retinopathy of prematurity (ROP).

A number of angiogenesis-related diseases are associated with the blood and lymph vessels including transplant arteriopathy and atherosclerosis, where plaques containing blood and lymph vessels form, vascular malformations, DiGeorge syndrome, hereditary hemorrhagic telangiectasia, cavernous hemangioma, cutaneous hemangioma, and lymphatic malformations.

Other angiogenesis diseases and disorders affect the bones, joints, and/or cartilage include, but are not limited to, arthritis, synovitis, osteomyelitis, osteophyte formation, and HIV-induced bone marrow angiogenesis.

The gastro-intestinal tract is also susceptible to angiogenesis diseases and disorders. These include, but are not limited to, inflammatory bowel disease, ascites, peritoneal adhesions, and liver cirrhosis.

Angiogenesis diseases and disorders affecting the kidney include, but are not limited to, diabetic nephropathy (early stage: enlarged glomerular vascular tufts).

Excess angiogenesis in the reproductive system is associated with endometriosis, uterine bleeding, ovarian cysts, ovarian hyperstimulation.

In the lung, excess angiogenesis is associated with primary pulmonary hypertension, asthma, nasal polyps, rhinitis, chronic airway inflammation, cystic fibrosis.

Diseases and disorders characterized by excessive or undesirable angiogenesis in the skin include psoriasis, warts, allergic dermatitis, scar keloids, pyogenic granulomas, blistering disease, Kaposi's sarcoma in AIDS patients, systemic sclerosis.

Obesity is also associated with excess angiogenesis (e.g., angiogenesis induced by fatty diet). Adipose tissue may be reduced by the administration of angiogenesis inhibitors.

Excess angiogenesis is associated with a variety of autoimmune disorders, such as systemic sclerosis, multiple sclerosis, Sjögren's disease (in part by activation of mast cells and leukocytes). Undesirable angiogenesis is also associated with a number of infectious diseases, including those associated with pathogens that express (lymph)-angiogenic genes, that induce a (lymph)-angiogenic program or that transform endothelial cells. Such infectious disease include those bacterial infections that increase HIF-1 levels, HIV-Tat levels, antimicrobial peptides, levels, or those associated with tissue remodeling.

Infectious diseases, such as viral infections, can cause excessive angiogenesis which is susceptible to treatment with agents of the invention. Examples of viruses that have been found in humans include, but are not limited to, Retroviridae (e.g. human immunodeficiency viruses, such as HIV-1 (also referred to as HDTV-III, LAVE or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

The present invention provides methods of treating diseases and/or disorders or symptoms thereof associated with excess or undesired angiogenesis, which comprise administering a therapeutically effective amount of a pharmaceutical composition comprising a compound of the formulae herein to a subject (e.g., a mammal, such as a human). Thus, one embodiment is a method of treating a subject suffering from or susceptible to an angiogenesis-related disease or disorder or symptom thereof. The method includes the step of administering to the mammal a therapeutic amount of an amount of a compound herein sufficient to treat the disease or disorder or symptom thereof (e.g., to prevent or reduce angiogenesis) under conditions such that the disease or disorder is treated.

The methods herein include administering to the subject (including a subject identified as in need of such treatment) an effective amount of a compound described herein (e.g., a peptide described herein, or mimetic, or analog thereof), or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which angiogenesis may be implicated.

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with angiogenesis, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Treatment of Neoplasia

The methods of the invention are particularly well suited for the treatment of neoplasias. By "neoplasia" is meant a disease that is caused by or results in inappropriately high levels of cell division, inappropriately low levels of apoptosis, or both. For example, cancer is an example of a proliferative disease. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors, such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). Lymphoproliferative disorders are also considered to be proliferative diseases.

Peptides of the Invention

The present invention utilizes powerful computational and bioinformatic approaches to identify therapeutic agents (e.g., polypeptides, peptides, analogs, and fragments thereof) having anti-angiogenic activity. The amino acid sequences of such agents are provided at Table 1 (below), which provides peptide sequences of peptides of the invention, as well as the names of the proteins from which they are derived, GenBank Accession Nos., and the amino acid positions of the sequences Amino acids are referred to herein by their commonly known one-letter symbols recommended by the IUPAC-IUB Biochemical Nomenclature Commission; they can also be referred to by their commonly known three letter symbols.

TABLE 1

Anti-Angiogenic Peptide sequences

| SEQ ID NO. | | | |
|---|---|---|---|
| Thrombospondin Containing Proteins | | | |
| 1 | ADAM-9 | Q13443: 649-661 | KCHGHGVCNSNKN |
| 2 | ADAM-12 | O43184: 662-675 | MQCHGRGVCNNRKN |
| 3 | ADAMTS-1 | Q9UHI8: 566-584 | GPWGDCSRTCGGGVQYTMR |
| 4 | ADAMTS-2 | CAA05880.1: 982-998 | GPWSQCSVTCGNGTQER |
| 5 | ADAMTS-3 | NP_055058.1: 973-989 | GPWSECSVTCGEGTEVR |
| 6 | ADAMTS-4 | CAH72146.1: 527-540 | GPWGDCSRTCGGGV |
| 7 | ADAMTS-4 | CAH72146.1: 527-545 | GPWGDCSRTCGGGVQFSSR |
| 8 | ADAMTS-5 | NP_008969.1: 882-898 | GPWLACSRTCDTGWHTR |
| 9 | ADAMTS-6 | NP_922932.2: 847-860 | QPWSECSATCAGGV |
| 10 | ADAMTS-6 | NP_922932.2: 847-863 | QPWSECSATCAGGVQRQ |
| 11 | ADAMTS-7 | AAH61631.1: 1576-1592 | GPWGQCSGPCGGGVQRR |
| 12 | ADAMTS-7 | AAH61631.1: 828-841 | GPWTKCTVTCGRGV |
| 13 | ADAMTS-8 | Q9UP79: 534-547 | GPWGECSRTCGGGV |
| 14 | ADAMTS-8 | Q9UP79: 534-552 | GPWGECSRTCGGGVQFSHR |
| 15 | ADAMTS-9 | Q9P2N4: 1247-1261 | WSSCSVTCGQGRATR |
| 16 | ADAMTS-9 | Q9P2N4: 1335-1351 | GPWGACSSTCAGGSQRR |
| 17 | ADAMTS-9 | Q9P2N4: 595-613 | SPFGTCSRTCGGGIKTAIR |
| 18 | ADAMTS-10 | Q9H324: 528-546 | TPWGDCSRTCGGGVSSSSR |
| 19 | ADAMTS-12 | P58397: 1479-1493 | WDLCSTSCGGGFQKR |
| 20 | ADAMTS-12 | P58397: 549-562 | SPWSHCSRTCGAGV |
| 21 | ADAMTS-13 | AAQ88485.1: 751-765 | WMECSVSCGDGIQRR |
| 22 | ADAMTS-14 | CAI13857.1: 980-994 | WSQCSATCGEGIQQR |
| 23 | ADAMTS-15 | CAC86014.1: 900-916 | SAWSPCSKSCGRGFQRR |
| 24 | ADAMTS-16 | Q8TE57: 1133-1149 | SPWSQCTASCGGGVQTR |
| 25 | ADAMTS-16 | Q8TE57: 1133-1150 | SPWSQCTASCGGGVQTRS |
| 26 | ADAMTS-18 | Q8TE60: 1131-1146 | PWQQCTVTCGGGVQTR |
| 27 | ADAMTS-18 | Q8TE60: 1131-1147 | PWQQCTVTCGGGVQTRS |
| 28 | ADAMTS-18 | Q8TE60: 998-1014 | GPWSQCSKTCGRGVRKR |
| 29 | ADAMTS-18 | Q8TE60: 596-614 | SKWSECSRTCGGGVKFQER |
| 30 | ADAMTS-19 | CAC84565.1: 1096-1111 | WSKCSITCGKGMQSRV |
| 31 | ADAMTS-20 | CAD56159.3: 1478-1494 | NSWNECSVTCGSGVQQR |
| 32 | ADAMTS-20 | CAD56159.3: 1309-1326 | GPWGQCSSSCSGGLQHRA |
| 33 | ADAMTS-20 | CAD56159.3: 1661-1675 | WSKCSVTCGIGIMKR |
| 34 | ADAMTS-20 | CAD56160.2: 564-581 | PYSSCSRTCGGGIESATR |
| 35 | BAI-1 | O14514: 361-379 | SPWSVCSSTCGEGWQTRTR |
| 36 | BAI-2 | O60241: 304-322 | SPWSVCSLTCGQGLQVRTR |
| 37 | BAI-3 | CAI21673.1: 352-370 | SPWSLCSFTCGRGQRTRTR |
| 38 | C6 | AAB59433.1: 30-48 | TQWTSCSKTCNSGTQSRHR |
| 39 | CILP | AAQ89263.1: 156-175 | SPWSKCSAACGQTGVQTRTR |
| 40 | CILP-2 | AAN17826.1: 153-171 | GPWGPCSGSCGPGRRLRRR |
| 41 | CTGF | CAC44023.1: 204-221 | TEWSACSKTCGMGISTRV |
| 42 | CYR61 | AAR05446.1: 234-251 | TSWSQCSKTCGTGISTRV |
| 43 | Fibulin-6 | CAC37630.1: 1574-1592 | SAWRACSVTCGKGIQKRSR |
| 44 | Fibulin-6 | CAC37630.1: 1688-1706 | QPWGTCSESCGKGTQTRAR |
| 45 | Fibulin-6 | CAC37630.1: 1745-1763 | ASWSACSVSCGGGARQRTR |
| 46 | NOVH | AAL92490.1: 211-228 | TEWTACSKSCGMGFSTRV |
| 47 | Papilin | NP_775733.2: 33-51 | SQWSPCSRTCGGGVSFRER |

TABLE 1 -continued

Anti-Angiogenic Peptide sequences

| SEQ ID NO. | | | |
|---|---|---|---|
| 48 | Papilin | NP_775733.2: 342-359 | GPWAPCSASCGGGSQSRS |
| 49 | Properdin | AAP43692.1: 143-161 | GPWEPCSVTCSKGTRTRRR |
| 50 | ROR-1 | CAH71706.1: 313-391 | CYNSTGVDYRGTVSVTKSGRQCQPWNSQYPHTHTFTALRFPEL NGGHSYCRNPGNQKEAPWCFTLDENFKSDLCDIPAC |
| 51 | ROR-1 | CAH71706.1: 310-391 | NHKCYNSTGVDYRGTVSVTKSGRQCQPWNSQYPHTHTFTALRF PELNGGHSYCRNPGNQKEAPWCFTLDENFKSDLCDIPAC |
| 52 | ROR-1 | CAH71706.1: 311-388 | HKCYNSTGVDYRGTVSVTKSGRQCQPWNSQYPHTHTFTALRFP ELNGGHSYCRNPGNQKEAPWCFTLDENFKSDLCDI |
| 53 | ROR-1 | CAH71706.1: 311-391 | HKCYNSTGVDYRGTVSVTKSGRQCQPWNSQYPHTHTFTALRFP ELNGGHSYCRNPGNQKEAPWCFTLDENFKSDLCDIPAC |
| 54 | ROR-1 | CAH71706.1: 312-392 | KCYNSTGVDYRGTVSVTKSGRQCQPWNSQYPHTHTFTALRFPE LNGGHSYCRNPGNQKEAPWCFTLDENFKSDLCDIPACD |
| 55 | ROR-2 | Q01974: 315-395 | QCYNGSGMDYRGTASTTKSGHQCQPWALQHPHSHHLSSTDFPE LGGGHAYCRNPGGQMEGPWCFTQNKNVRMELCDVPSCS |
| 56 | ROR-2 | Q01974: 314-391 | HQCYNGSGMDYRGTASTTKSGHQCQPWALQHPHSHHLSSTDFP ELGGGHAYCRNPGGQMEGPWCFTQNKNVRMELCDV |
| 57 | ROR-2 | Q01974: 314-394 | HQCYNGSGMDYRGTASTTKSGHQCQPWALQHPHSHHLSSTDFP ELGGGHAYCRNPGGQMEGPWCFTQNKNVRMELCDVPSC |
| 58 | ROR-2 | Q01974: 314-395 | HQCYNGSGMDYRGTASTTKSGHQCQPWALQHPHSHHLSSTDFP ELGGGHAYCRNPGGQMEGPWCFTQNKNVRMELCDVPSCS |
| 59 | ROR-2 | Q01974: 315-394 | QCYNGSGMDYRGTASTTKSGHQCQPWALQHPHSHHLSSTDFPE LGGGHAYCRNPGGQMEGPWCFTQNKNVRMELCDVPSC |
| 60 | Semaphorin 5A | NP_003957.1: 660-678 | GPWERCTAQCGGGIQARRR |
| 61 | Semaphorin 5A | NP_003957.1: 848-866 | SPWTKCSATCGGGHYMRTR |
| 62 | Semaphorin 5B | AAQ88491.1: 916-934 | TSWSPCSASCGGGHYQRTR |
| 63 | SCO-spondin | XP_379967.2: 3781-3799 | GPWEDCSVSCGGGEQLRSR |
| 64 | THSD1 | AAQ88516.1: 347-365 | QPWSQCSATCGDGVRERRR |
| 65 | THSD3 | AAH33140.1: 280-298 | SPWSPCSGNCSTGKQQRTR |
| 66 | THSD6 | AAH40620.1: 44-60 | WTRCSSSCGRGVSVRSR |
| 67 | TSP-2 | CAI23645.1: 444-462 | SPWSSCSVTCGVGNITRIR |
| 68 | TSP-2 | CAI23645.1: 501-519 | SPWSACTVTCAGGIRERTR |
| 69 | TSRC1 | AAH27478.1: 140-159 | SPWSQCSVRCGRGQRSRQVR |
| 70 | UNC5C | AAH41156.1: 267-285 | TEWSVCNSRCGRGYQKRTR |
| 71 | UNC5D | AAQ88514.1: 259-277 | TEWSACNVRCGRGWQKRSR |
| 72 | VSGP/F-spondin | BAB18461.1: 567-583 | WDECSATCGMGMKKRHR |
| 73 | VSGP/F-spondin | BAB18461.1: 621-639 | SEWSDCSVTCGKGMRTRQR |
| 74 | WISP-1 | AAH74841.1: 221-238 | SPWSPCSTSCGLGVSTRI |
| 75 | WISP-2 | AAQ89274.1: 199-216 | TAWGPCSTTCGLGMATRV |
| 76 | WISP-3 | CAB16556.1: 191-208 | TKWTPCSRTCGMGISNRV |

Collagens

| 77 | α1CIV | CAH74130.1: 1479-1556 | NERAHGQDLGTAGSCLRKFSTMPFLFCNINNVCNFASRNDYSY WLSTPEPMPMSMAPITGENIRPFISRCAVCEAPAM |
| 78 | α1CIV | CAH74130.1: 1494-1513 | LRKFSTMPFLFCNINNVCNF |
| 79 | α1CIV | CAH74130.1: 1504-1523 | FCNINNVCNFASRNDYSYWL |
| 80 | α1CIV | CAH74130.1: 1610-1628 | SAPFIECHGRGTCNYYANA |
| 81 | α2CIV | CAH71366.1: 1517-1593 | QEKAHNQDLGLAGSCLARFSTMPFLYCNPGDVCYYASRNDKSY WLSTTAPLPMMPVAEDEIKPYISRCSVCEAPAIA |
| 82 | α2CIV | CAH71366.1: 1542-1561 | YCNPGDVCYYASRNDKSYWL |
| 83 | α2CIV | CAH71366.1: 1646-1664 | ATPFIECNGGRGTCHYYAN |
| 84 | α4CIV | CAA56943.1: 1499-1575 | QEKAHNQDLGLAGSCLPVFSTLPFAYCNIHQVCHYAQRNDRSY WLASAAPLPMMPLSEEAIRPYVSRCAVCEAPAQA |
| 85 | α4CIV | CAA56943.1: 1514-1533 | LPVFSTLPFAYCNIHQVCHY |
| 86 | α4CIV | CAA56943.1: 1524-1543 | YCNIHQVCHYAQRNDRSYWL |
| 87 | α4CIV | CAA56943.1: 1628-1646 | AAPFLECQGRQGTCHFFAN |
| 88 | α5CIV | AAC27816.1: 1495-1572 | NKRAHGQDLGTAGSCLRRFSTMPFMFCNINNVCNFASRNDYSY WLSTPEPMPMSMQPLKGQSIQPFISRCAVCEAPAV |
| 89 | α5CIV | AAC27816.1: 1510-1529 | LRRFSTMPFMFCNINNVCNF |
| 90 | α5CIV | AAC27816.1: 1520-1539 | FCNINNVCNFASRNDYSYWL |
| 91 | α5CIV | AAC27816.1: 1626-1644 | SAPFIECHGRGTCNYYANS |
| 92 | α6CIV | CAI40758.1: 1501-1577 | QEKAHNQDLGFAGSCLPRFSTMPFIYCNINEVCHYARRNDKSY WLSTTAPIPMMPVSQTQIPQYISRCSVCEAPSQA |
| 93 | α6CIV | CAI40758.1: 1526-1545 | YCNINEVCHYARRNDKSYWL |
| 94 | α6CIV | CAI40758.1: 1630-1648 | ATPFIECSGARGTCHYFAN |

CXC Chemokines

| 95 | ENA-78/CXCL5 | AAP35453.1: 86-108 | NGKEICLDPEAPFLKKVIQKILD |
| 96 | ENA-78/CXCL5 | AAP35453.1: 48-103 | RCVCLQTTQGVHPKMISNLQVFAIGPQCSKVEVVASLKNGKEIC LDPEAPFLKKVI |
| 97 | ENA-78/CXCL5 | AAP35453.1: 51-107 | CLQTTQGVHPKMISNLQVFAIGPQCSKVEVVASLKNGKEICLDP EAPFLKKVIQKIL |
| 98 | GCP-2/CXCL6 | AAH13744.1: 86-109 | NGKQVCLDPEAPFLKKVIQKILDS |

TABLE 1-continued

Anti-Angiogenic Peptide sequences

| SEQ ID NO. | | | |
|---|---|---|---|
| 99 | GCP-2/CXCL6 | AAH13744.1: 47-106 | LRCTCLRVTLRVNPKTIGKLQVFPAGPQCSKVEVVASLKNGKQV CLDPEAPFLKKVIQKI |
| 100 | GCP-2/CXCL6 | AAH13744.1: 48-103 | RCTCLRVTLRVNPKTIGKLQVFPAGPQCSKVEVVASLKNGKQV CLDPEAPFLKKVI |
| 101 | GCP-2/CXCL6 | AAH13744.1: 51-107 | CLRVTLRVNPKTIGKLQVFPAGPQCSKVEVVASLKNGKQVCLDP EAPFLKKVIQKIL |
| 102 | GRO-α/CXCL1 | AAP35526.1: 80-103 | NGRKACLNPASPIVKKIIEKMLNS |
| 103 | GRO-α/CXCL1 | AAP35526.1: 42-97 | RCQCLQTLQGIHPKNIQSVNVKSPGPHCAQTEVIATLKNGRKAC LNPASPIVKKII |
| 104 | GRO-α/CXCL1 | AAP35526.1: 44-101 | QCLQTLQGIHPKNIQSVNVKSPGPHCAQTEVIATLKNGRKACLN PASPIVKKIIEKML |
| 105 | Gro-β/CXCL2 | AAH15753.1: 42-97 | RCQCLQTLQGIHLKNIQSVKVKSPGPHCAQTEVIATLKNGQKAC LNPASPMVKKII |
| 106 | GRO-γ/MIP-2β/CXCL3 | AAA63184.1: 79-100 | NGKKACLNPASPMVQKIIEKIL |
| 107 | GRO-γ/MIP-2β/CXCL3 | AAA63184.1: 43-100 | QCLQTLQGIHLKNIQSVNVRSPGPHCAQTEVIATLKNGKKACLN PASPMVQKIIEKIL |
| 108 | GRO-γ/MIP-2β/CXCL3 | AAA63184.1: 41-96 | RCQCLQTLQGIHLKNIQSVNVRSPGPHCAQTEVIATLKNGKKAC LNPASPMVQKII |
| 109 | IL-8/CXCL8 | AAP35730.1: 35-94 | QCIKTYSKPFHPKFIKELRVIESGPHCANTEIIVKLSDGRELCLDP KENWVQRVVEKFLK |
| 110 | IL-8/CXCL8 | AAP35730.1: 72-94 | DGRELCLDPKENWVQRVVEKFLK |
| 111 | IP-10/CXCL10 | AAH10954.1: 29-86 | RCTCISISNQPVNPRSLEKLEIIPASQFCPRVEIIATMKKKGEKRCL NPESKAIKNLL |
| 112 | MIG/CXCL9 | Q07325: 32-91 | SCISTNQGTIHLQSLKDLKQFAPSPSCEKIEIIATLKNGVQTCLNP DSADVKELIKKVVEK |
| 113 | PF-4/CXCL4 | AAK29643.1: 43-100 | CVKTTSQVRPRHITSLEVIKAGPHCPTAQLIATLKNGRKICLDLQ APLYKKIIKKLLE |
| 114 | THBG-β/CXCL7 | AAB46877.1: 100-121 | DGRKICLDPDAPRIKKIVQKKL |
| 115 | THBG-β/CXCL7 | AAB46877.1: 62-117 | RCMCIKTTSGIHPKNIQSLEVIGKGTHCNQVEVIATLKDGRKICL DPDAPRIKKIV |
| 116 | THBG-β/CXCL7 | AAB46877.1: 64-121 | MCIKTTSGIHPKNIQSLEVIGKGTHCNQVEVIATLKDGRKICLDP DAPRIKKIVQKKL |

Kringle Containing Proteins

| 117 | AK-38 protein | AAK74187.1: 14-93 | DCMFGNGKGYRGKKATTVTGTPCQEWAAQEPHRHSTFIPGTNK WAGLEKNYCRNPDGDINGPWCYTMNPRKLFDYCDIPLCA |
| 118 | AK-38 protein | AAK74187.1: 12-94 | QDCMFGNGKGYRGKKATTVTGTPCQEWAAQEPHRHSTFIPGTN KWAGLEKNYCRNPDGDINGPWCYTMNPRKLFDYCDIPLCA |
| 119 | AK-38 protein | AAK74187.1: 13-90 | DCMFGNGKGYRGKKATTVTGTPCQEWAAQEPHRHSTFIPGTNK WAGLEKNYCRNPDGDINGPWCYTMNPRKLFDYCDI |
| 120 | AK-38 protein | AAK74187.1: 14-93 | CMFGNGKGYRGKKATTVTGTPCQEWAAQEPHRHSTFIPGTNK WAGLEKNYCRNPDGDINGPWCYTMNPRKLFDYCDIPLC |
| 121 | Hageman fct/cf XII | AAM97932.1: 216-292 | SCYDGRGLSYRGLARTTLSGAPCQPWASEATYRNVTAEQARN WGLGGHAFCRNPDNDIRPWCFVLNRDRLSWEYCDL |
| 122 | Hageman fct/cf XII | AAM97932.1: 214-295 | KASCYDGRGLSYRGLARTTLSGAPCQPWASEATYRNVTAEQAR NWGLGGHAFCRNPDNDIRPWCFVLNRDRLSWEYCDLAQC |
| 123 | Hageman fct/cf XII | AAM97932.1: 215-296 | ASCYDGRGLSYRGLARTTLSGAPCQPWASEATYRNVTAEQARN WGLGGHAFCRNPDNDIRPWCFVLNRDRLSWEYCDLAQCQ |
| 124 | HGF | P14210: 127-206 | NCIIGKGRSYKGTVSITKSGIKCQPWSSMIPHEHSFLPSSYRGKDL QENYCRNPRGEEGGPWCFTSNPEVRYEVCDIPQC |
| 125 | HGF | P14210: 127-207 | NCIIGKGRSYKGTVSITKSGIKCQPWSSMIPHEHSFLPSSYRGKDL QENYCRNPRGEEGGPWCFTSNPEVRYEVCDIPQCS |
| 126 | HGF | P14210: 304-377 | ECIQGQGEGYRGTVNTIWNGIPCQRWDSQYPHEHDMTPENFKC KDLRENYCRNPDGSESPWCFTTDPNIRVGYC |
| 127 | HGF | P14210: 210-289 | ECMTCNGESYRGLMDHTESGKICQRWDHQTPHRHKFLPERYPD KGFDDNYCRNPDGQPRPWCYTLDPHTRWEYCAIKTCA |
| 128 | HGF | P14210: 304-383 | ECIQGQGEGYRGTVNTIWNGIPCQRWDSQYPHEHDMTPENFKC KDLRENYCRNPDGSESPWCFTTDPNIRVGYCSQIPNC |
| 129 | Hyaluronan binding | NP_004123.1: 192-277 | DDCYVGDGYSYRGKMNRTVNQHACLYWNSHLLLQENYNMFM EDAETHGIGEHNFCRNPDADEKPWCFIKVTNDKVKWEYCDVSA CS |
| 130 | Hyaluronan binding | NP_004123.1: 192-276 | DDCYVGDGYSYRGKMNRTVNQHACLYWNSHLLLQENYNMFM EDAETHGIGEHNFCRNPDADEKPWCFIKVTNDKVKWEYCDVSA C |
| 131 | KREMEN-1 | BAB40969.1: 31-114 | ECFTANGADYRGTQNWTALQGGKPCLFWNETFQHPYNTLKYP NGEGGLGEHNYCRNPDGDVS-PWCYVAEHEDGVYWKYCEIPAC |
| 132 | KREMEN-1 | BAB40969.1: 31-115 | ECFTANGADYRGTQNWTALQGGKPCLFWNETFQHPYNTLKYP NGEGGLGEHNYCRNPDGDVSPWCYVAEHEDGVYWKYCEIPAC Q |
| 133 | KREMEN-2 | BAD97142.1: 35-119 | ECFQVNGADYRGHQNRTGPRGAGRPCLFVVDQTQQHSYSSASDP HGRWGLGAHNFCRNPDGDVQ-PWCYVAETEEGIYWRYCDIPSC |
| 134 | KREMEN-2 | BAD97142.1: 34-119 | SECFQVNGADYRGHQNRTGPRGAGRPCLFWDQTQQHSYSSASD PHGRWGLGAHNFCRNPDGDVQPWCYVAETEEGIYWRYCDIPSC |

TABLE 1 -continued

Anti-Angiogenic Peptide sequences

| SEQ ID NO. | | | |
|---|---|---|---|
| 135 | Lp(a) | NP_005568.1: 1615-1690 | TEQRPGVQECYHGNGQSYRGTYSTTVTGRTCQAWSSMTPHSHS RTPEYYPNAGLIMNYCRNPDAVAAPYCYTRDPG |
| 136 | Lp(a) | NP_005568.1: 3560-3639 | QDCYYHYGQSYRGTYSTTVTGRTCQAWSSMTPHQHSRTPENYP NAGLTRNYCRNPDAEIRPWCYTMDPSVRWEYCNLTQC |
| 137 | Lp(a) | NP_005568.1: 4123-4201 | QCYHGNGQSYRGTFSTTVTGRTCQSWSSMTPHRHQRTPENYPN DGLTMNYCRNPDADTGPWCFTMDPSIRWEYCNLTRC |
| 138 | Lp(a) | NP_005568.1: 4225-4308 | EQDCMFGNGKGYRGKKATTVTGTPCQEWAAQEPHRHSTFIPGT NKWAGLEKNYCRNPDGDINGPWCYTMNPRKLFDYCDIPLCA |
| 139 | Macrophage stim. 1 | AAH48330.1: 188-268 | EAACVWCNGEEYRGAVDRTESGRECQRWDLQHPHQHPFEPGK FLDQGLDDNYCRNPDGSERPWCYTTDPQIEREFCDLPRC |
| 140 | Macrophage stim. 1 | AAH48330.1: 368-448 | QDCYHGAGEQYRGTVSKTRKGVQCQRWSAETPHKPQFTFTSEP HAQLEENFCRNPDGDSHGPWCYTMDPRTPFDYCALRRC |
| 141 | Macrophage stim. 1 | AAH48330.1: 368-449 | QDCYHGAGEQYRGTVSKTRKGVQCQRWSAETPHKPQFTFTSEP HAQLEENFCRNPDGDSHGPWCYTMDPRTPFDYCALRRCA |
| 142 | Macrophage stim. 1 | AAH48330.1: 370-448 | CYHGAGEQYRGTVSKTRKGVQCQRWSAETPHKPQFTFTSEPHA QLEENFCRNPDGDSHGPWCYTMDPRTPFDYCALRRC |
| 143 | Thrombin/cf II | AAL77436.1: 105-186 | EGNCAEGLGTNYRGHVNITRSGIECQLWRSRYPHKPEINSTTHP GADLQENFCRNPDSSTTGPWCYTTDPTVRRQECSIPVC |
| 144 | Thrombin/cf II | AAL77436.1: 106-186 | GNCAEGLGTNYRGHVNITRSGIECQLWRSRYPHKPEINSTTHPG ADLQENFCRNPDSSTTGPWCYTTDPTVRRQECSIPVC |
| 145 | Thrombin/cf II | AAL77436.1: 107-183 | NCAEGLGTNYRGHVNITRSGIECQLWRSRYPHKPEINSTTHPGA DLQENFCRNPDSSTTGPWCYTTDPTVRRQECSI |
| 146 | Thrombin/cf II | AAL77436.1: 107-186 | NCAEGLGTNYRGHVNITRSGIECQLWRSRYPHKPEINSTTHPGA DLQENFCRNPDSSTTGPWCYTTDPTVRRQECSIPVC |
| 147 | tPA | AAH95403.1: 214-293 | DCYFGNGSAYRGTHSLTESGASCLPWNSMILIGKVYTAQNPSAQ ALGLGKHNYCRNPDGDAKPWCHVLKSRRLTWEYCDV |
| 148 | tPA | AAH95403.1: 213-296 | SDCYFGNGSAYRGTHSLTESGASCLPWNSMILIGKVYTAQNPSA QALGLGKHNYCRNPDGDAKPWCHVLKSRRLTWEYCDVPSC |
| 149 | tPA | AAH95403.1: 213-297 | SDCYFGNGSAYRGTHSLTESGASCLPWNSMILIGKVYTAQNPSA QALGLGKHNYCRNPDGDAKPWCHVLKSRRLTWEYCDVPSCS |
| 150 | tPA | AAH95403.1: 214-296 | DCYFGNGSAYRGTHSLTESGASCLPWNSMILIGKVYTAQNPSAQ ALGLGKHNYCRNPDGDAKPWCHVLKSRRLTWEYCDVPSC |
| | | Somatotropins | |
| 151 | GH-1 | NP_000506.2: 26-160 | AFPTIPLSRLFDNAMLRAHRLHQLAFDTYQEFEEAYIPKEQKYSF LQNPQTSLCFSESIPTPSNREETQQKSNLELLRISLLLIQSWLEPVQ FLRSVFANSLVYGASDSNVYDLLKDLEEGIQTLMGRLEDGSPR |
| 152 | GH-2 | CAG46700.1: 26-160 | AFPTIPLSRLFDNAMLRARRLYQLAYDTYQEFEEAYILKEQKYSF LQNPQTSLCFSESIPTPSNRAKTQQKSNLELLRISLLLIQSWLEPV QLLRSVFANSLVYGASDSNVYRHLKDLEEGIQTLMWRLEDGSP R |
| 153 | Placental lactogen | AAP35572.1: 26-160 | AVQTVPLSRLFDHAMLQAHRAHQLAIDTYQEFEETYIPKDQKYS FLHDSQTSFCFSDSIPTPSNMEETQQKSNLELLRISLLLIESWLEPV RPLRSMFANNLVYDTSDSDDYHLLKDLEEGIQTLMGRLEDGSR R |
| 154 | Somatoliberin | AAH62475.1: 26-145 | AFPTIPLSRLFDNASLRAHRLHQLAFDTYQEFNPQTSLCFSESIPT PSMREETQQKSNLELLRISLLLIQSWLEPVQFLRSVFANSLVYGA SDSNVYDLLKDLEEGIQTLMGRLEDGSPR |
| | | TIMPs | |
| 155 | TIMP 3 | AAA21815.1: 148-171 | ECLWTDMLSNFGYPGYQSKHYACI |
| 156 | TIMP 4 | AAV38433.1: 175-198 | ECLWTDWLLERKLYGYQAQHYVCM |

Angiogenesis Assays

The biological activity of therapeutic agents of the invention is characterized using any method for assaying angiogenic activity known in the art. In vitro angiogenesis assays have been described in detail in recent reviews (Akhtar et al., Angiogenesis, 5:75-80, 2002; Auerbach et al., Cancer Metastasis Rev, 19:167-72, 2000; Auerbach et al., Clin Chem, 49:32-40, 2003; Staton et al., Int J Exp Pathol, 85:233-48, 2004; Vailhe et al., Lab Invest, 81:439-52, 2001). There are a number of different endothelial cell lineages that have been used in angiogenesis assays: bovine aortic, bovine retinal, rat and mouse microvascular, human aortic, human bladder microvascular, human cardiac microvascular, human dermal microvascular, human lung microvascular and human umbilical vein endothelial cells. All of these endothelial cells are capable of differentiating in vitro and forming capillary-like structures. This process occurs when the cells are cultured in a monolayer of extracellular matrix components, such as the Matrigel (extracellular matrix material similar to basement membrane), type I collagen, fibronectin or laminin. An endothelial cell lineage that is commonly used for testing the angiogenic response is the human umbilical vein endothelial cells (HUVECs). The National Cancer Institute (NCI) has issued guidelines for testing the anti-angiogenic efficacy of novel agents (<http://dtp.nci.nih.gov/aa-resources/aa_index.html>); they include proliferation, migration and tube formation assays using HUVECs.

Initially the anti-angiogenic effect of selected standard agents is assessed as a positive control by adding them into the wells containing cultured endothelial cells. Such standard anti-angiogenic agents include the fumigillin analog TNP-470 and paclitaxel that are available by request from NCI. The standard cell culture medium is usually used as a negative control. The experiments described below are repeated several times as required to obtain statistically significant and reproducible results. Once the platform is calibrated and tested for the known agents, the novel inhibitors are tested.

Cell Proliferation Assay

In these assays anti-angiogenic agents are tested for their ability to alter endothelial cell proliferation. A reduction in endothelial cell proliferation identifies an agent that inhibits angiogenesis. The viability and metabolic activity of the cells is measured in the presence of the anti-angiogenic peptides at different concentrations and various time steps. In one example, a cell proliferation reagent, MTT, is used in a substrate/assay that measures the metabolic activity of viable cells. The assay is based on the reduction of the yellow tetrazolium salt, MTT, by viable, metabolically active cells to form the insoluble purple formazan crystals, which are solubilized by the addition of a detergent. MTT is a colorimetric, non-radioactive assay that can be performed in a microplate. It is suitable for measuring cell proliferation, cell viability or cytotoxicity. The procedure involves three steps. First, the cells are cultured in a multi-well plate and then incubated with the yellow MTT for approximately 2 to 4 hours. During this incubation period, viable cells convert, in their mitochondria, the yellow MTT to the purple formazan crystals. The second step involves the solubilization of the crystals. A detergent solution is added to lyse the cells and solubilize the colored crystals. The final step of the assay involves quantifying changes in proliferation by measuring the changes in the color after lysing the cells. The samples are read using an ELISA plate reader at a wavelength of 570 nm. The amount of color produced is directly proportional to the number of viable cells present in a particular well. Other proliferation assays include WST-1, XTT, Trypan Blue, Alamar Blue and BrdU. In contrast to the MTT assay, in the WST-1 assay the formazan crystals do not need to be solubilized by the addition of a detergent; they are soluble to the cell medium.

In another example, cell proliferation is assayed by quantitating bromodeoxyuridine (BrdU) incorporation into the newly synthesized DNA of replicating cells. The assay is a cellular immunoassay that uses a mouse monoclonal antibody directed against BrdU. The procedure involves four steps. First, the cells are cultured in a microtiterplate and pulse-labeled with BrdU. Only proliferating cells incorporate BrdU into their DNA. The cells are then fixed in a denaturing solution. The genomic DNA is denatured, exposing the incorporated BrdU to immunodetection. The BrdU label is located in the DNA with a peroxidase-conjugated anti-BrdU antibody. The antibody is quantitated using a peroxidase substrate. To test anti-proliferative effects of the selected peptides, the endothelial cells are incubated in the presence of varying amounts of the peptides for different time intervals. After labeling of the cells with BrdU the cell proliferation reagent WST-1 is added, and the cells are reincubated. The formazan product is quantified at 450 nm with an absorbance reader. Subsequently, BrdU incorporation is determined using the colorimetric cell proliferation ELISA, BrdU. The results of this assay indicate the effects of the anti-angiogenic peptides either on DNA synthesis (anti-proliferative) or the metabolic activity (pro-apoptotic) of the cell. Kits for implementing these techniques are commercially available.

Preferably, an agent of the invention reduces cell proliferation by at least about 5%, 10%, 20% or 25%. More preferably, cell proliferation is reduced by at least 50%, 75%, or even by 100%.

Cell Apoptosis and Cell Cycle Assay

Agents having anti-angiogenic activity can also be identified in assay that measure the effect of a candidate agent on cell proliferation and survival using a mitogenic assay (incorporation of thymidine, or 5-bromodeoxyuridine) that measures alterations in cell number (direct counts or indirect colorimetric evaluation). Agents that reduce cell proliferation, cell survival, or that increase cell death are identified as having anti-angiogenic activity. Cell death by apoptosis can be measured using a TUNEL assay or by analyzing the expression of apoptosis markers, such as the caspases and annexin V (Fennell et al., *J Biomol Screen*, 11:296-302, 2006; Loo and Rillema, *Methods Cell Biol*, 57:251-64, 1998; Otsuki et al., *Prog Histochem Cytochem*, 38:275-339, 2003).

A number of methods have been developed to study apoptosis in cell populations. Apoptosis is a form of cell death that is characterized by cleavage of the genomic DNA into discrete fragments prior to membrane disintegration. Because DNA cleavage is a hallmark for apoptosis, assays that measure prelytic DNA fragmentation are especially attractive for the determination of apoptotic cell death. DNA fragments obtained from cell populations are assayed on agarose gels to identify the presence of absence of "DNA ladders" or bands of 180 bp multiples, which form the rungs of the ladders, or by quantifying the presence of histone complexed DNA fragments by ELISA.

Other indicators of apoptosis include assaying for the presence caspases that are involved in the early stages of apoptosis. The appearance of caspases sets off a cascade of events that disable a multitude of cell functions. Caspase activation can be analyzed in vitro by utilizing an enzymatic assay. Activity of a specific caspase, for instance caspase 3, can be determined in cellular lysates by capturing of the caspase and measuring proteolytic cleavage of a suitable substrate that is sensitive to the specific protease (Fennell et al., *J Biomol Screen*, 11:296-302, 2006; Loo and Rillema, *Methods Cell Biol*, 57:251-64, 1998; Otsuki et al., *Prog Histochem Cytochem*, 38:275-339, 2003). Agents that increase caspase activity or DNA fragmentation in endothelial cells are identified as useful in the methods of the invention.

In addition to in vitro techniques, apoptosis can be measured using flow cytometry. One of the simplest methods is to use propidium iodide (PI) to stain the DNA and look for sub-diploid cells (Fennell et al., *J Biomol Screen*, 11:296-302, 2006; Loo and Rillema, *Methods Cell Biol*, 57:251-64, 1998; Otsuki et al., *Prog Histochem Cytochem*, 38:275-339, 2003).

The most commonly used dye for DNA content/cell cycle analysis is propidium iodide (PI). PI intercalates into the major groove of double-stranded DNA and produces a highly fluorescent adduct that can be excited at 488 nm with a broad emission centered around 600 nm. Since PI can also bind to double-stranded RNA, it is necessary to treat the cells with RNase for optimal DNA resolution. Other flow cytometric-based methods include the TUNEL assay, which measures DNA strand breaks and Annexin V binding, which detects relocation of membrane phosphatidyl serine from the intracellular surface to the extracellular surface.

Cell Migration and Invasion Assay

Another anti-angiogenic activity is the ability to reduce endothelial cell migration towards an attractant that is present in a chemotactic gradient, such as a growth factor gradient. Endothelial cell motility or migration can be assessed using the Boyden chamber technique (Auerbach et al., *Cancer Metastasis Rev*, 19:167-72, 2000; Auerbach et al., *Clin Chem*, 49:32-40, 2003; Taraboletti and Giavazzi, *Eur J Cancer*, 40:881-9, 2004). In one example, a Boyden chamber assay is used to test endothelial cell migration from one side of the chamber in the presence of an activator. In brief, the lower compartment of the Boyden chamber is separated from the upper (containing the endothelial cells) by a matrix-coated polycarbonate filter with pores small enough to allow only the active passage of the cells (3-8 µm pore size). The matrix may include, for example, extracellular matrix proteins, such as collagen, laminin and fibronectin. Activators include but are not limited to growth factors, such as vascular endothelial growth factor and fibroblast growth factor-2 or conditioned medium (e.g. from tumor cells or NIH-3T3 fibroblasts). Migration typically occurs rapidly typically within 4-20 hours cells have migrated through the filter. The number of migrating cells is quantified using a cell-permeable fluorescent dye in the presence or absence of an inhibitor; it can also be quantified by any means of cell counting. A fluorescence plate reader is used to quantify the migrating cells by measuring the amount of fluorescence and directly correlating it to cell number. A decrease in cell migration identifies a peptide that inhibits angiogenesis. Preferably, cell migration or motility is reduced by at least about 5%, 10%, 20% or 25%. More preferably, cell migration or motility is reduced by at least about 50%, 75%, or even by 100%.

In other embodiments, anti-angiogenic agents of the invention alter the invasiveness of an endothelial cell, for example, by reducing the ability of an endothelial cell to degrade an extracellular matrix component. In one example, an anti-angiogenic inhibitor acts by reducing the proteolytic activity of a matrix metalloproteinase. Methods for assaying protease activity are known in the art. Quantification of the matrix metalloproteinase activity can be accomplished using a zymographic or gelatinase activity assay (Frederiks and Mook, *J Histochem Cytochem.* 52:711-22, 2004). Preferably, protease activity is reduced by at least about 5%, 10%, 20% or 25%. More preferably, protease activity is reduced by at least about 50%, 75%, or even by 100%.

In another example, the invasive activity of an endothelial cell is measured using a Boyden chamber invasion assay or by measuring phagokinetic tracks. The invasion assay is essentially as described above for the Boyden motility assay, except that the filter is coated with a layer of a matrix several microns thick, usually Matrigel or other basement membrane extracts, which the cells must degrade before migrating through the filter (Auerbach et al., *Cancer Metastasis Rev,* 19:167-72, 2000; Auerbach et al., *Clin Chem,* 49:32-40, 2003; Taraboletti and Giavazzi, *Eur J Cancer,* 40:881-9, 2004). Compounds that reduce extracellular matrix degradation or endothelial cell invasiveness are identified as useful in the methods of the invention.

Tube Formation Assay

Another method of identifying an agent having anti-angiogenic activity involves measuring the agent's ability to reduce or disrupt capillary tube formation. Various types of endothelial cells (e.g., HUVECs, HMVECs (human microvascular endothelial cells)) form tubes when cultured in wells uniformly coated with Matrigel, an extracellular matrix protein, or other substrates. Therefore the assay characterizes endothelial cell differentiation. The endothelial cells are cultured in the presence or the absence of a candidate agent. The agent may be added to the culture media or may be present or applied to the gel. Typically, the effect on tube formation is measured by incubating the cells for a period of time (e.g., one to four days) at 37° C. in 5% $CO_2$ atmosphere. Kits for implementing these techniques are commercially available.

The output of the experiments are images of capillary networks formed. A common metric used for the morphological characteristics of a capillary network is the angiogenic index. This index is calculated as the ratio of the total length of the connected tubes over the total monitored surface of the well. The change of the angiogenic index as a function of the concentration of the anti-angiogenic peptide will be the determinant for the effectiveness of the tested novel angiogenesis inhibitors.

Aortic Ring Assay

The aortic ring assay integrates the advantages of both in vivo and in vitro systems. It is a useful assay to test angiogenic factors or inhibitors in a controlled environment. More importantly, it recapitulates all of the necessary steps involved in angiogenesis (Staton et al., *Int J Exp Pathol,* 85:233-48, 2004).

In this quantitative method of studying angiogenesis, ring segments of aortas from various animals such as rats and mice are embedded in a three-dimensional matrix composed of fibrin or collagen, and cultured in a defined medium devoid of serum and growth factors. Microvessels sprout spontaneously from the surface of the aortic rings. This angiogenic process is mediated by endogenous growth factors produced from the aorta or can be assisted by applying exogenously specific concentrations of growth factors. The embedded aortas are incubated for 10-12 days and after the incubation period the newly formed vessels are quantified. Microvessels can be counted manually or quantified using computer-assisted image analysis. Test agents can be added to the culture medium to assay for angiogenic or anti-angiogenic activity. Also aortas from animals with different genetic background (e.g., knockout mice) can be used in order to assess specific mechanisms of the effect of the anti-angiogenic peptides on the neovessel formation process.

In Vivo Angiogenesis Assays

A recent review identified over 70 disease conditions that involve angiogenesis, about half of those characterized by abnormal or excessive angiogenesis or lymphangiogenesis (Carmeliet, *Nature,* 438:932-6, 2005). Agents identified as having anti-angiogenic activity are optionally tested in in vivo assays using animal models that exhibit abnormal or excessive angiogenesis or lymphangiogenesis.

Matrigel Plug Assay

In one in vivo approach, a candidate agent of the invention is tested for anti-angiogenic activity by implanting a polymer matrix subcutaneously in an animal and assaying the matrix for signs of neovascularization. In one embodiment, a Matrigel plug or a similar substrate containing tumor cells and an anti-angiogenic factor is used to study in vivo angiogenesis (Auerbach et al., *Cancer Metastasis Rev,* 19:167-72, 2000; Staton et al., *Int J Exp Pathol,* 85:233-48, 2004). Matrigel is a liquid at 4° C., but forms a solid gel at 37° C. A candidate agent is suspended together with an attractant, such as a growth factor, in the gel. The Matrigel is then injected subcutaneously where it forms a solid plug allowing for the prolonged local release of pro- or anti-angiogenic agents present in the gel. The plug is subsequently removed and neovascularization is assessed by any standard methods, including but not limited to, identifying the presence of endothelial cells or endothelial cell tubules in the plug using microscopy. In some embodiments, this approach is combined with an immuno-histological identification of endothelium specific proteins (e.g., CD-31/34 or integrins) on the newly formed vessels.

The Matrigel plug assay can be applied for testing the efficacy of the novel anti-angiogenic peptides identified herein. In one example, Matrigel is mixed with heparin (usually 20 U/ml) and a vascular endothelial growth factor at about 50 ng/ml in the presence or absence of a candidate peptide, which is supplied at a variety of concentrations (e.g., at the $IC_{50}$). A control animal receives the gel without the anti-angiogenic fragment. The Matrigel is injected into the mice subcutaneously and after one week the animals are sacrificed. The Matrigel plugs are then removed and fixed with 4% paraformaldehyde. The plugs are then embedded in paraffin, sectioned and stained with hematoxylin and eosin. The number of blood vessels as well as any other angiogenic indexes are estimated.

Directed In Vivo Angiogenesis Assay (DIVAA)

Directed in vivo angiogenesis assay (DIVAA) is a reproducible and quantitative in vivo method of assaying angiogenesis. It involves the preparation of silicon cylinders that are closed on one side filled with some type of extracellular matrix (for example Matrigel) with or without premixed angiogenic factors (Guedez et al., *Am J Pathol,* 162:1431-9, 2003) to form an angioreactor. The angioreactors are then implanted subcutaneously in mice. Vascular endothelial cells migrate into the extracellular matrix and form vessels in the angioreactor. As early as nine days post-implantation, there are enough cells present in the angioreactor to assay the effect of an angiogenic modulating factors. A candidate agent may be included in the matrix together with the angiogenic factors. The design of the angioreactor provides a standardized platform for reproducible and quantifiable in vivo angiogenesis assays.

Advantageously, the angioreactor prevents assay errors due to absorption of the basement membrane extract or the diffusion of the anti-angiogenic agent into the surrounding tissue; may be carried out using only a fraction of the materials required in the plug assay described above; and up to four angioreactors may be implanted in a single animal (e.g., mouse), providing more data for analysis. Vascularization response can be measured by intravenous injection of fluorescein isothiocyanate (FITC)-dextran before the recovery of the angioreactor, followed by spectrofluorimetry. Alternatively, to obtain a quantitative assessment of the angiogenic invasion, the content of the angioreactors, can be removed and the endothelial cells stained using FITC-Lectin. Fluorescence of the FITC-Lectin solution can be quantitated by measuring the fluorescence at 485 nm excitation and 510 nm emission using a fluorescence plate reader e.g., Victor 3V (Perkin Elmer). The intensity of the signal is directly proportional to the number of endothelial cells that are present in the angioreactors. The technique allows dose response analysis and identification of effective doses of angiogenesis-modulating factors in vivo.

Chorioallantoic Membrane Assay

The chorioallantoic membrane assay (CAM) is widely used as an angiogenesis assay Auerbach et al., *Cancer Metastasis Rev* 19:167-172, 2000; Staton et al., *Int J Exp Pathol* 85: 233-248, 2004; D'Amato, In: Voest, E. E., and D'Amore, P. A. (eds). *Tumor Angiogenesis and Microcirculation,* 2001, Marcel Dekker, New York-Basel). In one embodiment, the chorioallantoic membrane of a 7-9 day old chick embryos is exposed by making a window in the egg shell. A candidate agent is provided in a formulation that provides for its extended release (e.g., in a slow-release polymer pellets, absorbed on a gelatin sponge, or air-dried onto a plastic disc). The candidate agent formulation is implanted onto the chorioallantoic membrane through a window in the shell. The window is sealed and the egg is re-incubated. The lack of mature immune system in the 7 day old chick embryos allows the study of angiogenesis without any immunological interference. In the modified version of the in ovo assay, the entire egg content is transferred to a plastic culture dish. After 3-6 days of incubation the testing agents are applied and angiogenesis is monitored using various angiogenesis indexes.

In the case of testing the angiostatic peptides, polymer pellets can be loaded both with the growth factors and the anti-angiogenic fragments and be implanted in the chorioallantoic membrane. The modified version of the assay allows the application of a candidate agent using different strategies to identify effective therapeutic regimens. For example, a candidate agent is applied in a single bolus at a particular concentration; at different time points at lower concentrations; or in different formulations that provide for the extended release of an agent. This provides for the temporal control of candidate agent release and the delineation of temporal variations in drug administration on the angiostatic activity of the candidate agents.

Ocular Angiogenesis Models

The cornea is an avascular site and presumably any vessels penetrating from the limbus into the cornea stroma can be identified as newly formed. In this assay a pocket is created in the cornea stroma of the animal. An angiogenic response is usually initiated by implantation of a slow release pellet or polymer containing growth factors (Auerbach et al., *Cancer Metastasis Rev,* 19:167-72, 2000; Auerbach et al., *Clin Chem,* 49:32-40, 2003; D'Amato, *Tumor Angiogenesis and Microcirculation,* 103-110, 2001; Staton et al., *Int J Exp Pathol,* 85:233-48, 2004).

In order to test an angiogenesis inhibitor, the effect of a candidate agent on an angiogenic response in the cornea is assayed after the implantation of a pellet comprising an angiogenic agent in combination with a candidate inhibitor in the cornea pockets. Also the efficacy of an anti-angiogenic agent can be evaluated using the mouse model of ocular ischemic retinopathy to quantitatively assess antiangiogenic effects on retinal neovascularization. In addition, a mouse model of laser induced choroidal neovascularization can be used in order to quantitatively assess the anti-angiogenic effects of candidate agents on choroidal neovascularization. The tested peptides can be administered with a bolus injection or any other scheduled administration.

Chamber Assays

Other methods for studying the effect of a candidate agent in vivo on chronic angiogenesis involve the use of an implanted transparent chamber. The chamber is implanted in an accessible site (e.g., the rabbit ear, the dorsal skinfold and the cranial window chamber (Auerbach et al., *Clin Chem,* 49:32-40, 2003; Staton et al., *Int J Exp Pathol,* 85:233-48, 2004). In each of these systems a piece of skin (the ear or skinfold chamber) or part of the skull (cranial chamber) is removed from an anesthetized animal. Tumor cells or a pellet containing an angiogenesis stimulus is then placed on the exposed surface and covered by a glass. The animals are allowed to recover, and angiogenesis is subsequently monitored. The models allow for the continuous measurement of various angiogenesis as well as tissue parameters, such as pH or blood flow. Similarly to the corneal pocket assay, the angiostatic agents are administered orally, locally, or systemically using a predefined drug administration schedule. Agents that reduce angiogenesis in a chamber assay are identified as useful in the methods of the invention.

Tumor Models

Many different in vivo models have been developed to test the activity of potential anti-angiogenic or anti-cancer treatments, specifically on tumor vasculature. Tumors are implanted and can be grown syngeneically; i.e., subcutaneously, orthotopically in a tissue of origin, or as xenografts in immunodeficient mice (Auerbach et al., *Clin Chem,* 49:32-40, 2003; Staton et al., *Int J Exp Pathol,* 85:233-48, 2004). Any number of histological analyses may be used to examine the effect of a candidate agent on a blood vessel supplying the tumor. In one embodiment, the blood vessel density of a newly formed vasculature in the tumor is monitored; in another embodiment, the vascular architecture is monitored, for example, by counting the number of vascular branches per vessel unit length. In another embodiment, blood flow through the vasculature is measured.

The tumor models provide a variety of different conditions that can be analyzed to assay the efficacy of a candidate anti-angiogenic agent. For example, the effects of a candidate agent on the stability of a well vascularized vs. a poorly vascularized tumor can be assayed; the effect of a candidate agent on tumors of different origin, for example prostate and breast cancer, renal cell carcinoma, and including those of vascular origin such as the chemically induced hemangiosarcomas and Kaposi's sarcomas, can be analyzed. The study of in vivo tumor models provide the closest approximation of human tumor angiogenesis. Moreover, such models provide the opportunity to study the pharmacokinetics of the candidate drug as well as its efficacy simultaneously in a large scale model and under different administration carriers and strategies.

Anti-Angiogenic Peptides and Analogs

The invention is not limited to conventional therapeutic peptides having anti-angiogenic activity, but comprises a variety of modified peptides having properties that enhance their biodistribution, selectivity, or half-life. In particular, the invention provides peptides that are modified in ways that enhance their ability to inhibit angiogenesis in a cell, tissue, or organ in a subject in need thereof.

The invention provides methods for optimizing a transcription factor or protein transduction domain amino acid sequence or nucleic acid sequence by producing an alteration in the sequence. Such alterations may include certain mutations, deletions, insertions, or post-translational modifications. The invention further includes analogs of any naturally-occurring polypeptide of the invention. Analogs can differ from a naturally-occurring polypeptide of the invention by amino acid sequence differences, by post-translational modifications, or by both. Analogs of the invention will generally exhibit at least 85%, more preferably 90%, and most preferably 95% or even 99% identity with all or part of a naturally-occurring amino, acid sequence of the invention. The length of sequence comparison is at least 5, 10, 15 or 20 amino acid residues, preferably at least 25, 50, or 75 amino acid residues, and more preferably more than 100 amino acid residues. Again, in an exemplary approach to determining the degree of identity, a BLAST program may be used, with a probability score between $e^{-3}$ and $e^{-100}$ indicating a closely related sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring polypeptides of the invention by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine. "Amino acid analogs" refer to compounds that have the same basic chemical structure as a naturally occurring amino acid, i.e., a carbon that is bound to a hydrogen, a carboxyl group, an amino group, and an R group, for example, homoserine, norleucine, methionine sulfoxide, methionine methyl sulfonium. Such analogs have modified R groups (for example, norleucine) or modified peptide backbones, but retain the same basic chemical structure as a naturally occurring amino acid. "Amino acid mimetics" refers to chemical compounds that have a structure that is different from the general chemical structure of an amino acid, but that function in a manner similar to a naturally occurring amino acid. Amino acids and analogs are well known in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" apply to both amino acid and nucleic acid sequences. With respect to particular nucleic acid sequences, conservatively modified variants refers to those nucleic acids which encode identical or similar amino acid sequences and include degenerate sequences. For example, the codons GCA, GCC, GCG and GCU all encode alanine. Thus, at every amino acid position where an alanine is specified, any of these codons can be used interchangeably in constructing a corresponding nucleotide sequence. The resulting nucleic acid variants are conservatively modified variants, since they encode the same protein (assuming that is the only alternation in the sequence). One skilled in the art recognizes that each codon in a nucleic acid, except for AUG (sole codon for methionine) and UGG (tryptophan), can be modified conservatively to yield a functionally-identical peptide or protein molecule. As to amino acid sequences, one skilled in the art will recognize that substitutions, deletions, or additions to a polypeptide or protein sequence which alter, add or delete a single amino acid or a small number (typically less than about ten) of amino acids is a "conservatively modified variant" where the alteration results in the substitution of an amino acid with a chemically similar amino acid. Conservative substitutions are well known in the art and include, for example, the changes of alanine to serine; arginine to lysine; asparigine to glutamine or histidine; aspartate to glutamate; cysteine to serine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine. Other conservative and semi-conservative substitutions are known in the art and can be employed in practice of the present invention.

The terms "protein", "peptide" and "polypeptide" are used herein to describe any chain of amino acids, regardless of length or post-translational modification (for example, glycosylation or phosphorylation). Thus, the terms can be used interchangeably herein to refer to a polymer of amino acid residues. The terms also apply to amino acid polymers in which one or more amino acid residue is an artificial chemical mimetic of a corresponding naturally occurring amino acid.

Thus, the term "polypeptide" includes full-length, naturally occurring proteins as well as recombinantly or synthetically produced polypeptides that correspond to a full-length naturally occurring protein or to particular domains or portions of a naturally occurring protein. The term also encompasses mature proteins which have an added amino-terminal methionine to facilitate expression in prokaryotic cells.

The polypeptides and peptides of the invention can be chemically synthesized or synthesized by recombinant DNA methods; or, they can be purified from tissues in which they are naturally expressed, according to standard biochemical methods of purification. Also included in the invention are "functional polypeptides," which possess one or more of the biological functions or activities of a protein or polypeptide of the invention. These functions or activities include the ability to inhibit angiogenesis (e.g., by reducing endothelial cell proliferation, migration, survival, or tube formation). The functional polypeptides may contain a primary amino acid sequence that has been modified from that considered to be the standard sequence of a peptide described herein (e.g., SEQ ID Nos 1-156). Preferably these modifications are conservative amino acid substitutions, as described herein.

In addition to full-length polypeptides, the invention also includes fragments of any one of the polypeptides of the invention. As used herein, the term "a fragment" means at least 5, 10, 13, or 15 amino acids. In other embodiments a fragment is at least 20 contiguous amino acids, at least 21, 22, 23, 24, or 25 contiguous amino acids, or at least 30, 35, 40, or 50 contiguous amino acids, and in other embodiments at least 60 to 80 or more contiguous amino acids. Fragments of the invention can be generated by methods known to those skilled in the art or may result from normal protein processing (e.g., removal of amino acids from the nascent polypeptide that are not required for biological activity or removal of amino acids by alternative mRNA splicing or alternative protein processing events).

Non-protein transcription factor/protein transduction domain fusion analogs have a chemical structure designed to mimic the fusion proteins functional activity. Such analogs are administered according to methods of the invention. Fusion protein analogs may exceed the physiological activity of the original fusion polypeptide. Methods of analog design are well known in the art, and synthesis of analogs can be carried out according to such methods by modifying the chemical structures such that the resultant analogs increase the reprogramming or regenerative activity of a reference transcription factor/protein transduction domain fusion polypeptide. These chemical modifications include, but are not limited to, substituting alternative R groups and varying the degree of saturation at specific carbon atoms of a reference fusion polypeptide. Preferably, the fusion protein analogs are relatively resistant to in vivo degradation, resulting in a more prolonged therapeutic effect upon administration. Assays for measuring functional activity include, but are not limited to, those described in the Examples below.

Peptide-Design Approaches

Iterative design approaches (DeFreest et al., *J Pept Res*, 63:409-19, 2004) offer unique opportunities to optimize the structure and function of the candidate anti-angiogenic peptides. During iterative design an initial set of amino acids is substituted and the effect of the resulting agent on angiogenesis is assayed. The exploration of the structure-function relationships, but most importantly the conservation of the biophysical and biochemical characteristics of the peptides, during the iterative design and synthesis, is expected to contribute to the optimization of the anti-angiogenic activity. To determine which residues are essential to the bioactivity of the predicted peptide a series of analogs is prepared and evaluated.

In order to assess the types of substitutions within the amino acid sequence of the candidate peptide one can initially use computational methods. The most straightforward method for deciphering the importance of each amino acid is to investigate the conservation of these amino acids at multiple orthologues (same locus in different organisms). Amino acids that are conserved among different organisms are identified as functionally significant. From a biophysical point of view electrostatic interactions and hydrophobic partitioning act in concert to promote the interactions of the peptides with their receptors. In this sense, any point substitution should comply with the conservation of the net charge and hydrophobicity of the agent (DeFreest et al., *J Pept Res,* 63:409-19, 2004). Phage display technology can also be used for performing random substitutions at expressed peptides of 20-25 amino acids length (Scott and Smith, *Science,* 249:386-90, 1990). In each of the cases the resultant peptide is tested for its effect on angiogenesis using any of the assays described herein.

Design optimization of the activity of the predicted peptides can also be performed by altering specific structural characteristics of the agents. For example, it has been shown (DeFreest et al., *J Pept Res,* 63:409-19, 2004) that head-to-tail cyclization of the molecules confers an active dose range broader than the linear form of the molecules, and the peptide stability and shelf life are not compromised. The head-to-tail conjunction can occur either by a disulfide bond or by a peptide bond formation. The use of a peptide bond may be advantageous for purposes of shelf life, and elimination of dimers, trimers, and higher-order aggregates formation that can sometimes develop when peptides are stored or used in conditions where the redox state cannot be fully controlled. The cyclization approaches are discussed in the following section.

Cyclization of Linear Peptides

Cyclization of peptides has been shown to be a useful approach to developing diagnostically and therapeutically useful peptidic and peptidomimetic agents. Cyclization of peptides reduces the conformational freedom of these flexible, linear molecules, and often results in higher receptor binding affinities by reducing unfavorable entropic effects. Because of the more constrained structural framework, these agents are more selective in their affinity to specific receptor cavities. By the same reasoning, structurally constrained cyclic peptides confer greater stability against the action of proteolytic enzymes.

Methods for cyclization can be classified into the so called "backbone to backbone" cyclization by the formation of the amide bond between the N-terminal and the C-terminal amino acid residues, and cyclizations involving the side chains of individual amino acids (Li and Roller, *Curr Top Med Chem,* 2:325-41, 2002). Although many novel approaches have been developed to accomplish the head-to-tail cyclization of linear peptides and peptidomimetics, the most commonly used method is still the solution phase macro-cyclization using peptide coupling reagents. The results of the peptide cyclization are mainly influenced by the conformation of the linear peptide precursors in solution. Synthesis design is affected by the strategy of the ring disconnection, and the rational selection of peptide coupling reagents. A reasonable ring disconnection will significantly facilitate the peptide macro-cyclization reaction, while a poor selection of cyclization site may result in slow reaction speed and low yield accompanied by various side reactions such as racemization, dimerization, and oligomerization.

Cyclization involving the side chains of individual amino acids includes the formation of disulfide bridges between omega-thio amino acid residues (cysteine, homocysteine), the formation of lactam bridges between glutamic/aspartic acid and lysine residues, the formation of lactone or thiolactone bridges between amino acid residues containing carboxyl, hydroxyl or mercapto functional groups, and the formation of thio-ether or ether bridges between the amino acids containing hydroxyl or mercapto functional groups.

Recombinant Polypeptide Expression

The invention provides therapeutic peptides that are most commonly generated by routine methods for peptide synthesis. Such methods are known in the art and are described herein. If an alternative approach is desired, the peptides are expressed recombinantly, either alone, or as part of a larger fusion protein that includes an anti-angiogenic peptide operably linked to a polypeptide that facilitates expression. If desired, the peptide can subsequently be cleaved (e.g., enzymatically) from the fusion protein. Where the fusion protein does not interfere with the anti-angiogenic activity of the peptide such cleavage may not be necessary or even desirable. When the therapeutic peptide or fusion protein comprising the peptide contacts an endothelial cell, tissue, or organ comprising such a cell it reduces angiogenesis. Recombinant polypeptides of the invention are produced using virtually any method known to the skilled artisan. Typically, recombinant polypeptides are produced by transformation of a suitable host cell with all or part of a polypeptide-encoding nucleic acid molecule or fragment thereof in a suitable expression vehicle.

Those skilled in the field of molecular biology will understand that any of a wide variety of expression systems may be used to provide the recombinant protein. The precise host cell used is not critical to the invention. A polypeptide of the invention may be produced in a prokaryotic host (e.g., *E. coli*) or in a eukaryotic host (e.g., *Saccharomyces cerevisiae*, insect cells, e.g., Sf21 cells, or mammalian cells, e.g., NIH 3T3, HeLa, or preferably COS cells). Such cells are available from a wide range of sources (e.g., the American Type Culture Collection, Rockland, Md.; also, see, e.g., Ausubel et al., *Current Protocol in Molecular Biology*, New York: John Wiley and Sons, 1997). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

A variety of expression systems exist for the production of the polypeptides of the invention. Expression vectors useful for producing such polypeptides include, without limitation, chromosomal, episomal, and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof.

One particular bacterial expression system for polypeptide production is the *E. coli* pET expression system (e.g., pET-28) (Novagen, Inc., Madison, Wis.). According to this expression system, DNA encoding a polypeptide is inserted into a pET vector in an orientation designed to allow expression. Since the gene encoding such a polypeptide is under the control of the T7 regulatory signals, expression of the polypeptide is achieved by inducing the expression of T7 RNA polymerase in the host cell. This is typically achieved using host strains that express T7 RNA polymerase in response to IPTG induction. Once produced, recombinant polypeptide is then isolated according to standard methods known in the art, for example, those described herein.

Another bacterial expression system for polypeptide production is the pGEX expression system (Pharmacia). This system employs a GST gene fusion system that is designed for high-level expression of genes or gene fragments as fusion proteins with rapid purification and recovery of functional gene products. The protein of interest is fused to the carboxyl terminus of the glutathione S-transferase protein from *Schistosoma japonicum* and is readily purified from bacterial lysates by affinity chromatography using Glutathione Sepharose 4B. Fusion proteins can be recovered under mild conditions by elution with glutathione. Cleavage of the glutathione S-transferase domain from the fusion protein is facilitated by the presence of recognition sites for site-specific proteases upstream of this domain. For example, proteins expressed in pGEX-2T plasmids may be cleaved with thrombin; those expressed in pGEX-3X may be cleaved with factor Xa.

Alternatively, recombinant polypeptides of the invention are expressed in *Pichia pastoris*, a methylotrophic yeast. *Pichia* is capable of metabolizing methanol as the sole carbon source. The first step in the metabolism of methanol is the oxidation of methanol to formaldehyde by the enzyme, alcohol oxidase. Expression of this enzyme, which is coded for by the AOX1 gene is induced by methanol. The AOX1 promoter can be used for inducible polypeptide expression or the GAP promoter for constitutive expression of a gene of interest.

Once the recombinant polypeptide of the invention is expressed, it is isolated, for example, using affinity chromatography. In one example, an antibody (e.g., produced as described herein) raised against a polypeptide of the invention may be attached to a column and used to isolate the recombinant polypeptide. Lysis and fractionation of polypeptide-harboring cells prior to affinity chromatography may be performed by standard methods (see, e.g., Ausubel et al., supra). Alternatively, the polypeptide is isolated using a sequence tag, such as a hexahistidine tag, that binds to nickel column.

Once isolated, the recombinant protein can, if desired, be further purified, e.g., by high performance liquid chromatography (see, e.g., Fisher, *Laboratory Techniques In Biochemistry and Molecular Biology*, eds., Work and Burdon, Elsevier, 1980). Polypeptides of the invention, particularly short peptide fragments, can also be produced by chemical synthesis (e.g., by the methods described in *Solid Phase Peptide Synthesis*, 2nd ed., 1984 The Pierce Chemical Co., Rockford, Ill.). These general techniques of polypeptide expression and purification can also be used to produce and isolate useful peptide fragments or analogs (described herein).

Combinatorial Peptide Libraries

In addition to the synthetic solid state production of small peptides, the amino acid sequences of predicted fragments can be expressed and produced recombinantly using a variety of genetically modified organisms following insertion of the relevant DNA into their genome. One such widely used organism is *Escherichia coli*. Combinatorial biology depends on the ability to link peptides to their encoding DNA and create large libraries of encoded peptides. The methods for generating DNA-encoded peptide libraries can be divided into two groups. In vitro methods use libraries in which the peptides are accessible to exogenous ligands or cells. These libraries can be used in direct in vitro binding selections with cell cultures to enrich for peptides that induce particular phenotypes. In contrast, in vivo methods use peptide libraries that are expressed inside living cells. An interaction between a particular library member and the target protein is detected by virtue of an effect on the host cell, such as a selective growth advantage, or changes to a physical property of the host cell (Pelletier and Sidhu, *Curr Opin Biotechnol*, 12:340-7, 2001).

To optimize a set of peptides, such as those peptides identified herein, in vitro methods for creating and testing peptide libraries are suitable. In one embodiment, oligonucleotide directed mutagenesis of initial sequence is used. In another embodiment, a phage is used to display libraries of peptides.

Oligonucleotide Directed Mutagenesis

Oligonucleotide directed mutagenesis can be used in order to modify a single or multiple amino acids that compose the maternal sequence of the predicted anti-angiogenic fragments (Ryu and Nam, *Biotechnol Prog*, 16:2-16, 2000). Directed mutagenesis is based on the concept that an oligonucleotide encoding a desired mutation is annealed to one strand of a DNA of interest and serves as a primer for initiation of DNA synthesis. In this manner, the mutagenic oligonucleotide is incorporated into the newly synthesized strand. Mutagenic oligonucleotides incorporate at least one base change but can be designed to generate multiple substitutions, insertions or deletions.

Oligonucleotides can also encode a library of mutations by randomizing the base composition at sites during chemical synthesis resulting in degenerate oligonucleotides. The ability to localize and specify mutations is greatly enhanced by the use of synthetic oligonucleotides hybridized to the DNA insert-containing plasmid vector. The general format for site-directed mutagenesis includes several steps. Plasmid DNA containing the template of interest (cDNA) is denatured to produce single-stranded regions. A synthetic mutant oligonucleotide is annealed to the target strand. DNA polymerase is used to synthesize a new complementary strand, and finally DNA ligase is used to seal the resulting nick between the end of the new strand and the oligonucleotide. The resulting heteroduplex is propagated by transformation in *E. coli*.

Phage-Displayed Peptide Library Screening

Phage display is one method for in vitro combinatorial biology. The method stems from the observation that peptides fused to certain bacteriophage coat proteins are displayed on the surfaces of phage particles that also contain the cognate DNA (Landon et al., *Curr Drug Discov Technol*, 1:113-32, 2004).

Phage display describes a selection technique in which a library of variants of an initial peptide (e.g., a peptide described herein), is expressed on the outside of a phage virion, while the genetic material encoding each variant resides on the inside. This creates a physical linkage between each variant protein sequence and the DNA encoding it, which allows rapid partitioning based on binding affinity to a given target molecule by an in vitro selection process called panning. In its simplest form, panning is carried out by incubating a library of phage-displayed peptides with a plate containing a culture of cells, such as endothelial cells, washing away the unbound phage, and eluting the specifically bound phage. The eluted phage is then amplified and taken through additional binding/amplification cycles to enrich the pool in favor of specific phenotypes, such as suppression of proliferation, of the cells that are cultured. After 3-4 rounds, individual clones are characterized by DNA sequencing and ELISA.

Libraries of "fusion phages" are rapidly sorted to obtain clones with desired properties and phages can be readily amplified by passage through a bacterial host. Phage display was first demonstrated with the *Escherichia-coli*-specific M13 bacteriophage and this remains the most popular platform. Several other *E. coli* phages have also been adapted for phage display and eukaryotic systems have also been developed.

Screening Assays

Polypeptides and fragments of the invention are useful as targets for the identification of agents that modulate angiogenesis. In particular, the peptides identified herein (e.g., peptides listed in Table 1) are typically polypeptide fragments that are hidden within hydrophobic regions of a larger polypeptide. While the entire polypeptide may be pro-angiogenic, the peptides of the invention are typically anti-angiogenic. As such, the activity of these peptides, when exposed to the cellular or extracellular milleau, may reduce the pro-angiogenic function of the larger polypeptide. Where this antagonistic function is undesirable, agents that bind and/or inhibit the biological activity of these peptides are sought. Once identified, such agents are used to enhance angiogenesis. In another approach, anti-angiogenic agents are identified by screening for agents that bind to and enhance the activity of a peptide of the invention. Once identified, such agents are used to reduce angiogenesis.

Alternatively, or in addition, candidate agents may be identified that specifically bind to and inhibit a peptide of the invention. The efficacy of such a candidate compound is dependent upon its ability to interact with the peptide. Such an interaction can be readily assayed using any number of standard binding techniques and functional assays (e.g., those described in Ausubel et al., supra). For example, a candidate compound may be tested in vitro for interaction and binding with a polypeptide of the invention and its ability to modulate angiogenesis may be assayed by any standard assays (e.g., those described herein).

Potential antagonists include organic molecules, peptides, peptide mimetics, polypeptides, nucleic acid ligands, aptamers, and antibodies that bind to a peptide of the invention and thereby inhibit or extinguish its activity. Potential antagonists also include small molecules that bind to and occupy the binding site of the polypeptide thereby preventing binding to cellular binding molecules, such that normal biological activity is prevented.

In one particular example, a candidate compound that binds to a pathogenicity polypeptide may be identified using a chromatography-based technique. For example, a recombinant polypeptide of the invention may be purified by standard techniques from cells engineered to express the polypeptide, or may be chemically synthesized, once purified the peptide is immobilized on a column. A solution of candidate compounds is then passed through the column, and a compound specific for the peptide is identified on the basis of its ability to bind to the peptide and be immobilized on the column. To isolate the compound, the column is washed to remove non-specifically bound molecules, and the compound of interest is then released from the column and collected. Compounds isolated by this method (or any other appropriate method) may, if desired, be further purified (e.g., by high performance liquid chromatography). In addition, these candidate compounds may be tested for their ability to modulate angiogenesis (e.g., as described herein). Compounds isolated by this approach may also be used, for example, as therapeutics to treat or prevent the onset of a disease or disorder characterized by excess or undesirable angiogenesis. Compounds that are identified as binding to peptides with an affinity constant less than or equal to 1 nM, 5 nM, 10 nM, 100 nM, 1 mM or 10 mM are considered particularly useful in the invention.

Methods of the invention are useful for the high-throughput low-cost screening of polypeptides, biologically active fragments or analogs thereof that can be used to modulate angiogenesis. One skilled in the art appreciates that the effects of a candidate peptide on a cell (e.g., an endothelial cell) are typically compared to a corresponding control cell not contacted with the candidate peptide. Thus, the screening methods include comparing the expression profile, phenotype, or biological activity of a cell modulated by a candidate peptide to a reference value of an untreated control cell.

In one example, candidate peptides are added at varying concentrations to the culture medium of an endothelial cell. The survival, tube formation, apoptosis, proliferation, migration of the cell are assayed as indicators of angiogenesis. Peptides that reduce the survival, tube formation, proliferation, or migration of an endothelial cell are identified as useful anti-angiogenic agents. Alternatively, peptides that enhance the survival, tube formation, proliferation, or migration of an endothelial cell are identified as useful angiogenic agents. In another embodiment, the expression of a nucleic acid molecule or polypeptide characteristic of the vasculature is monitored. Typical cell surface markers include the fibronectin extra-domain B, large tenascin-C isoforms, various integrins, VEGF receptors, prostate specific membrane antigen, endoglin and CD44 isoforms and tumor endothelium marker (TEM). Peptides or other agents that alter the expression of such markers are identified as useful modulators of angiogenesis. An agent that reduces the expression of a characteristic polypeptide expressed in the vasculature is considered useful in the invention; such an agent may be used, for example, as a therapeutic to prevent, delay, ameliorate, stabilize, or treat an injury, disease or disorder characterized by an undesirable increase in neovascularization. In other embodiments, agents that increase the expression or activity of a marker characteristically expressed in an endothelial cell are used to prevent, delay, ameliorate, stabilize, or treat an injury, disease or disorder characterized by a reduction in angiogenesis. Agents identified according to the methods described herein maybe administered to a patient in need of angiogenesis modulation. Where such agents are peptides, such as those described herein, one skilled in the art appreciates that the invention further provides nucleic acid sequences encoding these peptides (e.g., those listed in Table 1).

Test Compounds and Extracts

In general, peptides are identified from large libraries of natural product or synthetic (or semi-synthetic) extracts or chemical libraries or from polypeptide or nucleic acid libraries, according to methods known in the art. Such candidate polypeptides or the nucleic acid molecules encoding them may be modified to enhance biodistribution, protease resistance, or specificity. The modified peptides are then screened for a desired activity (e.g., angiogenesis modulating activity). Those skilled in the field of drug discovery and development will understand that the precise source of test extracts or compounds is not critical to the screening procedure(s) of the invention. Agents used in screens may include known compounds (for example, known polypeptide therapeutics used for other diseases or disorders). Alternatively, virtually any number of unknown chemical extracts or compounds can be screened using the methods described herein. Examples of such extracts or compounds include, but are not limited to, plant-, fungal-, prokaryotic- or animal-based extracts, fermentation broths, and synthetic compounds, as well as the modification of existing polypeptides.

Libraries of natural polypeptides in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). Such polypeptides can be modified to include a protein transduction domain using methods known in the art and described herein. In addition, natural and synthetically produced libraries are produced, if desired, according to methods known in the art, e.g., by standard extraction and fractionation methods. Examples of methods for the synthesis of molecular libraries can be found in the art, for example in: DeWitt et al., *Proc. Natl. Acad. Sci. U.S.A.* 90:6909, 1993; Erb et al., *Proc. Natl. Acad. Sci. USA* 91:11422, 1994; Zuckermann et al., *J. Med. Chem.* 37:2678, 1994; Cho et al., *Science* 261:1303, 1993; Carrell et al., *Angew. Chem. Int. Ed. Engl.* 33:2059, 1994; Carell et al., *Angew. Chem. Int. Ed. Engl.* 33:2061, 1994; and Gallop et al., *J. Med. Chem.* 37:1233, 1994. Furthermore, if desired, any library or compound is readily modified using standard chemical, physical, or biochemical methods.

Numerous methods are also available for generating random or directed synthesis (e.g., semi-synthesis or total synthesis) of any number of polypeptides, chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, chemical compounds to be used as candidate compounds can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2nd ed., John Wiley and Sons (1991); L. Fieser and M. Fieser, Fieser and Fieser's *Reagents for Organic Synthesis*, John Wiley and Sons (1994); and L. Paquette, ed., *Encyclopedia of Reagents for Organic Synthesis*, John Wiley and Sons (1995), and subsequent editions thereof.

Libraries of compounds may be presented in solution (e.g., Houghten, *Biotechniques* 13:412-421, 1992), or on beads (Lam, *Nature* 354:82-84, 1991), chips (Fodor, *Nature* 364:555-556, 1993), bacteria (Ladner, U.S. Pat. No. 5,223,409), spores (Ladner U.S. Pat. No. 5,223,409), plasmids (Cull et al., *Proc Natl Acad Sci USA* 89:1865-1869, 1992) or on phage (Scott and Smith, *Science* 249:386-390, 1990; Devlin, *Science* 249:404-406, 1990; Cwirla et al. *Proc. Natl. Acad. Sci.* 87:6378-6382, 1990; Felici, *J. Mol. Biol.* 222:301-310, 1991; Ladner supra.).

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activity should be employed whenever possible.

When a crude extract is found to have angiogenesis modulating activity further fractionation of the positive lead extract is necessary to isolate molecular constituents responsible for the observed effect. Thus, the goal of the extraction, fractionation, and purification process is the careful characterization and identification of a chemical entity within the crude extract that alters angiogenesis (increases or decreases). Methods of fractionation and purification of such heterogeneous extracts are known in the art. If desired, compounds shown to be useful as therapeutics are chemically modified according to methods known in the art.

Therapeutic Methods

Therapeutic polypeptides, peptides, or analogs or fragments thereof, as well as the nucleic acid molecules encoding such molecules are useful for preventing or ameliorating a disease or injury associated with an undesirable increase or decrease in angiogenesis. Diseases and disorders characterized by excess angiogenesis may be treated using the methods and compositions of the invention. Such diseases and disorders include, but are not limited to, neoplasia, hematologic malignancies, rheumatoid arthritis, diabetic retinopathy, age-related macular degeneration, atherosclerosis, and pathologic obesity. In one embodiment, a peptide of the invention is delivered to one or more endothelial cells at a site of angiogenesis-associated disease or injury.

In other embodiments, a nucleic acid molecule encoding a peptide of the invention (e.g., a peptide listed in Table 1) is administered to a cell, tissue, or organ in need of a reduction in angiogenesis. If desired, the peptide is expressed as a fusion with a longer polypeptide. The peptide may then be cleaved from the polypeptide to achieve its desired therapeutic effect. Such cleavage is not required where the fusion protein does not interfere with the peptide's biological activity.

Transducing viral (e.g., retroviral, adenoviral, and adeno-associated viral) vectors can be used for somatic cell gene therapy, especially because of their high efficiency of infection and stable integration and expression (see, e.g., Cayouette et al., *Human Gene Therapy* 8:423-430, 1997; Kido et al., *Current Eye Research* 15:833-844, 1996; Bloomer et al., *Journal of Virology* 71:6641-6649, 1997; Naldini et al., *Science* 272:263-267, 1996; and Miyoshi et al., *Proc. Natl. Acad. Sci. U.S.A.* 94:10319, 1997). For example, a full length gene sialidase gene, or a portion thereof, can be cloned into a retroviral vector and expression can be driven from its endogenous promoter, from the retroviral long terminal repeat, or from a promoter specific for a target cell type of interest (e.g. endothelial cell). Other viral vectors that can be used include, for example, a vaccinia virus, a bovine papilloma virus, or a herpes virus, such as Epstein-Ban Virus (also see, for example, the vectors of Miller, *Human Gene Therapy* 15-14, 1990; Friedman, *Science* 244:1275-1281, 1989; Eglitis et al., *BioTechniques* 6:608-614, 1988; Tolstoshev et al., *Current Opinion in Biotechnology* 1:55-61, 1990; Sharp, *The Lancet* 337:1277-1278, 1991; Cornetta et al., *Nucleic Acid Research and Molecular Biology* 36:311-322, 1987; Anderson, *Science* 226:401-409, 1984; Moen, *Blood Cells* 17:407-416, 1991; Miller et al., *Biotechnology* 7:980-990, 1989; Le Gal La Salle et al., *Science* 259:988-990, 1993; and Johnson, *Chest* 107:77 S-83S, 1995). Retroviral vectors are particularly well developed and have been used in clinical settings (Rosenberg et al., *N. Engl. J. Med* 323:370, 1990; Anderson et al., U.S. Pat. No. 5,399,346). Most preferably, a viral vector is used to administer the gene of interest systemically or to a cell at the site of neovascularization.

Non-viral approaches can also be employed for the introduction of therapeutic to a cell of a patient having an angiogenesis related disease. For example, a nucleic acid molecule can be introduced into a cell by administering the nucleic acid in the presence of lipofectin (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., *Journal of Biological Chemistry* 263:14621, 1988; Wu et al., *Journal of Biological Chemistry* 264:16985, 1989), or by micro-injection under surgical conditions (Wolff et al., *Science* 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue at the site of disease or injury.

cDNA expression for use in such methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types, such as an intestinal epithelial cell, can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant therapeutic, such as a sialidase polypeptide, biologically active fragment, or variant thereof, either directly to the site of a potential or actual disease-affected tissue (for example, by administration to the intestine) or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions. Generally, between 0.1 mg and 100 mg, is administered per day to an adult in any pharmaceutically acceptable formulation.

Pharmaceutical Therapeutics

The invention provides a simple means for identifying compositions (including nucleic acids, peptides, small molecule inhibitors, and mimetics) capable of acting as therapeutics for the treatment of a disease associated with altered levels of angiogenesis. Accordingly, a chemical entity discovered to have medicinal value using the methods described herein is useful as a drug or as information for structural modification of existing compounds, e.g., by rational drug design. Such methods are useful for screening compounds having an effect on a variety of conditions characterized by undesired angiogenesis.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of a therapeutic agent described herein in a physiologically-acceptable carrier. Suitable carriers and their formulation are described, for example, in *Remington's Pharmaceutical Sciences* by E. W. Martin. The amount of the therapeutic agent to be administered varies depending upon the manner of administration, the age and body weight of the patient, and with the clinical symptoms of the disease or disorder. Generally, amounts will be in the range of those used for other agents used in the treatment of other diseases associated with alterations in angiogenesis, although in certain instances lower amounts will be needed because of the increased specificity of the compound. A compound is administered at a dosage that controls the clinical or physiological symptoms associated with angiogenesis as determined by a diagnostic method known to one skilled in the art.

It would be advantageous to administer therapeutic peptides in a formulation that would slow their elimination from the circulation through renal filtration, enzymatic degradation, uptake by the reticulo-endothelial system (RES), and accumulation in non-targeted organs and tissues. In addition, methods for administering agents that limits their widespread distribution in non-targeted organs and tissues allows lower concentrations of the agent to be administered reducing adverse side-effects and providing economic benefits. A variety of methods are available to slow the elimination of agents of the invention. In one embodiment, an implantable device is used to provide for the controlled release of an agent described herein. Such devices are known in the art and include, but are not limited to, polymeric gels and microfabricated chips. Some of these devices are already used in the clinic or are being tested in clinical trials (Moses et al., *Cancer Cell*, 4:337-41, 2003). Various delivery methods for anti-angiogenic agents are tissue specific, e.g., intraocular and periocular injection or gene transfer in the eye (Akiyama et al., *J Cell Physiol*, 2006; Saishin et al., *Hum Gene Ther*, 16:473-8, 2005). Numerous reviews on the subject of anti-angiogenic drug delivery are available.

Enhanced Permeability and Retention Effect

For the treatment of neoplasia or sites of neovascularization, the "enhanced permeability and retention effect" (EPR) constitutes a natural mechanism through which high molecular weight (40 kDa or higher) macromolecules with long circulation half-lives, including peptides and proteins conjugated with water-soluble polymers, accumulate (Shukla and Krag, *Expert Opin Biol Ther*, 6:39-54, 2006; Torchilin and Lukyanov, *Drug Discov Today*, 8:259-66, 2003). This effect occurs because of certain characteristics of those tissues. The first is that tumor or newly formed vasculature, unlike the vasculature of healthy tissues, is permeable to macromolecules with a MW up to 50 kDa or even higher. This allows macromolecules to enter into the interstitial space. Another characteristic is that in the case of many tumors the lymphatic system, which is responsible for the drainage of macromolecules from normal tissues, is impaired. Because of this, macromolecules that have entered a neo-vascularized tissue are retained there for a prolonged time. To enhance the retention of a low MW peptide described herein, the peptide may be conjugated to a suitable polymer or delivered using a micro-reservoir system.

Peptide and Protein Polymer Conjugation

Mechanisms that increase the MW of a peptide, such as conjugation with polymer chains or concentration of the drug in micro-reservoir systems tend to increase the retention time of the peptide in the tissue (Duncan, *Nat Rev Drug Discov*, 2:347-60, 2003). Moreover, renal filtration and excretion are mainly responsible for the rapid clearance from the systemic circulation of proteins with molecular weights (MW) of 40 kDa or lower. Rapid clearance and increased retention of a peptide of interest can be achieved by conjugating the peptides with water-soluble polymers. Preferably, the peptide-polymer conjugate has a molecular weight of at least about 30 kDA, 35 kDa, 40 kDa, 50 kDa, 75 kDa, or 100 kDa. Additional benefits of peptide and protein-polymer conjugation include increased resistance to enzymatic degradation and reduced immunogenicity.

Even endogenous proteins can be susceptible to protease degradation in the bloodstream and interstitial space or induce an immune response. Enzymatic degradation and an immune response against a protein result in its rapid elimination from the systemic circulation. In addition, the development of an immune response is potentially dangerous because of the possibility of allergic reactions and anaphylactic shock upon repetitive administrations. The mechanism of protein protection by polymer attachment is similar in both cases. Polymer molecules attached to the protein create steric hindrances, which interfere with binding to the active sites of proteases, and antigen-processing cells. Examples of peptide/protein-polymer conjugation include conjugates with poly(ethylene glycol) and conjugates with poly(styrene-co-maleic acid anhydride).

Conjugates with Poly(Ethylene Glycol)

Several polymers have been used for protein stabilization with varying degrees of success. Poly(ethylene glycol) (PEG) is one widely used polymer for the modification of proteins with therapeutic potential (Thanou and Duncan, *Curr Opin Investig Drugs*, 4:701-9, 2003; Vicent and Duncan, *Trends Biotechnol*, 24:39-47, 2006). This polymer is inexpensive, has low toxicity and has been approved for internal applications by drug regulatory agencies. PEG is commercially available in a variety of molecular weights and in chemically activated, ready-for-use forms for covalent attachment to proteins.

Conjugates with Poly(Styrene-Co-Maleic Acid Anhydride)

In some cases, the circulation time of drugs can be increased by conjugating with polymers that are not large enough to prevent renal clearance themselves, but which can attach themselves, with their conjugated drug, to natural long-circulating blood plasma components, such as serum albumin or lipoproteins (Thanou and Duncan, *Curr Opin Investig Drugs*, 4:701-9, 2003; Vicent and Duncan, *Trends Biotechnol*, 24:39-47, 2006).

Because of the small size and low molecular weight of the identified anti-angiogenic peptides and the high probability that the conjugated polymers, which are orders of magnitude larger than the peptides, may sterically hinder the activity of the fragments the method of protein conjugation may not be the most efficient method for increasing the retention of the agent in the neo-vascular site. A more attractive scenario is the administration of the peptide in a micro-reservoir delivery system.

Formulation of Pharmaceutical Compositions

The administration of a compound for the treatment of treatment of a disease or disorder associated with altered levels of angiogenesis may be by any suitable means that results in a concentration of the therapeutic that, combined with other components, is effective in ameliorating, reducing, or stabilizing a disease or disorder associated with altered levels of angiogenesis (e.g., an amount sufficient to reduce neovascularization). The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., *Remington: The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York).

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that allow for convenient dosing for metronomic therapy that would require taking small doses of the drug several times a week; (vii) formulations that target a disease or disorder associated with altered levels of angiogenesis by using carriers or chemical derivatives to deliver the therapeutic agent to a particular cell type (e.g., endothelial cell) whose function is perturbed in a disease or disorder associated with altered levels of angiogenesis.

For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Micro-Reservoir Delivery Systems

For some applications, micro-reservoir or micro-particulate carriers are used to deliver a peptide of the invention. Such systems include, but are not limited to, liposomes, micelles, polymer micro-particles, and cell ghosts. The use of such carriers results in a much higher ratio of active agent over carrier compared with direct molecular conjugates. They also provide a higher degree of protection against enzymatic degradation and other destructive factors upon parenteral administration because the carrier wall completely isolates drug molecules from the environment. An additional advantage of these carriers is that a single carrier can deliver multiple drug species so that they can be used in combination therapies. All micro-particulates are too large to be lost by renal filtration (Thanou and Duncan, *Curr Opin Investig Drugs*, 4:701-9, 2003) Exemplary micro-particulate delivery systems include, but are not limited to, liposomes and micelles.

Liposomes

Among particulate drug carriers, liposomes are the most extensively studied and possess suitable characteristics for peptide and protein encapsulation. Liposomes are vesicles formed by concentric spherical phospholipid bilayers encapsulating an aqueous space (Moses et al., *Cancer Cell*, 4:337-41, 2003). These particles are biocompatible, biologically inert and cause little toxic or antigenic reactions. Their inner aqueous compartment can be used for encapsulation of peptides and proteins. Many techniques for liposome preparation require only manipulations that are compatible with peptide and protein integrity (Allen and Cullis, *Science*, 303:1818-22, 2004). As with other micro-particulate delivery systems, cells of the RES rapidly eliminate conventional liposomes.

In one embodiment, surface-modified long-circulating liposomes grafted with a flexible hydrophilic polymer, such as PEG, are used. This approach prevents plasma protein adsorption to the liposome surface and the subsequent recognition and uptake of liposomes by the RES. Liposomes, in common with protein conjugated macromolecules, can accumulate in tumors of various origins via the EPR effect. Currently, liposomal forms of at least two conventional anticancer drugs, daunorubicin and doxorubicin, are used in the clinic (Torchilin and Lukyanov, *Drug Discov Today*, 8:259-66, 2003).

Micelles

In another approach, micelles or polymeric micelles, including those prepared from amphiphilic PEG-phospholipid conjugates, may be used to deliver an agent of the invention. Such formulations are of special interest because of their stability (Torchilin and Lukyanov, *Drug Discov Today*, 8:259-66, 2003). These particles are smaller than liposomes and lack the internal aqueous space. To load micelles, peptides can be attached to the surface of these particles or incorporated into them via a chemically attached hydrophobic anchor. An example of a biodegradable micelle developed for delivery of pharmacological agents are the poly{[(cholesteryl oxocarbonylamido ethyl)methyl bis(ethylene)ammonium iodide]ethyl phosphate} (PCEP) micelles (Wen, Mao et al., *J Pharm Sci.* 93:2142-57, 2004). Carrying a positive charge in its backbone and a lipophilic cholesterol structure in the side chain, PCEP self-assembles into micelles in aqueous buffer at room temperature with an average size of 60-100 nm. PCEP is an excellent platform for delivering ant-angiogenic agents as by itself shows lower cytotoxicity for endothelial cells than for poly-L-lysine and Lipofectamine.

Nanoparticles

An increasing number of agents are delivered with colloidal nanoparticles. Such formulations overcome non-cellular and cellular based mechanisms of resistance and increase the selectivity of agents to target cells while reducing their toxicity in normal tissues. Nanoparticles are typically submicron (<1 μm) colloidal systems. In some embodiments, nanoparticles are made of polymers (biodegradable or not). According to the process used for the preparation of the nanoparticles, nanospheres or nanocapsules can be obtained. Unlike nanospheres (matrix systems in which the drug is dispersed throughout the particles), nanocapsules are vesicular systems in which an agent is confined to an aqueous or oily cavity surrounded by a single polymeric membrane. Nanocapsules are one form of 'reservoir' system.

In some embodiments, nanoparticles are generated using hydrophilic polymers, (poly(ethylene glycol) (PEG), poloxamines, poloxamers, polysaccharides) to efficiently coat a nanoparticle surface. These coatings provide a dynamic 'cloud' of hydrophilic and neutral chains at the particle surface that repels plasma proteins. Hydrophilic polymers are introduced at the surface in two ways, either by adsorption of surfactants or by use of block or branched copolymers.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active therapeutic(s), the composition may include suitable parenterally acceptable carriers and/or excipients. The active therapeutic(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the invention may be in the form suitable for sterile injection. To prepare such a composition, the suitable active angiogenic modulating therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly(glycolic acid) or poly(ortho esters) or combinations thereof).

Solid Dosage Forms for Oral Use

Formulations for oral use include tablets containing the active ingredient(s) in a mixture with non-toxic pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug in a predetermined pattern (e.g., in order to achieve a controlled release formulation) or it may be adapted not to release the active drug until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active angiogenic modulating therapeutic). The coating may be applied on the solid dosage form in a similar manner as that described in *Encyclopedia of Pharmaceutical Technology*, supra.

At least two active angiogenic modulating therapeutics may be mixed together in the tablet, or may be partitioned. In one example, the first active in angiogenic modulating therapeutic is contained on the inside of the tablet, and the second active angiogenic modulating therapeutic is on the outside, such that a substantial portion of the second angiogenic modulating therapeutic is released prior to the release of the first angiogenic modulating therapeutic.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use are constructed to release the active angiogenic modulating therapeutic by controlling the dissolution and/or the diffusion of the active substance. Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/ or halogenated fluorocarbon.

A controlled release composition containing one or more therapeutic compounds may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the compound(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Polymeric Controlled-Release Implants

In another embodiment, an agent of the invention is delivered by implanting a biodegradable polymeric controlled-release device that stores the pharmaceutical agent and allows its delivery via diffusion into the surrounding tissue. Controlled release devices include Norplant and Gliadel, which are used clinically for the prevention of pregnancy and for brain tumor therapy, respectively. Local delivery of pro- or anti-angiogenic factors can be accomplished by encapsulating the agent within a biocompatible polymer matrix. The controlled-release polymer system is then implanted at the desired tissue site, where it releases the soluble factor directly into the interstitial space of the tissue. The diffusible agent can influence the survival or function of damaged cells within the local tissue, or provide a signal that elicits cell proliferation and migration or apoptosis and suppression of migration within the tissue region.

Controlled release implants are typically composed of inert, biocompatible polymers, such as poly(ethylene-co-vinyl acetate) (EVAc), or biodegradable polymers, such as poly(lactide-co-glycolide) (PLGA) (Torchilin and Lukyanov, *Drug Discov Today*, 8:259-66, 2003). EVAc-matrix systems have been used to release protein hormones, growth factors, antibodies, antigens and DNA. EVAc matrices allow a high degree of control over agent release, versatility in allowing the release of a wide range of agents, and good retention of biological activity. Biodegradable polymers have also been used to release growth factors, protein hormones, antibodies, antigens and DNA. Biodegradable materials disappear from the implant site after protein release. Polymer gels might also be useful for topical or localized protein delivery. Systems that release multiple protein factors are also possible (Saltzman and Olbricht, *Nat Rev Drug Discov*, 1:177-86, 2002; Torchilin and Lukyanov, *Drug Discov Today*, 8:259-66, 2003).

Biodegradable polymers include non-water-soluble polymers that are degraded by surface or bulk erosion in addition to water-soluble gels that dissolve and are cleared from the body without undergoing a decrease in molecular weight. There are many different types of biodegradable polymers that can potentially be used in the preparation of peptide delivery systems. They include both naturally derived and synthetic materials.

Biocompatibility of Polymeric Systems

Polymers used as drug delivery systems for protein pharmaceuticals need to exhibit biocompatible characteristics in terms of both the polymer's effect on the organism receiving the drug delivery system and the polymer's effect on the protein to be delivered. Several aspects of a polymeric delivery system ultimately contribute to its overall biocompatibility, or lack thereof. The polymer itself, which consists of a repeating monomeric species, may potentially be antigenic, carcinogenic, or toxic or have some inherent incompatibility with organisms. The shape of an implanted material has been implicated in its biocompatibility as well, smooth surfaces being less irritating and more biocompatible than rough surfaces (Saltzman and Olbricht, *Nat Rev Drug Discov*, 1:177-86, 2002).

Pharmaceutical Stability

Interactions between proteins and polymeric materials appear to be protein and polymer specific. At issue are the protein molecular weight, which is an important parameter with regard to diffusion characteristics and the iso-electric point of the protein (and polymer as well in some cases), which governs charge-charge interactions (protein-polymer and protein-protein). Moreover the presence of cysteines on the protein may facilitate the formation of intermolecular (i.e., protein-polymer) disulfide bonds. Furthermore, the primary amino acid sequence of the protein may be rendered susceptible to chemical modification in association with a polymeric material. The presence or absence of carbohydrates on the protein may enhance or prevent interaction with polymeric materials and affect the protein's hydrodynamic volume. The relative hydrophobicity of a protein could interact with hydrophobic sites on a polymer. Finally the heterogeneity of protein pharmaceuticals often exists for proteins produced by recombinant methods (Bilati et al., *Eur J Pharm Biopharm*, 59:375-88, 2005; Gombotz and Pettit, *Bioconjug Chem*, 6:332-51, 1995; Saltzman and Olbricht, *Nat Rev Drug Discov*, 1:177-86, 2002).

Bulk Erosion Polymers

Poly(lactic-co-glycolic acid)

Poly(lactic-co-glycolic acid) (PLGA) has been used successfully for several decades in biodegradable structures and more recently as drug delivery micro-carriers, and as a result of the extended use, much is known about their biocompatibility and physicochemical characteristics. PLGA copolymers are well suited for use in delivery systems since they can be fabricated into a variety of morphologies including films, rods, spheres by solvent casting, compression molding and solvent evaporation techniques. Examples of peptide drug delivery systems made from PLGA copolymers, have successfully met FDA approval and they are available as marketed products are Lupron Depot, Zoladex and Decapeptyl (Frokjaer and Otzen, *Nat Rev Drug Discov,* 4:298-306, 2005).
Block Copolymers of PEG and PLA Copolymers of PEG and PLA have been synthesized for use in delivery systems. The net result is a biodegradable polymer with a reduced amount of hydrophobicity that is an inherent property of PLA systems. These copolymer systems can be composed of random blocks of the two polymers, two blocks in which case the molecules are amphiphilic, or triblocks in which hydrophilic microphases are present. Peptides that are incorporated into devices made from these copolymers are less likely to adsorb to the delivery system through hydrophobic interactions. The polymers were shown to swell very rapidly due to microphase separation, and degradation occurred over 2-3 weeks (Bilati et al., *Eur J Pharm Biopharm,* 59:375-88, 2005; Gombotz and Pettit, *Bioconjug Chem,* 6:332-51, 1995).

Poly(cyanoacrylates)

Poly(cyanoacrylates) have received attention as delivery systems for proteins and peptides. They undergo spontaneous polymerization at room temperature in the presence of water, and their erosion has been shown to be controlled by the length of the monomer chain and the pH. Once formed, the polymer is slowly hydrolyzed, leading to a chain scission and liberation of formaldehyde. While the polymers are not toxic, the formaldehyde released as the degradation byproduct does create a toxicity concern. A characteristic example of their use are delivery systems for insulin prepared by the interfacial emulsion polymerization of alkyl cyanoacrylate (Gombotz and Pettit, *Bioconjug Chem,* 6:332-51, 1995).

Surface Erosion Polymers
Poly(anhydrides)

Poly(anhydrides) represent a class of surface eroding polymers. Hydrolysis of the anhydride bond is suppressed by acid, which results in an inhibition of bulk erosion by the acidity of the carboxylic acid products of the polymer hydrolysis process. By varying the ratio of their hydrophobic components, one can control degradation rates ranging from days to years. Several proteins have been successfully incorporated into, and released, from poly-(anhydride) delivery systems. The incorporation of insulin and myoglobin has successfully been achieved in poly(anhydride) microspheres using both a hotmelt microencapsulation technique or microencapsulation by solvent removal (Gombotz and Pettit, *Bioconjug Chem,* 6:332-51, 1995).

Poly(ortho Esters)

Poly(ortho esters) are another example of surface-eroding polymers that have been developed for drug delivery systems. Several proteins and peptides have been incorporated into poly(ortho-ester) delivery systems including the LHRH analog nafarelin, insulin and lysozyme.

Hydrogels

The use of biodegradable hydrogels as delivery systems for proteins is of particular interest due to their biocompatibility and their relative inertness toward protein drugs (Gombotz and Pettit, *Bioconjug Chem,* 6:332-51, 1995). Hydrogels are the only class of polymer that can enable a protein to permeate through the continuum of the carrier. The initial release rate of proteins from biodegradable hydrogels is therefore generally diffusion controlled through the aqueous channels of the gel and is inversely proportional to the molecular weight of the protein. Once polymer degradation occurs, and if protein still remains in the hydrogel, erosion-controlled release may contribute to the system. Several disadvantages must be considered when using a biodegradable hydrogel system for the release of proteins. Their ability to rapidly swell with water can lead to very fast release rates and polymer degradation rates. In addition, hydrogels can rapidly decrease in mechanical strength upon swelling with water. Examples of hydrogels include, pluronic polyols, poly(vinyl alcohol), poly(vinylpyrolidone), malein anhydride, callulose, hyaluronic acid derivatives, alginate, collagens, gelatin, starches and dextrans.

Selective Drug Delivery

Selective delivery of therapeutic agents includes any methodology by which the functional concentration of drug is higher at the target site than in normal tissue. A wide variety of methods may fall under the category of "selective delivery," including interventions as simple and mechanical as selective vascular administration in which the drug is physically isolated in a neovascularized area. An example of that type of mechanical selectivity is also the EPR effect.

Most strategies, however, are pharmaceutical. In these approaches, the differences in the biochemical and physiological nature of normal and the targeted cells and their microenvironment are exploited for selective delivery. In one embodiment, a carrier is used to deliver a peptide of the invention that because of its physical properties, accumulates preferentially at a target site. In another embodiment, a ligand is conjugated to a peptide of the invention that binds to a tissue-associated antigen. In another embodiment, an agent of the invention is maintained in an inactive form that can be activated preferentially at the tissue site. In yet another embodiment, external energy irradiation is used to release a peptide at the delivery site.

A variety of technologies using combinations of different approaches are constantly being developed for selective delivery of therapeutics. These delivery systems employ different targets such as cancer cell and neovascular antigens, hypoxia, or high osmotic pressure; targeting agents such as monoclonal antibodies (mAbs), single chain variable fragments (scFvs), peptides and oligonucleotides; effectors like chemical or biological toxins, radioisotopes, genes, enzymes, immunomodulators, oligonucleotides, imaging and diagnostic agents; vehicles the already mentioned colloidal systems, including liposomes, emulsions, micelles, nanoparticles, polymer conjugates or implants; and drug-releasing switches such as systems that utilize thermal, radiation, ultrasound or magnetic fields (Allen and Cullis, *Science,* 303:1818-22, 2004; Gombotz and Pettit, *Bioconjug Chem,* 6:332-51, 1995; Moses et al., *Cancer Cell,* 4:337-41, 2003; Neri and Bicknell, *Nat Rev Cancer,* 5:436-46, 2005; Saltzman and Olbricht, *Nat Rev Drug Discov,* 1:177-86, 2002).

Tumor Marker Targeting

The advent of aptamer and antibody technology has facilitated the use of cancer-specific monoclonal antibodies and aptamers to deliver peptides of the invention to a selected target tissue. Of special interest are antibodies and aptamers that target, in vivo, tumor endothelium. Those targets include, but are not limited to, the fibronectin extra-domain B, large tenascin-C isoforms, various integrins, VEGF receptors, prostate specific membrane antigen, endoglin and CD44 isoforms (Shukla and Krag, *Expert Opin Biol Ther,* 6:39-54, 2006). Alternatively, the tumor itself may be targeted, exemplary tumor markers include CA-125, gangliosides G(D2), G(M2) and G(D3), CD20, CD52, CD33, Ep-CAM, CEA, bombesin-like peptides, PSA, HER2/neu, epidermal growth factor receptor, erbB2, erbB3, erbB4, CD44v6, Ki-67, cancer-associated mucin, VEGF, VEGFRs (e.g., VEGFR3), estrogen receptors, Lewis-Y antigen, TGFβ1, IGF-1 receptor, EGFα, c-Kit receptor, transferrin receptor, IL-2R and CO17-1A. Aptamers and antibodies of the invention can recognize tumors derived from a wide variety of tissue types, including, but not limited to, breast, prostate, colon, lung, pharynx, thyroid, lymphoid, lymphatic, larynx, esophagus, oral mucosa, bladder, stomach, intestine, liver, pancreas, ovary, uterus, cervix, testes, dermis, bone, blood and brain. In the context of the present invention, a tumor cell is a neoplastic (e.g., cancer) cell or a mass of cancer cells, which can also encompass cells that support the growth and/or propagation of a cancer cell, such as vasculature and/or stroma, but not necessarily macrophages. For instance, therefore, the present invention envisages compositions and methods for reducing growth of a tumor cell in a subject, wherein antibodies or aptamers bind with specificity to cell surface epitopes (or epitopes of receptor-binding molecules) of a cancer cell or a cell that is involved in the growth and/or propagation of a cancer cell such as a cell comprising the vasculature of a tumor or blood vessels that supply tumors and/or stromal cells. Methods of this invention are particularly suitable for administration to humans with neoplastic diseases.

Antibodies

Antibodies are well known to those of ordinary skill in the science of immunology. Particularly useful in the methods of the invention are antibodies that specifically bind a polypeptide that is expressed in a tumor or endothelial cell. As used herein, the term "antibody" means not only intact antibody molecules, but also fragments of antibody molecules that retain immunogen binding ability. Such fragments are also well known in the art and are regularly employed both in vitro and in vivo. Accordingly, as used herein, the term "antibody" means not only intact immunoglobulin molecules but also the well-known active fragments $F(ab')_2$, and Fab. $F(ab')_2$, and Fab fragments which lack the Fc fragment of intact antibody, clear more rapidly from the circulation, and may have less non-specific tissue binding of an intact antibody (Wahl et al., *J. Nucl. Med.* 24:316-325, 1983). The antibodies of the invention comprise whole native antibodies, bispecific antibodies; chimeric antibodies; Fab, Fab', single chain V region fragments (scFv) and fusion polypeptides.

In one embodiment, an antibody that binds polypeptide is monoclonal. Alternatively, the antibody is a polyclonal antibody. The preparation and use of polyclonal antibodies are also known to the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "$F(ab')_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab' fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing an HSP27 polypeptide or a polypeptide described in Table 1, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding an HSP27 polypeptide or a polypeptide described in Table 1, or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding an an HSP27 polypeptide or a polypeptide described in Table 1, or immunogenic fragments thereof, can be expressed in cells in vitro, followed by isolation of the polypeptide and administration of the receptor to a suitable host in which antibodies are raised.

Using either approach, antibodies can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Aptamers

Nucleic acid aptamers are single-stranded nucleic acid (DNA or RNA) ligands that function by folding into a specific globular structure that dictates binding to target proteins or other molecules with high affinity and specificity, as described by Osborne et al., *Curr. Opin. Chem. Biol.* 1:5-9, 1997; and Cerchia et al., *FEBS Letters* 528:12-16, 2002. By "aptamer" is meant a single-stranded polynucleotide that binds to a protein. Desirably, the aptamers are small, approximately ~15 KD. The aptamers are isolated from libraries consisting of some $10^{14}$-$10^{15}$ random oligonucleotide sequences by a procedure termed SELEX (systematic evolution of ligands by exponential enrichment). See Tuerk et al., *Science*, 249:505-510, 1990; Green et al., *Methods Enzymology.* 75-86, 1991; Gold et al., *Annu. Rev. Biochem.*, 64: 763-797, 1995; Uphoff et al., *Curr. Opin. Struct. Biol.*, 6: 281-288, 1996. Methods of generating aptamers are known in the art and are described, for example, in U.S. Pat. Nos. 6,344,318, 6,331,398, 6,110,900, 5,817,785, 5,756,291, 5,696,249, 5,670,637, 5,637,461, 5,595,877, 5,527,894, 5,496,938, 5,475,096, 5,270,163, and in U.S. Patent Application Publication Nos. 20040241731, 20030198989, 20030157487, and 20020172962.

An aptamer of the invention is capable of binding with specificity to a polypeptide expressed by a cell of interest (e.g., a tumor cell or an endothelial cell supplying a tumor). "Binding with specificity" means that non-tumor polypeptides are either not specifically bound by the aptamer or are only poorly bound by the aptamer. In general, aptamers typically have binding constants in the picomolar range. Particularly useful in the methods of the invention are aptamers having apparent dissociation constants of 1, 10, 15, 25, 50, 75, or 100 nM.

In one embodiment, an antigen expressed on a blood vessel supplying a tumor is the molecular target of the aptamer. Because aptamers can act as direct antagonists of the biological function of proteins, aptamers that target such polypeptide can be used to modulate angiogenesis, vasculogenesis, blood vessel stabilization or remodeling. The therapeutic benefit of such aptamers derives primarily from the biological antagonism caused by aptamer binding.

The invention encompasses stabilized aptamers having modifications that protect against 3' and 5' exonucleases as well as endonucleases. Such modifications desirably maintain target affinity while increasing aptamer stability in vivo. In various embodiments, aptamers of the invention include chemical substitutions at the ribose and/or phosphate and/or base positions of a given nucleobase sequence. For example, aptamers of the invention include chemical modifications at the 2' position of the ribose moiety, circularization of the aptamer, 3' capping and 'spiegelmer' technology. Aptamers having A and G nucleotides sequentially replaced with their 2'-OCH3 modified counterparts are particularly useful in the methods of the invention. Such modifications are typically well tolerated in terms of retaining aptamer affinity and specificity. In various embodiments, aptamers include at least 10%, 25%, 50%, or 75% modified nucleotides. In other embodiments, as many as 80-90% of the aptamer's nucleotides contain stabilizing substitutions. In other embodiments, 2'-OMe aptamers are synthesized. Such aptamers are desirable because they are inexpensive to synthesize and natural polymerases do not accept 2'-OMe nucleotide triphosphates as substrates so that 2'-OMe nucleotides cannot be recycled into host DNA. A fully 2'-O-methyl aptamer, named ARC245, was reported to be so stable that degradation could not be detected after 96 hours in plasma at 37° C. or after autoclaving at 125° C. Using methods described herein, aptamers will be selected for reduced size and increased stability. In one embodiment, aptamers having 2'-F and 2'-OCH3 modifications are used to generate nuclease resistant aptamers. Other modifications that stabilize aptamers are known in the art and are described, for example, in U.S. Pat. No. 5,580,737; and in U.S. Patent Application Publication Nos. 20050037394, 20040253679, 20040197804, and 20040180360.

Using standard methods tumor markers or endothelial cell-specific aptamers can be selected that bind virtually any tumor marker or endothelial cell-expressed polypeptide known in the art.

The Fibronectin Extra-Domain B (EDB)

Fibronectin is a large glycoprotein that is present in large amounts in the plasma and tissues. EDB is a 91-amino-acid type III homology domain that becomes inserted into the fibronectin molecule under tissue-remodeling conditions by a mechanism of alternative splicing at the level of the primary transcript. EDB is essentially undetectable in healthy adult individuals. EDB-containing fibronectin is abundant in many aggressive solid tumors and in neo-vascularized endothelium, and displays either predominantly vascular or diffuse stromal patterns of expression, depending on the tissue.

Large Tenascin-C Isoforms

Tenascins are a family of four extracellular matrix glycoproteins that are found in vertebrates. They are typically present in many different connective tissues. Tenascins contribute to matrix structure and influence the behavior of cells that are in contact with the extracellular matrix. Several isoforms of tenascin-C can be generated as a result of different patterns of alternative splicing in the region between domains A1 and D. It has been known for some time that spliced isoforms containing extra domains are tumor-associated antigens, which show a more restricted pattern of expression in normal tissues compared with the "small" tenascin isoforms. The C domain of tenascin-C is the extra domain that shows the most restricted pattern of expression. In normal adult tissue it is undetectable by immunohistochemistry and northern-blot analysis, but it is strongly expressed in aggressive brain tumors and some lung tumors, with a prominent perivascular pattern of staining.

Integrins

During vascular remodeling and angiogenesis, endothelial cells show increased expression of several cell-surface molecules that potentiate cell invasion and proliferation. One such molecule is the integrin $\alpha v$-$\beta 3$, which has a key role in endothelial cell survival during angiogenesis in vivo and which might serve as a target for therapeutic molecules, particularly those that require internalization in endothelial cells. Monoclonal antibodies to the $\alpha v$-$\beta 3$ have been shown to display anti-angiogenic activities and to preferentially stain tumor blood vessels.

VEGFs and their Receptors

VEGFs represent a class of proteins that promote angiogenesis, increase vascular permeability and contribute to endothelial-cell survival in blood and lymphatic vessels. The contribution of VEGFA to cancer progression has been highlighted by the recent approval of the humanized anti-VEGF monoclonal antibody bevacizumab (Avastin; Genentech) for first-line cancer treatment. The overexpression of VEGFs and VEGF receptors in tumors is well documented. The selective tumor localization of monoclonal antibodies to VEGFA, VEGF receptor 2 and the VEGFA-VEGF receptor 2 complex can be used as an excellent selectivity mechanism for targeting the angiogenic vasculature.

Prostate-Specific Membrane Antigen

Prostate-specific membrane antigen (PSMA) is a membrane glycoprotein with proteolytic activity. PSMA is predominantly expressed in the prostate and serum concentrations are often increased in patients with prostate cancer. Several studies have reported overexpression of PSMA in the neo-vasculature of different solid tumors, whereas expression in normal vasculature is limited to some vessels of the breast, duodenum, kidney and prostate.

Endoglin

Endoglin (CD105) is a transforming growth factor-beta (TGF) co-receptor that is overexpressed in tumor neo-vasculature and is used as a marker for the tumor endothelium.

CD44 Isoforms

CD44 is a cell-surface receptor of great molecular heterogeneity, which is due to both alternative splicing and extensive post-translational modification. The radio-labeled monoclonal antibody TES-23, which is specific to an isoform of CD44, has shown impressive performance in tumor-targeting experiments in animal models. TES-23 recognizes a widely distributed form of CD44 that lacks variant exons, known as CD44H.

Tumor Endothelial Markers (TEMs)

TEMs is a family of genes encoding proteins that serve as tumor endothelial markers (Carson-Walter, Watkins, et al, *Cancer Res.* 61:6649-55, 2001). These genes display elevated expression during tumor angiogenesis. From both biological and clinical points of view, TEMs associated with the cell surface membrane are of particular interest. Accordingly, four such genes are characterized, TEM1, TEM5, TEM7, and TEM8, all of which contain putative transmembrane domains. TEM5 appears to be a seven-pass transmembrane receptor, whereas TEM1, TEM7, and TEM8 span the membrane once. Three of these TEMs (TEM1, TEM5, and TEM8) are abundantly expressed in tumor vessels in mouse tumors, embryos, and adult tissues as well as in the vasculature of the developing mouse embryo. The expression of these TEMs in normal adult mice tissues is undetectable.

Selective Delivery Through Pro-Drug Activation

Selective delivery of agents of the invention can be achieved by administering a pro-drug form that is converted into an active drug at the target site. Most pro-drugs are designed to have a "trigger," "linker" and "effector." The "trigger," following the tissue-specific metabolism, modifies the "linker," resulting in an activation of the "effector." There are several mechanisms potentially exploitable for selective activation. Some utilize unique aspects of the tissue physiology, such as selective enzyme expression or hypoxia in the case of tumors, whereas others are based on tissue antigen-specific delivery techniques.

Targeting Secreted Enzymes from Cells

The approach uses pro-drugs that are "hidden" from the cells until cleaved by an enzyme produced and secreted preferentially by the cells. A typical example of an enzyme used for pro-drug activation is MMP-9.

Targeting Tumor Hypoxia

Advances in the chemistry of bio-reductive drug activation have led to the design of hypoxia-selective drug delivery systems. These pro-drugs initially undergo one-electron reduction by reductases to give the radical anion, which in normal cells are re-oxidized to the parent compound, but in hypoxic tumor cells they are further reduced to more hydrophilic species and trapped inside. These drugs can be selectively delivered to tumors with defined hypoxic fractions rich in the required activating enzymes.

Antibody-Directed Enzyme Pro-Drug Therapy

Antibody-directed pro-drug therapy (ADEPT) is a 2-step approach in which first the antibody-enzyme construct is administered intravenously. This is composed of an antibody against a tissue-specific target linked to an enzyme that activates a pro-drug. In the second step, after the unbound antibody-enzyme conjugate construct is cleared from the circulation, a pro-drug is administered intravenously. The pro-drug is an agent that has been rendered less active by chemical addition of enzyme-cleavable moieties. The pro-drug is converted to an active form by the tumor-bound antibody-enzyme, which results in local accumulation of the fully active form of the agent.

External Energy-Controlled Delivery

Some selective delivery strategies involve focusing external energy for concentrating or delivering therapeutics at the tissue site. A variety of delivery systems in this category are in the experimental stage, although some have been used in clinical trials as well. Those strategies include selective delivery through photodynamic therapy, magnetically targeted delivery, selective delivery through X-ray exposure, radiation-induced selective delivery and ultrasound-guided delivery.

Methods of Ocular Delivery

The compositions of the invention (e.g., peptides listed in Table 1) are also particularly suitable for treating ocular diseases, such as age-related macular degeneration, choroidal neovascularization, persistent hyperplastic vitreous syndrome, diabetic retinopathy, and retinopathy of prematurity that are characterized by excess angiogenesis.

In one approach, the compositions of the invention are administered through an ocular device suitable for direct implantation into the vitreous of the eye. The compositions of the invention may be provided in sustained release compositions, such as those described in, for example, U.S. Pat. Nos. 5,672,659 and 5,595,760. Such devices are found to provide sustained controlled release of various compositions to treat the eye without risk of detrimental local and systemic side effects. An object of the present ocular method of delivery is to maximize the amount of drug contained in an intraocular device or implant while minimizing its size in order to prolong the duration of the implant. See, e.g., U.S. Pat. Nos. 5,378,475; 6,375,972, and 6,756,058 and U.S. Publications 20050096290 and 200501269448. Such implants may be biodegradable and/or biocompatible implants, or may be non-biodegradable implants. Biodegradable ocular implants are described, for example, in U.S. Patent Publication No. 20050048099. The implants may be permeable or impermeable to the active agent, and may be inserted into a chamber of the eye, such as the anterior or posterior chambers or may be implanted in the schlera, transchoroidal space, or an avascularized region exterior to the vitreous. Alternatively, a contact lens that acts as a depot for compositions of the invention may also be used for drug delivery.

In a preferred embodiment, the implant may be positioned over an avascular region, such as on the sclera, so as to allow for transcleral diffusion of the drug to the desired site of treatment, e.g. the intraocular space and macula of the eye. Furthermore, the site of transcleral diffusion is preferably in proximity to the macula. Examples of implants for delivery of a composition include, but are not limited to, the devices described in U.S. Pat. Nos. 3,416,530; 3,828,777; 4,014,335; 4,300,557; 4,327,725; 4,853,224; 4,946,450; 4,997,652; 5,147,647; 5,164,188; 5,178,635; 5,300,114; 5,322,691; 5,403,901; 5,443,505; 5,466,466; 5,476,511; 5,516,522; 5,632,984; 5,679,666; 5,710,165; 5,725,493; 5,743,274; 5,766,242; 5,766,619; 5,770,592; 5,773,019; 5,824,072; 5,824,073; 5,830,173; 5,836,935; 5,869,079; 5,902,598; 5,904,144; 5,916,584; 6,001,386; 6,074,661; 6,110,485; 6,126,687; 6,146,366; 6,251,090; and 6,299,895, and in WO 01/30323 and WO 01/28474, all of which are incorporated herein by reference.

Examples include, but are not limited to the following: a sustained release drug delivery system comprising an inner reservoir comprising an effective amount of an agent effective in obtaining a desired local or systemic physiological or pharmacological effect, an inner tube impermeable to the passage of the agent, the inner tube having first and second ends and covering at least a portion of the inner reservoir, the inner tube sized and formed of a material so that the inner tube is capable of supporting its own weight, an impermeable member positioned at the inner tube first end, the impermeable member preventing passage of the agent out of the reservoir through the inner tube first end, and a permeable member positioned at the inner tube second end, the permeable member allowing diffusion of the agent out of the reservoir through the inner tube second end; a method for administering a compound of the invention to a segment of an eye, the method comprising the step of implanting a sustained release device to deliver the compound of the invention to the vitreous of the eye or an implantable, sustained release device for administering a compound of the invention to a segment of an eye; a sustained release drug delivery device comprising: a) a drug core comprising a therapeutically effective amount of at least one first agent effective in obtaining a diagnostic effect or effective in obtaining a desired local or systemic physiological or pharmacological effect; b) at least one unitary cup essentially impermeable to the passage of the agent that surrounds and defines an internal compartment to accept the drug core, the unitary cup comprising an open top end with at least one recessed groove around at least some portion of the open top end of the unitary cup; c) a permeable plug which is permeable to the passage of the agent, the permeable plug is positioned at the open top end of the unitary cup wherein the groove interacts with the permeable plug holding it in position and closing the open top end, the permeable plug allowing passage of the agent out of the drug core, through the permeable plug, and out the open top end of the unitary cup; and d) at least one second agent effective in obtaining a diagnostic effect or effective in obtaining a desired local or systemic physiological or pharmacological effect; or a sustained release drug delivery device comprising: an inner core comprising an effective amount of an agent having a desired solubility and a polymer coating layer, the polymer layer being permeable to the agent, wherein the polymer coating layer completely covers the inner core.

Other approaches for ocular delivery include the use of liposomes to target a compound of the present invention to the eye, and preferably to retinal pigment epithelial cells and/or Bruch's membrane. For example, the compound may be complexed with liposomes in the manner described above, and this compound/liposome complex injected into patients with an ocular disease, using intravenous injection to direct the compound to the desired ocular tissue or cell. Directly injecting the liposome complex into the proximity of the retinal pigment epithelial cells or Bruch's membrane can also provide for targeting of the complex with some forms of ocular PCD. In a specific embodiment, the compound is administered via intra-ocular sustained delivery (such as VITRASERT or ENVISION). In a specific embodiment, the compound is delivered by posterior subtenons injection. In another specific embodiment, microemulsion particles containing the compositions of the invention are delivered to ocular tissue to take up lipid from Bruch's membrane, retinal pigment epithelial cells, or both.

For optical applications, nanoparticles are a colloidal carrier system that has been shown to improve the efficacy of the encapsulated drug by prolonging the serum half-life. Polyalkylcyanoacrylates (PACAs) nanoparticles are a polymer colloidal drug delivery system that is in clinical development, as described by Stella et al., *J. Pharm. Sci.*, 2000. 89: p. 1452-1464; Brigger et al., *Int. J. Pharm.*, 2001. 214: p. 37-42; Calvo et al., *Pharm. Res.*, 2001. 18: p. 1157-1166; and Li et al., *Biol. Pharm. Bull.*, 2001. 24: p. 662-665. Biodegradable poly (hydroxyl acids), such as the copolymers of poly (lactic acid) (PLA) and poly (lactic-co-glycolide) (PLGA) are being extensively used in biomedical applications and have received FDA approval for certain clinical applications. In addition, PEG-PLGA nanoparticles have many desirable carrier features including (i) that the agent to be encapsulated comprises a reasonably high weight fraction (loading) of the total carrier system; (ii) that the amount of agent used in the first step of the encapsulation process is incorporated into the final carrier (entrapment efficiency) at a reasonably high level; (iii) that the carrier have the ability to be freeze-dried and reconstituted in solution without aggregation; (iv) that the carrier be biodegradable; (v) that the carrier system be of small size; and (vi) that the carrier enhance the particles persistence.

Nanoparticles are synthesized using virtually any biodegradable shell known in the art. In one embodiment, a polymer, such as poly (lactic-acid) (PLA) or poly (lactic-co-glycolic acid) (PLGA) is used. Such polymers are biocompatible and biodegradable, and are subject to modifications that desirably increase the photochemical efficacy and circulation lifetime of the nanoparticle. In one embodiment, the polymer is modified with a terminal carboxylic acid group (COOH) that increases the negative charge of the particle and thus limits the interaction with negatively charge nucleic acid aptamers. Nanoparticles are also modified with polyethylene glycol (PEG), which also increases the half-life and stability of the particles in circulation. Alternatively, the COOH group is converted to an N-hydroxysuccinimide (NHS) ester for covalent conjugation to amine-modified aptamers.

Biocompatible polymers useful in the composition and methods of the invention include, but are not limited to, polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetage phthalate, carboxylethyl cellulose, cellulose triacetate, cellulose sulphate sodium salt, poly(methyl methacrylate), poly(ethylmethacrylate), poly(butylmethacrylate), poly(isobutylmethacryla-te), poly(hexlmethacrylate), poly(isodecylmethacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene, polyvinylpryrrolidone, polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutylmethacrylate), poly(hexlmethacrylate), poly(isodecl methacrylate), poly(lauryl methacrylate), poly(phenyl methacrylate), poly(methyl acrylate), poly(isopropyl acrylate), poly(isobutyl acrylate), poly(octadecl acrylate) and combinations of any of these. In one embodiment, the nanoparticles of the invention include PEG-PLGA polymers.

Compositions of the invention may also be delivered topically. For topical delivery, the compositions are provided in any pharmaceutically acceptable excipient that is approved for ocular delivery. Preferably, the composition is delivered in drop form to the surface of the eye. For some application, the delivery of the composition relies on the diffusion of the compounds through the cornea to the interior of the eye.

Those of skill in the art will recognize that the best treatment regimens for using compounds of the present invention to treat an ocular PCD can be straightforwardly determined. This is not a question of experimentation, but rather one of optimization, which is routinely conducted in the medical arts. In vivo studies in nude mice often provide a starting point from which to begin to optimize the dosage and delivery regimes. The frequency of injection will initially be once a week, as has been done in some mice studies. However, this frequency might be optimally adjusted from one day to every two weeks to monthly, depending upon the results obtained from the initial clinical trials and the needs of a particular patient.

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher doses may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Combination Therapies

Optionally, an angiogenic modulating therapeutic as described herein may be administered in combination with any other standard active angiogenic modulating therapeutics; such methods are known to the skilled artisan and described in *Remington's Pharmaceutical Sciences* by E. W. Martin. For example, an anti-angiogenic peptide of the invention may be administered in combination with any other anti-angiogenic peptide, or with known anti-angiogenic agent. Such agents are listed below (Folkman, *Annu Rev Med.* 57:1-18, 2006).

| Agent | Clinical Trials |
|---|---|
| 1. Alphastatin | |
| 2. Angiostatin | |
| 3. Arresten | |
| 4. Anti-thrombin III (truncated) | |
| 5. Canstatin | |
| 6. Endostatin | Phase II |
| 7. Fibulin-5 | |
| 8. Fragment of histidine-rich glycoprotein | |
| 9. Interferon-β | Phase III |
| 10. Maspin | |
| 11. 2-methoxyestradiol | Phase II |
| 12. PEX | |
| 13. Pigment epithelial-derived factor (PEDF) | |
| 14. Platelet factor 4 (PF4) | |
| 15. Semaphorin 3F | |
| 16. sFlt-1 | |
| 17. Tetrahydrocortisol | Phase III |
| 18. Thrombospondin-1 (and -2) | Phase II |
| 19. TIMP-2 | |
| 20. Troponin I | |
| 21. Tumstatin | |
| 22. Vasostatin | |

For the treatment of a neoplasia, a peptide of the invention (e.g., any one or more of those listed in Table 1) is administered in combination with any conventional treatment (e.g., chemotherapy, radiotherapy, hormonal therapy, surgery, cryosurgery). A pharmaceutical composition of the invention may, if desired, include one or more chemotherapeutics typically used in the treatment of a neoplasm, such as abiraterone acetate, altretamine, anhydrovinblastine, auristatin, bexarotene, bicalutamide, BMS184476,2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, thalidomide, tretinoin, vinblastine, vincristine, vindesine sulfate, and vinflunine. Other examples of chemotherapeutic agents can be found in *Cancer Principles and Practice of Oncology* by V. T. Devita and S. Hellman (editors), 6th edition (Feb. 15, 2001), Lippincott Williams & Wilkins Publishers.

Kits

The invention provides kits for the treatment or prevention of diseases or disorders characterized by excess or undesirable angiogenesis. In one embodiment, the kit includes a therapeutic or prophylactic composition containing an effective amount of one or more peptides of Table 1 (SEQ ID Nos. 1-156) in unit dosage form. In some embodiments, the kit comprises a sterile container that contains a therapeutic or prophylactic vaccine; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired a peptide of the invention is provided together with instructions for administering it to a subject having or at risk of developing excess or undesired angiogenesis. The instructions will generally include information about the use of the composition for the treatment or prevention of ischemia or for enhancing angiogenesis to a tissue in need thereof. In other embodiments, the instructions include at least one of the following: description of the expression vector; dosage schedule and administration for treatment or prevention of ischemia or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Methods of the Invention

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "*Molecular Cloning: A Laboratory Manual*", second edition (Sambrook, 1989); "*Oligonucleotide Synthesis*" (Gait, 1984); "*Animal Cell Culture*" (Freshney, 1987); "*Handbook of Experimental Immunology*" (Weir, 1996); "*Gene Transfer Vectors for Mammalian Cells*" (Miller and Calos, 1987); "*Current Protocols in Molecular Biology*" (Ausubel, 1987); "*PCR: The Polymerase Chain Reaction*", (Mullis, 1994); "*Current Protocols in*

*Immunology*" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

EXAMPLES

Example 1

Bioinformatics Approach to Identifying Angiogenesis Inhibitors

During the last two decades, a large number of endogenous regulators have been identified that either stimulate or inhibit the process of angiogenesis. Disturbance of the fine regulation of these stimulating and inhibiting elements leads to pathologic conditions. One of the hallmarks of cancer progression is the shift of these regulatory elements towards the pro-angiogenic components, often referred to as the angiogenic switch (Folkman, *Semin Oncol,* 29:15-8, 2002).

The angiogenesis-promoting regulatory elements include various growth factors. Growth factor signaling promotes the expression of extracellular matrix (ECM)-processing enzymes such as the freely diffusing and membrane-bound matrix metalloproteinases (MMPs), plasmin, and various serine, cysteine and aspartic acid proteinases (cathepsins). While the importance of these enzymes, particularly the cell-secreted proteases, in processing the extracellular matrix has been demonstrated both experimentally (Neri and Bicknell, *Nat Rev Cancer,* 5:436-46, 2005) and theoretically (Karagiannis and Popel, *J Biol Chem,* 279:39105-14, 2004), there are indications that this role may not be unique. Only recently has it been realized that the proteolytic processing of the ECM components results in the exposure of biologically active protein fragments, known as cryptic fragments (Davis et al., *Am J Pathol,* 156:1489-98, 2000). These fragments are fully functional moieties or include active sites within larger sequences that are normally hidden from the extracellular environment inside the structure of the ECM macromolecules. Proteolytic processing of the macromolecules reveals these fragments that, once released, can act as modulators of angiogenesis. Most of these fragments have anti-angiogenic and pro-apoptotic activities; they act as endogenous inhibitors of angiogenesis. Others have pro-angiogenic properties. The present invention is focused on angiogenesis inhibitors.

The amino-acid sequences of the known potent anti-angiogenic fragments were compiled after extensive searching of the relevant literature. In total 36 proteins with known anti-angiogenic and pro-apoptotic activities were found (Table 2).

TABLE 2

36 target sequences with anti-angiogenic or pro-apoptotic properties.

| | Length of known active domain | | |
|---|---|---|---|
| | 20-60 aa | 100-150 aa | >150 aa |
| Candidate antiangiogenic proteins or protein fragments | Endorepellin/LG3 | Angiostatin K5 | ADAMTS-1 |
| | Kininogen frg | BCA-1 | Angiostatin K1-4 |
| | PF-4 | Endostatin | Angiotensinogen |
| | Timp2/loop 6 | Gro-β | Antithrombin |
| | TSP1/Mal-II | Growth Hormone | Arresten |
| | TSP1/Mal-III | IP-10 | BAI-1 |

TABLE 2-continued 36 target sequences with anti-angiogenic or pro-apoptotic properties.

| | Length of known active domain | | |
|---|---|---|---|
| | 20-60 aa | 100-150 aa | >150 aa |
| | Tumstatin/Tum2 | I-TAC | BAI-2 |
| | Tumstatin/Tum3 | Kininogen/D5 | BAI-3 |
| | Tumstatin/Tum4 | Lactogen | Calreticulin |
| | Tumstatin/Tum7 | MIG | Canstatin |
| | | Prolactin | Kallistatin |
| | | | Maspin |
| | | | PEDF |
| | | | Restin |
| | | | Vastatin |

The proteins are categorized according to the information known about the length of the amino acid sequence within which their activity is localized. The proteins are listed alphabetically.

Based on the information inferred from the amino acid sequences of the known anti-angiogenic proteins, these proteins were systematically categorized by protein family. After observing that most of the known anti-angiogenic active domains were localized within conserved protein domains, the proteins were classified according to these conserved domains. Along with this classification, the information from the amino acid sequences of the active fragments was used to evaluate sequence similarities and predict novel proteins that likely induce anti-angiogenic effects.

These proteins were divided into three classes by length of known active fragment (i.e., 20-60 amino acids; 100-150 amino acids; or greater than 150 amino acids) according to the known information regarding the active fragment and the localization of their anti-angiogenic activity. Some of these thirty-six proteins have known "active domains," which have up to approximately 20 amino acids, that are known to exhibit potent anti-angiogenic activity. Others are protein fragments of 100-150 amino acids with identified activity but an unknown active domain, and still others are full-length proteins or large protein domains, having more than 150 contiguous amino acid sequences, that are known to be potent angiogenesis inhibitors.

The top 202 identified similarity hits for the proteins or protein fragments with known anti-angiogenic activity are displayed in Table 3. Of the 202 hits, some of which are duplicated among the queries, over 150 distinct novel anti-angiogenic protein segments. The queries that include the proteins from Table 2 are displayed in the first column and organized alphabetically. Among the Table 2 proteins, those with identified similarities and lengths of 20-60 amino acids were platelet factor-4, with 7 similar protein domains; various fragments of thrombospondin 1, each of which with 45 identified similar fragments; and various tumstatins, with approximately 5 similar fragments each. The proteins with identified similarities and lengths of 100-150 amino acids included the angiostatin kringles; the CXC chemokines Gro-β, IP-10, and MIG, each with approximately 8 top similar protein sites; growth hormone-1 and placental lactogen with 3 similar fragments each; as well as kininogen, with a single identified similarity. The hits are displayed along with their identification numbers and the corresponding part of their sequence that is similar. They are organized in three columns according to the degree of similarity with the query, in descending order of similarity. The similarity notations "identical," "highly similar," and "similar" correspond to the scaled score: Proteins with a score of 80-100% were "identical," 60-80% "highly similar" and 45-60% "similar."

TABLE 3

Sequences identified by similarity to pro-angiogenic polypeptides.

|  | Identical | Highly Similar | Similar |
|---|---|---|---|
| PF-4 |  | GCP-2/CXCL6 (AAH13744.1: 86-109) | GRO-β/CXCL2 (AAH15753, 1: 80-103) |
|  |  | ENA-78/CXCL5 (AAP35453.1: 86-108) | GRO-γ/MIP-2β/CXCL3 (AAA63184.1: 79-100 |
|  |  | GRO-α/CXCL1 (AAP35526.1: 80-103) | IL-B/CXCL8 (AAP35730, 1: 72-94) |
|  |  | THBG-β/CXCL7 (AAB46877.1: 100-121) |  |
| TIMP2/ LOOP 6 |  | TIMP 4 (AAV38433.1: 175-193) | TIMP 3 (AAA21815.1: 148-171) |
| TSP-1/ Mal-II | TSP-2 (CAI23645.1: 444-462) | THSD1 (AAQ88516.1: 347-365) | Properdin (AAP43692.1: 143-161) |
|  |  | WISP-1 (AAH74841.1: 221-238) | ADAMTS-9 (NP891550.1: 595-613) |
|  |  | BAI-2 (O60241: 304-322) | ADAMTS-10 (NP112219.2: 554-572) |
|  |  | ADAMTS-16 (Q8TE57: 1133-1149) | ADAMTS-14 (CAI13857.1: 980-994) |
|  |  | CILP (AAQ89263.1: 156-175) | ADAMTS-13 (AAQ88485.1: 751-765) |
|  |  | VSGP/F-Spondin (BAB18461.1; 621-639) | Papilin (AAH42057.1: 33-51) |
|  |  | BAI-3 (CAI21673.1: 352-370) | ADAMTS-1 (Q9UHI8: 566-584) |
|  |  | ADAMTS-18 (AAH83283.1: 1131-1146) | WISP-2 (AAQ89274.1: 199-216) |
|  |  | ADAMTS-2 (CAA05880.1: 982-998) | ADAMTS-4 (CAH72146.1: 527-540) |
|  |  | ADAMTS-3 (NP055058.1: 973-989) | ADAMTS-6 (NP922932.2: 847-860) |
|  |  | ADAMTS-9 (Q9P2N4: 1247-1261) | ADAMTS-8 (BAD92954.1: 62-75) |
|  |  | Semaphorin 5A (NP003957.1: 848-868) | ADAMTS-20 (CAD56160.2: 564-581) |
|  |  | TSRC1 (AAH27478.1: 140-159) | Semaphorin 5B (AAQ88491.1: 916-934) |
|  |  | Fibulin-6 (CAC37630.1: 1688-1706) | WISP-3 (CAB16556.1: 191-208) |
|  |  | CYR61 9 (AAR05446.1: 234-251) | THSD6 (AAH40620.1: 44-60) |
|  |  | ADAMTS-19 (CAC84565.1: 1096-1111) | THSD3 (AAH33140.1: 280-298) |
|  |  | ADAMTS-12 (CAC20419.1: 549-562) | NOVH (AAL92490.1: 211-228 |
|  |  | ADAMTS-20 (CAD56159.3: 1611-1675) | C6 (AAB59433.1: 30-48) |
|  |  | CTGF (CAC44023.1: 204-221) | UNC5D (AAQ88514.1: 259-277) |
|  |  | ADAMTS-18 (NP620685.2: 997-1013) | CILP-2 (AAN17826.1: 153-171) |
|  |  | ADAMTS-7 (AAH61631.1: 828-841) | ADaMTS-15 (CAC86014.1: 900-916) |
|  |  |  | ADAMTS-5 (NP008969.1: 882-898) |
|  |  |  | UNC5C (AAH41156.1: 267-285) |
| TSP-1/ Mal-III |  | ADAMTS-like 3 (NP_997400.1: 425-442) | Semaphorin 5B (AAQ88491.1: 731-747) |
|  |  | Fibulin-6 (CAC37630.1: 1574-1592) | VSGP/F-spondin (BAB18461.1: 621-639) |
|  |  | ADAMTS-18 (AAH63283.1: 1131-1147) | UNC5C (AAH41156.1: 267-285) |
|  |  | BAI-2 (O60241: 304-322) | TSRC1 (AAH71852.1: 140-156) |
|  |  | TSP-2 (CAI23645.1: 501-519) | Propordin (AAP43692.1: 143-161) |
|  |  | SCO-spondin (XP379967.2: 3781-3799) | ADAMTS-20 (CAD56160.2: 1309-1326) |
|  |  | ADAMTS-16 (Q8TE57: 1133-1150) | ADAMTS-7 (Q9UKP4: 545-563) |
|  |  | ADAMTS-12 (NP112217.2: 1480-1495) | WISP-1 (AAH74841.1: 221-237) |
|  |  | BAI-1 (O14514: 361-379) | ADAMTS-15 (Q8TE58: 848-863) |
|  |  | ADAMTS-like 1 (NP443098.2: 383-400) | THSD3 (AAJ01020.1: 333-351) |
|  |  | ADAMTS-16 (CAC86015.1: 593-611) | ADAMTS-17 (Q8TE56: 928-945) |
|  |  | Semaphorin 5A (NP003957.1: 660-878) | ADAMTS-3 (O15072: 973-989) |
|  |  | ADAMTS-4 (CAH72146.1: 527-545) | ADAMTS-19 (Q8TE59: 1096-1110) |
|  |  | ADAMTS-10 (Q9H324: 528-546) | ADAMTS-14 (CAI13857.1: 980-994) |
|  |  | Papilin (NP775733.2: 342-359) | ADAMTS-13 (AAQ88465.1: 751-765) |
|  |  | BAI-3 (CAI21673.1: 352-370) | TSRC1 (AAH27478.1: 267-283) |
|  |  | THSD1 (AAQ88516.1: 347-365) | ADAMTS-like 2 (AAH50544.1: 54-72) |
|  |  | ADAMTS-7 (AAH61631.1; 1576-1592) | UNC5B (NP891550.1: 595-613) |
|  |  | ADAMTS-20 (CAD56159.3: 1478-1494) | ADAMTS-5 (NP008969.1: 576-588) |
|  |  | ADAMTS-1 (Q9UHI8: 566-584) | THSD6 (AAH40620.1: 44-60) |
|  |  | CILP (AAQ89263.1: 156-175) | C6 (AAB59433.1: 30-48) |
|  |  | VSGP/F-spondin (BAB18461.1: 567-583) | CILP-2 (AAN17826.1: 153-171) |
|  |  | ADAMTS-8 (Q9UP79: 534-552) | CTGF (CAC44023.1: 204-220) |
|  |  | ADAMTS-6 (NP922932.2: 847-863) | CYR61 (AAR05446.1: 234-250) |
|  |  | UNC5D (AAQ88514.1: 259-277) | WISP-3 (CAB16556.1: 191-207) |
|  |  | ADAMTS-9 (Q9P2N4: 1335-1351) | WISP-2 (AAQ89274.1: 199-215) |
|  |  | ADAMTS-18 (CAC83612.1: 997-113) |  |
| Tum2 | α1(CIV) (CAH74130.1: 1479-1556) | α2(CIV) (CAH71366.1: 1517-1593) | α4(CIV) (CAA56943.1: 1499-1575) |
|  | α5(CIV) (AAC27816.1: 1495-1572) | α6(CIV) (CAI40758.1: 1501-1577) |  |
| Tum3 | α5(CIV) (AAC27816.1: 1510-1529) | α6(CIV) (CAI40758.1: 1516-1535) | α4(CIV) (CAA56943.1: 1514-1533) |
|  | α1(CIV) (CAH74130.1: 1494-1513) | α2(CIV) (CAH71366.1: 1532-1551) |  |
| Tum4 | α5(CIV) (AAC27816.1: 1626-1644) | α2(CIV) (CAH71366.1: 1646-1664) | ADAM-12 (O43184: 662-674) |
|  | α1(CIV) (CAH74130.1: 1610-1628) | α6(CIV) (CAI40758.1: 1630-1648) | ADAM-9 (13443: 649-661) |
|  |  | α4(CIV) (CAA56943.1: 1628-1646) |  |
| Tum7 | α1(CIV) (CAH74130.1: 1504-1523) | α6(CIV) (CAI40758.1: 1526-1545) |  |
|  | α5(CIV) (AAC27516.1: 1520-1539) | α2(CIV) (CAH71366.1: 1542-1561) |  |
|  |  | α4(CIV) (CAA58943.1: 1524-1543) |  |

TABLE 3-continued

Sequences identified by similarity to pro-angiogenic polypeptides.

| | Identical | Highly Similar | Similar |
|---|---|---|---|
| Angio-statin K1 | | Macrophage stim. 1 (AAH48330.1: 368-448)<br>Thrombin/cf II (AAL77436.1: 106-186)<br>HGF (P14210: 127-206)<br>LP(a) (NP005568.1: 4123-4201) | tPA (AAO34406.1: 213-286)<br>ROR-1 (CAH71706.1: 312-392)<br>ROR-2 (Q01974: 315-394)<br>KREMEN-1 (BAB40969.1: 31-115)<br>Hyaluronan binding (NP004123.1: 192-276)<br>Hageman fct/cf XII (AAM97932.1: 215-296) |
| Angio-statin K2 | | HGF (P14210: 304-383)<br>Macrophage stim. 1 (AAH48330.1: 188-268)<br>Lp(a) (NP005568.1: 3560-3639) | AK-38 protein (AAK74187.1: 11-93)<br>ROR-1 (CAH71706.1: 310-391)<br>Thrombin/cf II (AAL77436.1: 105-186)<br>ROR-2 (Q01974: 314-394)<br>tPA (AAO34406.1: 214-296)<br>KREMEN-2 (BAD97142.1: 35-119) |
| Angio-statin K3 | Lp(a) (NP005568.1: 1615-1690) | HGF (P14210: 304-377)<br>Macrophage stim. 1 (AAH48330.1: 370-448) | AK-38 protein (AAK74187.1: 13-90)<br>ROR-2 (Q01974: 314-391)<br>ROR-1 (CAH71706.1: 311-388)<br>Thrombin/cf II (AAL77436.1: 107-183)<br>Hageman fct/cf XII (AAM97932.1: 216-292)<br>KREMEN-1 (BAB40969.1: 31-114)<br>tPA (AAO3446.1.1: 214-293) |
| Angio-statin K4 | Lp(a) (NP005568.1: 4225-4308) | HGF (P14210: 304-383)<br>AK-38 protein (AAK74187.1: 12-94)<br>Macrophage stim. 1 (AAH48330.1: 368-449)<br>ROR-2 (Q01974: 314-395) | ROR-1 (CAH71706.1: 311-391)<br>Thrombin/cf II (AAL77436.1: 107-186)<br>KREMEN-1 (BAB40969.1: 31-114)<br>tPA (AAO34406.1: 213-297)<br>Hageman fct/cf XII (AAM97932.1: 214-295)<br>Hyaluronan binding (NP004123.1: 192-277) |
| Angio-statin K5 | Lp(a) (NP005568.1: 1615-1690)<br>AK-38 protein (AAK74187.1: 14-93) | Macrophage stim. 1 (AAH48330.1: 370-448) | HGF (P14210: 127-207)<br>Tpa (AAM52248.1: 5-89)<br>Thrombin/cf II (AAL77436.1: 105-186)<br>ROR-2 (Q01974: 315-395)<br>ROR-1 (CAH71706.1: 313-391)<br>KREMEN-1 (BAB40969.1: 31-114)<br>KREMEN-2 (BAD97142.1: 34-119)<br>Hageman fct/cf XII (AAM97932.1: 214-295) |
| Gro-β/CXCL2 | GRO-γ/MIP/2β/CXCL3 (AAA63184.1: 43-100)<br>GRO-α/CXCL1 (AAP35526.1: 44-101) | THBG-β/CXCL7 (AAB46877.1: 64-121)<br>ENA-78/CXCL5 (AAP35453.1: 51-107) | GCP-2/CXCL6 (AAH13744.1: 51-107)<br>MIG/CXCL9 (Q07325: 91)<br>PF-4/CXCL4 (AAK29643.1: 43-100)<br>IL-8/CXCL8 (AAP35730.1: 35-94) |
| GH-1 | GH-2 (CAG46700.1: 260-160)<br>Placental lactogen (AAP35572.1: 26-160)<br>Somatoliberin (gi225905: 26-145) | | |
| IP-10/CXCL10 | | | GCP-2/CXCL6 (AAH13744.1: 47-106) |
| Kininogen | | | Hemopexin (P02780: 233-246) |
| Lactogen | GH-1 (NP000506.2: 26-160)<br>GH-2 (CAG46700.1: 26-160) | Somatoliberin (gi225905: 26-145) | |
| MIG/CXCL9 | | | Gro-β/CXCL2 (AAH15753.1: 42-97)<br>GRO-γ/MIP-2β/CXCL3 (AAA63184.1: 41-96)<br>ENA-78/CXCL5 (AAP35453.1: 48-103)<br>GRO-α/CXCL1 (AAP35526.1: 42-97)<br>THBG-β/CXCL7 (AAB46877.1: 62-117)<br>IP-10/CXCL10 (AAH10954.1: 29-86)<br>GCP-2/CXCL6 (AAH13744.1: 48-103) |

Table 3 shows identified similarity hits with respect to the proteins or protein fragments with known anti-angiogenic activity. Similarities with the anti-angiogenic proteins or protein fragments of 20-60 amino acids (PF-4, TIMP-2/loop6, TSPs, and Tums) and of 100-150 amino acids (angiostatin kringles, CXCs, somatotropins and kininogen) were identified in a BLAST search against the human proteome. The results were filtered and similarities, based on a scaled score, of 80-100% are identified as "identical," 60-80% as "highly similar," and 45-60% as "similar." The queries (first column) are listed alphabetically. The hits are displayed with their identification number and the corresponding part of their sequence that is identical. They are organized according to the degree of similarity with the query.

In order to identify the conserved domains present within a query sequence, the NCBI's conserved domain (CD) search option (Marchler-Bauer and Bryant, *Nucleic Acids Res,* 32:W327-31, 2004) was used as part of the protein BLAST algorithm. The EMBL's SMART (Letunic et al., *Nucleic Acids Res,* 32:D142-4, 2004) sequence analysis was then used to identify conserved domains. Information for each hit, including localization within the protein as well as the protein's biological function, was collected using the EMBL's Harvester database (Liebel et al., *Bioinformatics,* 20:1962-3, 2004). In the case of proteins with known active domains, the total query protein sequence was used and not just the 20-amino acid fragment. Subsequently, the active domains were localized within the query and classified as to whether they belonged to or included specific conserved domains.

For sequence similarity searches, the p-BLAST algorithm was used. Each search was performed for human proteins using the default options of the algorithm, except that the expectation value was increased from 10 to 1000 and the word size was decreased from 3 to 2. These modifications were made because the small length of some queries (15-20 amino acids) suggested that results calculated using these low-level criteria might be significant and therefore should not be rejected ab initio. Proteins with significant similarities were initially identified using these low-level criteria. For each of the queries, approximately 1000 initial hits having sequence similarity were identified. The results included high-similarity hits, such as the maternal protein from which the anti-angiogenic fragment originated, as well as intermediate and low-level similarity results.

A Monte Carlo-type algorithm was used to filter the initial hits once the e-values of the results as provided by the NCBI's p-BLAST were considered. The proteins with e-values smaller than 0.1 where collected. Given that these hits were found using the p-BLAST search, there was some evidence for similarity between the query and the hit. It was therefore reasonable to expect that the score for the alignment of a truly similar p-BLAST hit with the initial query would be higher than the scores obtained by aligning a random sequence of amino acids with this same p-BLAST hit.

By conserving the amino acid composition of the initial query, i.e. the original anti-angiogenic protein, and after randomly permuting the amino acid locations, a set of 100 new random sequences for each of the queries was created. These random sequences were later used to determine a cut off value designating the random vs. non random identities. The cut-off value for a random alignment was determined as follows. A set of 100 random sequences was created for each of the queries by randomly altering an amino acid position within each sequence. The similarity of each of these 100 artificial sequences to each of the initial p-BLAST hits was calculated and the resulting scores were fitted to an extreme value distribution probability density function. This distribution describes the probability that the alignment score is a random hit, rather than a significant hit. The scores for the original protein's local alignment with each of the p-BLAST hits was then superimposed on the scores of each of the random sequences, and those having scores greater than the random sequence cut-off value were retained. The percentage identity score of the random sequences was less than 20%. The sequences with score greater than 50% only were retained. As significant identity, a score greater than 80% was considered.

Local alignments were performed with the Smith-Waterman algorithm using the BLOSUM 50 substitution matrix as the scoring matrix. The BLOSUM 50 matrix identifies highly similar proteins that are likely to share similar overall structure whether they have distant evolutionary origins or are closely related sequences (Pearson, *Methods Mol Biol*, 132: 185-219, 2000). The resulting score for each alignment, in bits, was scaled using as a scaling factor the score of the alignment of the initial query with itself. As a threshold for similarity a scaled score above 40% was used. All the algorithms were implemented in Matlab (Mathworks, Natick, Mass.).

The results in Table 3 are presented in the three sections corresponding to the classifications shown in Table 1: (1) anti-angiogenic proteins with a conserved domain and known active fragment; (2) anti-angiogenic proteins with a conserved domain and unknown active fragment; and (3) anti-angiogenic proteins without conserved domains. The top 202 identified similarity hits for the proteins or protein fragments with known anti-angiogenic activity are displayed in Table 3. The first column includes the query sequence.

Anti-Angiogenic Proteins with a Conserved Domain and Known Active Fragment

Based on the characteristic domains contained within the anti-angiogenic fragments or containing these fragments, eight protein families with established anti-angiogenic effects were identified. These protein families are: the type 1 thrombospondin containing proteins, the C-X-C chemokines, the collagens, the somatotropins, the serpins, the Laminin Globular (LG) domain containing proteins, the kringle containing proteins and the complement component 1 (C1q) containing proteins. Others that do not contain a characteristic domain, such as the tissue inhibitors of metalloproteinases (TIMPs) were also identified. While each of these proteins may contain multiple conserved domains, the proteins are categorized here by the conserved domain that is most likely to have anti-angiogenic activity based on its proximity to a known anti-angiogenic sequence. Once the proteins were categorized by characteristic domains, they were compared to all the known human protein sequences that contain the same conserved domains, and the results were clustered based on similarity criteria.

Proteome Query

The identification of similarities was also extended beyond the proteins with similar conserved domains to all of the proteome. Thus, the conserved domains identified in the first column of Table 3, were used to query all sequences present in the human proteome; the results were filtered in order to identify truly similar hits. The result of this procedure was the identification of a set of peptides that may exert anti-angiogenic effects, based on similarity to the known active fragments of the anti-angiogenic proteins listed in Table 1. This set of identified anti-angiogenic proteins/peptides is displayed in Table 3. The function of these proteins, including their anti-angiogenic properties, is described below.

Anti-Angiogenic Peptides Related to Thrombospondins

Thrombospondins (TSPs) 1 and 2 are matricellular proteins with the well-characterized ability to inhibit angiogenesis in vivo and to inhibit the migration and proliferation of cultured microvascular endothelial cells in vitro (Carpizo and Iruela-Arispe, *Cancer Metastasis Rev*, 19:159-65, 2000; de Fraipont et al., *Trends Mol Med*, 7:401-7, 2001). Angiogenesis in developing tumors and in various models of wound healing is diminished or delayed by the presence of thrombospondin 1 or 2 (de Fraipont et al., *Trends Mol Med*, 7:401-7, 2001). Both of these proteins have similar structural organizations and contain three copies of a similar conserved domain, the type I TSP domain. These conserved domains are designated TSP1.1, TSP1.2 and TSP1.3, starting at the amino terminus, according to their localization within the thrombospondin sequence. Other proteins with known anti-angiogenic properties and type I TSP domains, include the Brain-specific Angiogenesis Inhibitors (BAI-1, BAI-2 and BAI-3) and the ADAMTS-1 and 8 (METH-1 and METH-2). BAI-1, a known potent angiogenesis inhibitor, which contains five TSP1 domains while BAI-2 and BAI-3 have four. ADAMTS-1/METH-1 contains three TSP1 domains and ADAMTS-8/METH-2 two.

BAI-1 is a p53 inducible gene (Nishimori et al., *Oncogene*, 15:2145-50, 1997), that encodes a transmembrane protein that is primarily expressed in normal but not cancerous brain tissue. BAI-1 is proteolytically cleaved at a conserved domain, the G-protein coupled receptor proteolytic cleavage site (GPS), releasing a 120 kDa extracellular fragment, vasculostatin (Kaur et al., *Oncogene,* 24:3632-42, 2005). Vasculostatin contains all five TSP1 domains and exhibits potent anti-angiogenic activity (Koh et al., *Exp Cell Res,* 294:172-84, 2004).

ADAMTS-1/METH-1 and ADAMTS-8/METH-2 belong to the metallospondin family of proteins, a growing family of matrix metalloproteinases (MMPs). These two proteins show similarities to the reprolysin subfamily, which includes the ADAM proteins. METH-1 and METH-2 display anti-angiogenic properties and inhibit endothelial cell proliferation (Iruela-Arispe et al., *Ann N Y Acad Sci,* 995:183-90, 2003; Luque et al., *J Biol Chem,* 278:23656-65, 2003; Rodriguez-Manzaneque et al., *J Biol Chem,* 275:33471-9, 2000; Vazquez et al., *J Biol Chem,* 274:23349-57, 1999). The catalytic activity of METH-1 has been experimentally shown to be required for its anti-angiogenic effects, although TSP1 repeats alone are able to suppress VEGF-induced angiogenesis in vitro (Luque et al., *J Biol Chem,* 278:23656-65, 2003). These results indicate that there are at least two potential mechanisms to account for the METH-1 activity. It is hypothesized that the catalytic domain is required for the cleavage and release of the TSP1 domains, either directly in an autocatalytic manner or indirectly after binding to another METH-1 and cleaving its active fragment (Iruela-Arispe et al., *Ann N Y Acad Sci,* 995:183-90, 2003).

Another of the known anti-angiogenic proteins with TSP1 domains, thrombospondin 1, has been extensively mapped and its activity has been localized (Tolsma et al., *J Cell Biol,* 122:497-511, 1993). Several peptides derived from thrombospondin 1 have been shown to possess anti-angiogenic properties. The pro-collagen domain of the protein has been shown to exert anti-migrational effects, whereas the two active domains MAL-II and MAL-III, residing within the TSP1.2 and TSP1.3 conserved domains, respectively, are anti-angiogenic (Tolsma et al., *J Cell Biol,* 122:497-511, 1993).

Given that the TSP1 conserved domain is the main locus of anti-angiogenic activity in TSP1-containing proteins, the similarity between all the known TSP1 domains in the proteome and thrombospondin's 1 TSP1.2 and TSP1.3 was queried. These two domains, as well as the corresponding active fragments MAL-II and MAL-III, exhibit high similarity to the TSP1 conserved domains of hemicentin, semaphorin 5A and 5B, and a plethora of ADAMTS enzymes including ADAMTS-2, 4, 6, 7, 10, 12, 13, 14, 16, and 20 (FIG. 1). Similarities were also identified within papilin, CILP-2 and the netrin receptors UNC-5B, 5C, and 5D. The TSP1.1 domain of thrombospondin 1 shares no similarity with any of these proteins (FIG. 1).

TSP1.1 of the ADAMTS Proteins

The high similarity of the TSP1.1 of the ADAMTS proteins with MAL-II and MAL-III indicates that this specific domain is likely to act as a potent anti-angiogenic regulator. The first type I TSP motif is not clustered with the other domains, but is positioned upstream from the other TSP1 domains, which are usually clustered downstream. This unique localization presumably makes it more accessible to cleavage. Furthermore, in most of the ADAMTS molecules the TSP1.1 domain is located near a cysteine-rich, also conserved, domain that functionally regulates the binding affinity of the molecule.

Hemicentin (Fibulin 6), CILP-1 and 2, Papilin, and UNCs

The above-described strategy also identified the following proteins: hemicentin (fibulin 6), CILP-1 and 2, papilin, and UNCs, which are of particular interest. Hemicentin is a membrane-bound cell adhesion molecule with 48 tandem Ig modules. Hemicentin is expressed in fibroblasts, retinal pigment epithelial cells, and endothelial cells. It affects the mechanical stabilization of the germline syncytium, the anchorage of mechanosensitive neurons to the epidermis and the organization of hemidesmosomes. Cartilage Intermediate Layer Protein 1 and 2 (CILP-1 and CILP-2) are primarily expressed in articular chondrocytes and are secreted proteins that affect the cartilage scaffolding; papilin is a proteoglycan sulfated protein. UNCs are transmembrane netrin receptors that direct axon extension and migration during neural development. Because of their high similarity to the anti-angiogenic fragments of thrombospondin 1, fragments of these proteins represent potential angiogenesis inhibitors.

TSP1.2 of BAI-2 and BAI-3 and TSP1.3 of BAI-1

Although BAIs have been shown to exhibit anti-angiogenic activity, this activity has not been previously localized within the molecule. The sequence similarities of each of the BAI's TSP1 domains to the analogous domains of MAL-II and MAL-III and the clustering of similarities of BAIs with the predicted hits obtained using the MAL sequences (FIG. 1) suggest that the second TSP1 domain (TSP1.2) of BAI-2 and BAI-3 and the third TSP1 domain of BAI-1 is likely to have anti-angiogenic acitivity. TSP1.2 shows diffuse similarity with most of the predicted proteins (FIG. 1). The BAI-2 TSP1.2 domains are also highly similar to thrombospondin's 1 TSP1.2 while the BAI-3 TSP1.2 domain is similar to thrombospondin's 1 TSP1.2 and TSP1.3. For BAI-1, it is the third thrombospondin domain (TSP1.3) that exhibits similarity.

WISP-1, F-Spondin, Properdin, C6, NOVH and CYR61

Finally, a BLAST search of the active domains MAL-II and MAL-III against the whole proteome, identified a number of hits that included proteins with TSP conserved domains (Table 2). These hits include WISP-1, F-spondin, properdin, the complement component C6, the neuroblastoma expressed-NOVH and CYR61 (Table 3). WISP-1, NOVH, and CYR61 belong to the connective tissue growth factor family and have been previously identified as having pro-angiogenic activity. Based on their similarity to the anti-angiogenic MAL-II and MAL-III, the results reported herein indicate that proteolytic processing of these proteins is likely to yield angiostatic fragments.

CXC Proteins

The second cluster of proteins belongs to the CXC protein family and contains the CXC conserved domain. These proteins include the Platelet Factor 4 (PF-4/CXC ligand 4), the Monochine Induced by Gamma interferon (MIG/CXC ligand 9), the Interferon gamma induced Protein 10 (IP-10/CXC ligand 10), the Interferon inducible T-cell Alpha Chemoattractant (ITAC/CXC ligand 11) and the B-Cell Attracting Chemokine 1 (BCA-1/CXC ligand 13) (Belperio et al., *J Leukoc Biol,* 68:1-8, 2000; Romagnani et al., *Trends Immunol,* 25:201-9, 2004; Strieter et al., *Semin Cancer Biol,* 14:195-200, 2004).

CXC chemokines are heparin-binding proteins that contain four conserved cysteines, with the first two separated by a non-conserved residue (i.e. C-X-C). The N-terminal portion of most CXC chemokines contains three amino acid residues, Glu-Leu-Arg (ELR); this ELR motif precedes the first cysteine of the primary structure of these cytokines. It has been speculated that CXC cytokines that contain the ELR motif ($ELR^+$) are potent promoters of angiogenesis (Romagnani et al., *Trends Immunol,* 25:201-9, 2004); in contrast, those lacking the ELR motif ($ELR^-$) are potent inhibitors of angiogenesis (Romagnani et al., *Trends Immunol,* 25:201-9, 2004). However, it has also been shown that in Lewis lung carcinoma cells, an $ELR^+$ protein, the beta GRO protein (CXC ligand 2) is an angiogenesis inhibitor (Cao et al., *J Exp Med,* 182:2069-77, 1995).

The most well-studied CXC angiostatic protein is PF-4 (Bikfalvi, *Semin Thromb Hemost*, 30:379-85, 2004; Bikfalvi and Gimenez-Gallego, *Semin Thromb Hemost*, 30:137-44, 2004). The ability of PF-4 to bind heparin and heparan sulfate glycosaminoglycans (GAGs) with high affinity appears to be important for several of its biological functions. PF-4 inhibits endothelial cell migration, proliferation, and in vivo angiogenesis in response to bFGF and VEGF by binding to their receptors or by forming PF4-VEGF and PF4-bFGF heterodimers that impair the binding of growth factors to their receptors (Bikfalvi, *Semin Thromb Hemost*, 30:379-85, 2004). There are several known isoforms of PF-4; the numbering here refers to the originally reported sequence (Deuel et al., *Proc Natl Acad Sci USA*, 74:2256-8, 1977). The PF-4$^{17-70}$ fragment is the naturally occurring fragment produced by proteolytic processing of full length PF-4 by elastase. The 1-17 amino acid domain remains attached to the cleaved protein through a disulfide bond. PF-4$^{47-70}$/CTF, the C-terminal fragment of full-length PF-4, is a very potent angiostatic fragment (Bikfalvi and Gimenez-Gallego, *Semin Thromb Hemost*, 30:137-44, 2004). This fragment is contained within the CXC conserved domain.

Figure 2A:
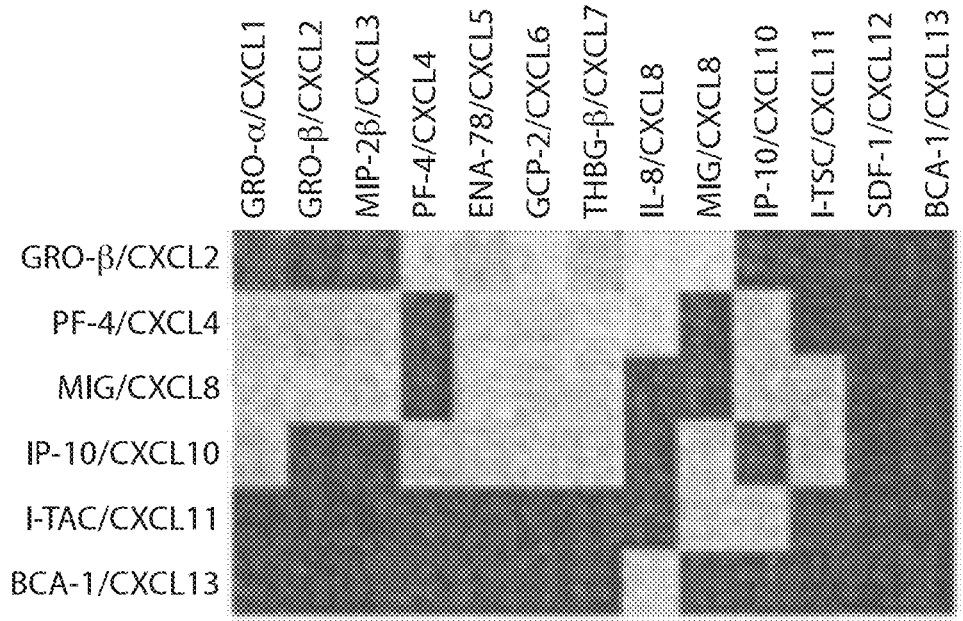
FIGS. 2A-2E show scaled similarity scores (bits) for different families of proteins classified based on the existence of a common conserved domain.

The active fragment of other CXC family members has not been previously identified. Hypothesizing that a peptide fragment having anti-angiogenic activity resides within their CXC conserved domains, the similarities of each of these CXC domains with the corresponding domains of putative anti-angiogenic proteins was determined. The CXC domain of GRO-β, although an ELR$^+$ protein, is considered to be anti-angiogenic as well. FIG. 2A illustrates the notably high similarity between the CXC domains of known angiostatic proteins and those of ELR$^+$ proteins such as GRO-α, GRO-β, ENA-78 and GCP-2. This similarity suggests that even though the full-length proteins may be angiogenic, fragments within their CXC domains are angiostatic PF-4's anti-angiogenic activity was localized to a specific portion of the CXC domain and the sequence of this active fragment was used to search for similar protein fragments. These similarities were identified first for the pool of all CXC domains and then for the total human proteome. Surprisingly, the active domain of PF-4 was found to share similarity with fragments of the CXC domains of GRO-α, GRO-β, GCP-2, ENA-78, and THBG-2 (FIG. 2A), which are ELR$^+$ proteins, providing support for the proposition that fragments of these proteins may be anti-angiogenic.

A BLAST search of the active domain of PF-4 against the whole proteome was performed and the results of this search were filtered using the Monte Carlo algorithm. These results are summarized in Table 3. Excluding the CXC-related proteins, the hits include the CC motif chemokines 1, 2, and 19 and lymphotactin, all of which exhibited relatively low similarities but were still above the similarity threshold. Finally, the CXC domains of the chemokines with known anti-angiogenic activities, but unknown active fragments are also searched against the proteome and the results are filtered. The results indicated that the CXC domain of BCA-1 shares similarities with proteins other than CXC, such as the CC motif ligands 3, 7, and 13. The corresponding domains of the other members of the CXC family showed no significant similarities.

Collagen Type IV-Derived Fragments

A significant source of anti-angiogenic fragments is the non-collagenous/NC1 domain of various type IV-collagen α fibrils. There are six type IV-collagen α fibrils; α1-α6. Each is composed of a cysteine-rich 7S domain at the N-terminal of the protein, which is involved in the covalent assembly of four type IV collagen fibers into a planar macrostructure; a central triple-helical collagenous domain; and a C-terminal NC1 domain, that is involved in the self-assembly of α chains into heterotrimers. The α1 and α2 chains are the predominantly expressed forms in most of the tissues; the α3-α6 are found in specialized basement membranes.

Fragments of α1(CIV) NC1 (arresten) (Colorado et al., *Cancer Res*, 60:2520-6, 2000), α2(CIV) NC1 (canstatin) (Kamphaus et al., *J Biol Chem*, 275:1209-15, 2000), α3(CIV) NC1 (tumstatin) (Maeshima et al., *J Biol Chem*, 276:15240-8, 2001) have been shown to inhibit angiogenesis and tumor cell proliferation, although the corresponding domains of the rest of the α(CIV) fibrils have not yet been shown to exhibit similar properties. From the aforementioned domains, the anti-angiogenic property of tumstatin has been localized to four specific fragments of α3(CIV) NC1: Tum2, Tum3, Tum4, and Tum7 (Maeshima et al., *J Biol Chem*, 275:21340-8, 2000; Maeshima et al., *J Biol Chem*, 276:31959-68, 2001).

The NC1 domains of all the type IV collagen α fibrils comprise two copies of the conserved C-terminal tandem repeated in the type IV procollagen domain, C4.1 and C4.2. Surprisingly, the active domains of tumstatin can be localized within and do not span both of the conserved domains. Each of them independently belongs to either C4.1 or C4.2. Moreover, the most potent fragments, Tum2, Tum3, and Tum7, are localized only to C4.1 while the remaining Tum4 to C4.2.

Figure 2B:
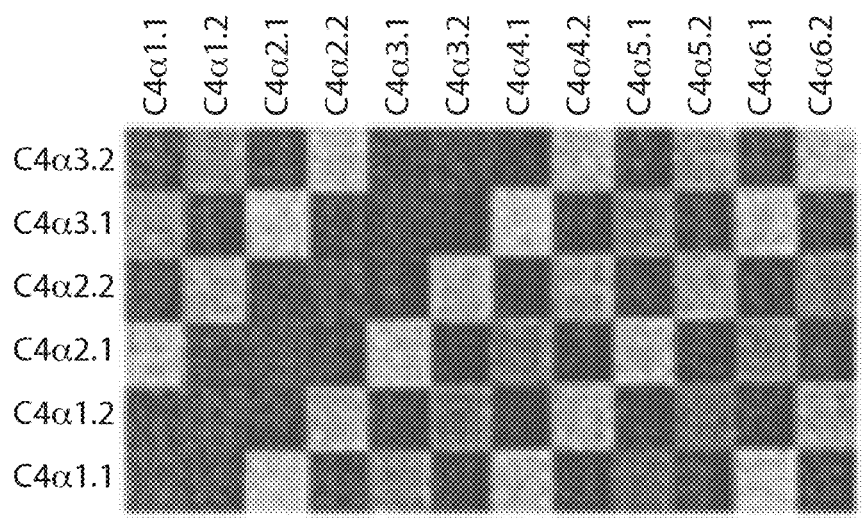

A bioinformatics approach was used to test the similarities of the various C4 domains of all the type IV collagen α fibrils to the active fragments of tumstatin. Similarity criteria were used to predict (FIG. 2B) that the C4.1 domains of α5 and α6 fibrils might exhibit anti-angiogenic effects. It is likely that their angiostatic potential resides within the specific fragment of the NC1 domain and not the total sequence. Furthermore, each of the C4.1 and C4.2 domains was found to bear similarity only to the corresponding domains of the collagen fibrils (FIG. 2B).

When tumstatin's active domains were compared with the whole proteome, only Tum4 produced significant hits. It shares similarity with ADAM-9 and ADAM-12 and to a lower degree with tenascin C. ADAM-9 and -12 are membrane-anchored proteins implicated in a variety of biological processes involving cell-cell and cell-matrix interactions, including fertilization, muscle development, and neurogenesis. For both of these proteins, the similarity regions are localized to the extracellular portion of the molecule. Tenascin C is a substrate adhesion molecule that appears to inhibit cell migration and is a ligand for most of the integrins. From its sequence similarity to tumstatin it also appears that a fragment of the molecule may be anti-angiogenic.

Anti-Angiogenic Proteins with a Conserved Domain and Unknown Active Fragment

In all of the aforementioned protein families, at least one member has a known active domain, and the anti-angiogenic activity was localized within an approximately 20-amino acid domain. This information was used to predict the function of similar domains in related family members. In addition, using information regarding the site of the active domain, similarities were identified with other members of the protein family as well as with more distantly related proteins that possessed this domain.

Below, protein families are classified by their conserved domains. These proteins have been shown to exhibit anti-angiogenic effects, but their active domains have not yet been localized. It is likely that their active domains are hidden within the sequence of their common conserved domains and similarities were identified based on this hypothesis. The fact that these queries have thus far identified anti-angiogenic activity within these conserved domains supports this hypothesis.

Serpins

Serine proteinase inhibitors (serpins) modulate the activity of serine proteinases that function in coagulation, fibrinolysis, complement activation, and phagocytosis (van Gent et al., *Int J Biochem Cell Biol,* 35:1536-47, 2003). Members of this family with potent angiostatic activity include Pigment Epithelium Derived Factor (PEDF), maspin, antithrombin, kallistatin and a fragment of angiotensinogen.

Figure 2C:
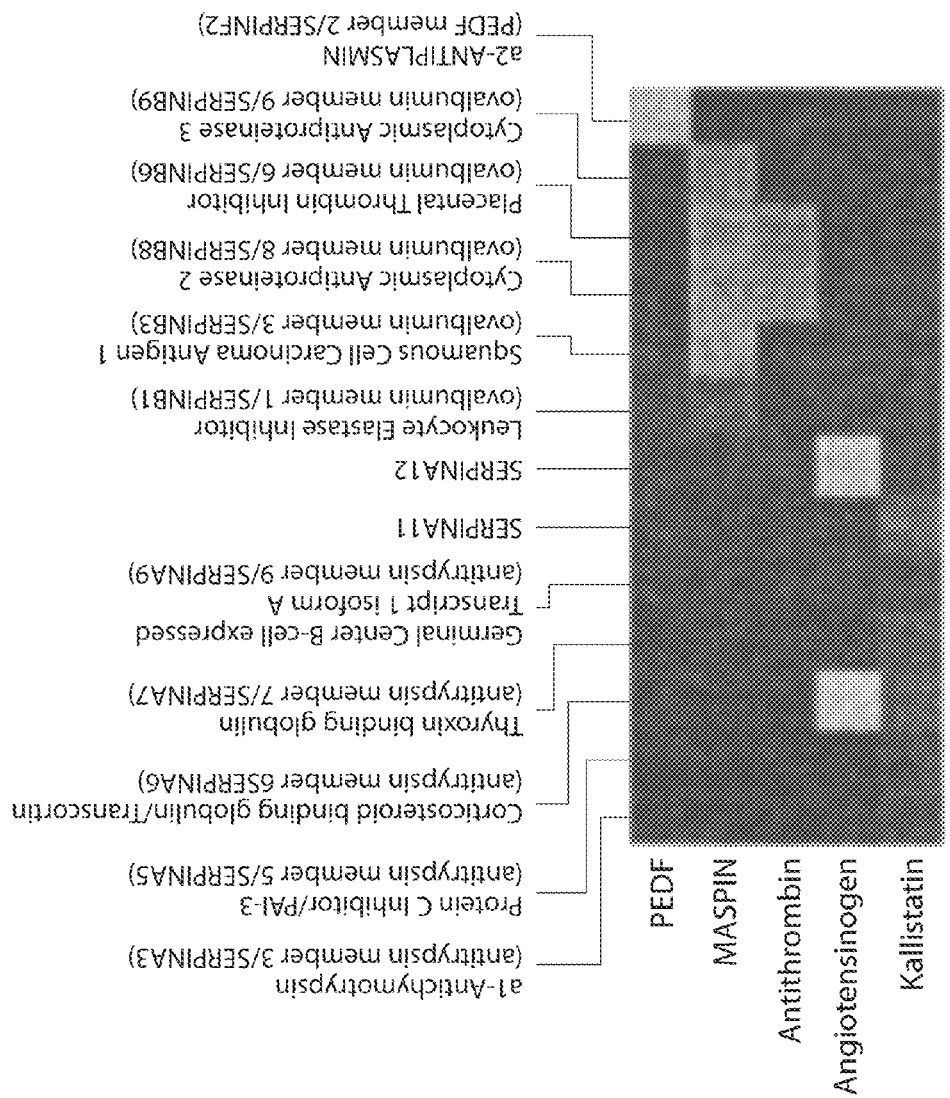

The anti-angiogenic activity of PEDF selectively effects newly forming vessels, while sparing existing vessels (Bouck, *Trends Mol Med,* 8:330-4, 2002). In vivo, PEDF blocks angiogenesis that has been induced in the retina by ischemia or by growth factors in the cornea. In both cases, PEDF causes endothelial cells involved in forming new vessels to initiate apoptosis (Abe et al., *Am J Pathol,* 164:1225-32, 2004). PEDF's serpin domain is unique; it does not share significant similarity with any other serpin domain and shares only minor similarity with α2 antiplasmin's serpin (FIG. 2C). Both of the proteins belong to the same clade, clade F of the serpins. α2 antiplasmin is a serine protease inhibitor that inhibits plasmin and trypsin and inactivates chymotrypsin. Recently, two functional anti-angiogenic protein sites were identified in PEDF: a 34 amino acid sequence and a TGA domain of 10 amino acids were shown to be responsible for the anti-angiogenic properties of the protein (Filleur et al., *Cancer Res,* 65:5144-52, 2005). These sites extend beyond the serpin domain. The 34 amino acid sequence and the TGA domain sequence were used to directly search for similarities with other proteins within the proteome. Interestingly, this search yielded no similarity hits. PEDF is unique at both the level of its serpin domain and of its anti-angiogenic protein sites.

Maspin (mammary serpin) is a member of the serpin super family and a novel protease inhibitor related to other inhibitors such as plasminogen activator inhibitor and α1-antitrypsin, as well as to non-inhibitor serine proteins such as ovalbumin (Maass et al., *Acta Oncol,* 39:931-4, 2000). In vitro invasion assays have demonstrated that endogenous and exogenous maspin inhibits invasion of endothelial cells through the basement membrane matrix (Maass et al., *Acta Oncol,* 39:931-4, 2000; Schaefer and Zhang, *Curr Mol Med,* 3:653-8, 2003). Maspin belongs to clade B of the serpins, and is similar in its conserved domain to leukocyte elastase inhibitor, squamous cell carcinoma antigen 1, cytoplasmic antiproteinases 2 and 3, and placental thrombin inhibitor (FIG. 2C). Interestingly, these proteins are all cytoplasmic. The squamous cell carcinoma antigen is secreted into plasma by tumor cells. These proteins exhibit serine-type endopeptidase inhibitor activity. Leukocyte elastase inhibitor regulates the activity of the neutrophil proteases elastase, cathepsin G and proteinase 3. Placental thrombin inhibitor inhibits thrombin while the cytoplasmic antiproteinase 3 inhibits granzyme B. They have no known anti-angiogenic function, but specific fragments of the proteins may have such a function.

Antithrombin is a plasma-derived, single-chain glycoprotein. A complex molecule with multiple biologically important properties, it is a potent anticoagulant and also has anti-inflammatory properties, several of which are related to its participation in the coagulation cascade. Both the reactive loop of antithrombin resulting from cleavage by thrombin and its latent form exhibit anti-angiogenic activity (O'Reilly et al., *Science,* 285:1926-8, 1999). Antithrombin belongs to clade C of serpins. Its conserved domain is similar to the corresponding serpin domain of cytoplasmic proteinase inhibitor 2 and placental thrombin inhibitor (FIG. 2C).

Kallistatin is found in vascular smooth muscle cells and in endothelial cells of human blood vessels. It has multiple biological functions including blood pressure regulation, protection against inflammation, vasculature relaxation, and stimulation of neointimal hyperplasia. Kallistatin also possesses anti-angiogenic properties (Miao et al., *Blood,* 100:3245-52, 2002; Miao et al., *Am J Physiol Cell Physiol,* 284:C1604-13, 2003). Wild-type kallistatin, but not a mutant form lacking the heparin binding activity that resides within the conserved serpin domain, inhibits VEGF-induced proliferation, growth, and migration of human microvascular endothelial cells (Miao et al., *Am J Physiol Cell Physiol,* 284:C1604-13, 2003). Kallistatin belongs to clade A and its conserved serpin domain is similar to the corresponding domains of α1-antichymotrypsin, protein C inhibitor/PAI-3, corticosteroid binding globulin, thyroxine binding globulin and germinal center B-cell expressed protein (FIG. 2C). All of these hits are extracellular serine-type endopeptidase inhibitors, and function as part of the coagulation cascade. α1-antichymotrypsin inhibits neutrophil cathepsin G and cell chymase while both protein C inhibitor and germinal center B-cell expressed protein inhibit protein C and plasminogen activators. Corticosteroid and thyroxin binding globulins are major hormone transport proteins, circulating in the blood of most vertebrates.

Angiotensinogen is the precursor of angiotensin I, an inactive decapeptide that is converted into angiotensin II, the main effector of the renin-angiotensin system. Full length angiotensinogen ($AGT^{1-452}$), des[Ang I] angiotensinogen ($AGT^{11-452}$), and RCL-cleaved angiotensinogen ($AGT^{1-412}$), a C-terminal cleaved product of the protein are anti-angiogenic (Celerier et al., *Hypertension,* 39:224-8, 2002). Search for similarities between angiotensinogen's serpin domains and other serpin motifs did not produce any significant results (FIG. 2C). Similarly, no significant similarities were found to proteins from the whole proteome.

Somatotropin Hormones

The somatotropins share a conserved domain but the active anti-angiogenic fragment has not been previously identified. This family includes growth hormone, lactogen, and prolactin, which are proteins with known angiostatic effects.

Prolactin (PRL) is a polypeptide hormone synthesized and secreted primarily by the lactotroph cells of the anterior pituitary. It is also synthesized at extrapituitary sites including the mammary epithelium, placenta, uterus, brain, and immune system (Harris et al., *Ann Med,* 36:414-25, 2004). PRL participates in the regulation of reproduction, osmoregulation, and immunomodulation. Growth hormone (GH) is involved in regulating growth and morphogenesis. Growth hormone is produced in large part by the anterior pituitary in all vertebrates. The human placenta expresses two structural homologs of hGH, human placental lactogen (hPL) and a variant of hGH (hGH-V). Members of the PRL/GH family and derived peptides have been reported to both stimulate and inhibit angiogenesis (Struman et al., *Proc Natl Acad Sci USA,* 96:1246-51, 1999). In general, the full length members of the human PRL/GH family, i.e., hPRL, hPL, and hGH stimulate vessel formation whereas their cleaved 16-kDa N-terminal fragments are anti-angiogenic both in vivo and in vitro. Proteolytic cleavage of PRL occurs at sites of PRL production via cathepsin D, resulting in two fragments of 16 kDa (16K-hPRL) and 6 kDa. It can also be cleaved by kallikerin producing a 22 kDa fragment. It is the 16K-hPRL (N-terminal fragment) that possesses anti-angiogenic properties and inhibits prostate tumor growth in mice by suppressing blood vessel formation. Cleaved PRL has been observed in mouse, rat, and human serum, whereas free 14- and 16-kDa PRL appear to be secreted by the hypothalamoneurohypophyseal system of the rat. Human GH is cleaved by plasmin, thrombin, and subtilisin, yielding similar fragments (Struman et al., *Proc Natl Acad Sci USA*, 96:1246-51, 1999).

These three anti-angiogenic proteins, the 16-kDa fragments of growth hormone, placental lactogen and prolactin contain the somatotropin hormone conserved domain in their sequences. Similarity identification was directed towards proteins that contained the somatotropin hormone conserved domain. The identified proteins are somatotropin hormone family isoforms of the initial set of three queries. In all of the cases the somatotropin conserved domain or a large part of it is contained within the 16-kDa fragments, already known to have anti-angiogenic properties.

Figure 2D:
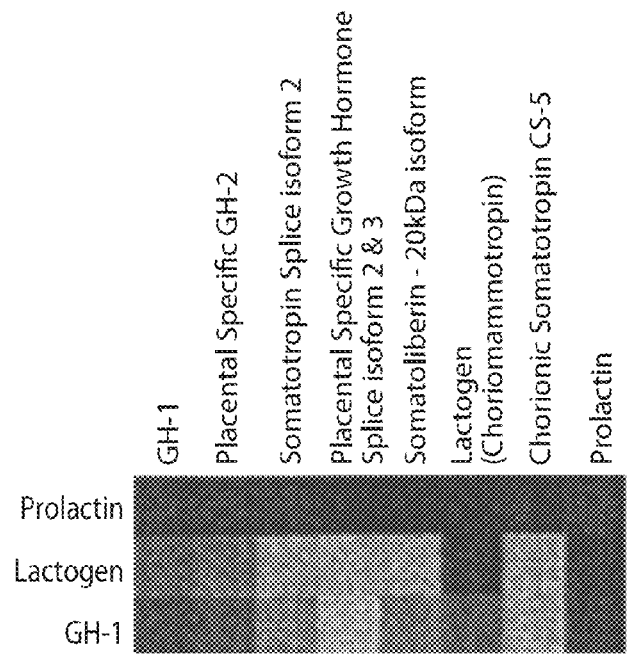

Interestingly, the somatotropin domain of prolactin exhibits no similarity with any of the domains of the same family; it seems to be a unique moiety (FIG. 2D). In contrast, both GH and PRL share significant similarities with the somatotropin domains of most of the other family members. Specifically, the somatotropin domains of both pituitary and placental specific growth hormone are highly similar to each other and also share similarities with the corresponding domains of lactogen and the lactogen (chorionic somatomammotropin) CS-5. The conserved domain of lactogen is similar to the somatotropin domains of the two growth hormone isoforms and lactogen's CS-5 (FIG. 2D).

The most interesting result arose from a direct search for similarities of the 16-kDa anti-angiogenic fragments within the total proteome. Again, prolactin's 16-kDa fragment showed no similarity with any other protein; surprisingly, however, the 16-kDa fragments of growth hormone and lactogen were found to be highly similar to somatoliberin (growth hormone releasing factor). Somatoliberin belongs to the glucagon protein family and is secreted from the hypothalamus as a pre-protein that is cleaved to a 44-amino acid fragment that stimulates growth hormone release from the pituitary. As noted above, the full-length somatotropins are pro-angiogenic; somatoliberin is considered to be an angiogenesis stimulator. The high similarity of somatoliberin to the 16-kDa anti-angiogenic fragments indicates that this protein may exhibit anti-angiogenic behavior.

Each of these protein families with shared conserved domains and unknown active fragments comprises multiple protein members. Four of the known anti-angiogenic proteins contain a characteristic conserved domain within their sequences, although only single members of the corresponding protein families have been identified as angiostatic. These proteins are perlecan's fragment endorepellin, which contains the laminin globular conserved domain and angiostatin which contains the kringle domain, both discussed in the following sections.

Laminin Globular Domain-Containing Proteins

Perlecan is a major basement membrane heparan sulfate proteoglycan. It is involved in the stabilization of other basement membrane molecules and regulates cell adhesion as well as vessel permeability. The C-terminal of perlecan, endorepellin, has been shown to inhibit endothelial cell migration, tube formation in collagen and angiogenesis in CAM and matrigel assays (Bix and Iozzo, *Trends Cell Biol*, 15:52-60, 2005; Mongiat et al., *J Biol Chem*, 278:4238-49, 2003). Endorepellin consists of three LamG conserved domains LamG1 (LG1), LamG2 (LG2), and LamG3 (LG3), which are separated by two EGF-like domains within each pair of LamG modules. Physiologically endorepellin is cleaved proteolytically by MMP-1 and MMP-3 releasing either the three-LamG domain cassette or the last LamG domain, LamG3.

The similarity of the globular laminin domains of endorepellin to other sequences of the same family is insignificant. The second and third domains, LamG2 and LamG3, both displayed similarity only with the LamG1 and LamG2 domains of another proteoglycans, agrin. Agrin is another basement membrane protein that induces the aggregation of acetylcholine receptors and other post-synaptic proteins in muscle fibers and it is crucial for the formation of the neuromuscular junctions. The structural similarity of the C-terminal of agrin to endorepellin, as manifested by three consecutive LamG domains, separated by two EGF-like motifs, suggests that the C-terminal region may also possess anti-angiogenic activity.

A direct search for similarities between the LamG domains of perlecan and the whole proteome did not provid any additional significant results.

Kringle Containing Proteins

One of the most thoroughly studied angiogenesis inhibitor is angiostatin (O'Reilly et al., *Cell*, 79:315-28, 1994). The structure of angiostatin includes the first four kringle (K) domains of plasminogen. Kringle structures exist in many proteins, and such proteins can contain anywhere from one to several kringles. The primary amino acid sequence of each kringle domain consists of approximately 80 amino acids. Kringle proteins do not share a common function, but act as growth factors, proteases, or coagulation factors. Although most kringle-containing proteins have only one kringle domain, the glycoprotein, apolipoprotein (a), is unusual in containing 38 kringle domains. Plasminogen, the parent protein of angiostatin, contains a total of five kringle domains and the fifth domain is excluded from angiostatin. Like other individual kringle domains, the K5 domain of human plasminogen contains 80 amino acid residues. Primary structure alignment shows that K5 exhibits remarkable sequence identity (~60%) with K1, although K2, K3, and K4 also share significant homologies with K5. Both proteolytic/denatured and appropriately folded recombinant K5 displays more potent pro-apoptotic effects on endothelial cells than do the other individual kringle domains. In fact, K5 alone exhibits a several-fold greater effect than do the K1-4 of angiostatin. This unexpected finding suggests that K5 might inhibit endothelial cell growth via a separate mechanism, or that K5 is a more potent inducer of inhibitory targets on endothelial cells. It has been shown in various in vitro studies that the ranking order for kringle potency in inducing endothelial cell apoptosis is K5>K1·K2·K3 complex>K1·K2·K4 complex>K1>K3>K2>K4 (Cao and Xue, *Semin Thromb Hemost*, 30:83-93, 2004).

The bioinformatics approach described herein has proven useful in identifying fragments similar to angiostatin's kringles. The most potent angiogenesis inhibitor, Kringle 5, was found to share similarities with the following kringle-containing proteins: Macrophage stimulating factor 1, hepatocyte growth factor, lipoprotein/Lp(a), receptor tyrosine kinase like orphan receptor 1 and 2, coagulation factor II (thrombin) and XII (Hageman factor), hyaluronan binding protein 2, tissue plasminogen activator and the kringle containing proteins KREMEN-1 and 2.

Figure 2E:
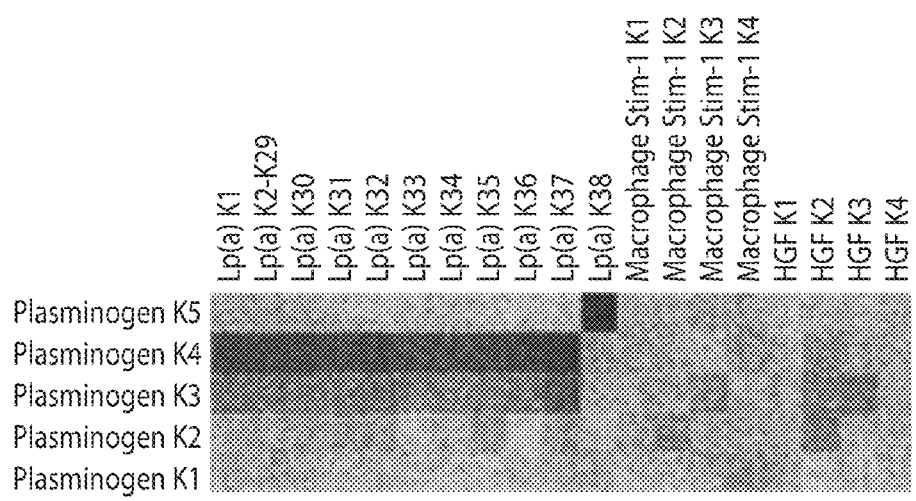

Kringles 1-4 are similar to a smaller group of proteins including macrophage stimulating factor 1, hepatocyte growth factor and lipoprotein/Lp(a). All of the aforementioned proteins contain multiple kringle domains within their sequences and plasminogen exhibits similarity with most of them. In particular, K5 is extremely similar to the last $38^{th}$ kringle of apolipoprotein localized next to a trypsin-like serine protease domain as well as to the anti-angiogenic protein AK-38, a protein that consists only of the last kringle of apolipoprotein (FIG. 2E). Lipoprotein which consists of 38 kringles (kringles 2 to 29 are identical) demonstrates different modes of similarity with plasminogen's kringles. All of its kringles, apart from the 38$^{th}$, are notably similar to plasminogen's K3 and K4, whereas only the last kringle is similar to plasminogen's K5. The clustering of the lipoprotein's similarities around different plasminogen's kringles suggests that K5 is a separate moiety, distinct from kringles 1-4.

Another candidate is macrophage stimulating factor 1, which belongs to the family of granulocyte/macrophage colony-stimulating factors. These are cytokines that contribute to hematopoiesis by controlling the production, differentiation, and function of the white cells of the blood including the granulocytes and the monocytes/macrophages. It plays a role in immunological defense, bone metabolism, lipoproteins clearance, fertility, and pregnancy. The four kringles of macrophage stimulating factor principally display similarities to plasminogen's K1, K2 and K3 (FIG. 2E).

Hepatocyte growth factor (HGF) is a potent mitogen for mature parenchymal hepatocytes. It also seems to be a hepatotrophic factor and acts as growth factor for a broad spectrum of tissues and cell types. HGF contains four kringles; among them kringles 2 and 3, which exhibit significant similarities to plasminogen's K2, 3, and 4 (FIG. 2E). It is therefore likely that they have potent anti-angiogenic activity. Other proteins with significant similarities to plasminogen's kringle 5 are receptor tyrosine kinase-like orphan receptors 1 and 2, thrombin, Hageman factor (cf XII), hyaluronan binding protein 2, and tissue plasminogen activator (Table 2). All of these proteins may possess anti-angiogenic properties in addition to their known role as mediators of the blood coagulation cascade.

Complement Component C1q Containing Proteins

Type VIII collagen has been demonstrated to contain fragments with potent anti-angiogenic. This protein is an ECM component that is synthesized by endothelial cells, keratinocytes, mast cells and tumor cells. It is a hetero-trimer composed of two α1 and one α2 fibrils. The NC1 domain of the α1(CVIII) fibril displays anti-angiogenic activity like that of endostatin (Xu et al., *Biochem Biophys Res Commun*, 289: 264-8, 2001). However, the activity has not yet been mapped to a specific site on the protein.

Interestingly, the α1(CVIII) NC1 domain contains a conserved domain, the complement component C1q domain, that spans most of the fragments and possibly differentiates it functionally from endostatin. The bioinformatics approach described above was used to investigate the similarity between the C1q conserved domain contained within the angiostatic fragment of type VIII collagen and other C1q domains. This domain is highly similar to the corresponding domains of the α2 fibril of collagen VIII and the α1 fibril of collagen X. Thus, both of these fragments may possess angiostatic properties similar to those of α1(CVIII) NC1. A direct search for similarities between the C1q domain of the α1(CVIII) NC1 and of the full-length NC1 fragment and the whole proteome also identified this same group of proteins.

Anti-Angiogenic Proteins without Conserved Domains

Finally, there is a very small group of known angiogenesis inhibitors for which the angiostatic activity is precisely mapped to specific active domains within the sequence of the protein. The proteins do not contain any previously identified conserved domains within their sequences. Most of the angiostatic active domains are approximately 20-60 amino acids long (Table 1) including kininogen, loop 6 of tissue inhibitor of metalloproteinases 2, calreticulin and the collagen XVIII and XV endostatins.

High-molecular-weight kininogen (HK) is a plasma protein with a variety of physiological functions. Originally identified as a precursor of bradykinin, a bioactive peptide that regulates many cardiovascular processes, HK is now known to play important roles in fibrinolysis, thrombosis, and inflammation. HK binds to endothelial cells where it can be cleaved by plasma kallikrein to release bradykinin (BK). The remaining portion of the molecule, cleaved HK, is designated cleaved high-molecular-weight kininogen or HKa (Guo and Colman, *J Thromb Haemost*, 3:670-6, 2005). While BK has been intensively studied, the physiological implications of HKa generation are not clear. Recent studies have revealed that HKa inhibits angiogenesis while BK promotes it (Guo and Colman, *J Thromb Haemost*, 3:670-6, 2005). Mapping studies have indicated that a peptide (HK$^{486-502}$) in the D5 region of HK inhibits cell migration, while the peptide HK$^{440-455}$ is responsible for inhibiting cell proliferation (Colman et al., *Blood*, 95:543-50, 2000; Guo et al., *Arterioscler Thromb Vasc Biol*, 21:1427-33, 2001). Our search for similarities between the HK$^{440-455}$ active domain and other protein fragments within the proteome identified hemopexin, which binds heme and transports it to the liver for breakdown and iron recovery, as well as the relatively less similar isoforms of the solute carrier family 39 protein, which is an integral membrane protein with zinc transport properties.

Moses and colleagues (Fernandez et al., *J Biol Chem*, 278:40989-95, 2003) have demonstrated the uncoupling of the MMP-inhibitory and anti-angiogenic activities of TIMP-2 using the *Pichia pastoris* expression system to engineer and produce both the N- and C-terminal domains of TIMP-2. They found that although both domains inhibited angiogenesis in the embryonic CAM assay, the C-terminal domain and wild-type TIMP-2 were more effective inhibitors of angiogenesis in the mouse corneal pocket assay than was the N-terminal TIMP-2 domain. Furthermore, the inhibitory ability of the N-terminal domain was dependent on MMP-inhibitory activity. The ability of TIMP-2 to inhibit endothelial cell proliferation was localized to the C-terminal domain of TIMP-2, and specifically to the C-terminal disulfide loop, loop 6. Loop 6 showed significant similarities to the corresponding domains of TIMP-4 and TIMP-3 and, to a lower degree to, TIMP-1.

Calreticulin is a unique endoplasmic reticulum (ER) luminal-resident protein. This protein affects many cellular functions, both within the ER lumen and outside the ER environment. In the ER lumen, calreticulin performs two major functions: chaperoning and regulating Ca$^{2+}$ homeostasis. Vasostatin, the N-terminal domain of calreticulin inclusive of amino acids 1-180, is an angiogenesis inhibitor that shows antitumor effects in vivo (Pike et al., *J Exp Med*, 188:2349-56, 1998; Pike et al., *Blood*, 94:2461-8, 1999) Like vasostatin, the whole protein, calreticulin, selectively inhibits endothelial cell proliferation and angiogenesis, but not cells of other lineages. Calreticulin lacking its N-terminal 1-120 amino acids inhibits endothelial cell proliferation that is comparable to that of vasostatin. The internal fragment 120-180 of calreticulin inhibits angiogenesis and is probably the protein fragment responsible for the angiostatic effects of vasostatin. Vasostatin showed no similarity to any other protein except for a distal hit, calnexin, which is also an ER calcium-binding protein.

A very significant source of a potent anti-angiogenic fragment, endostatin, is type XVIII collagen (O'Reilly et al., *Cell* 88; 277-85, 1997). The 20- to 22-kDa fragment of NC1 of the α1 chain of CXVIII was identified as endostatin. A similar fragment of the NC1 domain of the a1 chain of CXV has been shown to have properties similar to those of CXVIII-endostatin (Sasaki, et al., *J Mol Biol* 301; 1179-90, 2000; Ramchandran et al., *Biochem Biophys Res Commun* 255; 735-9, 1999). The 22-kDa fragment of NC10 of the α1 chain of CXV was identified as restin, which shows anti-angiogenic effects similar to those of endostatin. These two fragments apart from their similarity to one another did not show any other significantly similar hits in a BLAST search and filtering against the whole proteome.

The present invention provides a systematic means of classifying known endogenous anti-angiogenic proteins and protein fragments. Based on similarity criteria a number of similar sequences were identified. These similarities suggest that the polypeptides and fragments identified exhibit anti-angiogenic properties. In the case of most of the proteins identified using the bioinformatic analysis, the relationships to known anti-angiogenic proteins and fragments have not been previously identified. These newly identified proteins and fragments constitute novel drug candidates for anti-angiogenesis therapeutics.

To date, the identification of potentially anti-angiogenic proteins has been performed purely empirically. Selected proteins were proteolytically processed by proteases and the cleaved fragments tested in various in vitro and in vivo angiogenesis protocols. This process has yielded a number of proteins and considerable information regarding the localization of the anti-angiogenic protein site, i.e., the protein region responsible for a particular effect. In some cases a specific protein site of 20-60 amino acids length has been identified; however, in most cases the anti-angiogenic behavior has been attributed to longer fragments of 100-150 amino acids length or even to the whole protein. The identification of protein sites and the observation that these sites are localized within the considered conserved domains suggests that the anti-angiogenic behavior is localized within this conserved domain. Identification of similarities between the conserved domains of multiple proteins belonging to the same protein family and the anti-angiogenic fragments has yielded novel candidates that may exhibit similar functions. This conclusion was based solely on the amino acid sequences of the hits and not on structural criteria. Moreover, in the case of proteins for which the active anti-angiogenic site has not yet been mapped, similarity criteria has been used to identify putative regions of their amino acid sequence in which angiostatic activity is localized.

Based on the bioinformatic analysis of the whole human proteome, the pool of anti-angiogenic candidates consists of extracellular matrix-residing or circulating proteins. In some cases the novel hits are fragments of proteins with known pro-angiogenic activity. As shown for the somatotropin hormones, it is likely that while the whole protein promotes angiogenesis, small fragments of the protein are anti-angiogenic. This property defines a novel category of proteins with dual behavior. Without wishing to be bound by theory, it is likely the expression of enzymes that processes the initial protein into smaller fragments that controls the function of such proteins.

It is also possible that the shift from the pro-angiogenic to the anti-angiogenic function is controlled by a small subset of amino acids. For proteins identified herein, the proteins with known pro-angiogenic behavior that show similarity to known anti-angiogenic fragments are highly similar to these known fragments but not identical to them. Again, without wishing to be bound by theory, it is possible that the subset of amino acids that differ between the two proteins controls their angiogenic properties. Potential mutations within these subsets could provide a control mechanism for the transition between the two totally different properties.

This analysis is the first computational approach that attempts to identify novel endogenous angiogenesis inhibitors. The knowledge of specific protein sites at which the anti-angiogenic behavior resides provides for the identification of novel candidates. These computationally identified candidates are then tested experimentally for anti-angiogenic properties as described herein. This process of mining angiogenesis inhibitors requires combined computational and experimental efforts. Such an integrative approach results in a systematic and efficient identification of anti-angiogenic protein fragments as well as advancing current understanding of the control of the angiogenic switch.

Example 2

Results of Proliferation Experiments

As described above, computational bioinformatic algorithms were used to identify a set of protein fragments of naturally occurring, endogenous proteins that may possess potent anti-AM angiogenic properties. The algorithms identified approximately 200 similarity hits for the proteins or protein fragments with known anti-angiogenic activity. Of the 200 hits, some of which are duplicated, over 150 represent distinct novel putative anti-angiogenic protein fragments. Among the novel fragments, there were hits similar to platelet factor-4, with 7 identified similar protein domains; various fragments of thrombospondin 1, each of which having 45 identified similar fragments; and various tumstatins, with approximately 5 similar fragments each. The proteins with identified similarities and lengths of 100-150 amino acids included the angiostatin kringles; the CXC chemokines Gro-β, IP-10, and MIG, each with approximately 8 top similar protein sites; growth hormone-1 and placental lactogen with 3 similar fragments each; as well as kininogen, with a single identified similarity.

An experimental medium-throughput platform was used to test the identified polypeptides and peptides biological activity. Following the NCI (National Cancer Institute) guidelines for testing the anti-angiogenic efficacy of novel agents (<http://dtp.nci.nih.gov/aa-resources/aa_index.html>), an endothelial cell proliferation assay was used. Endothelial cell proliferation is important for new capillary sprout formation; thus, inhibiting proliferation should be sufficient for a complete or partial inhibition of angiogenesis. Where the active domains of proteins have not been identified, fragments that exhibit similarities to known anti-angiogenic fragments or proteins are assayed to identify amino acid sequences having anti-angiogenic activity. Peptides not exhibiting activity in the proliferation assays described below, will be tested for angiogenesis modulating activity in functional assays described herein. In addition to proliferation assay, examples of a migration assay are presented below as well as a Directed In Vivo Angiogenesis Assay (DIVAA).

Peptide Synthesis and Handling

The peptides are produced using the custom peptide synthesis facility in the Department of Oncology, Johns Hopkins University, and a commercial providers (Abgent, San Diego, Calif.; New England Peptide, Inc., Gardner, Mass.) using a solid phase synthesis technique. For each peptide HPLC and mass spectroscopy analysis is performed and proof of identity and purity is provided. The procedure yields 10 mg of >95% pure peptide. 10 mg are aliquoted, by the manufacturer, in single mg vials and shipped. Each single mg of peptide was diluted in 100 μl final solution, which provides a 10,000 μg/ml peptide concentration. The 100 μl is aliquoted in 10×10 μl stock solutions and frozen.

In order to predict the proper solvent that is required to solubilize the peptide, the hydrophobicity of the aminoacid chains is calculated. The more hydrophobic peptides require polar solvents, such as DMSO. Otherwise the peptides are diluted in a commercially available balanced salt solution, Hanks balanced salt solution (HBSS). Where the peptide is neither strongly hydrophobic nor highly hydrophilic then the solvent is empirically determined by testing the peptides solubility in small volumes of solvents starting with 20 μl of HBSS. Where a peptide is not soluble in HBSS a small solid pellet is formed at the bottom of the tube. This separation of phases is a sufficient indication that HBSS is not the proper solvent. We then use another 80 μl of DMSO and repeat the process. If the peptide is soluble in the 20 μl of HBSS we add another 80 μl to final volume 100 μl. So far in all of the cases this procedure has proven satisfactory in establishing the solubility of the solid peptides in different solvents.

For all solvents, 9×10 μl of stock solutions are stored in −80° C. and the tenth 10 μl is used to provide a working solution. In the single vial containing 10 μl of 10,000 μg/ml of peptide 90 μl of HBSS was added to generate 100 μl of 1,000 μg/ml solution. Those 100 μl were aliquoted in 10×10 μl and stored at −80° C.

Experimental Protocol

The effect of the various peptides on cell proliferation was assayed, by administering the peptides to human umbilical vein endothelial cells (HUVECs) in culture. 45 peptides belonging to four distinct families of proteins including the thrombospondin-1 containing proteins, the C-X-C chemokines, collagen derived peptides and peptides from tissue inhibitors of metalloproteinases were tested.

Figure 4:
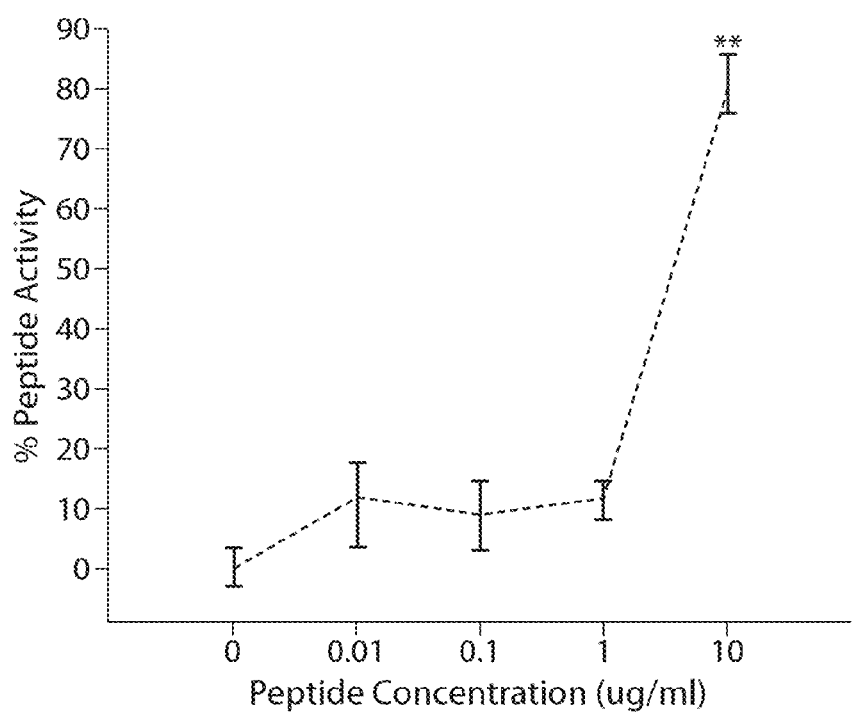
FIG. 4 is a graph showing the activity of the exemplary peptide of FIG. 3 applied to a HUVEC cell culture at four different concentrations in in vitro cell proliferation assays; the activity is scaled using as 0% the optical density reading from the negative control (application full medium only to the cell culture), and as 100% activity the optical density reading from the positive control (application of full medium and 100 ng/ml of TNP-470). All of the subsequent in vitro proliferation results are presented in this format.

The potency of each of the peptides was tested using the proliferation assay at 2 days and 4 days following administration of the peptides and a similar assay using a different cell density at 3 days. In the four-day experiments, the cell medium was changed after the second day of incubation and the peptide was replaced at the initial concentration together with the medium. TNP-470 is an antiangiogenic compound that was used as a positive control for assessing anti-angiogenic efficacy. The activity of each polypeptide was, therefore, expressed as a percentage of TNP-470 activity, i.e., the optical density obtained experimentally is scaled such that the negative control is 0% and the positive control is 100% as explained below (FIG. 4). Each plate included a well having HUVEC cells that received 0.1 μg/ml TNP-470. For example, a peptide having the same effect on endothelial cell proliferation would have 100% of the activity of TNP-470. Note that activity could exceed 100%.

The observed activity of the tested peptides in many of the cases reached 40% of the TNP-470 activity, and in some cases reached 80%. At higher peptide concentrations the activities of some of the peptides are likely to increase further. Also some peptides have biphasic activity. A peptide having "biphasic activity" has maximum activity at an intermediate concentration, but this anti-angiogenic activity was diminished at very high or very low concentrations. This biphasic activity maybe time-dependent. Peptides that show biphasic behavior at two days may change this characteristic after four days with a concomitant gain of activity. In most cases, peptides gain activity over time, or maintain a constant level of activity.

Statistical significance was tested using one way and two way ANOVA; $p<0.001$ is indicated by **, $p<0.05$ by *.

Analysis of the Proliferation Experimental Results

In this assay, the effects of the predicted anti-angiogenic fragments on the ability of HUVECs to proliferate was characterized. A decrease in the proliferation rate of the cells indicates that those agents are capable of disrupting the angiogenic process. A commonly used methodology to test for proliferation is to monitor the viability and metabolic activity of endothelial cells, in the presence of the anti-angiogenic fragments at different concentrations and various time steps. The cell proliferation reagent WST-1 was used as a substrate/assay to measure the metabolic activity of viable cells. WST-1 is a colorimetric, non-radioactive assay and can be performed in a microplate. It is suitable for measuring cell proliferation, cell viability or cytotoxicity. The assay is based on the reduction a red tetrazolium salt, WST-1, by viable, metabolically active, cells to form the yellow formazan crystals soluble in the cell medium. In contrast to other formazan based assays, such as MTT, the formazan crystals do not need to be solubilized by the addition of a detergent; they are solvable in the cell medium.

The cells are cultured described above. Once cells have reached 80% confluence they are trypsinized and resuspended in EGM-2. The cell density is estimated using a hemocytometer. All of the endothelial cells used were from passage 4 to passage 8.

Figure 3:
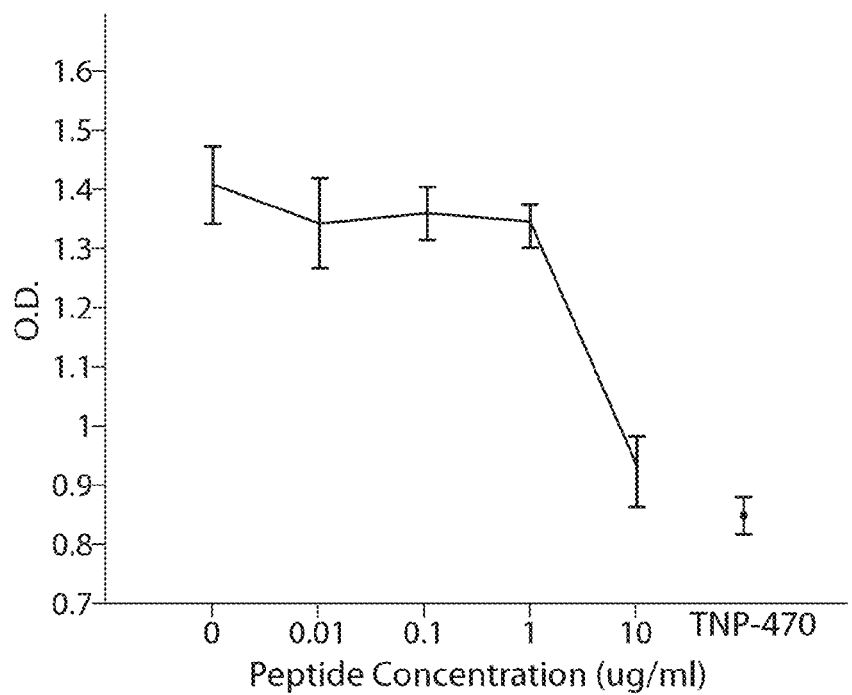
FIG. 3 is a graph showing an exemplary optical density reading for a peptide derived from the alpha 5 fibril of type 4 collagen applied to a Human Umbilical Vein Endothelial Cells (HUVEC) cell culture at four different concentrations in in vitro cell proliferation assays.

The proliferation assay involved two steps. During the first step the cells, approximately 5,000 cells per well for a 96-well plate, were seeded without any extracellular matrix substrate on the wells overnight (8 hours). The initial cell culture medium was removed using a multichannel pipetor and the candidate peptides were applied. A logarithmic scale of four different concentrations of 0.01 μg/ml, 0.1 μg/ml, 1 μg/ml and 10 μg/ml of each peptide was used. Each of the concentrations was tested in quadruplicate. The viability of the cells was challenged at 2 and 4 days upon the application of the peptide. As a positive control for decreased viability, 0.1 μg/ml of TNP-470 (O-(chloro-acetyl-carbamoyl) fumagillol, a synthetic analogue of fumagillin; TNP-470 was provided by NCI, was provided along with the medium, and as a negative control for normal viability, the cells were cultured without the addition of any agent. The cells were then incubated with 10 μl per well of the red WST-1 reagent for approximately 2 to 4 hours. During this incubation period, viable cells converted, in their mitochondria, the red WST-1 to the yellow formazan crystals which dissolve in the medium. The second step of the assay involved the quantification of the changes in proliferation which was performed by measuring the change in color after lysing the cells. The samples were read using the ELISA plate reader Victor3 V (Perkin Elmer) at a wavelength of 570 nm. The amount of color produced is directly proportional to the number of viable cells. For each plate, this value was compared to background by measuring the signal in a cell-free well containing only cell culture medium and dye. This background signal was subtracted from the signal from each cell-containing well. The resulting signal was expressed as optical density (O.D.). A typical example of an optical density output from a measurement of a single peptide that was applied to cells in culture for two days is shown in FIG. 3.

In this figure the optical density was plotted for each of 4 wells/sample for each concentration of administered peptide. The value was expressed as the average of the four measurements along with the standard deviation. The first point, which is denoted as 0 peptide concentration, represented the background signal present in the negative control cell-free well. The last point, denoted as TNP-470, represents the collections of wells where 0.1 µg/ml of TNP-470 was applied. This well served as a positive control.

The optical density results are scaled using the positive and negative controls. Each of the optical density measurements, from each well, was divided by the average optical density of the negative control (only full medium) and the results were scaled from 0% to 100%. A scaling where 100% represents the activity of TNP-470 and 0% represents zero anti-proliferative activity as measured in the negative control wells was used. Using this scaling method FIG. 3 was used to generate a measure of peptide activity as shown in FIG. 4. Note that the 2-day and 4-day results were scaled by their own negative and positive control values.

In addition to the 2 and 4 day proliferation experiment where 5,000 cells per well were seeded, the effects of the peptides on the proliferating ability of HUVECs were also studied using cells seeded at a density of 2,000 cells per well. This lower cell seeding density allowed the experiment to be extend for an additional day without changing the cell medium. The effects of the peptides when applied to the cells for 3 consecutive days is also reported herein. The proliferation assay again involved two steps. During the first step 2,000 cells per well for a 96-well plate were seeded without any extracellular matrix substrate on the wells overnight (8 hours). The initial cell culture medium was removed using a multichannel pipetor. To synchronize the cells, the cells were serum starved for 4 hours and the candidate peptides were applied. During serum starvation the cell culture medium was changed from a "full" medium to the "basal" medium, which contained no growth factors or serum. Serum starvation for 4 hours had no effect on the proliferation of the cells. For this assay, the logarithmic scale of four different concentrations of 0.01 µg/ml, 0.1 µg/ml, 1 µg/ml and 10 µg/ml of peptide was used. In addition, a larger concentration of 30 µg/ml peptide was also applied. Each of the concentrations was again tested in quadruplicate.

After the third day of peptide application the WST-1 dye was applied for approximately 2 to 4 hours (usually after 3 hours the color saturates). The proliferation was later tested on the ELISA plate reader as described for the 2 and 4 day assay. Note that the 2- and 4-day and the 3-day protocols differed in that 5,000 cells/well versus 2,000 cells/well seeded, respectively.

Peptides from four families of proteins, two of the families containing a conserved domain (the TSP-1 containing proteins and the C-X-C chemokines), and two families without a conserved domain (the collagens and the TIMPs) were experimentally screened in order to determine the anti-angiogenic activity of the computationally predicted fragments.
Peptides Derived from Thrombospondin-1 Containing Proteins Thirty two peptides that contain a thrombospondin-1 domain (TSP-1) were tested in proliferation assays as described above. The results of these tests follow.
THSD-1

Figure 5A:
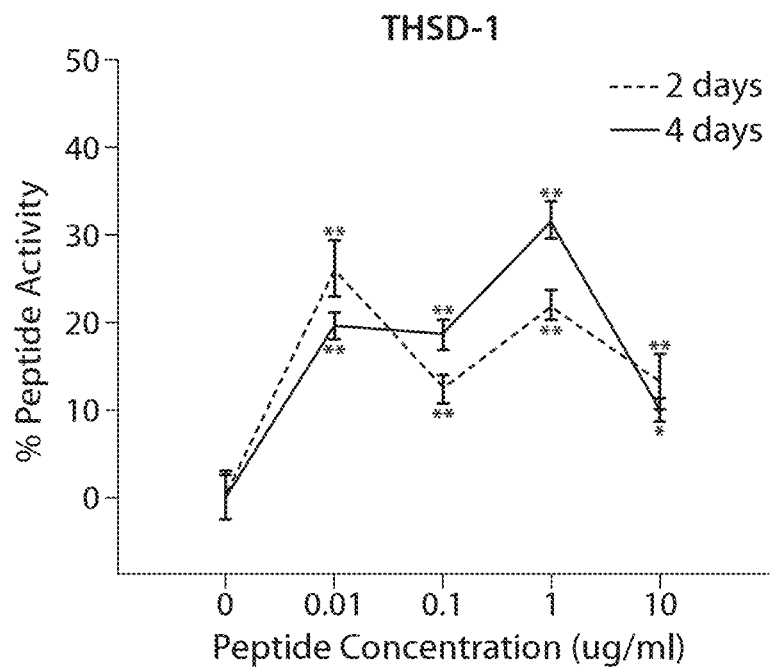
FIGS. 5A and 5B are graphs showing the activity of THSD-1 in in vitro cell proliferation assays.
Figure 5B:
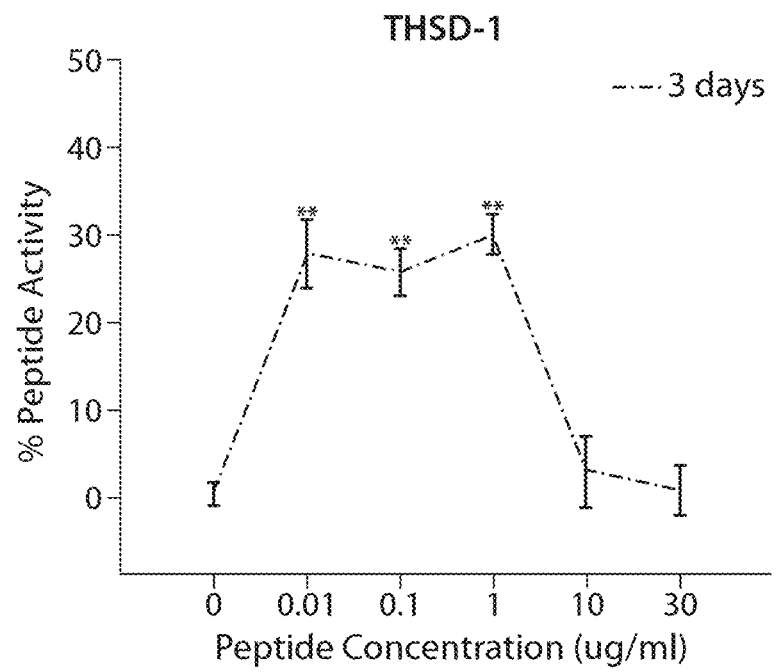

Thrombospondin, type I, domain containing 1 (THSD-1) is a cell surface protein that contains a domain similar to thrombospondin-1. The predicted anti-angiogenic fragment (QPWSQCSATCGDGVRERRR) (SEQ ID NO: 64) showed approximately 20% activity. This activity was fairly constant throughout the 4 days of the peptide application as shown in FIG. 5A for all the applied concentrations. THSD-1 maximum activity was attained at a low peptide concentration (0.01 µg/ml). Similar activity was observed in the 3-day assay (FIG. 5B). There was a substantial increase in activity at the higher concentration of 30 µg/ml.

THSD-3

Figure 6A:
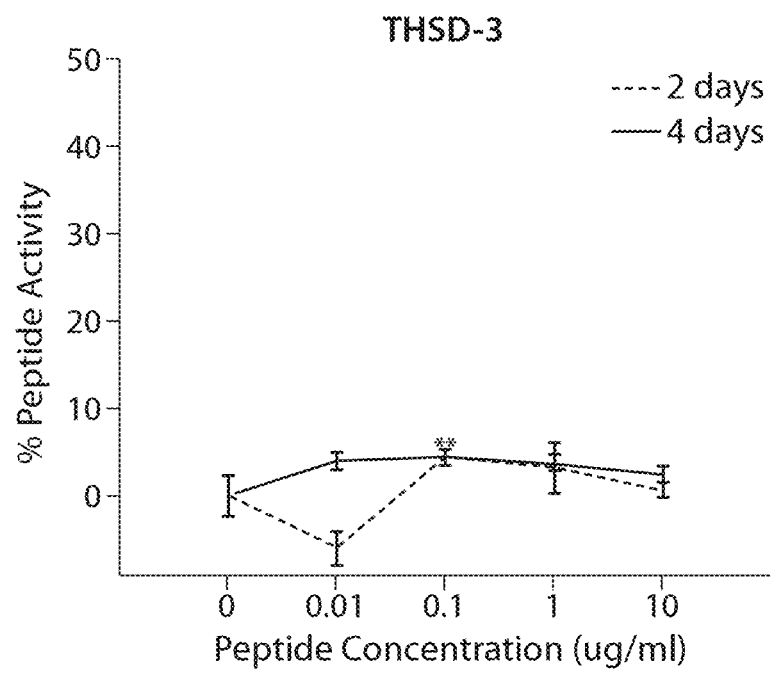
FIGS. 6A and 6B are graphs showing the activity of THSD-3 in in vitro cell proliferation assays.
Figure 6B:
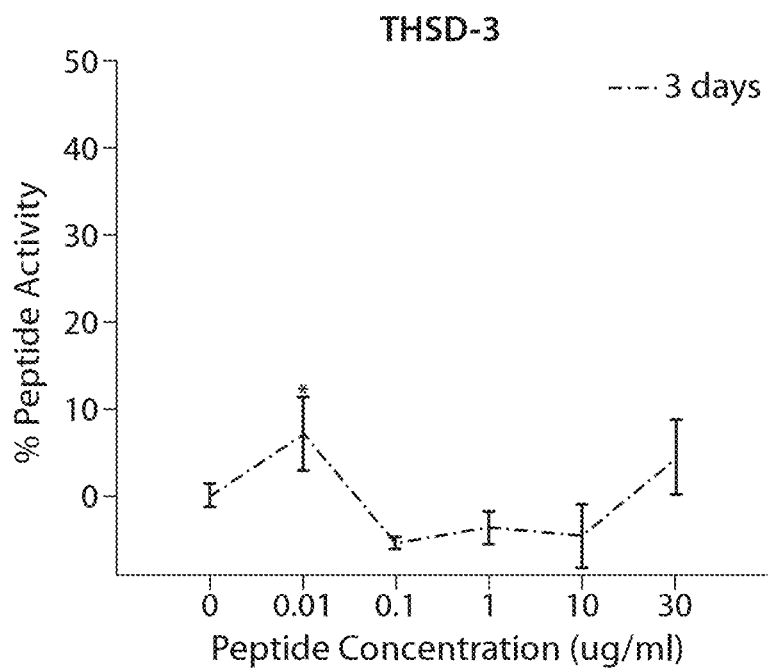

A second isoform of the thrombospondin, type I, domain containing proteins (THSD) that contains a domain predicted to possess anti-angiogenic activity is THSD-3. The THSD-3 fragment (SPWSPCSGNCSTGKQQRTR) (SEQ ID NO: 65) did not effect endothelial cell proliferation in the two, three, or four day assay (FIGS. 6A and 6B).
THSD-6

Figure 7A:
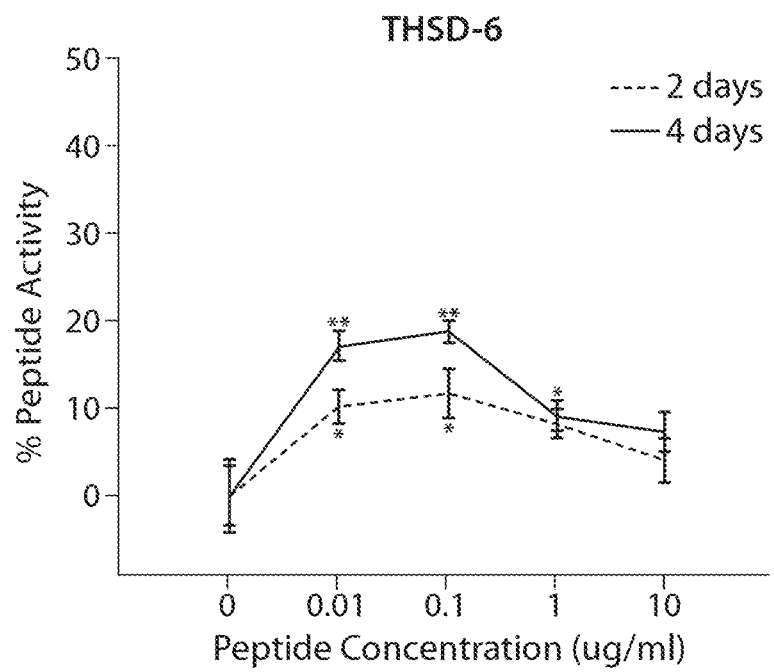
FIGS. 7A and 7B are graphs showing the activity of THSD-6 in in vitro cell proliferation assays.
Figure 7B:
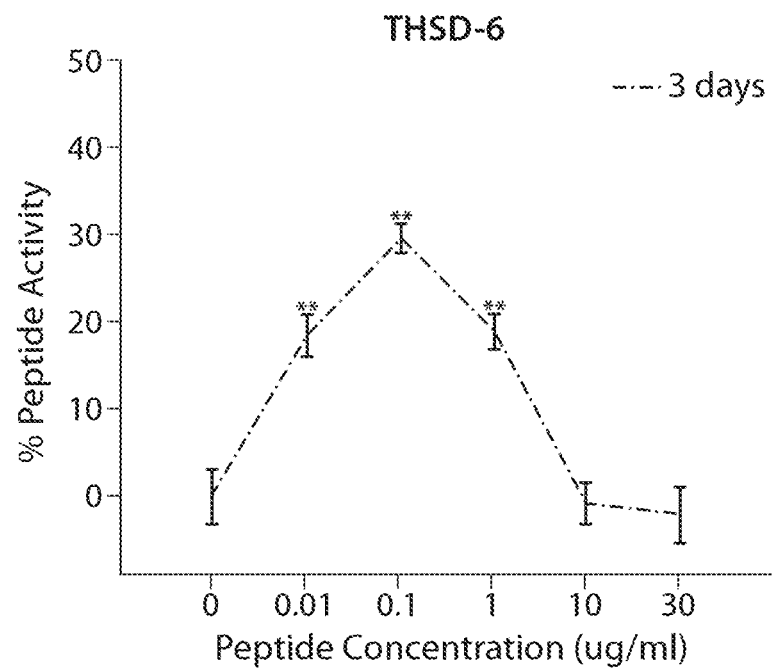
Figure 8A:
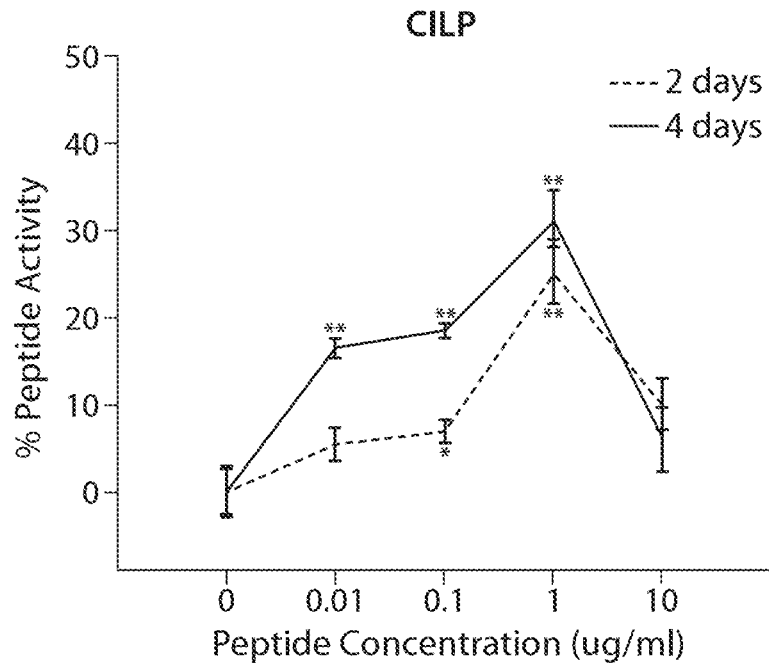
FIGS. 8A and 8B are graphs showing the activity of CILP in in vitro cell proliferation assays.
Figure 8B:
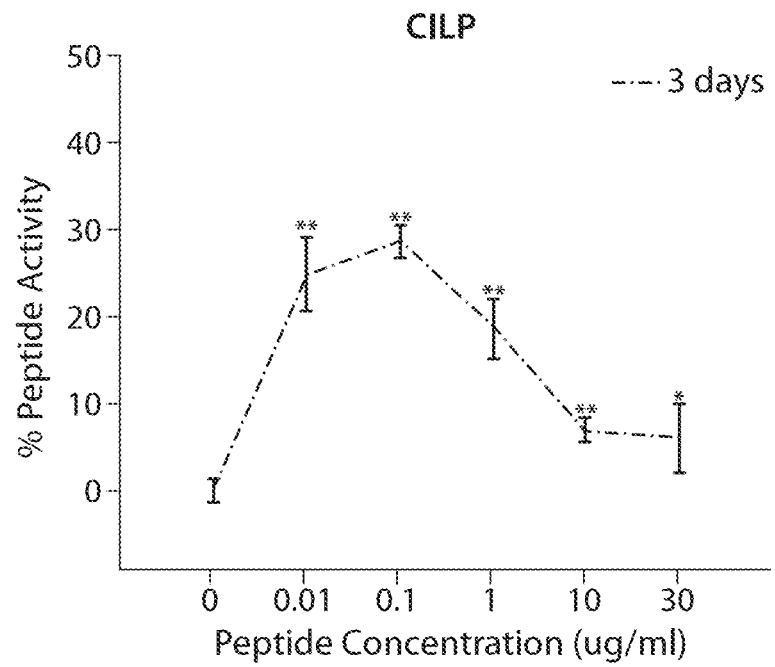

A third isoform of the thrombospondin, type I, domain containing proteins (THSD) that contains a domain predicted to exert anti-angiogenic activity is THSD-6. The THSD-6 fragment (WTRCSSSCGRGVSVRSR) (SEQ ID NO: 66) attained a maximum activity of approximately 20% at 2 days and 30% at 3 days. This activity was biphasic in the two, three, and four day assay (FIGS. 7A and 7B). THSD-6 showed maximum potency when administered at 0.1 µg/ml.
CILP CILP is the cartilage intermediate layer protein. It contains a TSP-1 domain and the predicted anti-angiogenic fragment (SPWSKCSAACGQTGVQTRTR) (SEQ ID NO: 39). CILP showed biphasic activity that was consistently maintained throughout the four days that the cells were incubated with peptide application (FIG. 8A). The maximum activity of the peptide (~30%) is observed at 1 µg/ml concentration. At lower concentrations (0.01 and 0.1 µg/ml) the activity falls to 15% and at higher concentrations (10 µg/ml) the activity is also diminished (5%). For the 3 day assay (FIG. 8B) a similar biphasic response was observed. In the 3-day assay, maximum activity was observed at 0.1 µg/ml peptide concentration.
WISP-1

WISP-1 is the WNT1 inducible signaling pathway protein 1. It is a cell secreted protein that belongs to the connective tissue growth factor (CTGF) family. It is expressed at a high level in fibroblast cells, and overexpressed in colon tumors. It attenuates p53-mediated apoptosis in response to DNA damage through activation of the Akt kinase. The predicted anti-angiogenic fragment (SPWSPCSTSCGLGVSTRI) (SEQ ID NO: 74) shows intermediate activity (~20%) after four days of application whereas after two days its activity is not statistically significant (FIG. 9A). The WISP-1 activity for the 3 day assay retained intermediate levels but reached higher values at 30 µg/ml (FIG. 9D).
WISP-2

Another isoform of the WNT1 inducible signaling pathway protein 1 is WISP-2. The fragment that is derived from WISP-2, TAWGPCSTTCGLGMATRV (SEQ ID NO: 75), was quite potent at small concentrations of 0.01 µg/ml and shows a biphasic response after the second day of the peptide application (FIG. 9B). For the 3 day assay the WISP-2 peptide retained intermediate activity of 20% (FIG. 9E).
WISP-3

Figure 10A:
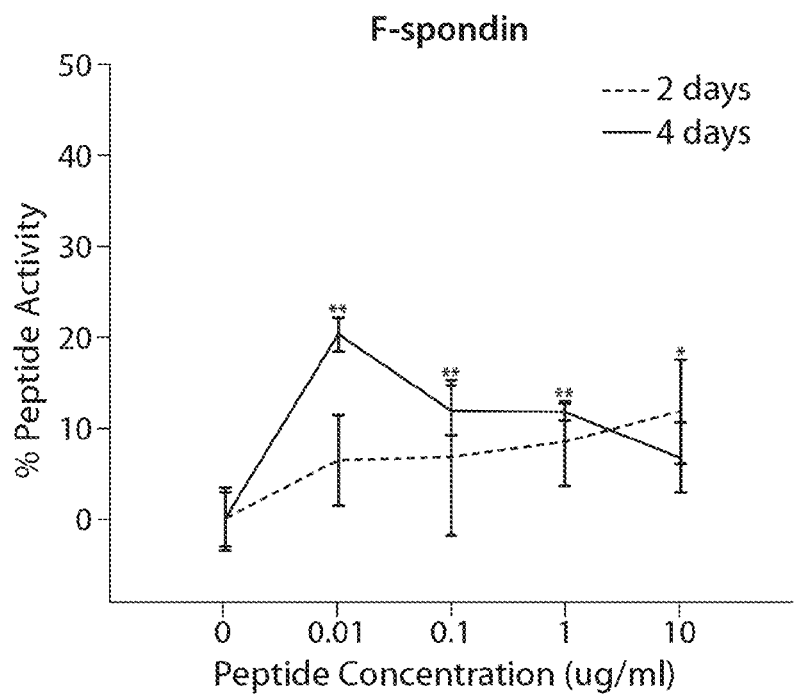
FIGS. 10A-10D are graphs showing the activity of two F-spondin fragments in in vitro cell proliferation assays.
Figure 10B:
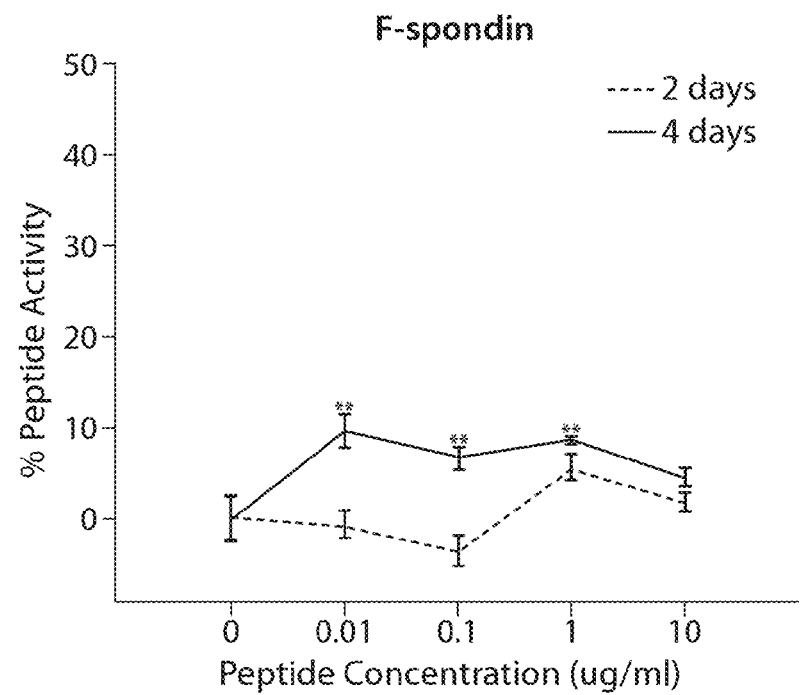
Figure 10C:
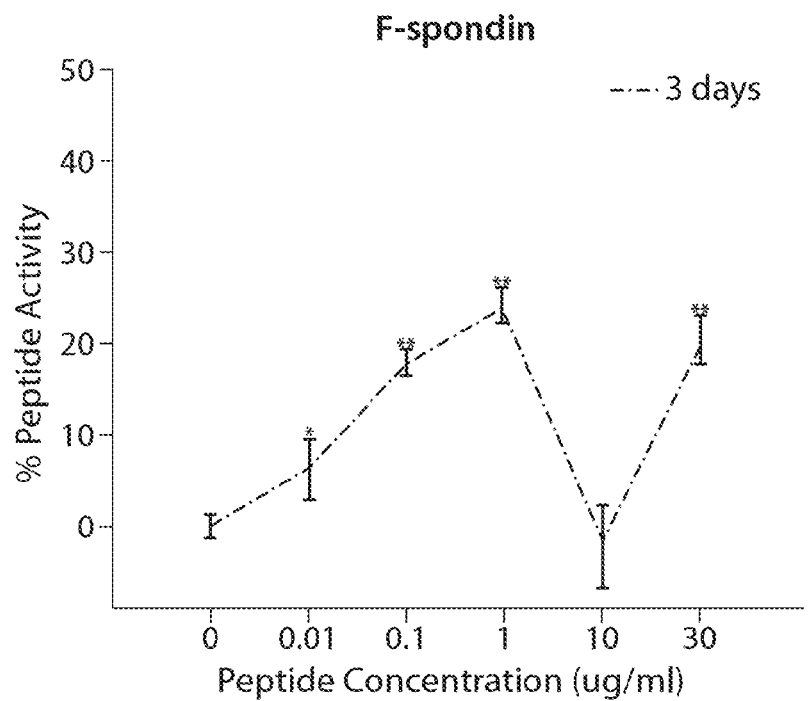
Figure 10D:
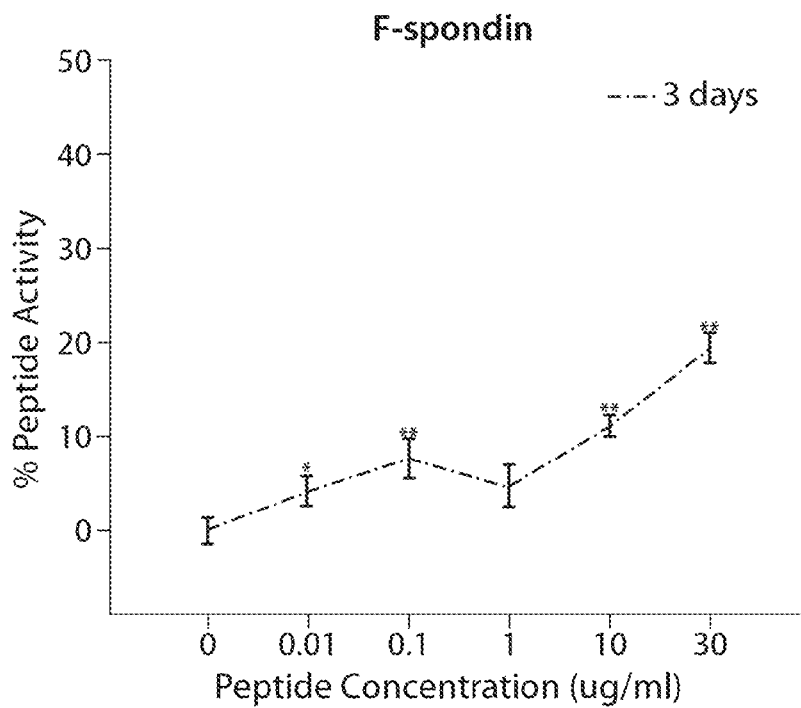

A third isoform of the same family of proteins that was predicted to contain a fragment with putative anti-angiogenic effects is WISP-3. Similarly to WISP-2, the fragment of WISP-3, TKWTPCSRTCGMGISNRV (SEQ ID NO: 76), shows potency at small peptide concentration of 0.01 µg/ml which was also biphasic (FIG. 9C). During the three day application assay, the peptide activity increased significantly as the concentration increased (FIG. 9F)
F-Spondin F-spondin, or vascular smooth muscle cell growth-promoting factor, contains a thrombospondin domain that is predicted to be anti-angiogenic. Two fragments of F-spondin were identified as having putative anti-angiogenic activity. For the first fragment of the protein, SEWSDCSVTCGKGMRTRQR (SEQ ID NO: 73), the activity of the peptide after two days of application was not statistically significant. After four days there was a notable activity which was predominant at low peptide concentration (0.01 µg/ml) and shifts the activity of the peptide to a biphasic profile (FIG. 10A). Interestingly at a high peptide concentration, during the 3 day assay, the peptide shows increased activity (FIG. 10C). The second predicted fragment of F-spondin WDECSATCGMGMKKRHR (SEQ ID NO: 72), shows a small activity after four days of application that reached a maximum of 10% (FIG. 10B). Its activity during the two-day assay was not statistically significant (FIG. 10C) but it exhibited activity in the 3-day assay (FIG. 10D).

CTGF

Figure 11A:
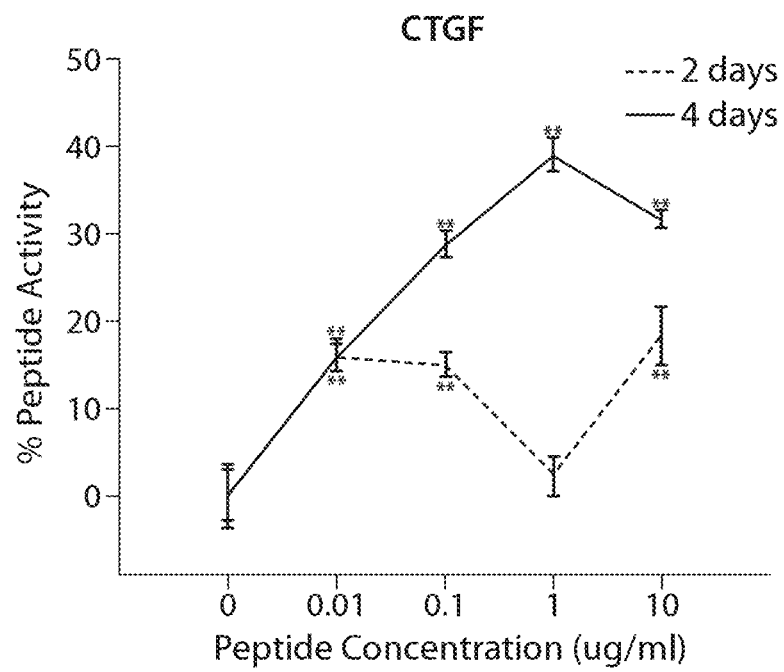
FIGS. 11A and 11B are graphs showing the activity of CTGF in in vitro cell proliferation assays.
Figure 11B:
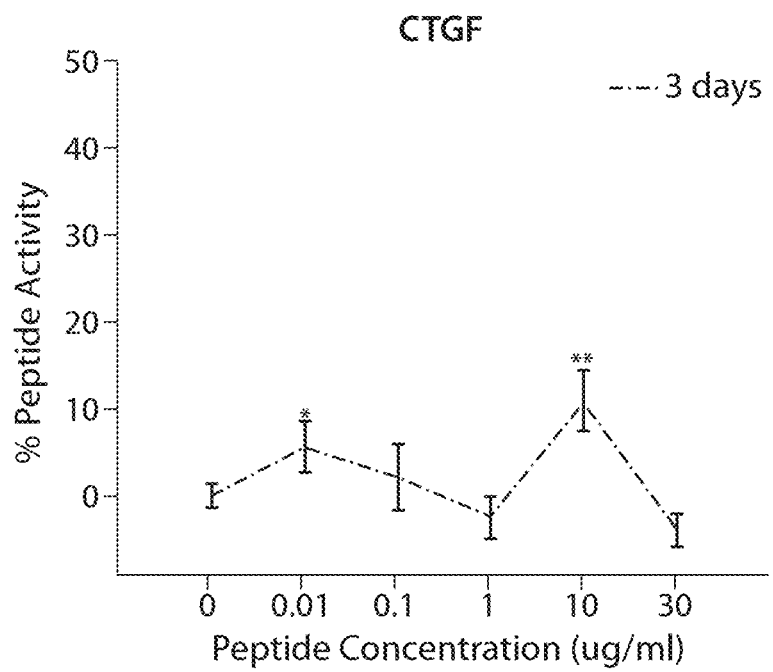

CTGF, connective tissue growth factor, is the prototype for a family of proteins that promotes proliferation and differentiation of chondrocytes. It also mediates heparin- and divalent cation-dependent cell adhesion in many cell types including fibroblasts, myofibroblasts, endothelial and epithelial cells. The peptide that is predicted to be anti-angiogenic (TEWSACSKTCGMGISTRV) (SEQ ID NO: 41) attained 40% activity after four days of application (FIG. 11A) and the activity appeared to saturate at an intermediate concentration (1 µg/ml). The peptide's potency after two days was low (FIG. 11A). CTGF showed increased activity over time. The results of the 3-day assay resembled those observed in the 2-day assay (FIG. 11B).

Fibulin-6

Fibulin-3 and fibulin-5 proteins have been shown to be anti-angiogenic. These fibulins belong to the EGF superfamily. Fibulin-6, or hemicentin-1, which belongs to the immunoglobulin superfamily, contains multiple TSP-1 domains that are predicted to have anti-angiogenic activity. Two distinct domains of fibulin-6 were identified by the bioinformatic analysis as having putative anti-angiogenic properties. One of these (ASWSACSVSCGGGARQRTR) (SEQ ID NO: 45) showed activity of approximately 30% in the four-day assay (FIG. 12A). Interestingly, in the two-day assay the peptide showed biphasic activity. It attained maximum activity at a low concentration (0.1 µg/ml), whereas at lower or higher concentrations it was less active. During the 3-day assay the peptide showed similar activity to that observed after 2 days (i.e., a biphasic response that reached a 20% maximum at 0.1 µg/ml peptide concentration (FIG. 12D). The second fragment derived from fibulin-6 (QPWGTCSESCGKGTQTRAR) (SEQ ID NO: 44) showed even greater potency. It attained maximum activity (~40%) four days after application (FIG. 12B). The second fragment also exhibited biphasic behavior after the four days of application. Its maximum activity was observed at the lowest tested concentration of 0.01 µg/ml. Interestingly, in the 3-day assay, anti-angiogenic activity increased with increasing peptide concentration (FIG. 12E). The third fragment of fibulin-6 (SAWRACSVTCGKGIQKRSR) (SEQ ID NO: 43) was characterized by activity that reached 30% (FIG. 12C). A similar response was observed in the 3 day assay (FIG. 12F) with peptide activity increasing as concentration increased.

CYR61

Figure 13A:
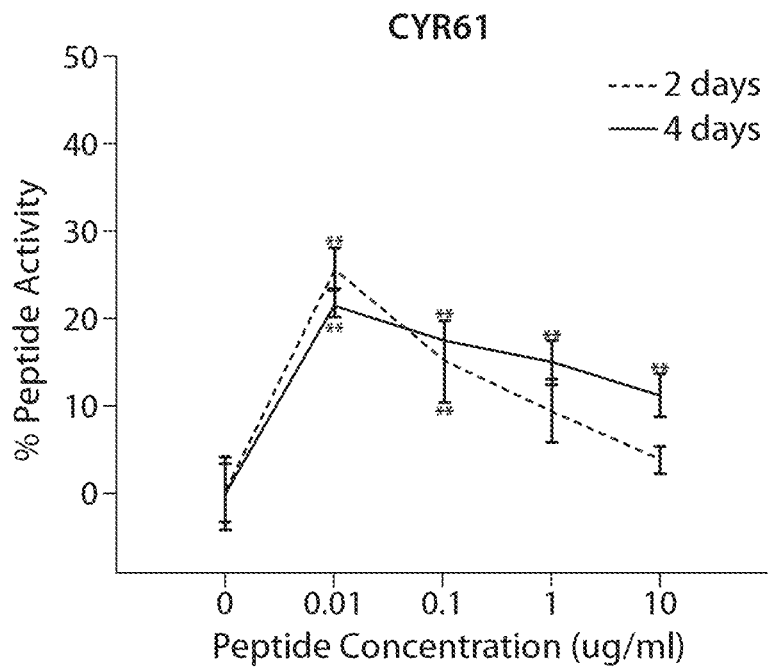
FIGS. 13A and 13B are graphs showing the activity of CYR61 in in vitro cell proliferation assays.
Figure 13B:
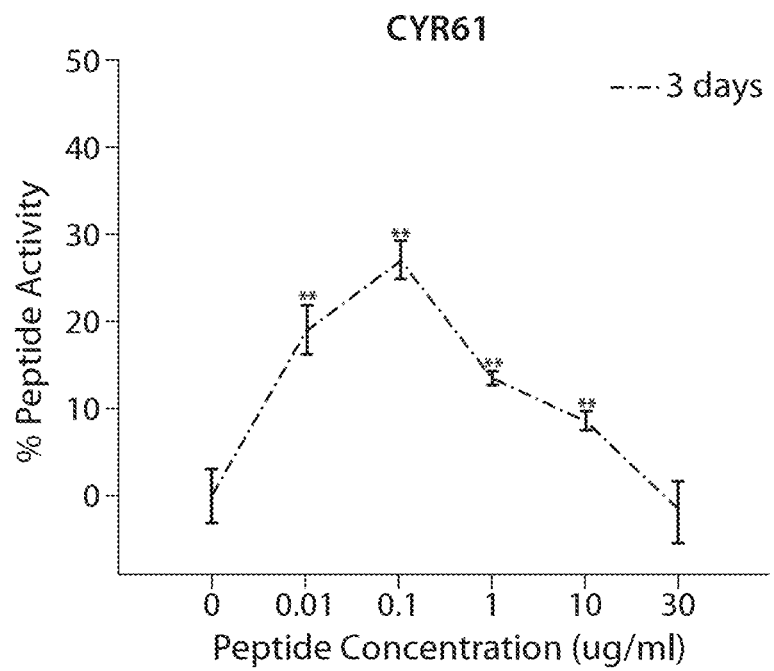

CYR61, or cysteine-rich angiogenic inducer 61, is a secreted, cysteine-rich, heparin-binding protein encoded by a growth factor-inducible immediate-early gene. It is an extracellular matrix-associated signaling molecule. CYR61 promotes the adhesion of endothelial cells through interaction with integrin and augments growth factor-induced DNA synthesis. The predicted fragment (TSWSQCSKTCGTGISTRV) (SEQ ID NO: 42) showed biphasic anti-proliferative activity on the endothelial cells. Maximum (30%) activity was observed at 0.01 µg/ml (FIG. 13A). In the 3-day assay (FIG. 13B), the activity of the peptide was similar, attaining maximum activity of 30% at 0.1 µg/ml concentration.

NOVH

Figure 14A:
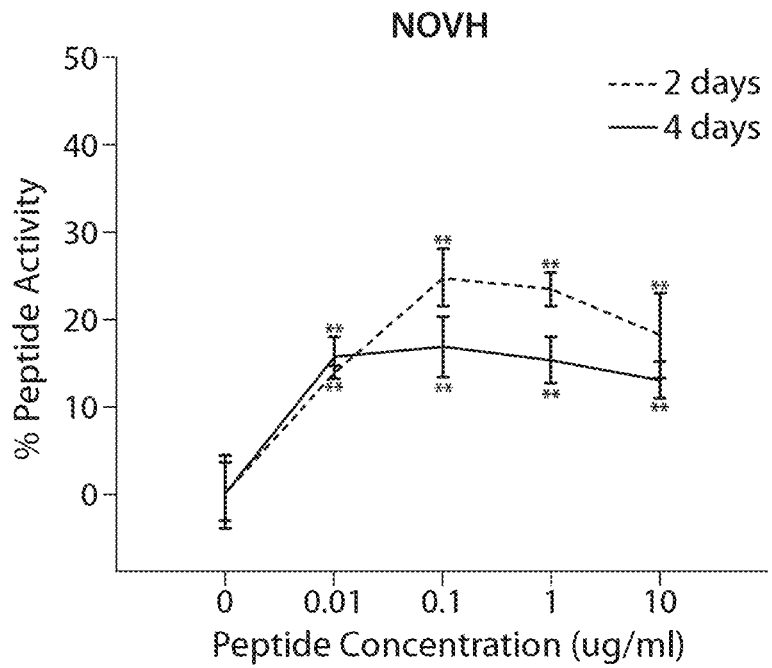
FIGS. 14A and 14B are graphs showing the activity of NOVH after 2 and 4 days of peptide application.
Figure 14B:
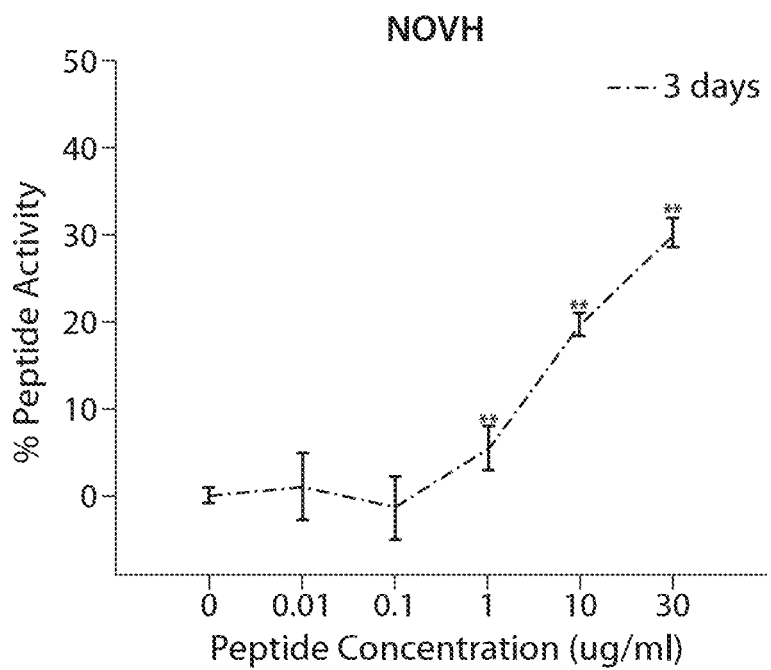

NOVH, or the nephroblastoma overexpressed protein, is an immediate-early protein that plays a role in tumor cell growth regulation. The TSP-1 domain of NOVH was predicted to exert anti-angiogenic activity. The predicted anti-angiogenic fragment (TEWTACSKSCGMGFSTRV) (SEQ ID NO: 46) reached 20% maximum activity (FIG. 14A) at small peptide concentrations (0.01 µg/ml) and the activity was retained throughout the four days of the peptide application. In the 3-day assay the activity showed a monotonic increase with concentration (FIG. 14B).

UNC-5C and UNC-5D

Figure 15A:
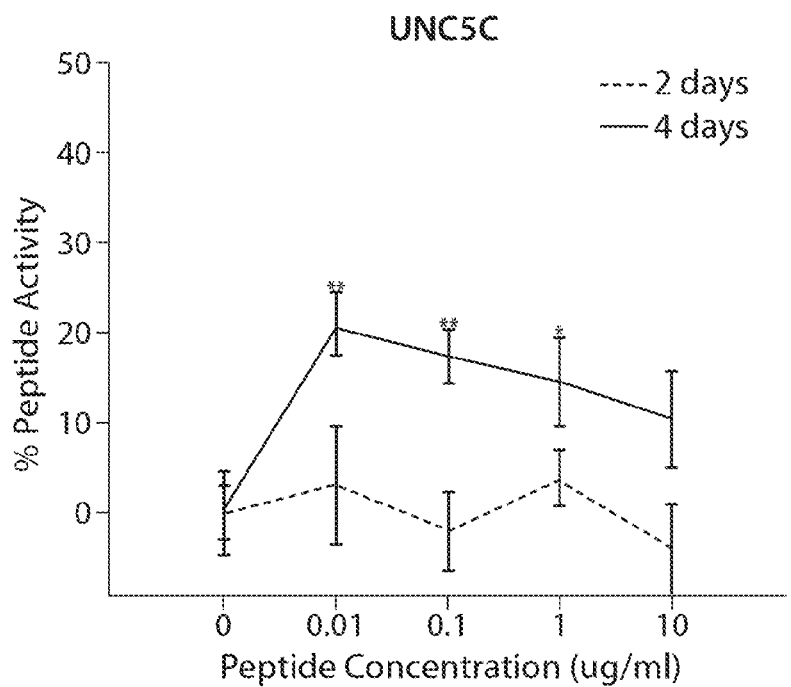
FIGS. 15A-15D are graphs showing the activity of two isoforms of UNC-5 in an in vitro cell proliferation assay.
Figure 15B:
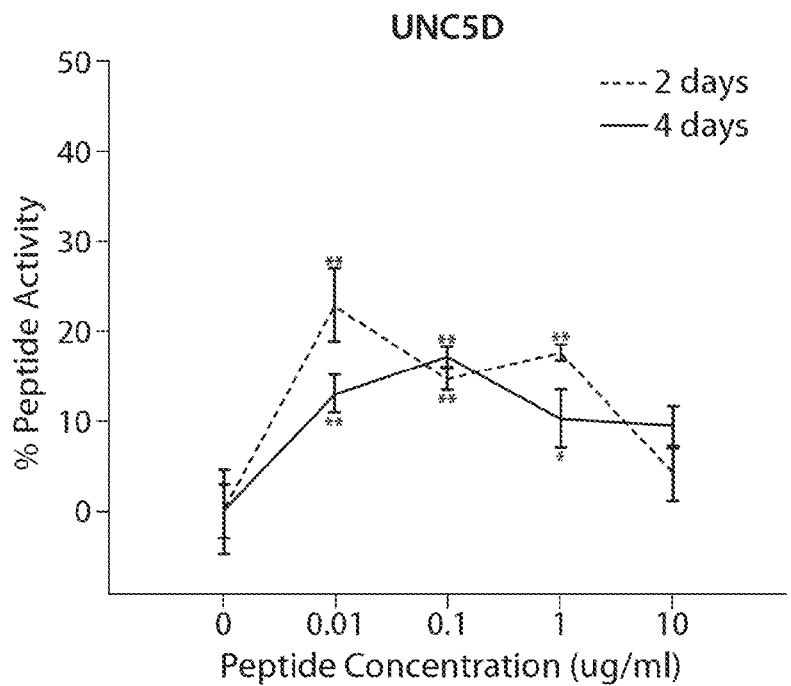
Figure 15C:
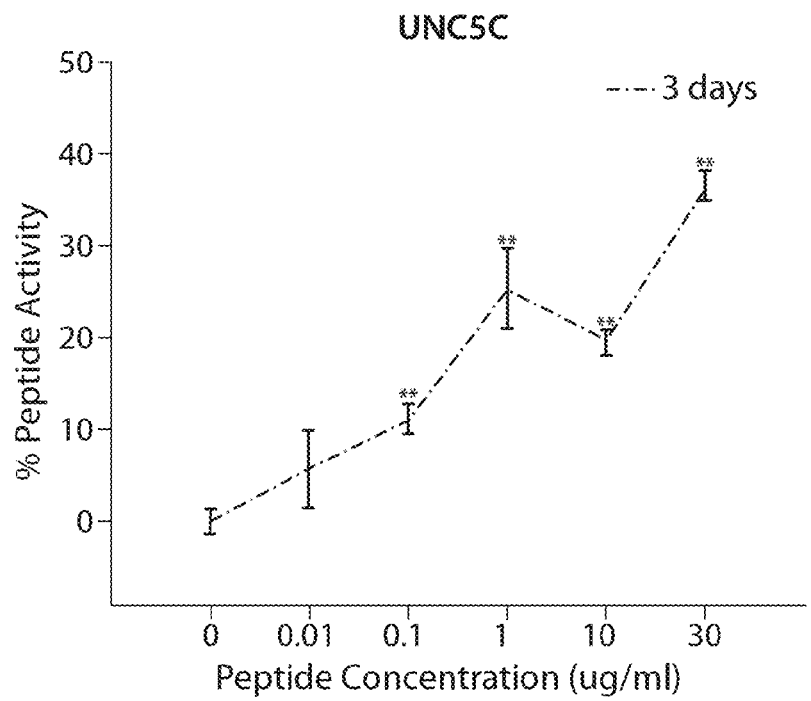
Figure 15D:
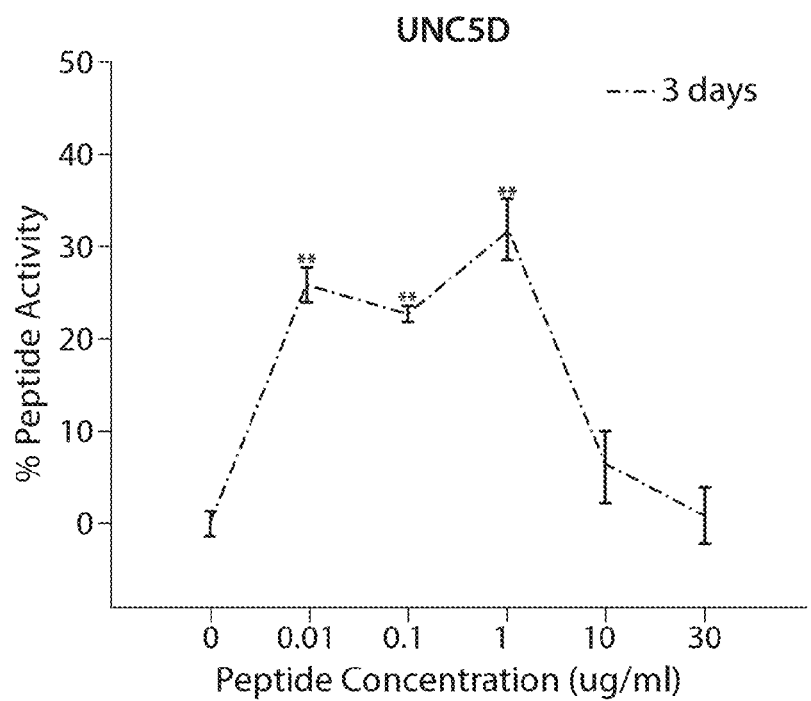

UNC-5C and UNC-5D belong to the UNC-5 family of netrin receptors. Netrins are secreted proteins that direct axon extension and cell migration during neural development. They are bifunctional proteins that act as attractants for some cell types and as repellents for others, and these opposite actions are thought to be mediated by two classes of receptors. The UNC-5 family of receptors mediate the repellent response to netrin; they are transmembrane proteins containing 2 immunoglobulin (Ig)-like domains and 2 type I thrombospondin domains (TSP-1) in the extracellular region. Fragments of the TSP-1 domains are predicted to exert anti-angiogenic activity. The fragment derived from UNC5-C (TEWSVCNSRCGRGYQKRTR) (SEQ ID NO: 70) has negligible activity at the two days of the peptide application whereas it reached 20% activity after four days (FIG. 15A). For the 3 day application experiment the peptide response was similar to the 4 days of application with a 20% maximum at 10 µg/ml. At 30 µg/ml the peptide activity increases to 40% (FIG. 15C). The fragment from UNC5-D (TEWSACNVRCGRGWQKRSR) (SEQ ID NO: 71) has constant activity throughout the four days assay and the activity reached 20% (FIG. 15B). The activity of UNC5-D in the 3-day assay was similarly biphasic, but now the maximum reached 30% at 0.1 to 1 µg/ml (FIG. 15D).

SCO-Spondin

Figure 16A:
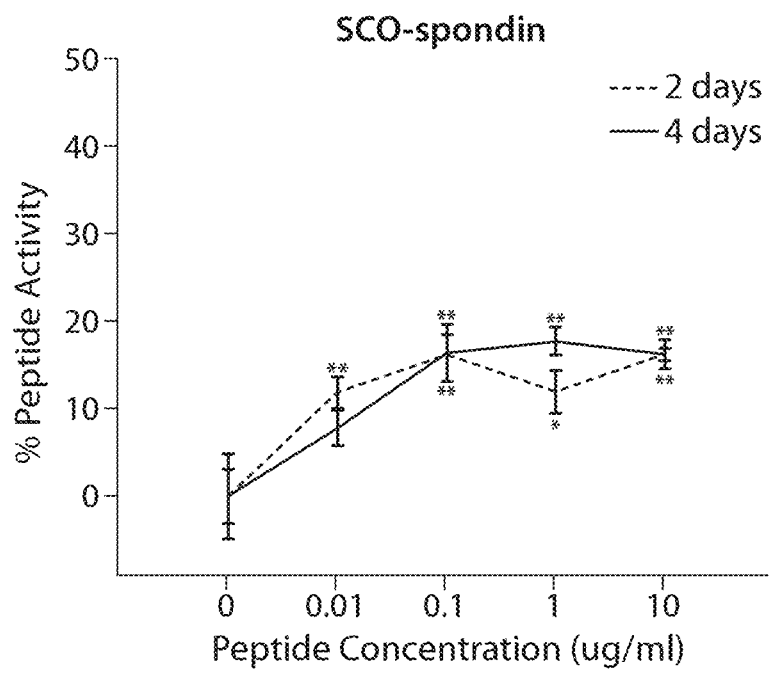
FIGS. 16A and 16B are graphs showing the activity of SCO-spondin in in vitro cell proliferation assays.
Figure 16B:
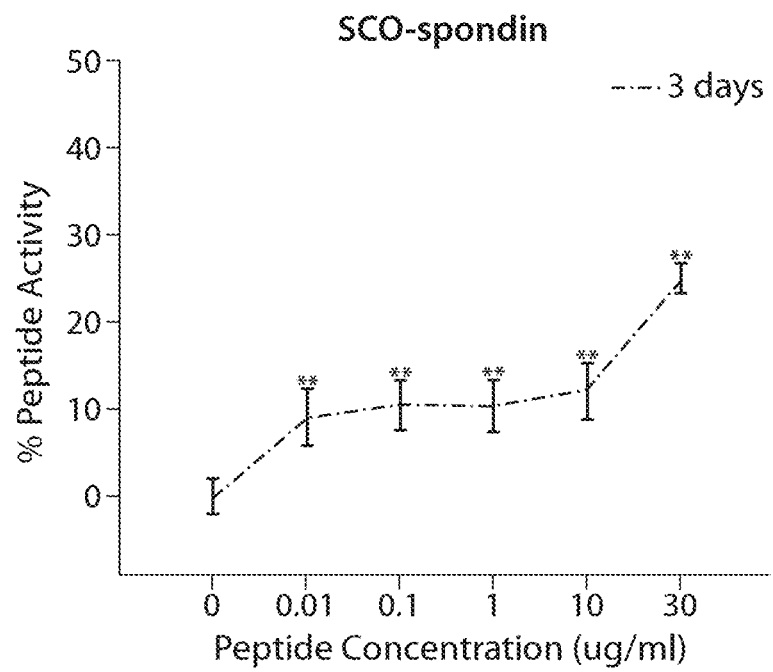

SCO-spondin is a relative of the thrombospondin family and corresponds to glycoproteins secreted by the subcommissural organ (SCO). SCO-spondin is also known to modulate neuronal aggregation. The TSP-1 peptide fragment that is predicted to be anti-angiogenic (GPWEDCSVSCGGGEQLRSR) (SEQ ID NO: 63) showed low anti-proliferative activity which reached maximum efficiency ~15% at high peptide concentrations for both of the 2-4 and 25% for 3-day assays (FIGS. 16A and 16B).

Properdin

Figure 17A:
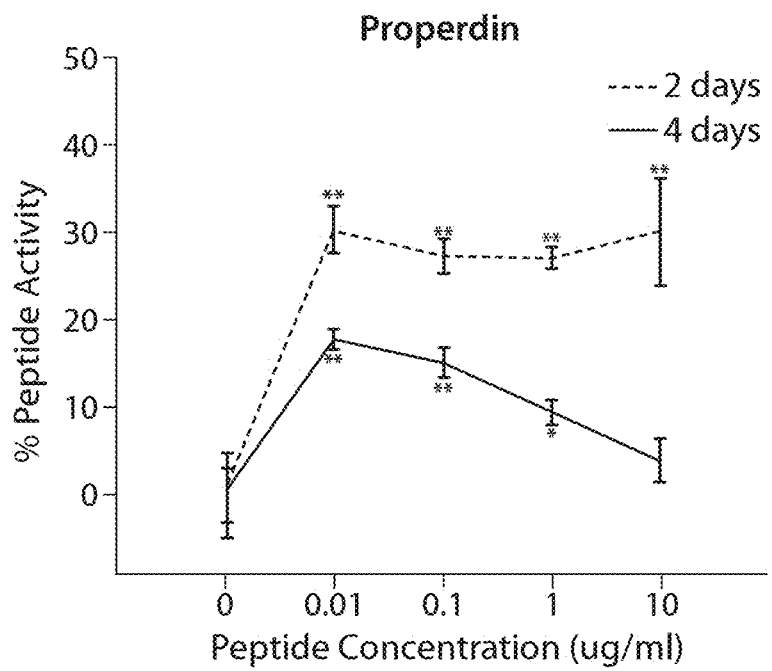
FIGS. 17A and 17B are graphs showing the activity of properdin in in vitro cell proliferation assays.
Figure 17B:
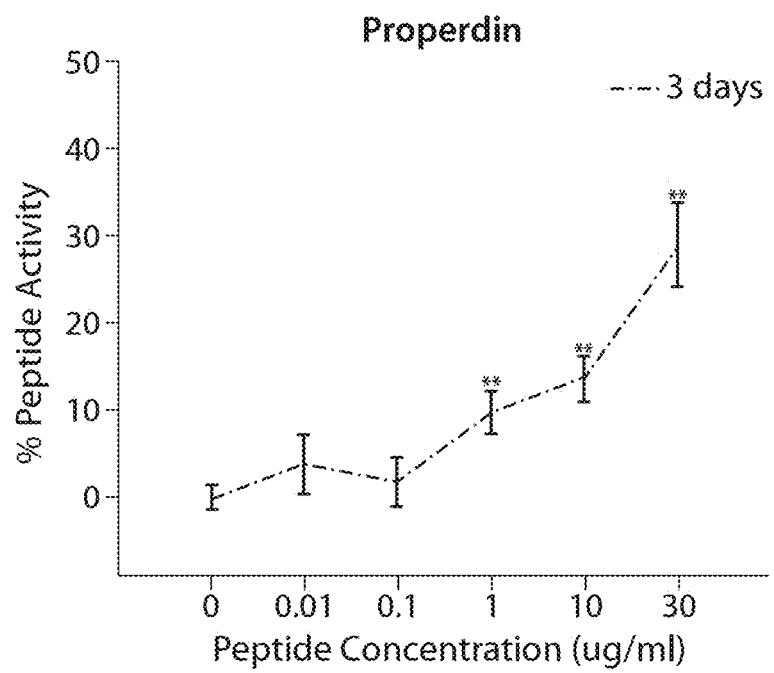

Properdin or factor P, is a plasma protein that is active in the alternative complement pathway of the innate immune system. A fragment from its TSP-1 domain (GPWEPCSVTCSKGTRTRRR) (SEQ ID NO: 49) was predicted to exert anti-angiogenic activity. The peptide attained maximum activity 30% at the lowest tested concentration (0.01 µg/ml) (FIG. 17A). After four days of peptide application, it showed a biphasic response with maximum activity 20% observed at low concentrations (0.01 µg/ml and 0.1 µg/ml). In the 3-day proliferation assay (FIG. 17B) the activity significantly increased at 30 µg/ml.

C6

Figure 18A:
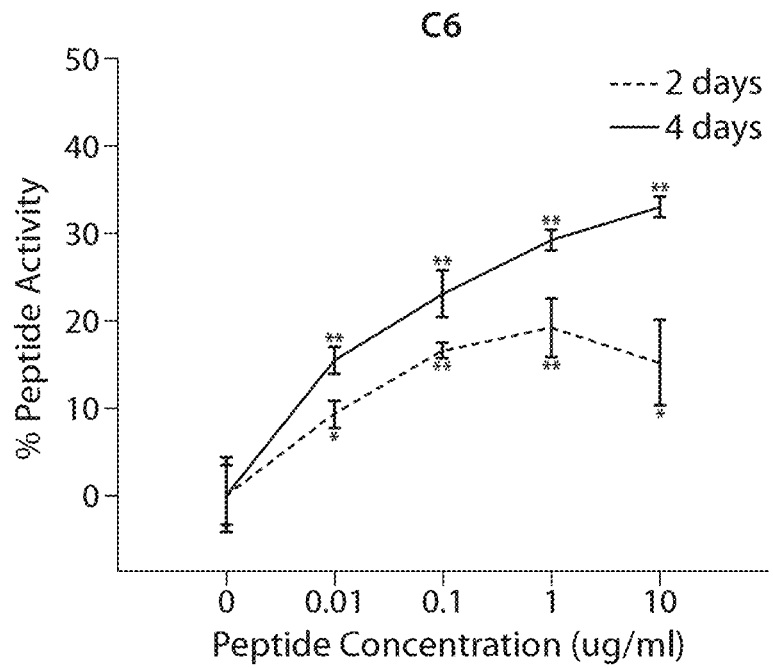
FIGS. 18A and 18B are graphs showing the activity of C6 in in vitro cell proliferation assays.
Figure 18B:
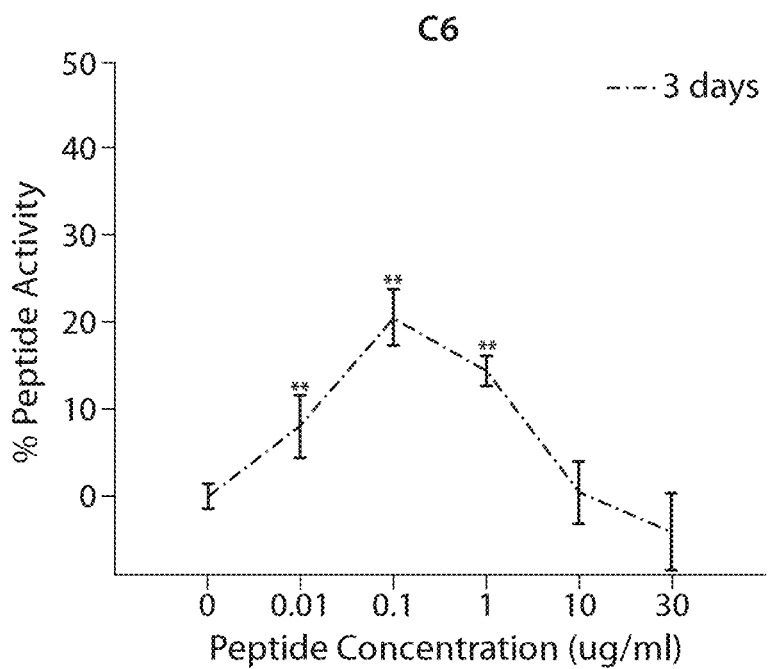

Another protein that functions as part of the immune system is the complement component 6 protein (C6). C6 is a component of complement cascade. It is part of the membrane attack complex that can insert into the cell membrane and cause cell to lyse. The predicted anti-angiogenic fragment (TQWTSCSKTCNSGTQSRHR) (SEQ ID NO: 38), which is part of the TSP-1 domain that C6 contains, exhibited maximum activity of 35% at high peptide concentrations after four days of incubation with cells (FIG. 18A). The activity of C6 was different from the activity observed in properdin, the other peptide fragment that belongs to the immune response pathway. The proliferation results in the 3-day assay (FIG. 18B) were similar to those observed in the 2 day assay. The activity was biphasic with a 25% maximum reached at intermediate peptide concentrations (FIG. 18B).

ADAMTS Family

A large portion of the fragments that contain TSP-1 domains and are predicted to exert anti-angiogenic activity belong to the ADAMTS family of proteins. Members of the family share several distinct protein modules, including a propeptide region, a metalloproteinase domain, a disintegrin-like domain, and a thrombospondin type 1 (TSP-1) motif. The peptides tested that belong to this protein family are thrombospondin repeat containing 1 protein (TRSC1) or ADAMTS-like-4, ADAMTS-4, ADAMTS-8, ADAMTS-16 and ADAMTS-18.

TRSC1

Figure 19A:
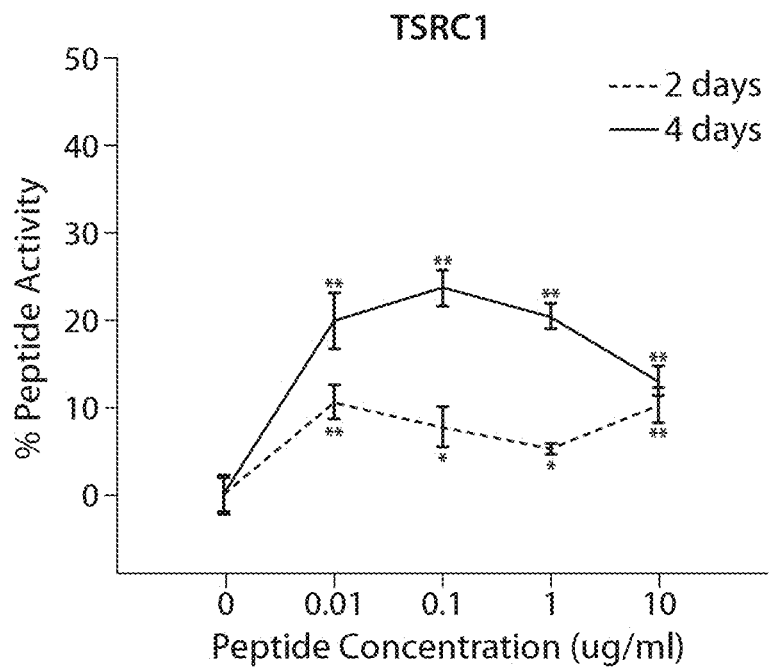
FIGS. 19A and 19B are graphs showing the activity of TSRC1 in in vitro cell proliferation assays.
Figure 19B:
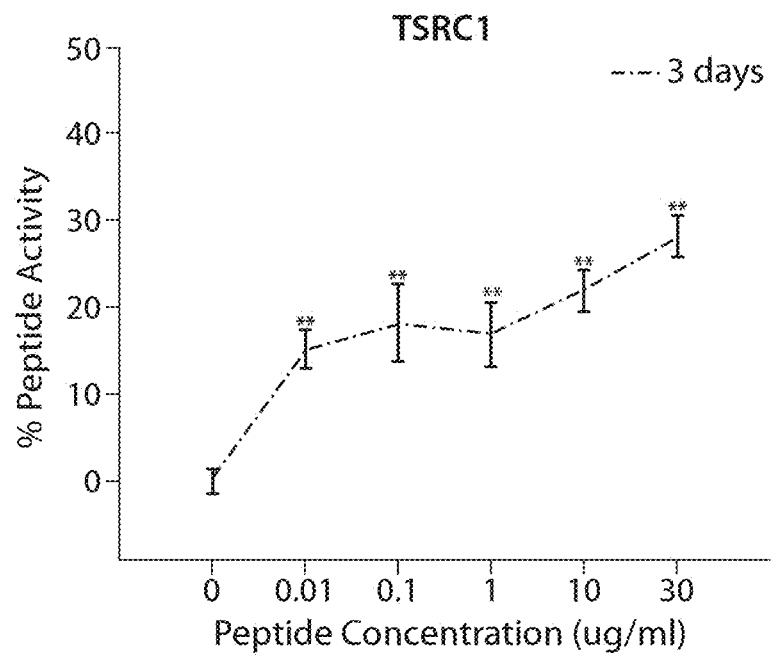

TSRC1 or ADAMTS-like-4, is a protein with a predicted anti-angiogenic fragment (SPWSQCS-VRCGRGQRSRQVR) (SEQ ID NO: 69) that showed minimal activity on the endothelial cell proliferation ability after two days of the peptide application. After four days there was prominent activity at intermediate peptide concentrations. The activity profile was biphasic and reached a maximum of 25% at 0.1 µg/ml (FIG. 19A). The experimental results for the 3-day assay (FIG. 19B) were similar to those in the 4-day assay. The peptide activity increased at the highest applied concentrations of 30 µg/ml.

ADAMTS-4

Figure 20A:
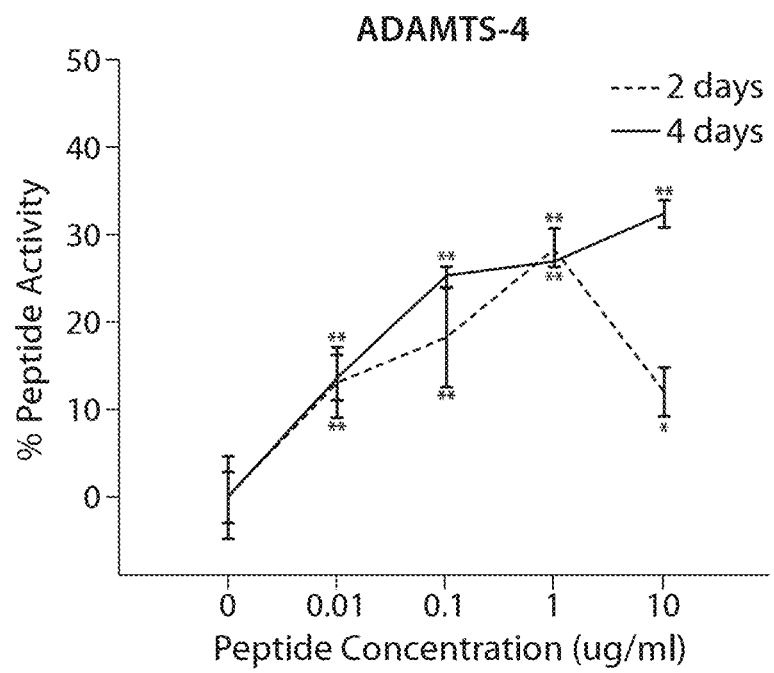
FIGS. 20A and 20B are graphs showing the activity of ADAMTS-4 in in vitro cell proliferation assays.
Figure 20B:
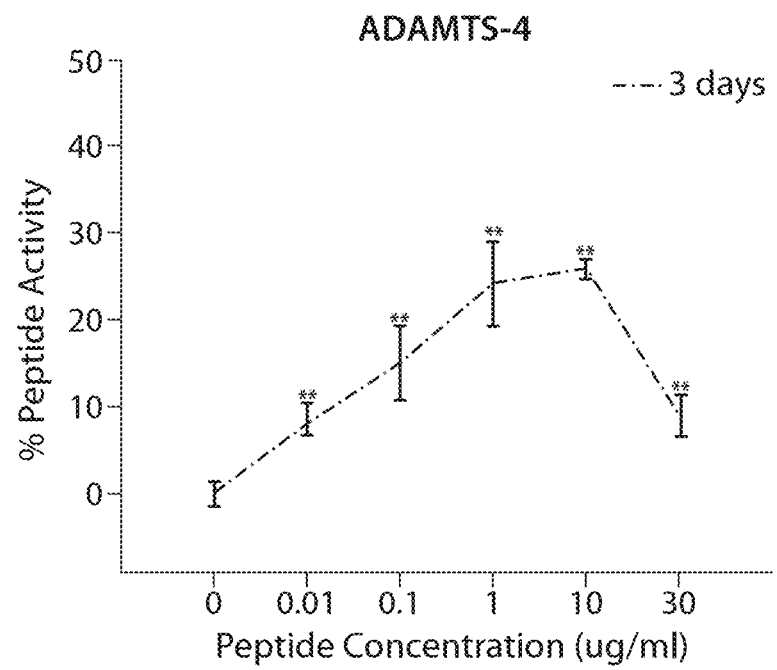

The ADAMTS-4 protein contains a TSP-1 domain (GP-WGDCSRTCGGGVQFSSR) (SEQ ID NO: 7) that is predicted to be anti-angiogenic. When tested for its anti-proliferative activity the ADAMTS-4 fragment reached a maximum of 35% efficiency at its highest tested concentration (10 µg/ml) after four days of the peptide application (FIG. 20A). Similar results were observed in the 3 day assay (FIG. 20B).

ADAMTS-8

Figure 21A:
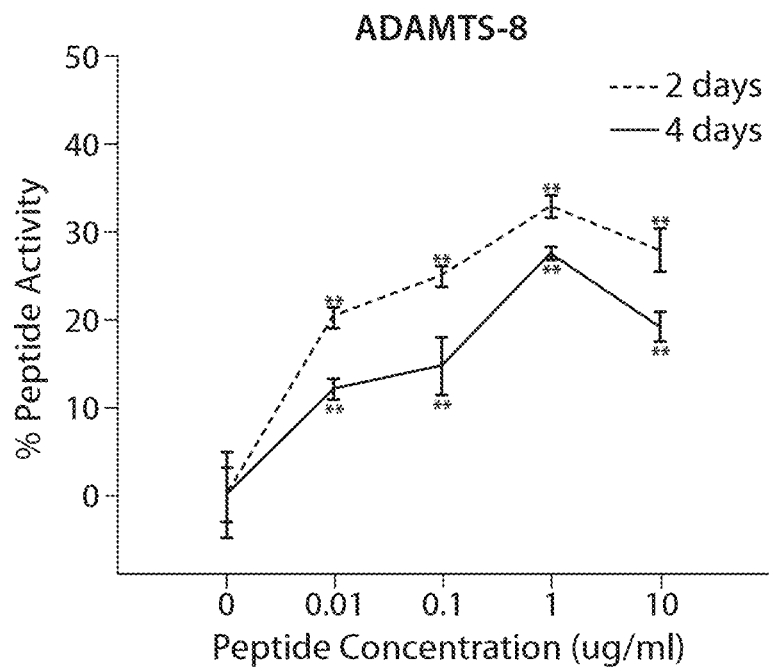
FIGS. 21A and 21B are graphs showing the activity of ADAMTS-8 in in vitro cell proliferation assays.
Figure 21B:
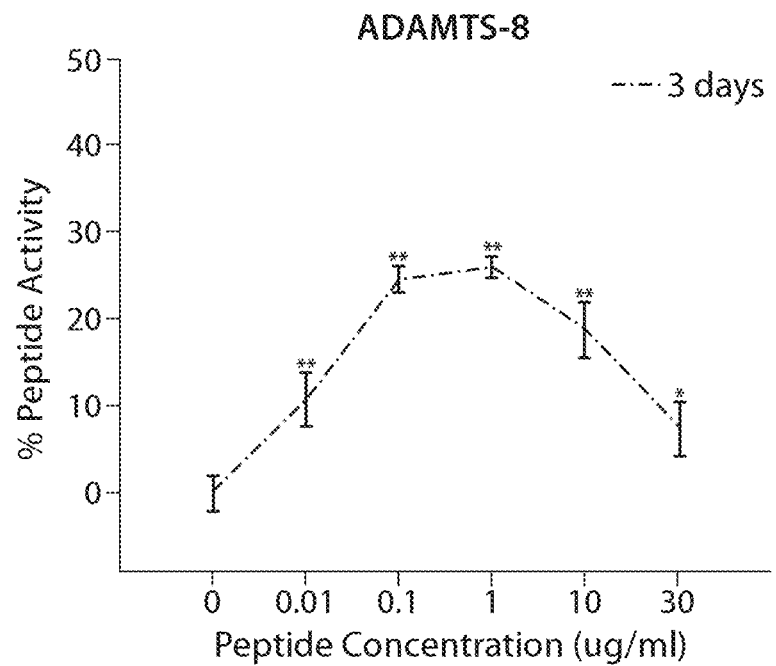

The second protein that belongs to the ADAMTS family and contains a TSP-1 domain that is predicted to be anti-angiogenic is ADAMTS-8. The fragment from ADAMTS-8 (GPWGECSRTCGGGVQFSHR) (SEQ ID NO: 14) exerted maximum activity of 35% at concentration 1 µg/ml after two days of the peptide application (FIG. 21A). A maximum activity of 30% at 1 µg/ml was observed in the 4-day assay also. The peptide's activity was reduced at the maximum tested concentration of 10 µg/ml relative to its activity at lower concentrations. This biphasic response was observed in the two, three, and four day assays (FIGS. 21A and 21B).

ADAMTS-16

Figure 22A:
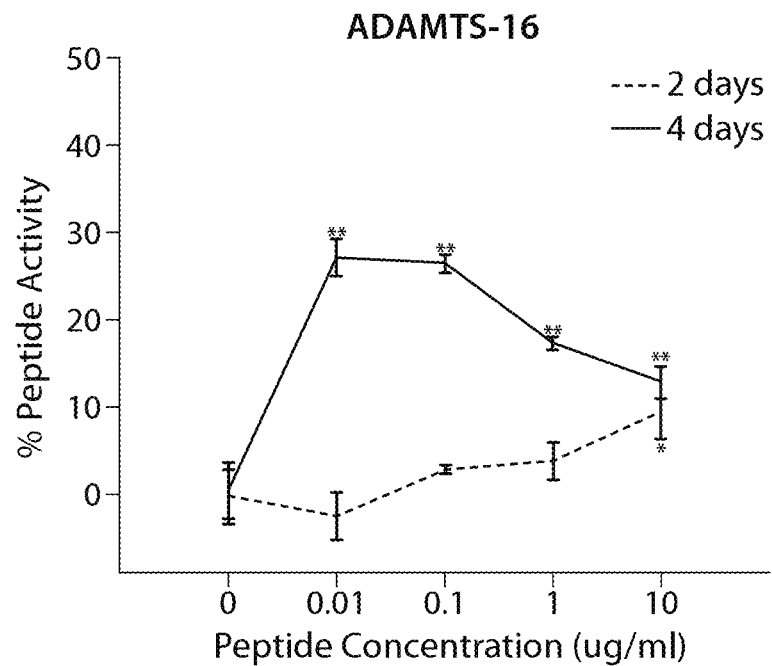
FIGS. 22A and 22B are graphs showing the activity of ADAMTS-16 in in vitro cell proliferation assays.
Figure 22B:
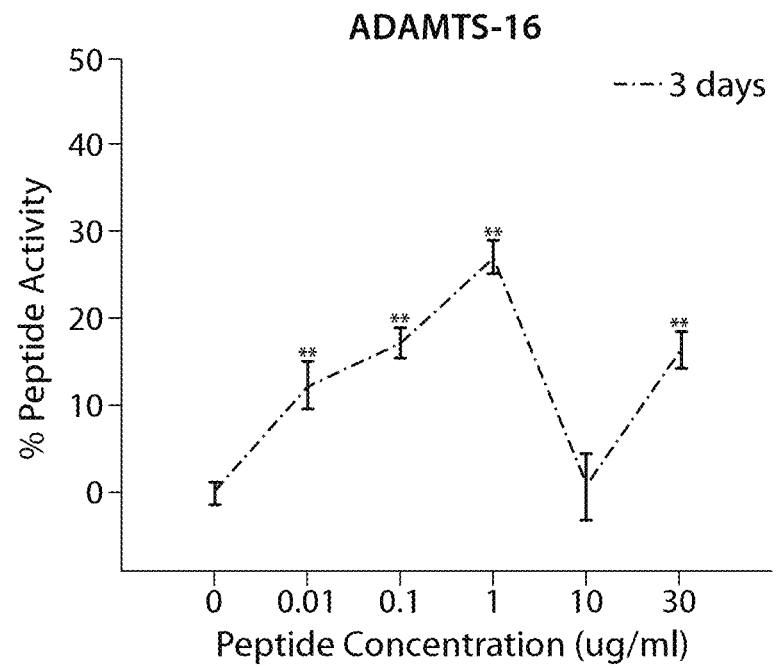

ADAMTS-16 is another protein that contains a TSP-1 domain that is predicted to be anti-angiogenic. The ADAMTS-16 fragment (SPWSQCTASCGGGVQTR) (SEQ ID NO: 24) showed strong activity at four days and exhibited a biphasic response with a maximum 30% observed at 0.01 µg/ml and 0.1 µg/ml concentrations (FIG. 22A). At concentrations greater than 0.1 µg/ml the activity of the peptide was reduced. In the 3-day assay, an increase in peptide activity was observed at the highest applied concentration of 30 µg/ml (FIG. 22B).

ADAMTS-18

Figure 23A:
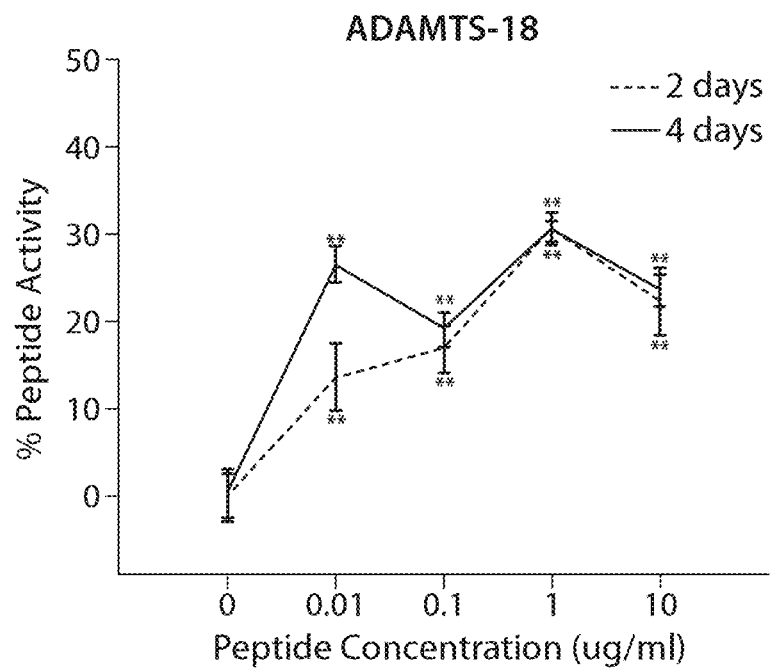
FIGS. 23a and 23B are graphs showing the activity of ADAMTS-18 in in vitro cell proliferation assays.
Figure 23B:
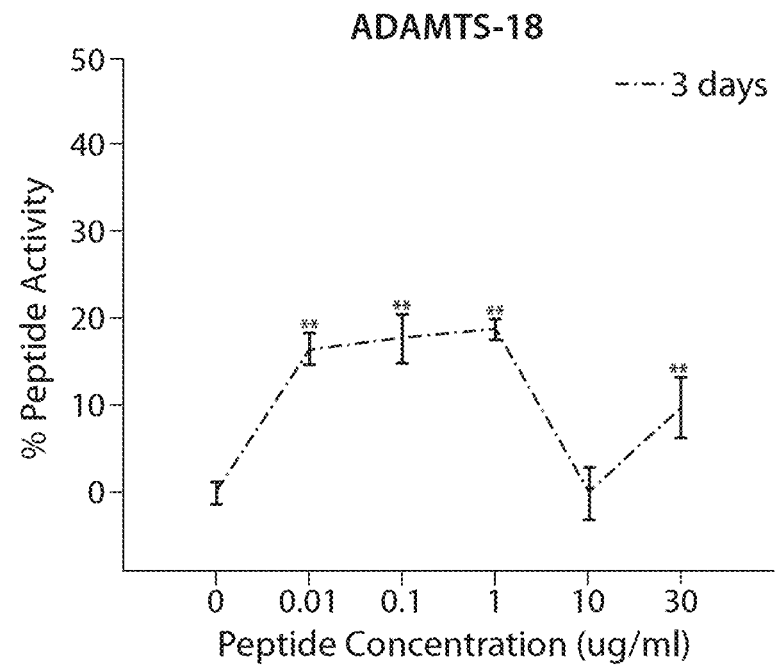

ADAMTS-18 is another protein containing a TSP-1 domain that was experimentally tested for its anti-proliferative activity. The activity of the ADAMTS-18 derived fragment (SKWSECSRTCGGGVKFQER) (SEQ ID NO: 29) was similar to that of ADAMTS-8 (FIG. 23A). The peptide exhibited 30% activity at 1 µg/ml after two days of incubation with cells (FIG. 23A). As was observed for ADAMTS-8, the peptide's activity was reduced at 10 µg/ml relative to its activity at lower concentrations. This biphasic response was observed in the two and four day assays. In the 3-day assay at the highest peptide concentration (30 µg/ml) the peptide's activity was significantly increased.

Semaphorins

The semaphorins are another family of proteins that contain a TSP-1 domain. Two fragments of semaphorin 5A and one fragment of semaphorin 5B were predicted to have anti-angiogenic activity. Semaphorins are involved in axonal guidance during neural development and some of them have been shown to possess anti-angiogenic activity, although Semaphorin 5A and 5B have not been identified as anti-angiogenic agents.

Semaphorin 5A and 5B

The first semaphorin 5A fragment (GP-WERCTAQCGGGIQARRR) (SEQ ID NO: 60) exhibited minimum anti-proliferative activity after two days of the peptide application and showed intermediate activity in the 4-day assay. The activity reached a maximum of 25% at concentrations higher than 1 µg/ml (FIG. 24A) for the 2 and 4 day assay whereas reached 35% in the 3 day assay (FIG. 24D). The second semaphorin 5A fragment tested SPWTKC-SATCGGGHYMRTR (SEQ ID NO: 61) showed no anti-proliferative activity (FIGS. 24B and 24E). The semaphorin 5B fragment, TSWSPCSASCGGGHYQRTR (SEQ ID NO: 62) showed 10% anti-proliferative activity (FIG. 24C). Similar results were obtained in the 3-day assay (FIGS. 24D-F).

Papilin

Figure 25A:
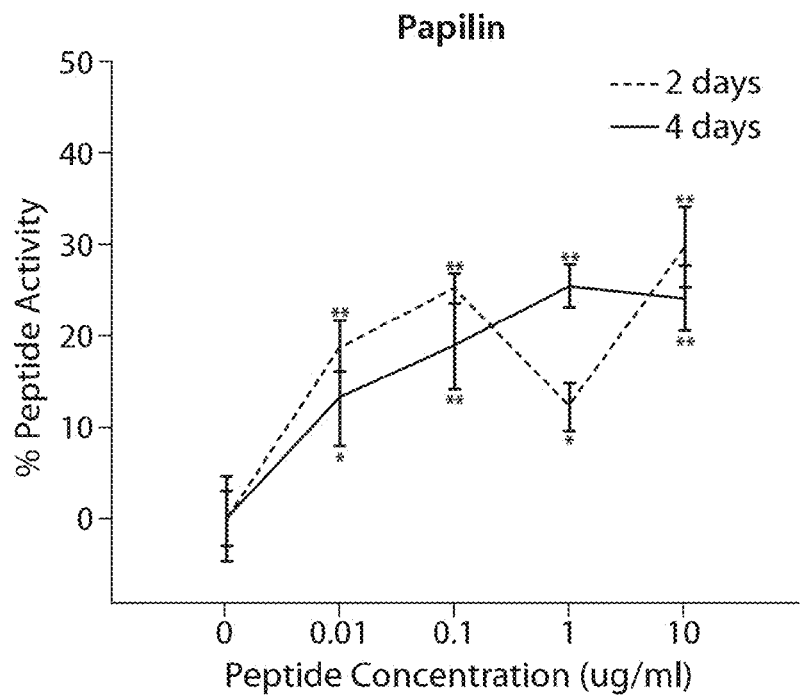
FIGS. 25A-25D are graphs showing the activity of two different papilin fragments in in vitro cell proliferation assays.
Figure 25B:
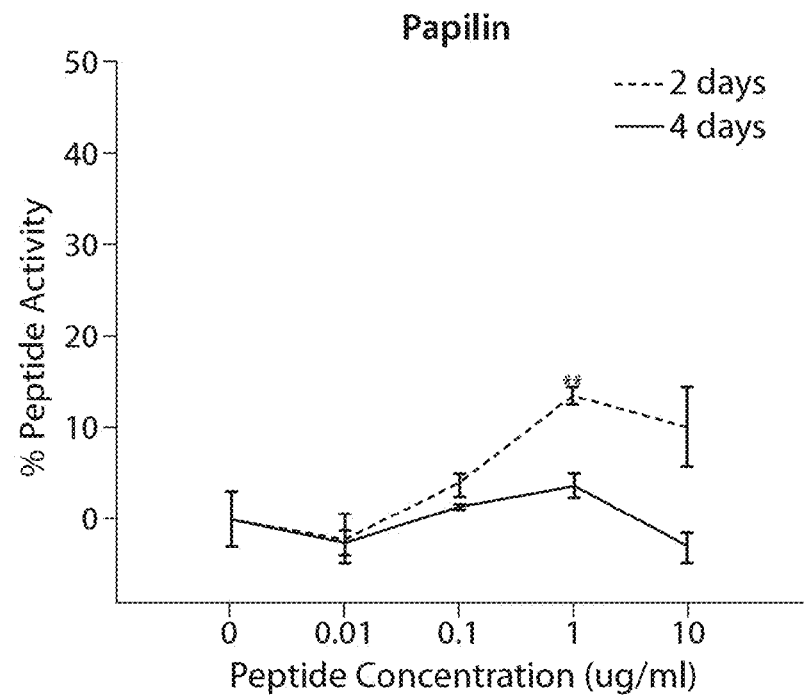
Figure 25C:
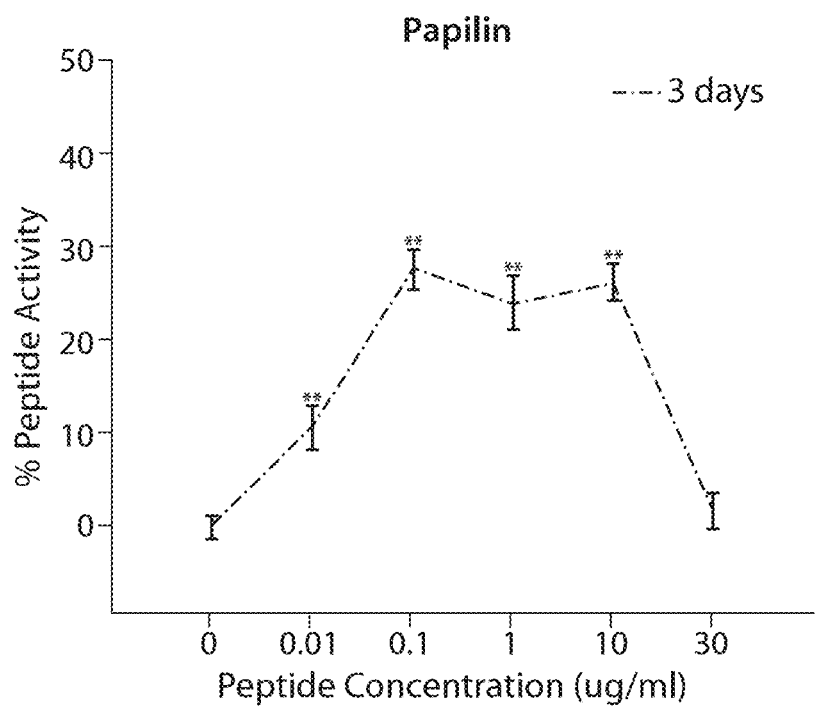
Figure 25D:
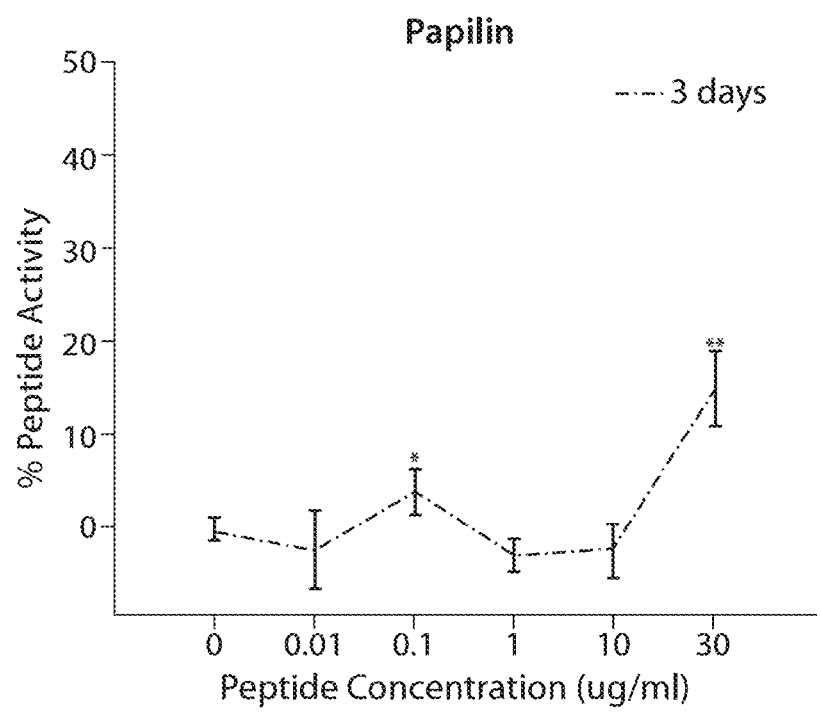

Another protein that belongs to the TSP-1 containing proteins is papilin. Papilin is a proteoglycan-like sulfated glycoprotein that functions during development. Two fragments of papilin contained within distinct TSP-1 domains of the protein sequence were tested experimentally for their ability to suppress endothelial cell proliferation. The first fragment of papilin, GPWAPCSASCGGGSQSRS (SEQ ID NO: 48), showed potent anti-proliferative activity of 30% (FIG. 25A). The second fragment of papilin, SQWSPCSRTCGGGVS-FRER (SEQ ID NO: 47), was less potent and showed only minimal anti-proliferative activity (FIG. 25B). Similar results were obtained for these fragments in the 3-day assay (FIGS. 25C and 25D).

ADAMs

Another family of proteins that contain a TSP-1 domain are the ADAMs. Members of this family are membrane-anchored proteins and have been implicated in a variety of biologic processes involving cell-cell and cell-matrix interactions, including fertilization, muscle development, and neurogenesis. ADAM proteins interact with SH3 domain-containing proteins, bind mitotic arrest deficient 2 beta protein, and are also involved in TPA-induced ectodomain shedding of membrane-anchored heparin-binding EGF-like growth factor.

ADAM-9

Figure 26A:
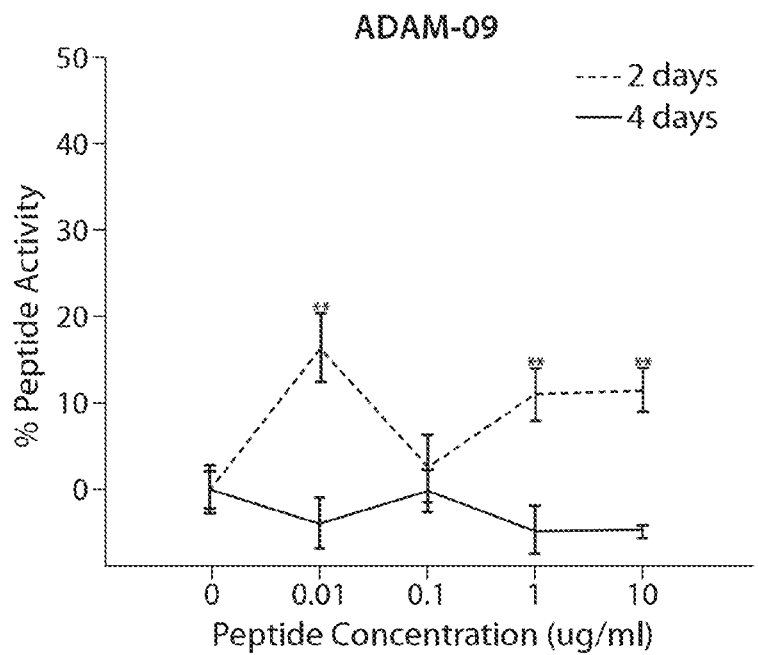
FIGS. 26A-26D are graphs showing the activity of fragments derived from ADAM-9 and ADAM-12 in in vitro cell proliferation assays.

A putative anti-angiogenic fragment was identified in ADAM-9. The protein fragment, KCHGHGVCNSNKN (SEQ ID NO: 1), showed ~20% antiproliferative activity (FIG. 26A). Similar activity was observed in the 3-day proliferation assay (FIG. 26C).

ADAM-12

Figure 26B:
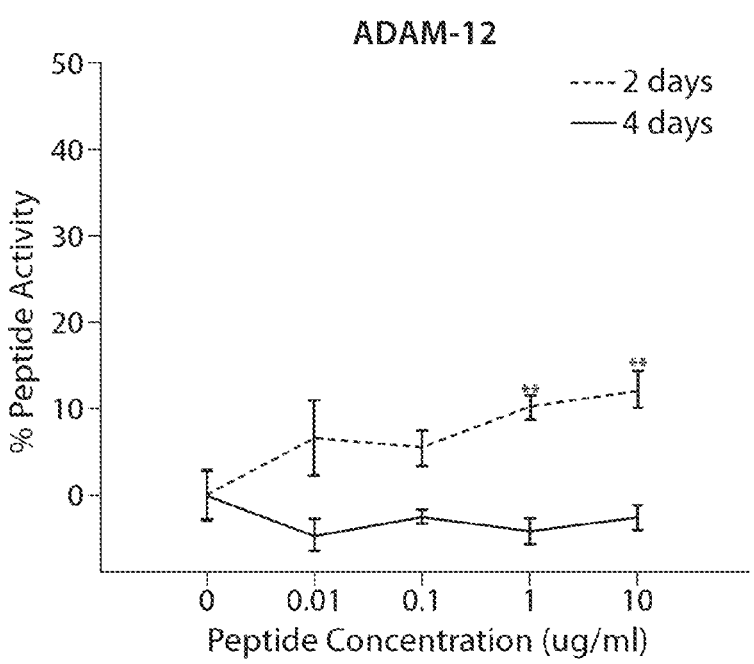
Figure 26C:
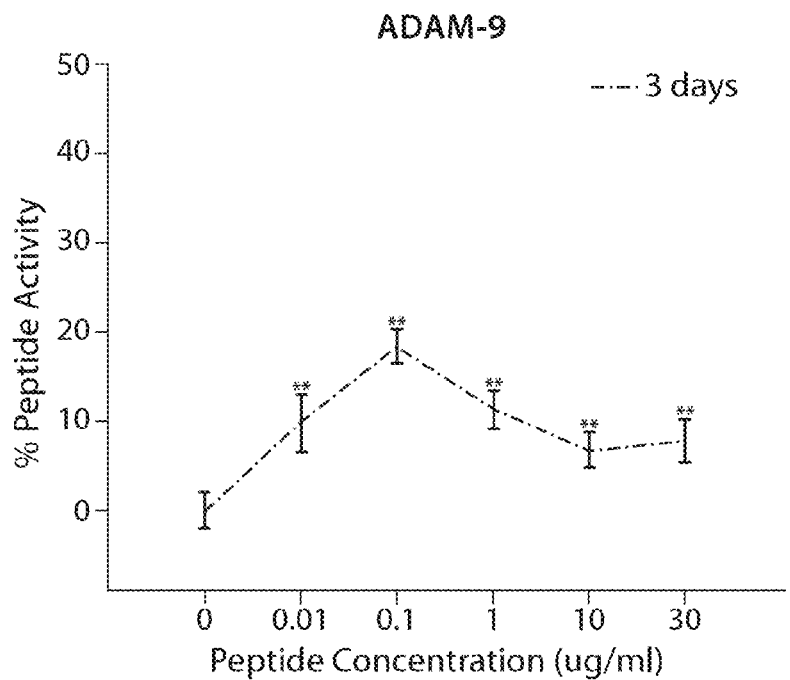
Figure 26D:
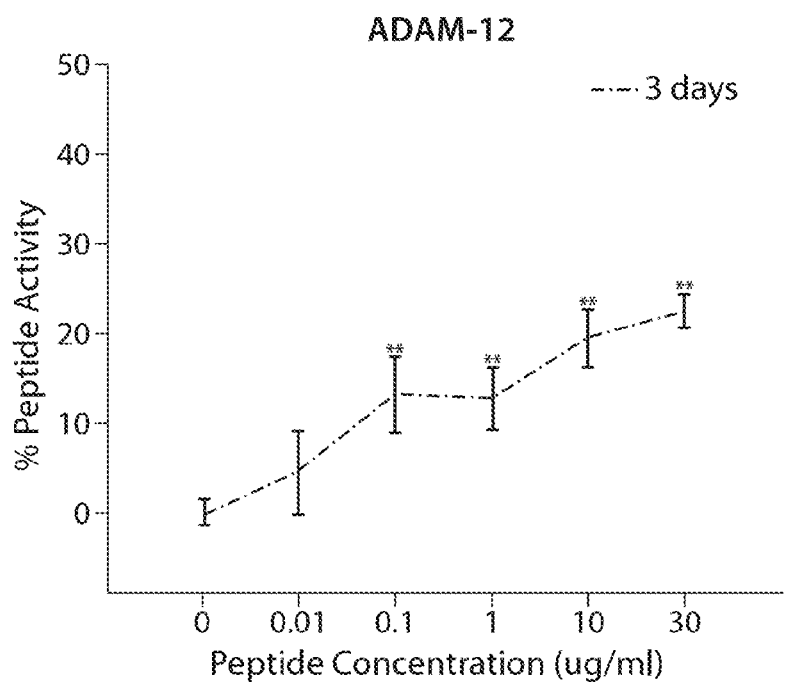

A fragment derived from the ADAM-12 isoform, MQCH-GRGVCNNRKN (SEQ ID NO: 2), showed activity at 2 days at concentrations of 1 and 10 µg/ml (FIG. 26B). Similar results were observed in the 3-day assay, with the activity increasing as the peptide concentration increased (FIG. 26D).

Peptides Derived from C-X-C Chemokines

Six peptides derived from C-X-C chemokines were predicted to exhibit anti-angiogenic activity based on their similarity to known anti-angiogenic protein fragments of this family.

Gro-α/CXCL1

Figure 27A:
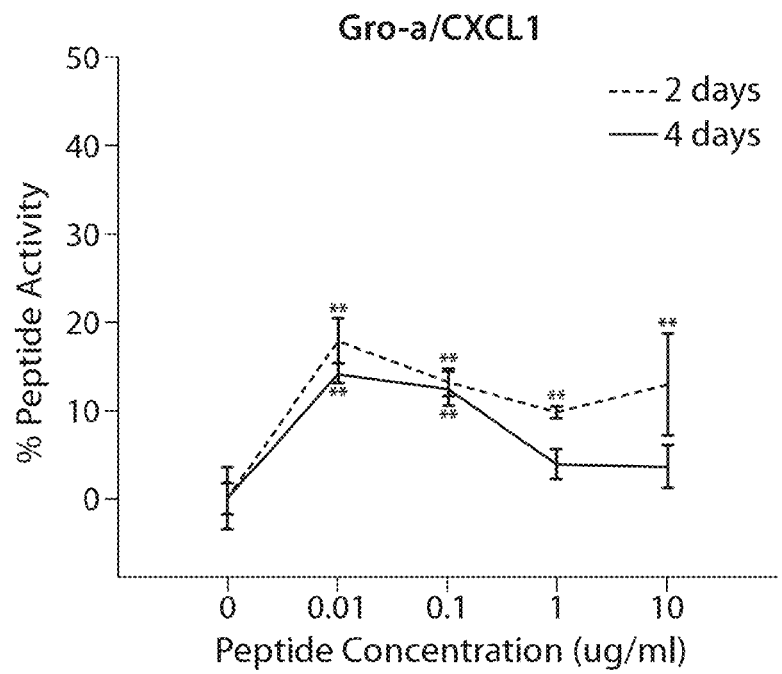
FIGS. 27A and 27B are graphs showing the activity of Gro-α in in vitro cell proliferation assays.
Figure 27B:
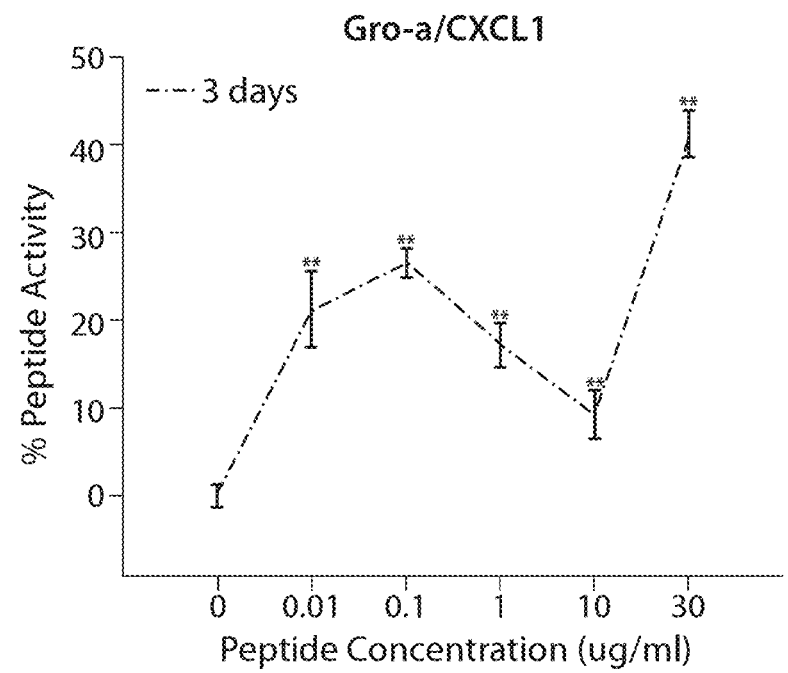

Gro-α or CXCL1 exhibits chemotactic activity for neutrophils. It also plays a role in inflammation and showed its effects on endothelial cells in an autocrine fashion. The peptide fragment (NGRKACLNPASPIVKKIIEKMLNS) (SEQ ID NO: 102) predicted to exert anti-angiogenic properties showed an anti-proliferative activity of 15%. This activity remained constant for the four days of testing (FIG. 27A). The peptide showed maximum activity at 0.01 and 0.1 μg/ml but showed reduced activity at higher concentrations. At the maximum tested peptide concentration, 10 μg/ml, its activity was statistically insignificant. In the 3-day proliferation assay, the peptide activity was significantly increased at the highest tested concentration of 30 μg/ml (FIG. 27B).

Gro-γ/CXCL3

Figure 28A:
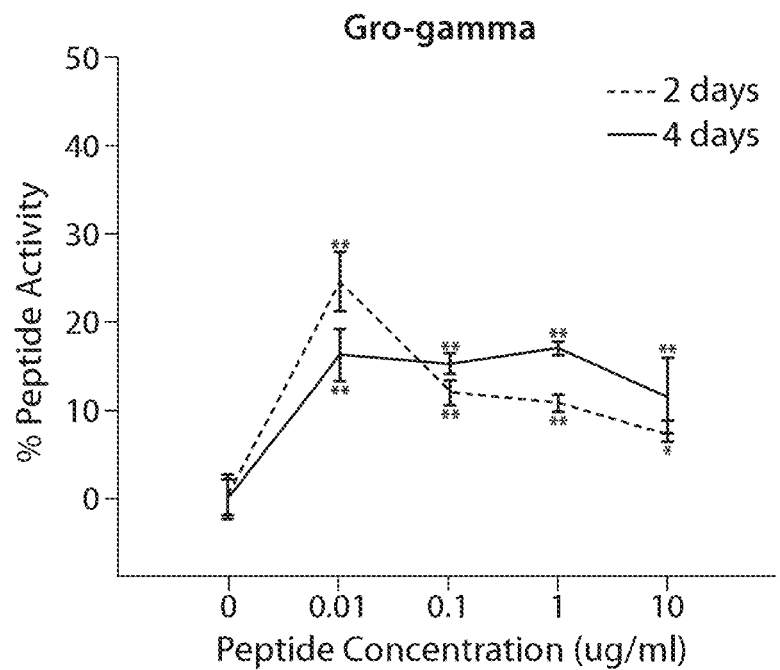
FIGS. 28A and 28B are graphs showing the activity of Gro-γ in in vitro cell proliferation assays.
Figure 28B:
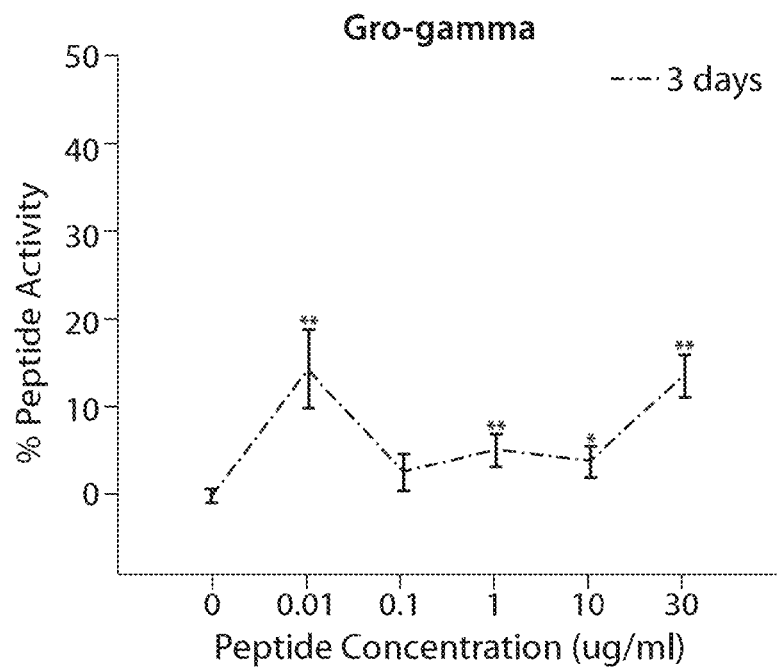

Gro-γ or CXCL3 showed similar chemotactic properties to Gro-α. The predicted anti-angiogenic fragment, NGKKACLNPASPMVQKIIEKIL (SEQ ID NO: 106), showed 15% activity after four days of incubation and exhibited a slight gain of activity during two extra days of incubation. Maximum activity was observed at the lowest applied peptide concentration of 0.01 μg/ml both at the 2 and 4 and 3 day assays (FIGS. 28A and 28B).

THBG/CXCL7

Figure 29A:
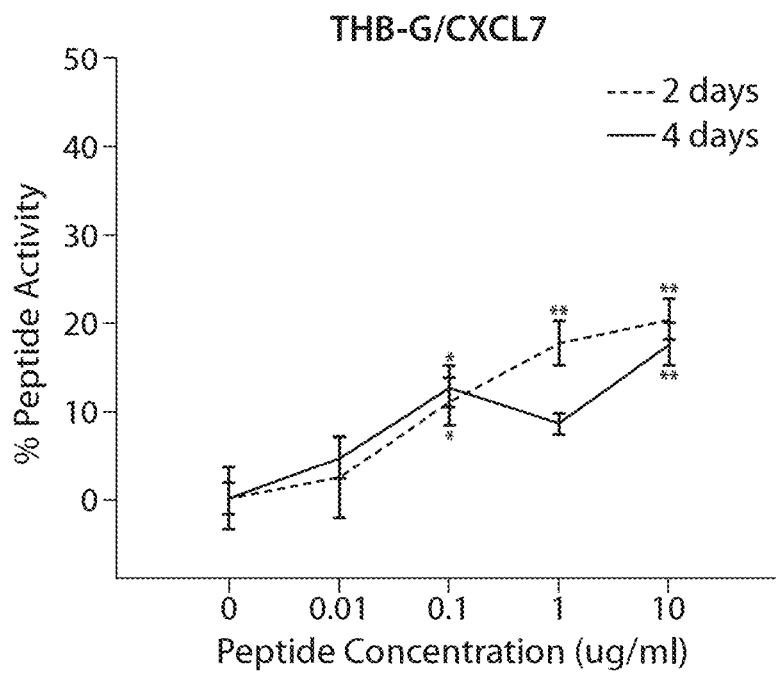
FIGS. 29A and 29B are graphs showing the activity of THBG in in vitro cell proliferation assays.
Figure 29B:
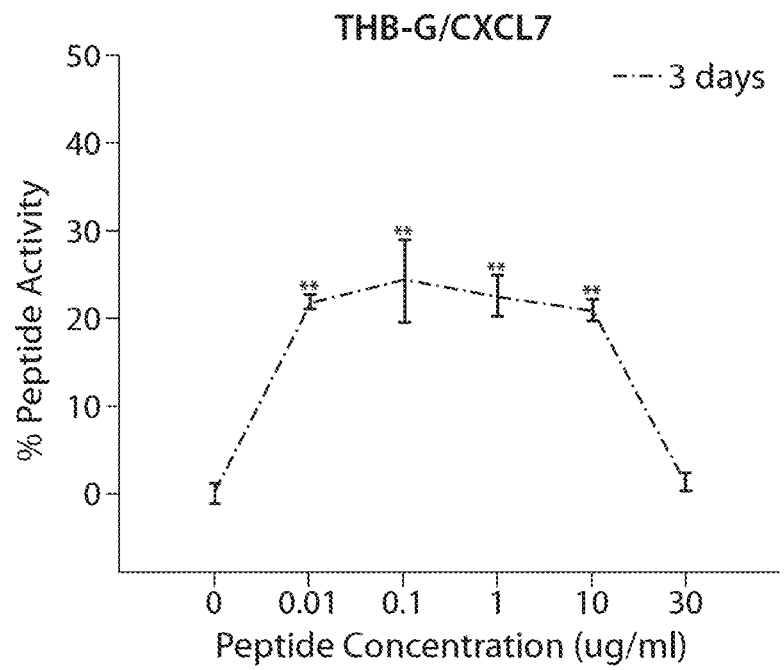

Beta thromboglobulin (THBG), or CXCL7, is a platelet-derived growth factor that belongs to the C-X-C chemokine family. It is a potent chemoattractant and activator of neutrophils. It has been shown to stimulate various cellular processes, including DNA synthesis, mitosis, glycolysis, intracellular cAMP accumulation, prostaglandin E2 secretion, and synthesis of hyaluronic acid and sulfated glycosaminoglycan. The peptide, DGRKICLDPDAPRIKKIVQKKL (SEQ ID NO: 114), was predicted to have anti-angiogenic activity. It showed 15% activity (FIG. 29A) at 10 μg/ml. Similar activity was observed in the 3-day assay (FIG. 29B).

IL-8/CXCL8

Figure 30A:
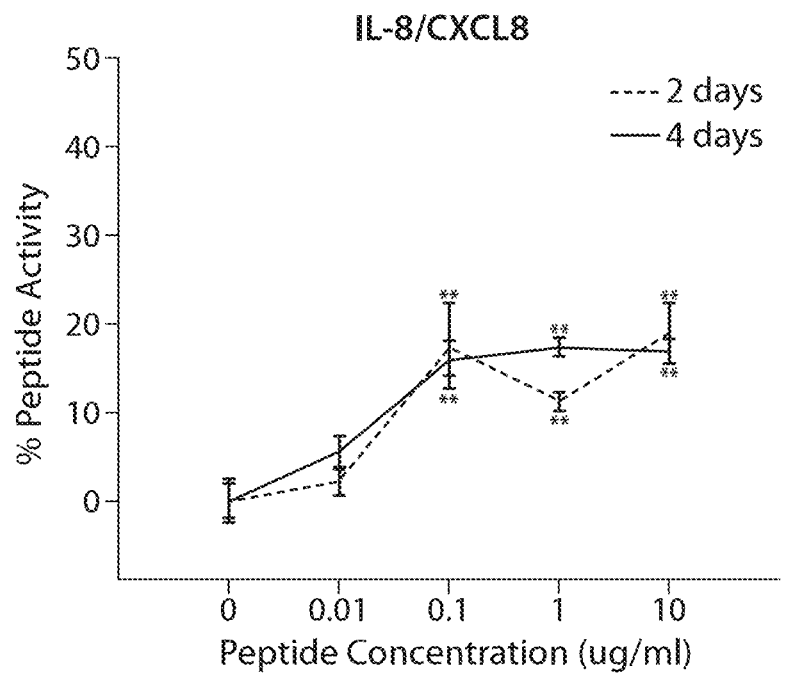
FIGS. 30A and 30B are graphs showing the activity of the IL-8 fragment in in vitro cell proliferation assays.
Figure 30B:
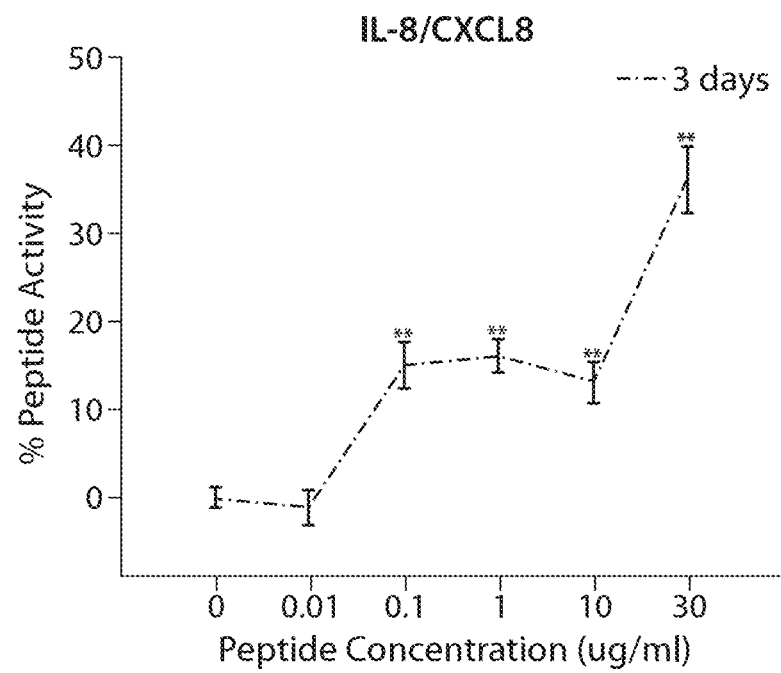

Interleukin 8 (IL-8) or CXCL8 is one of the major mediators of the inflammatory response. This chemokine is secreted by several cell types. It functions as a chemoattractant, and is also a potent angiogenic factor. A peptide fragment derived from IL-8, DGRELCLDPKENWVQRVVEKFLK (SEQ ID NO: 110), showed 20% anti-proliferative activity at its maximum applied concentration (10 μg/ml) at the 2 and 4 day assay (FIG. 30A). During the 3-day assay its activity is higher at 30 μg/ml (FIG. 30B).

ENA-78/CXCL5

Figure 31A:
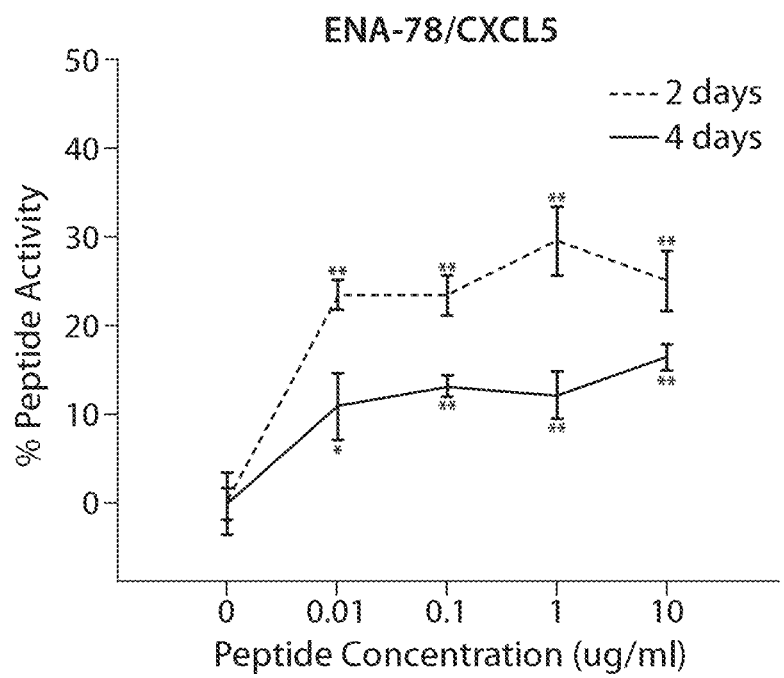
FIGS. 31A and 31B are graphs showing the activity of the ENA-78 fragment in in vitro cell proliferation assays.
Figure 31B:
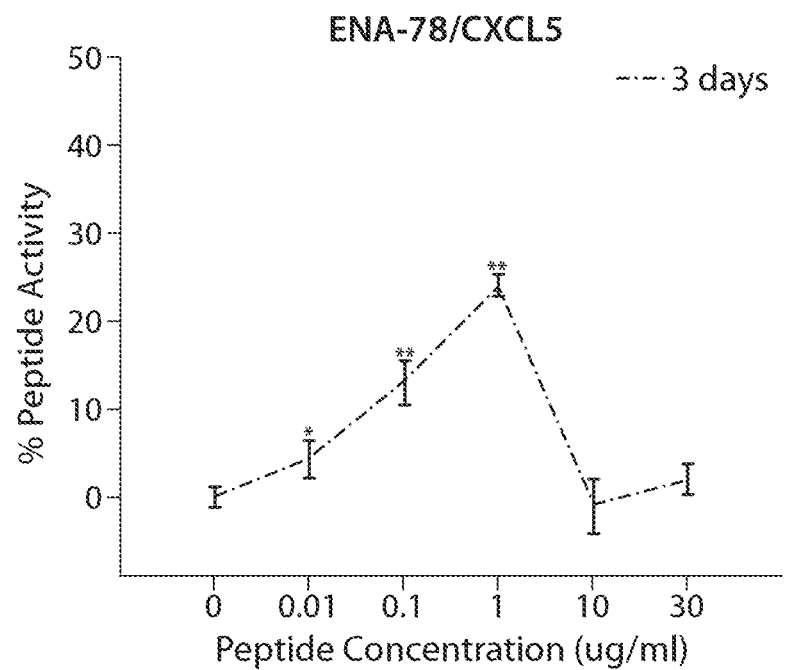

ENA-78 or CXCL5 is an inflammatory chemokine that also belongs to the C-X-C chemokine family. This chemokine is produced concomitantly with interleukin-8 (IL-8) in response to stimulation with either interleukin-1 (IL-1) or tumor necrosis factor-alpha (TNF-a). This chemokine is a potent chemotaxin involved in neutrophil activation. The ENA-78 derived peptide, NGKEICLDPEAPFLKKVIQKILD (SEQ ID NO: 95), was predicted to be anti-angiogenic. It showed approximately 30% activity at 2 days even at the lowest tested concentration tested (0.01 μg/ml) (FIG. 31A). In the 3 day assay this activity was reproducible over all tested concentrations (FIG. 31B). At highest concentrations of 30 μg/ml the peptide showed high activity.

GCP-2/CXCL6

Figure 32A:
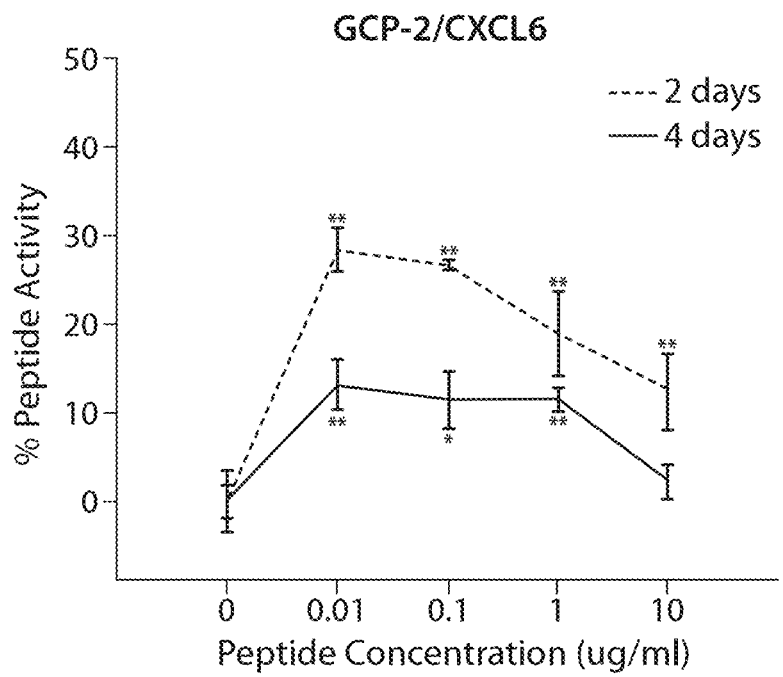
FIGS. 32A and 32B are graphs showing the activity of the GCP-2 fragment in in vitro cell proliferation assays.
Figure 32B:
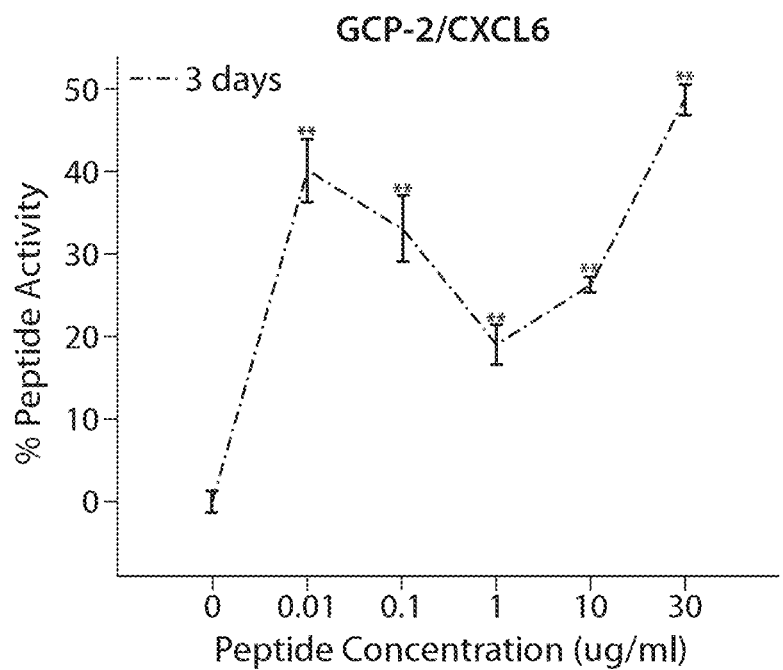

A fragment derived from a C-X-C chemokine, CXCL6, showed similar activity in the 2-4 day and in the 3-day assay. GCP-2 or CXCL6 is a chemotactic protein that contains a fragment predicted to be anti-angiogenic (NGKQVCLDPEAPFLKKVIQKILDS) (SEQ ID NO: 98) (FIGS. 32A and 32B). The peptide derived from GCP-2 showed biphasic behavior in both the 2-4 and in the 3-day assays. It showed 30% activity at 2 days at 0.01 μg/ml. At higher peptide concentrations peptide activity was reduced. Virtually no anti-proliferative activity was observed at 10 μg/ml. In the 3-day assay its activity was increased at 30 μg/ml (FIG. 32B).

Peptides Derived from Collagen

The anti-angiogenic activity of two peptides derived from collagen sequences was tested. A peptide from the alpha 6 fibril of type 4 collagen and a peptide from alpha 5 fibril of type 4 collagen.

Alpha 6 Fibril of Type 4 Collagen

Figure 33A:
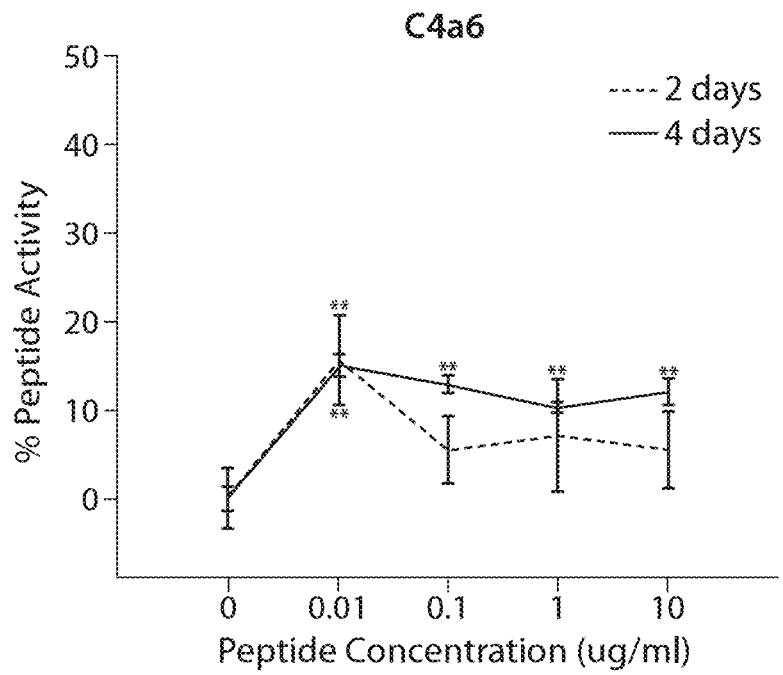
FIGS. 33A and 33B are graphs showing the activity of the C4-alpha6 fragment in in vitro cell proliferation assays.
Figure 33B:
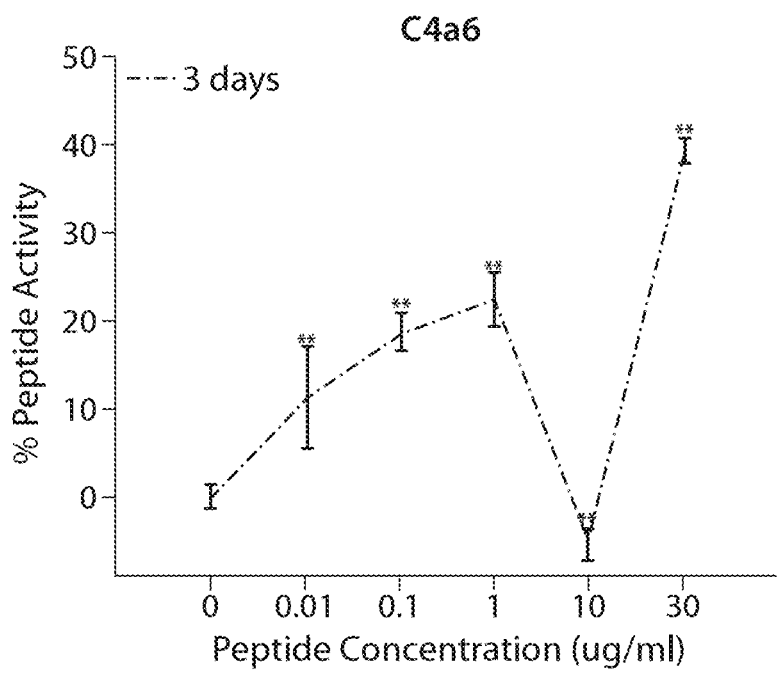

The first peptide was derived from the alpha 6 fibril of type 4 collagen (C4α6). A peptide having the sequence: YCNINEVCHYARRNDKSYWL (SEQ ID NO: 93) showed 15% anti-proliferative activity at four days (FIG. 33A). A similar profile was observed in the 3-day proliferation assay as well (FIG. 33B) though at 30 μg/ml concentration, the peptide activity increased to 80%.

Alpha 5 Fibril of Type 4 Collagen

Figure 34A:
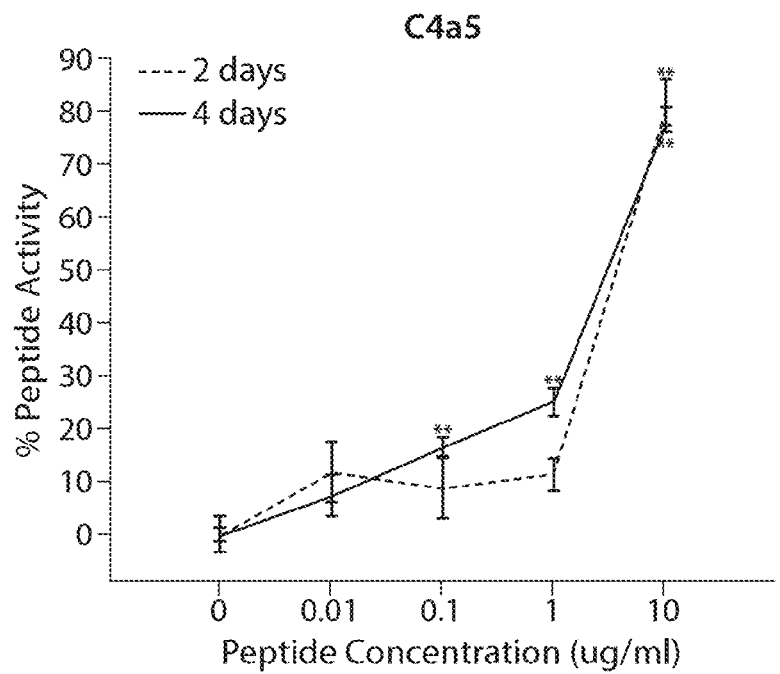
FIGS. 34A-34D are graphs showing the activity of the C4-alpha5 fragments in in vitro cell proliferation assays.
Figure 34B:
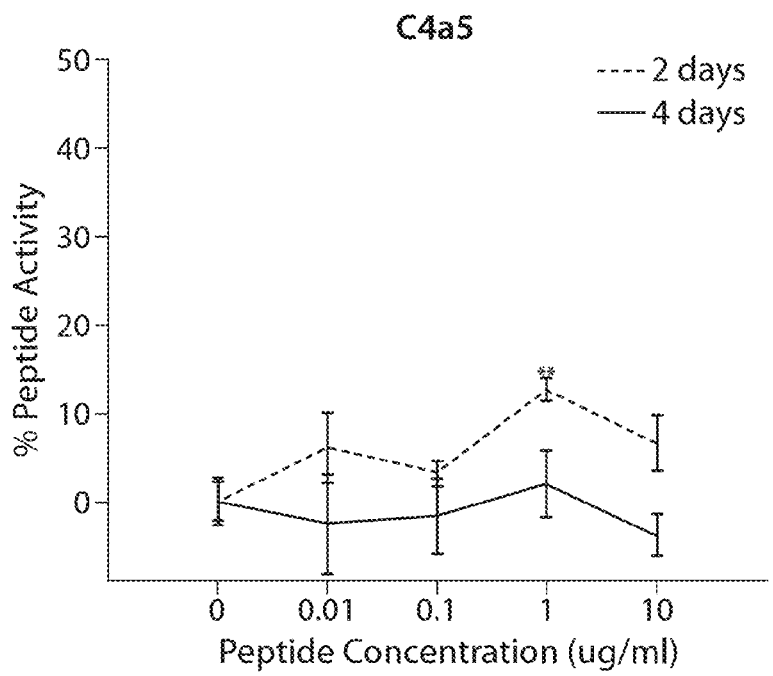
Figure 34C:
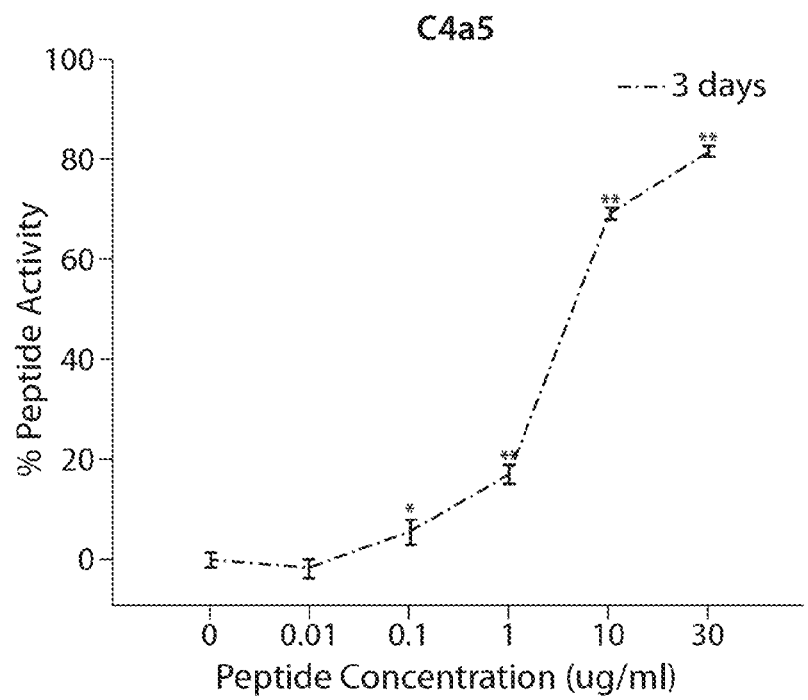
Figure 34D:
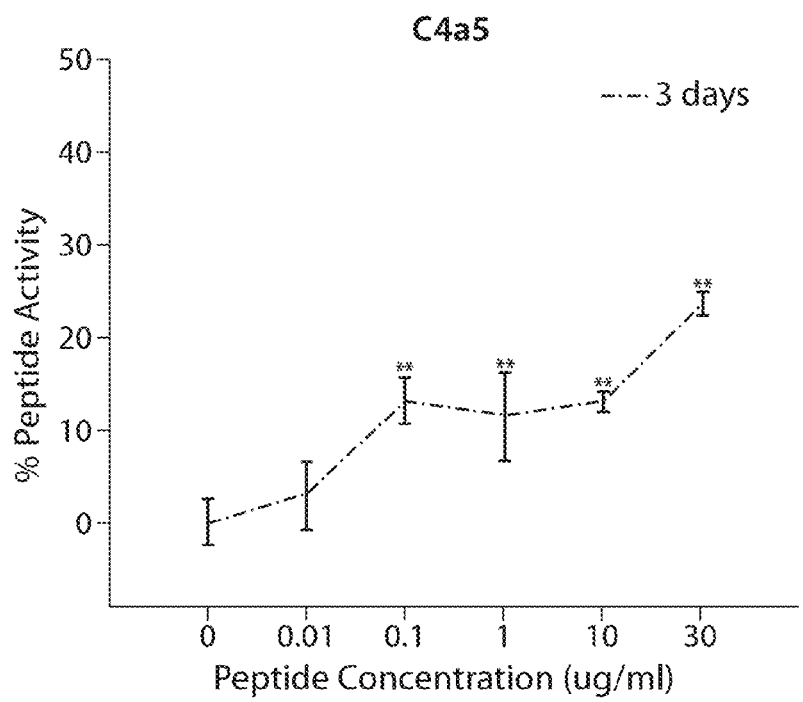

The second set of peptides derived from a collagen sequence that was predicted to have anti-angiogenic activity was derived from the alpha 5 fibril of type 4 collagen (C4α5). There are two such peptides. The first peptide, LRRFSTMPFMFCNINNVCNF (SEQ ID NO: 89), showed 80% activity at its highest applied concentration, 10 μg/ml (FIG. 34A) for the 2- and 4-day proliferation assay. In the 3-day assay, the peptide activity for the common concentrations was reproducible and increased even more when testing the higher concentration of 30 μg/ml (FIG. 34C). The second peptide, SAPFIECHGRGTCNYYANS (SEQ ID NO: 91), showed low activity at two or four days though during the 3-day assay its activity increases at the highest applied concentration of 30 μg/ml (FIGS. 34B and 34D).

Alpha 4 Fibril of Type 4 Collagen

The third set of peptides derived from collagens with putative anti-angiogenic activity are derived from the alpha 4 fibril of type 4 collagen (C4α4). The first peptide, AAPFLECQGRQGTCHFFAN (SEQ ID NO: 87), has intermediate activity following two days of incubation (FIG. 35A). The activity was similar during the 3-day assay (FIG. 35D) though the activity increased with increasing the applied peptide concentration. The second peptide, LPVFSTLPFAYCNIHQVCHY (SEQ ID NO: 85), exhibited similar behavior (FIGS. 35B and 35E). The third peptide YCNIHQVCHYAQRNDRSYWL (SEQ ID NO: 86) showed low anti-proliferative activity at 2 or 4 days (FIG. 35C). In the 3-day assay its activity was greater and was increasing at higher peptide concentrations (FIG. 35F).

Tissue Inhibitors of Metalloperoteinases (TIMP)

Figure 36A:
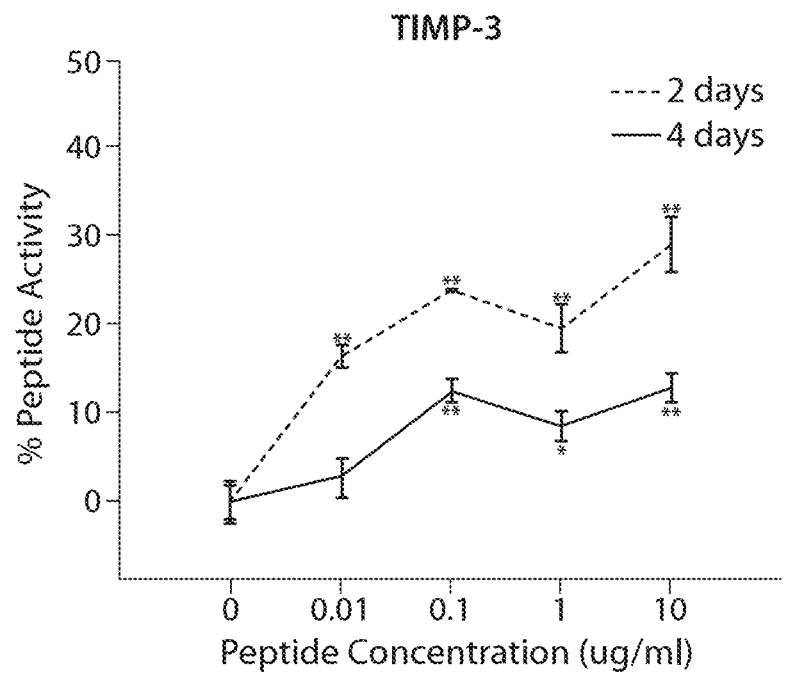
FIGS. 36A and 36B are graphs showing the activity of the TIMP-3 fragment in in vitro cell proliferation assays.
Figure 36B:
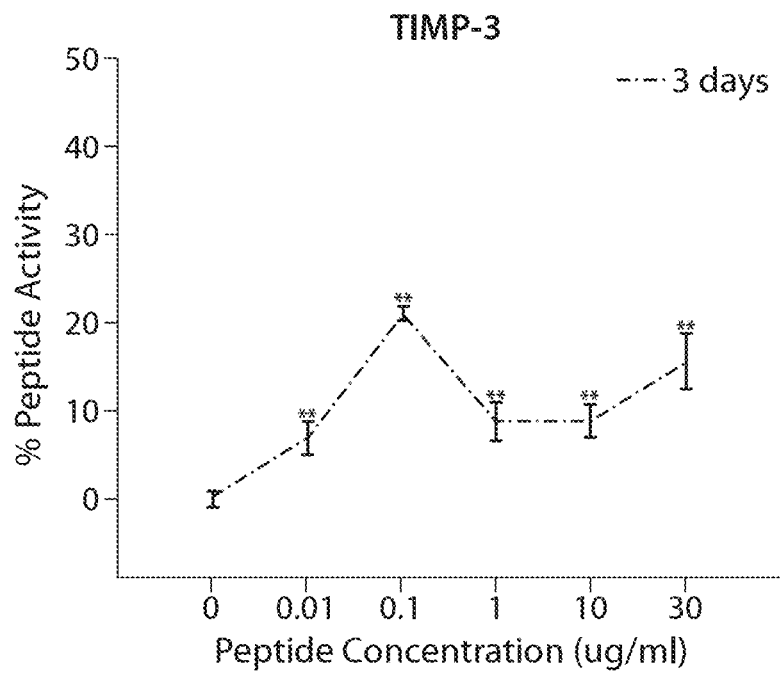

A peptide derived from a sequence of a tissue inhibitor of metalloproteinases (TIMP) was tested. The peptide, which was derived from TIMP-3, ECLWTDMLSNFGYPGYQSKHYACI (SEQ ID NO: 155), was predicted to have anti-angiogenic activity. This fragment showed a maximum 30% activity at two days (FIG. 36A). A similar response was observed during the 3-day assay (FIG. 36B).

Scrambled Peptides

Figure 37A:
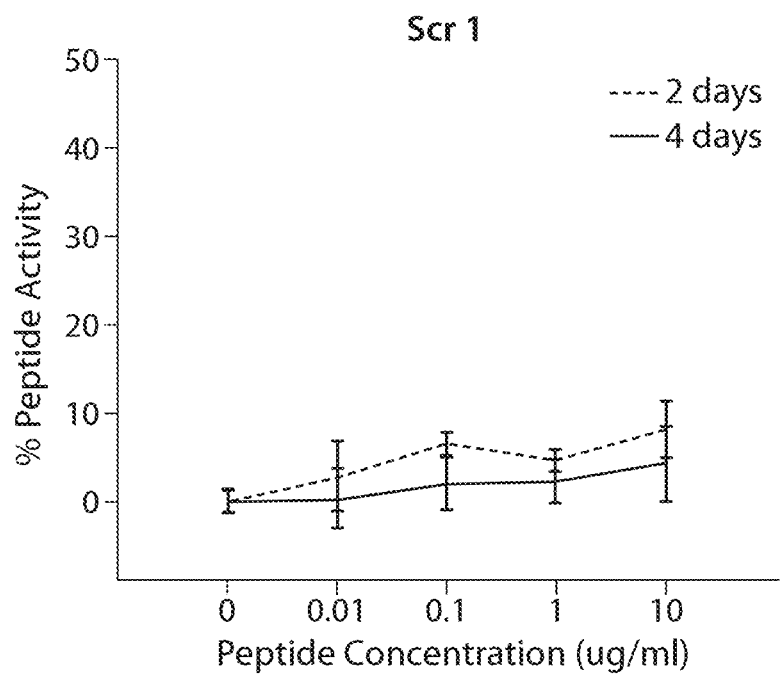
FIGS. 37A and 37B are graphs showing the activity of two scrambled peptides in in vitro cell proliferation assays.
Figure 37B:
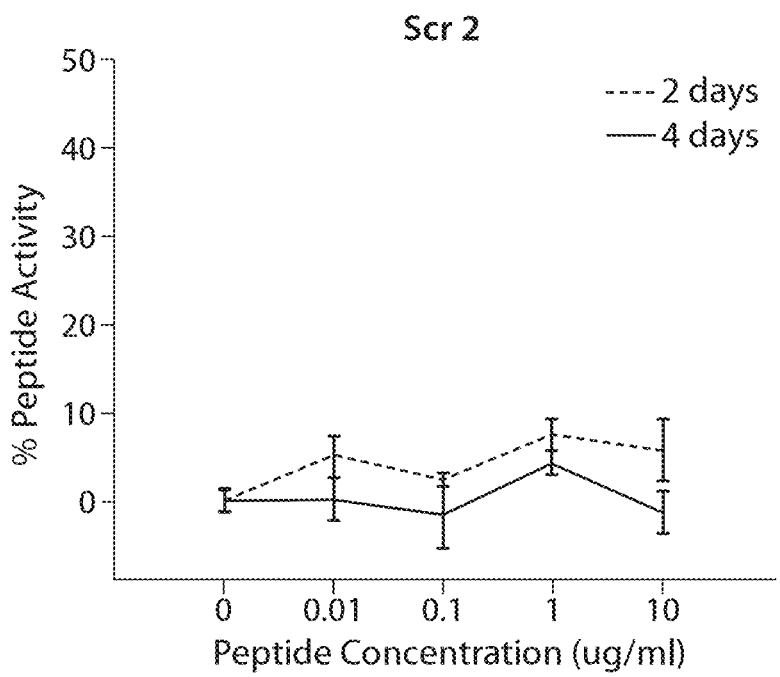

To determine if the anti-proliferative activity was specific, the effect of scrambled peptides was examined. These peptides contained the same amino acids as the studied peptides but the order of the amino acids within the peptide sequence was randomly permuted. For example, the C-X-C derived GCP-2/CXCL6 with the original sequence NGKQVCLD-PEAPFLKKVIQKILDS (SEQ ID NO: 98), which showed a biphasic response having 35% maximum anti-proliferative activity was permuted to the random sequence QDVFNKDGKVILLSPQAICLPKEK (SEQ ID NO: 158). Also, the TIMP3 derived peptide, ECLWTDMLSNF-GYPGYQSKHYACI (SEQ ID NO: 155), which showed 30% maximum anti-proliferative activity was randomly permuted to LCMTKSDCYQPAWYIHEGFYNLSG (SEQ ID NO: 159). The anti-proliferative effects of these randomly scrambled peptides was not statistically significant at any concentration for the 2- and 4-day assays (FIGS. 37A and 37B).

Example 3

Results of In-Vivo Screening

A directed in vivo anti-angiogenesis assay (DIVAA) was used to test the anti-angiogenic efficacy of the alpha 5 fibril of collagen type 4, which had the sequence: SAPFIECH-GRGTCNYYANS (SEQ ID NO: 91). This peptide showed anti-angiogenesis activity that increased as its concentration increased in in vitro assays. This peptide showed only intermediate activity in in vitro screening assays. The peptide was solubilized in buffer solution at 200 µg/ml without an organic solvent. DIVAA is a reproducible and quantitative in-vivo method of assaying angiogenesis. It involves preparation of silicon cylinders of 20 µl volume, closed on one side, filled with some type of extracellular matrix (for example Matrigel or BME-basement membrane extract) with or without pre-mixed angiogenic factors. These angioreactors are then implanted subcutaneously in the dorsal flank of mice. Accompanied with the onset of angiogenesis, vascular endothelial cells migrate into the extracellular matrix and form vessels in the angioreactor. As early as nine days post-implantation, there are enough cells to determine an effective dose response to angiogenic modulating factors.

A set of DIVAA angioreactors was prepared. Each of them was filled with a basement membrane extract (extracellular matrix) containing the peptides and growth factors. The basement membrane extract used was the Culturex® extract (Trevigen, Inc., Gaithersburg, Md.), which is a soluble form of basement membrane purified from Engelbreth-Holm-Swarm (EHS) tumor. The extract gels at 37° C. to form a reconstituted basement membrane. The major components of the Basement Membrane Extract include laminin I, collagen IV, entactin, and heparan sulfate proteoglycans. The extract used was growth factor free, which means that the matrix does not contain any inherent growth factors that are applied exogenously. As a positive control, 37.5 ng of bFGF and 12.5 ng of VEGF per 200 µl of the basement membrane extract in accordance with the manufacturer's directions (Trevigen, Inc., Gaithersburg, Md.). As a negative control a bioreactor containing the reduced growth factor only basement membrane extract was used. For the peptide application, the extracellular matrix was mixed with the positive control constituents, 37.5 ng of bFGF and 12.5 ng of VEGF per 200 µl of matrix, and with 200 µg/ml of the alpha 5 fibril of collagen type 4 peptide (sequence: SAPFIECHGRGTCNYYANS) (SEQ ID NO: 91). Two reactors per condition and per mouse were used. Each condition was repeated in quadruplicate. The DIVAA reactors were implanted subcutaneously in the abdomen of C57BL/6 female mice. Two angioreactors were implanted per mouse, one on either side of the abdomen, 4 mice were used per condition tested.

Figure 38A:
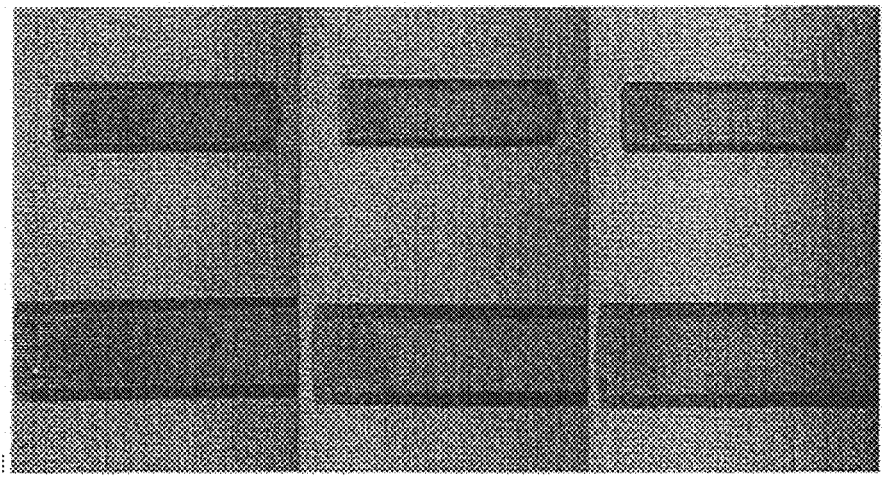
FIGS. 38A and 38B show in vivo angiogenesis inhibition in C57BL/6 mice in an experiment using subcutaneously implanted basement-membrane-extract filled DIVAA angioreactors.

Eleven days after implantation the mice were sacrificed and the angioreactors were removed from their abdomens. FIG. 38A shows microphotographs from the angioreactors for each of the conditions. Fewer endothelial cells invaded the extracellular matrix containing the inhibitory peptide than were observed in the negative control. In the panel at the far left, the positive control angio-reactors having well developed vasculature is shown. In the middle panel is the angioreactor containing the inhibitory peptide and at the right is the negative control. The figure shows that the peptide strongly inhibited angiogenesis.

To obtain a quantitative assessment of the angiogenic invasion, the content of the angioreactors was removed from the cylinder and the endothelial cells were stained using FITC-Lectin (FIG. 38A) Once the tubes were extracted from the mice, the inside of the angioreactors was rinsed with 300 µl of a 36 kDa, bacillus-derived neutral metalloproteinase which is commercially available as Cellsperse (Trevigen, Inc., Gaithersburg, Md.), an extracellular matrix digesting solution and the content of the reactors as well as the rinse was transferred into a microtube. After one hour of incubation, the tubes were centrifuged at 250×g for 5 minutes at room temperature. The cell pellets and insoluble fractions were retained. The pellet was resuspended in 500 µl of full cell medium (EGM-2, Clonetics) to allow for cell surface receptor recovery, and incubated at 37° C. for one hour. The cells were then centrifuged at 250×g for 5 minutes at room temperature to collect cell pellets. The pellets were resuspended in a FITC-Lectin solution, and incubated at 4° C. overnight.

Figure 38B:
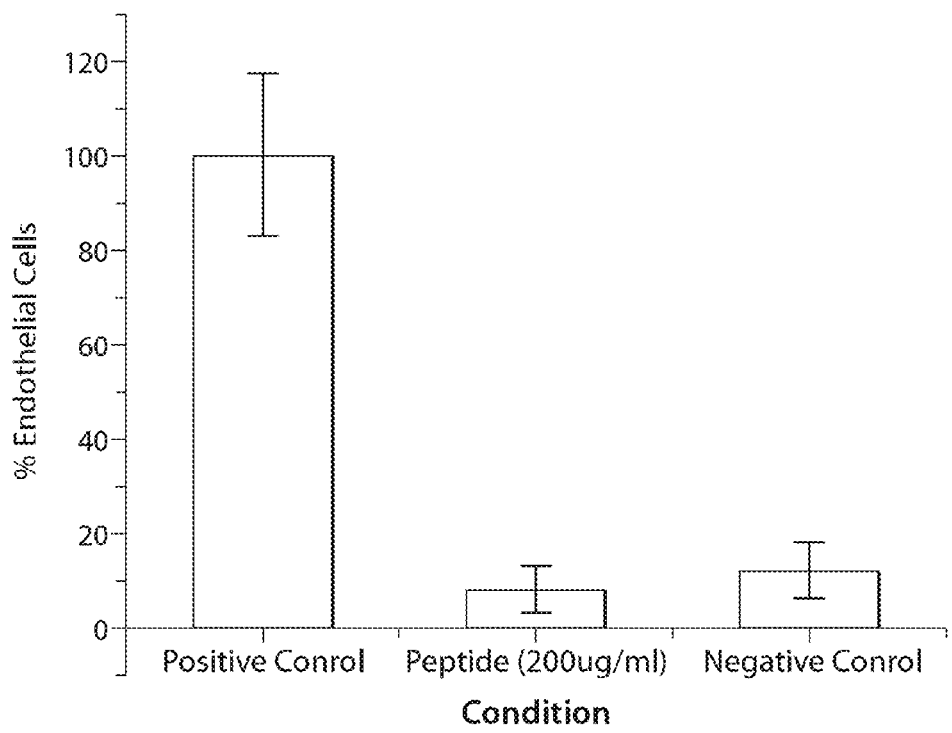

Fluorescence of the FITC-Lectin solution was quantitated by measuring the fluorescence at 485 nm excitation and 510 nm emission using a fluorescence plate reader (Victor 3V, Perkin Elmer). The intensity of the signal was directly proportional to the number of endothelial cells that were present in the angioreactors. The results were scaled to a percentage scale so that 100% would represent the mean of the positive controls (FIG. 38B).

Example 4

Analysis of Peptide Motifs

By performing multiple sequence alignment to the sequences of the predicted peptides, the conservation of specific motifs that were common in many of the sequences was observed. Multiple sequence alignment were performed using the ClustalW algorithm to the sequences of the peptides that belong to the different families. In order to perform the alignments a critical number of peptide sequences are required. Thus the families investigated are the thrombospondin-1 containing peptides and the peptides that belong to the C-X-C chemokines family. This analysis was also extended to the families of collagen and TIMPs. In order to represent the motifs single letter abbreviations of the amino acids that are common and the letter "X" to denote a non-common amino acid that intervenes the common letters. If there is more than one non-common amino acid in between, the letter "X" is followed by the number of the non-common amino acids. For example, if there are three non-common amino acids between two conserved letters, this is denoted "a-X3-b", where a and b are conserved residues. This notation is commonly used to represent motifs.

Initially, multiple sequence alignments were performed with peptides showing experimentally demonstrated anti-angiogenic activity. This calculation was subsequently extended to all the theoretically predicted fragments to determine whether the motifs calculated for the experimentally tested fragments are conserved and reproduced in all of the anti-angiogenic predictions. The results of this analysis are organized by protein family.

Thrombospondin-1 (TSP-1) Domain Containing Peptides

Figure 39:
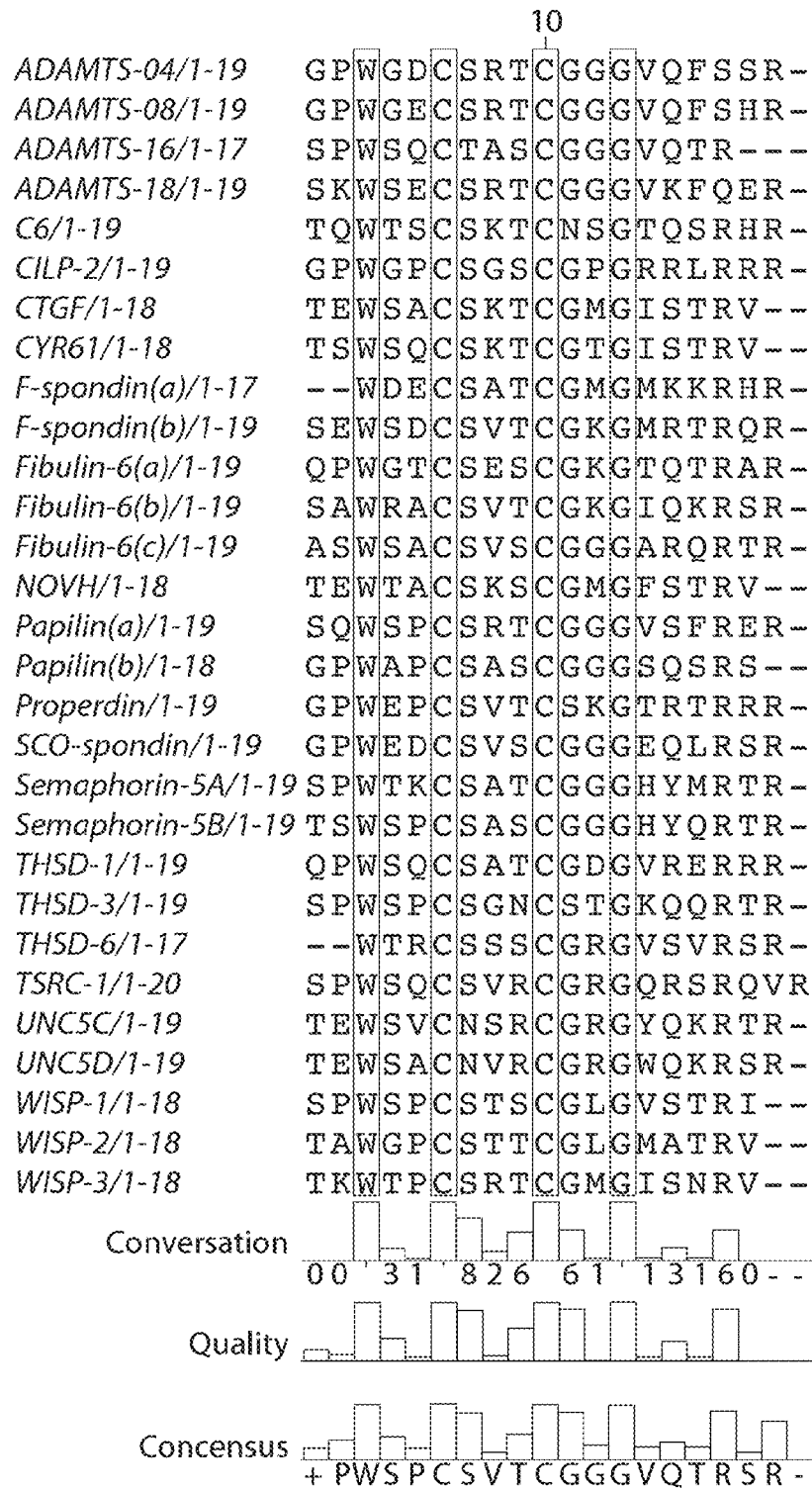
FIG. 39 shows the 4-letter motif common in all the experimentally tested TSP-1 containing proteins. (SEQ ID NOS 7, 14, 24, 29, 38, 40-42, 72, 73, 44, 43, 45-49, 63, 61, 62, 64-66, 69-71 & 74-76 are disclosed respectively in order of appearance.)
Figure 40A:
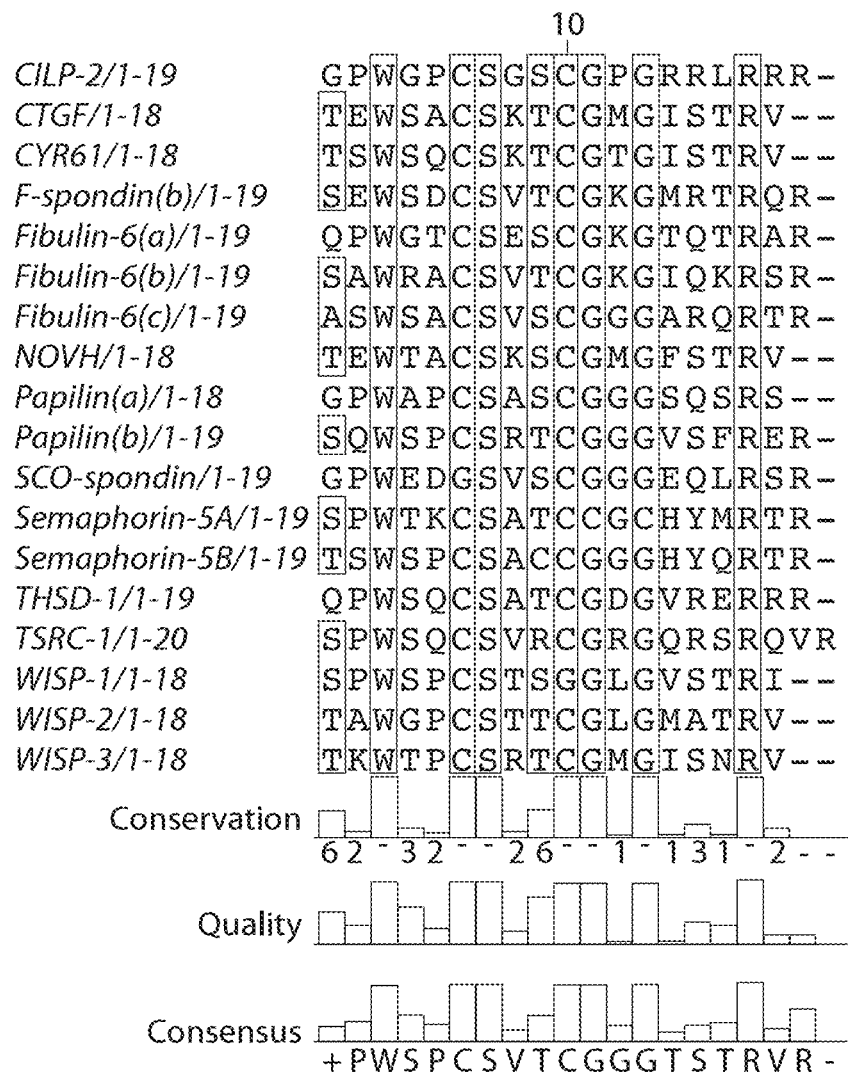
FIG. 40 shows common motifs of the TSP-1 containing peptides using a threshold of 60% (A) (SEQ ID NOS 40-42, 73, 44, 43, 45, 46, 48, 47, 63, 61, 62, 64, 69, & 74-76 are disclosed respectively in order of appearance) and 45% (B) (SEQ ID NOS 24, 7, 14, 40, 44, 48, 49, 63, 61, 64, 65, 69 & 74 are disclosed respectively in order of appearance.)
Figure 40B:
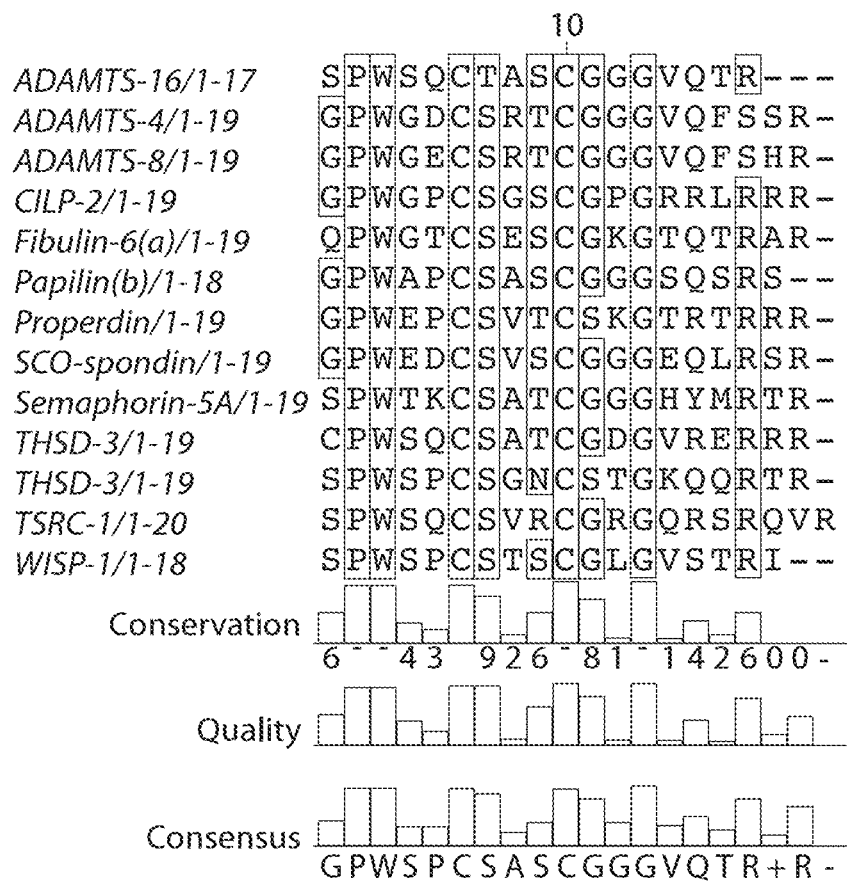

Of the thirty-one predicted and experimentally tested TSP-1 containing short peptides, twenty-nine share a global 4 residue common motif which is the X2-W-X2-C-X3-C-X2-G-X7 (SEQ ID NO: 180), or W-X2-C-X3-C-X2-G (SEQ ID NO: 161) after removing the uncommon edges, resulting in the generic TSP-1 containing 20-mer (FIG. 39). The first motif with 45% threshold, common in 13 sequences, is the 5 letter motif X1-P-W-X2-C-X3-C-X2-G-X7 (SEQ ID NO: 185). The common alterations of this motif can be described as (S/G/Q)-P-W-X2-C-(T/S)-X2-C-(G/S)-X1-G-X3-(R/S)-X3 (SEQ ID NO: 186) (FIG. 40B).

In addition to calculating the motifs that are present within the sequences of the predicted fragments one can analyze all the possible amino acids that are present within the 29 peptide sequences from which the motifs were calculated. This 20-mer with all the possible substitutions is presented in the following table (Table 4) along with the frequencies that each amino acid is present in the 29 sequences.

TABLE 4

The TSP-1 containing 20-mer with all the possible amino acid substitutions (SEQ ID NO: 162)

| AA1 | AA2 | AA3 | AA4 | AA5 | AA6 | AA7 | AA8 | AA9 | AA10 | AA11 | AA12 |
|---|---|---|---|---|---|---|---|---|---|---|---|
| S(9) | P(13) | W(29) | S(14) | P(9) | C(29) | S(26) | V(7) | T(15) | C(29) | G(26) | G(10) |
| T(9) | E(5) | | T(5) | A(5) | | N(2) | A(6) | S(10) | | S(2) | K(4) |
| G(6) | S(3) | | G(5) | Q(4) | | T(1) | R(5) | R(3) | | N(1) | R(4) |
| Q(2) | A(2) | | E(2) | D(3) | | | K(4) | N(1) | | | M(4) |
| A(1) | Q(1) | | D(1) | E(3) | | | G(2) | | | | T(2) |
| | K(1) | | R(1) | K(1) | | | S(2) | | | | L(2) |
| | | | A(1) | R(1) | | | T(2) | | | | D(1) |
| | | | | V(1) | | | E(1) | | | | S(1) |
| | | | | | | | | | | | P(1) |

| AA13 | AA14 | AA15 | AA16 | AA17 | AA18 | AA19 | AA20 |
|---|---|---|---|---|---|---|---|
| G(29) | V(8) | Q(11) | T(10) | R(26) | S(5) | R(15) | R(1) |
| | I(4) | S(7) | F(4) | S(2) | T(5) | V(1) | |
| | M(3) | R(6) | K(3) | Q(1) | V(5) | | |
| | T(3) | K(2) | Q(3) | | R(3) | | |
| | H(2) | Y(2) | S(3) | | H(3) | | |
| | A(1) | A(1) | L(2) | | E(2) | | |
| | E(1) | | E(1) | | Q(2) | | |
| | F(1) | | M(1) | | A(1) | | |
| | K(1) | | N(1) | | I(1) | | |
| | R(1) | | V(1) | | | | |
| | S(1) | | | | | | |
| | Q(1) | | | | | | |
| | W(1) | | | | | | |
| | Y(1) | | | | | | | amino acid that succeeds the first cysteine of the motif, or the seventh amino acid of the sequence can alternate between T, S and N. Thus a more generic description of this motif is X2-W-X2-C-(T/S/N)-X2-C-X2-G-X7 (SEQ ID NO: 181) with threonine or serine the most abundant alteration for the seventh amino acid position.

By altering the threshold of the conserved amino acids that are common among the sequences of the predicted peptides subsets of peptide families having individual common motifs of greater length than the global 4-letter motif are identified. The threshold is defined as the percentage of the peptides that share a common motif. Such a subgroup of peptides is one that consists of 18 TSP-1 containing predictions (threshold 60%) that share a seven amino acid long common motif. The motif is the X2-W-X2-C-S-X2-C-G-X1-G-X3-R-X3 (SEQ ID NO: 182). A common alteration occurs in the 19$^{th}$ amino acid which can be either an arginine or a valine with arginine the most abundant amino acid. In that case the motif is written X2-W-X2-C-S-X2-C-G-X1-G-X3-R-X1-(R/V)-X1 (SEQ ID NO: 183). Similarly the ninth amino acid can be altered by either arginine, serine or threonine. In that case the motif can be represented as X2-W-X2-C-S-X1-(S/R/T)-C-G-X1-G-X3-R-X1-(R/V)-X1 (SEQ ID NO: 184) with threonine the most abundant amino acid (FIG. 40A). Similarly another The above motifs, for both the TSP-1 containing proteins were identified from the sequences of the peptide fragments that have already been experimentally tested in the proliferation assay. The specific approach for identification of motifs within groups of sequences can be generalized for the case of all the theoretically predicted anti-angiogenic fragments. For the TSP-1 containing fragments the multiple sequence alignment calculations are repeated, but now all of the theoretically predicted fragments are included.

Figure 41:
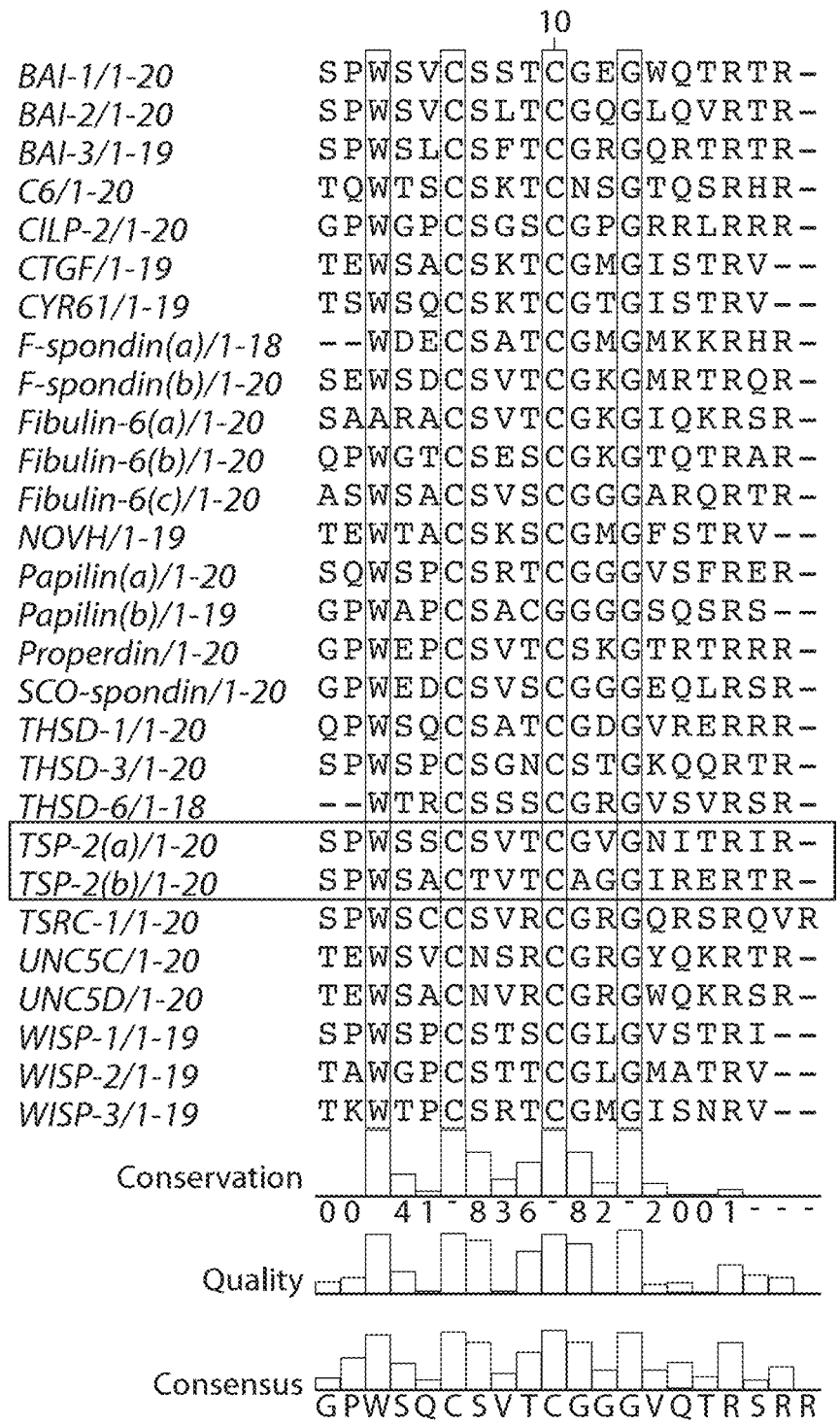
FIG. 41 shows the 4-letter motif common in all the theoretically predicted TSP-1 containing proteins. In the shaded insert the predicted motif is identified within TSP-2 domains as well. (SEQ ID NOS 3-16, 18-33, 35-38, 40-42, 72, 73, 43-49, 63-71, & 74-76 are disclosed respectively in order of appearance.)

For the cases of all the theoretically predicted TSP-1 containing proteins, multiple sequence alignment yielded a common motif within 97% of all the tested sequences. This motif, as described above, W-X2-C-X3-C-X2-G (SEQ ID NO: 161) (FIG. 41) and a generic 20-mer can be expressed as X2-W-X2-C-X3-C-X2-G-X7 (SEQ ID NO: 180). It is interesting that this motif is not a characteristic of only the TSP-1 domains, in other words it is not a signature domain of TSP-1 proteins. Rather, it appears to be present not only in a subset of TSP-1 proteins that are associated with anti-angiogenic activity, but also within the type-2 thrombospondin containing proteins (TSP-2) that are associated with anti-angiogenic activity. Thus, the W-X2-C-X3-C-X2-G (SEQ ID NO: 161) motif is associated with anti-angiogenic activity that spans at least two protein families (i.e., TSP-1 and TSP-2 containing proteins). Moreover, in both experimentally tested fragments and in theoretically predicted fragments, the amino acid following the first cysteine of the motif can alternate between T, S and N. Thus a more specific description of the motif is the W-X2-C-(T/S/N)-X2-C-X2-G (SEQ ID NO: 163) with serine and threonine being the predominant amino acids in the position following the first cysteine.

A common alteration occurs in the 19$^{th}$ amino acid of the 20-mer which can be either an arginine or a valine with arginine the most abundant amino acid. In that case the motif is written X2-W-X2-C-(T/S/N)-X2-C-X2-G-X5-(R/V)-X (SEQ ID NO: 187).

Peptides Derived from C-X-C Chemokines

Figure 42:
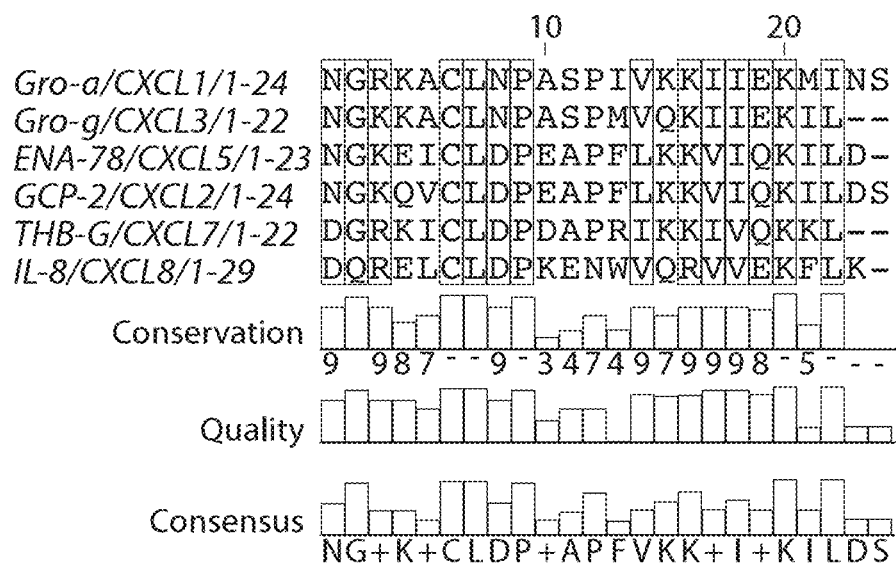
FIG. 42 shows the 6-letter motif common in all the experimentally tested C-X-C containing proteins. (SEQ ID NOS 102, 106, 95, 98, 114 & 110 are disclosed respectively in order of appearance.)

Based on the six predicted and experimentally tested C-X-C chemokines, all of them contain a six amino acid common motif. This motif can be described as X-G-X3-C-L-X-P-X10-K-X-L (SEQ ID NO: 188) (FIG. 42). There are few common alterations that occur within the sequences of the predicted fragments. For all those cases the motif can be re-written as (N/D)-G-(R/K)-X2-C-L-(N/D)-P-X2-(P/N)-X2-(K/Q)-(K/Q)-(I/V)-(I/V)-(E/Q)-K-X-L (SEQ ID NO: 173).

The generic 22-mer of the predicted C-X-C chemokines including all the possible substitutions is presented in the following table (Table 5).

Figure 44A:
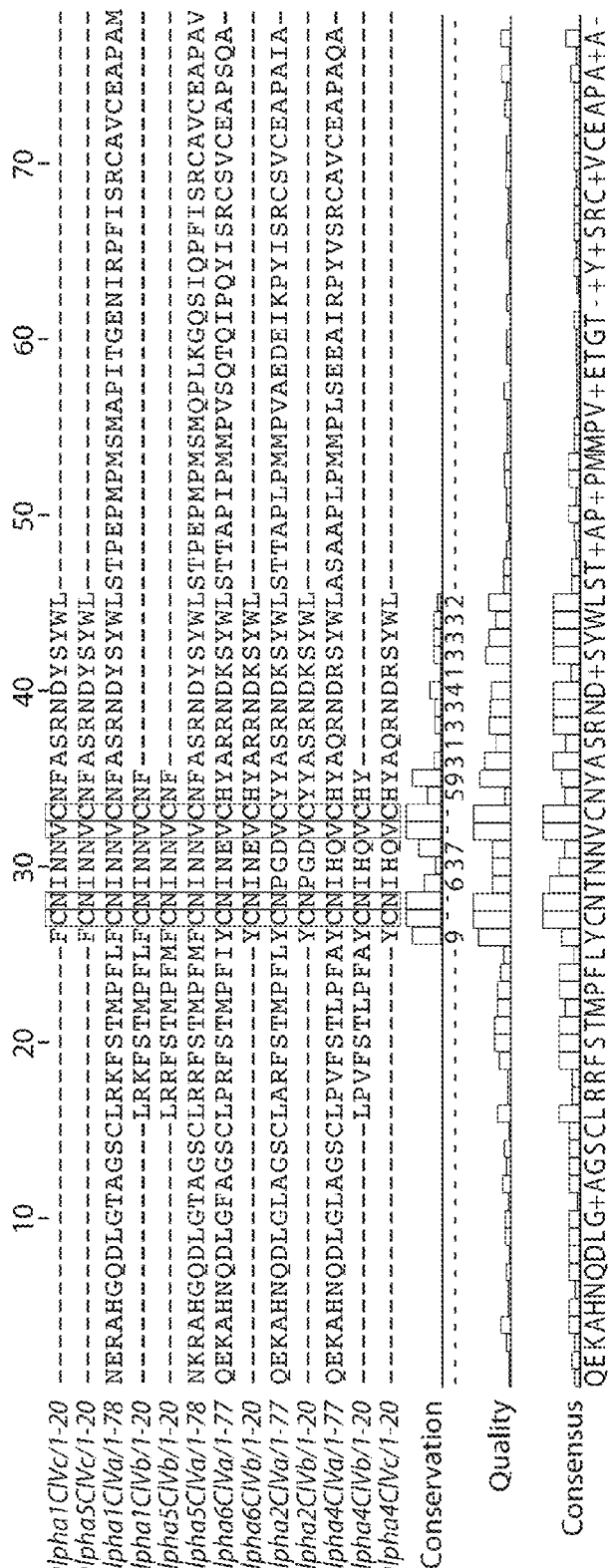
FIGS. 44A-44C show the most abundant motif in the theoretically predicted anti-angiogenic collagen derived peptide fragments.
Figure 44B:
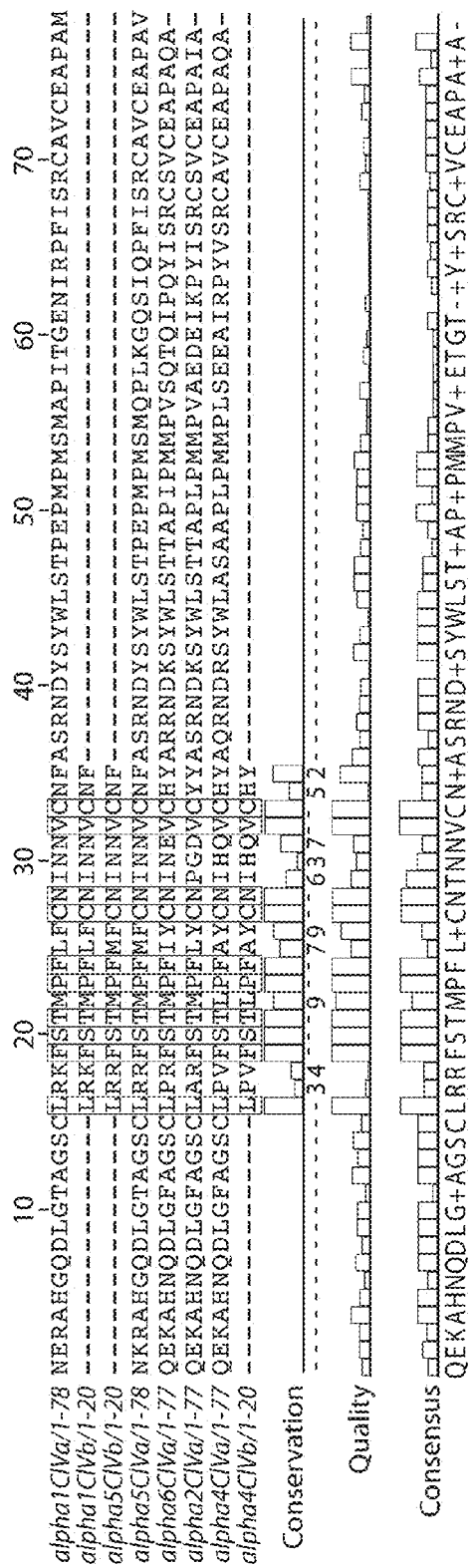

4-letter motif appears upstream of C-N-X3-V-C-X2-A-X-R-N-D-X-S-Y-W-L (SEQ ID NO: 176) (FIG. 44B). The 4-residue motif appears downstream of the L-X2-F-S-T-X-P-F-X2-C-N-X3-V-C (SEQ ID NO: 177) (FIG. 44C) motif.

Figure 45:
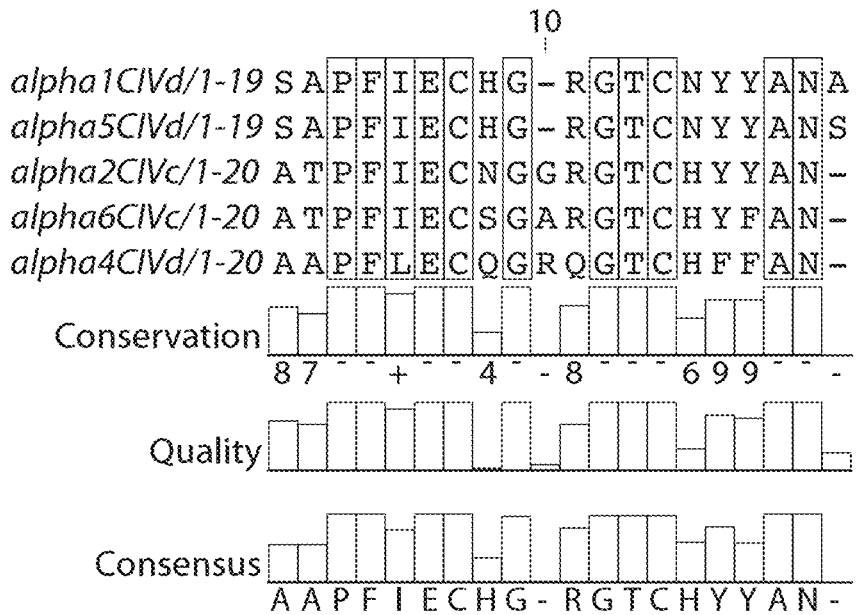
FIG. 45 shows a less common motif within the sequences of collagen derived peptide fragments. SEQ ID NOS 80, 91, 83, 94, & 87 are disclosed respectively in order of appearance.

In addition to the aforementioned 7-mer there is another motif that is present in a smaller subset of collagen derived peptides. Those peptides do not include the C-N-X3-V-C (SEQ ID NO: 174). This motif is described by the generic sequence X2-P-F-X-E-C-X-G-X5-A-N (SEQ ID NO: 189). Common modifications can be described by the sequence X2-P-F-(I/L)-E-C-X-G-X-(R/G)-X-(Y/F)-(Y/F)-A-N (SEQ ID NO: 190) (FIG. 45).

Peptides Derived from TIMPs

Figure 46:
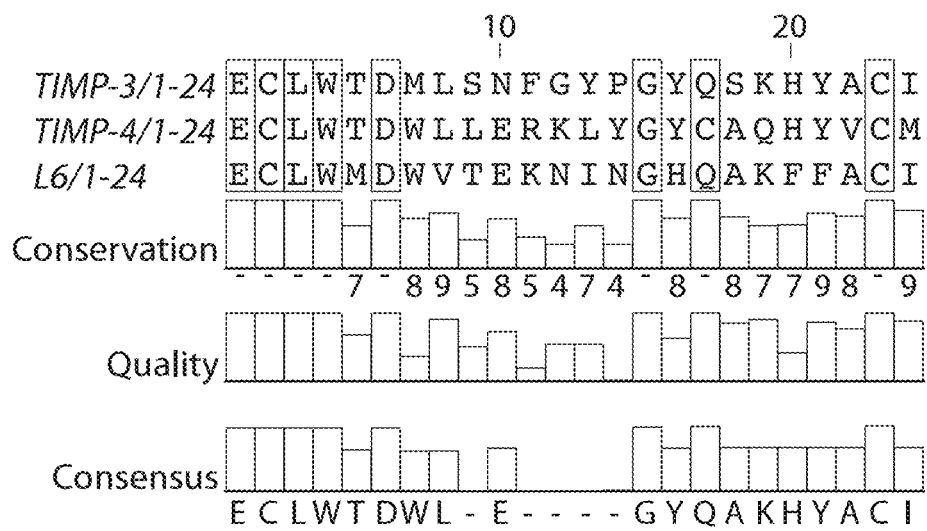
FIG. 46 shows the common motif in all the predicted anti-angiogenic fragments derived from TIMPs. SEQ ID NOS 155, 156, & 160 are disclosed respectively in order of appearance.

Finally, motifs found within peptides derived from tissue inhibitors of metalloproteinases were identified. The peptides used included the loop-6 fragment of TIMP-2, which has been shown to have anti-angiogenic activity. This analysis indicated that a motif having the sequence E-C-L-W-X-D-X8-G-X-Y-X5-C (SEQ ID NO: 179) is present in TIMP peptides as shown in Figure (FIG. 46).

No anti-angiogenic motifs have as yet been identified for the kringle containing peptides and the somatotropins.

TABLE 5

The C-X-C chemokine 22-mer with all the possible amino acid substitutions (SEQ ID NO: 171)

| AA1 | AA2 | AA3 | AA4 | AA5 | AA6 | AA7 | AA8 | AA9 | AA10 | AA11 | AA12 |
|---|---|---|---|---|---|---|---|---|---|---|---|
| N(4) | G(6) | R(3) | K(3) | A(2) | C(6) | L(6) | D(4) | P(6) | A(2) | A(3) | P(6) |
| D(2) |  | K(3) | E(2) | I(2) |  |  | N(2) |  | E(2) | S(2) |  |
|  |  |  | Q(1) | L(1) |  |  |  |  | D(1) | E(1) |  |
|  |  |  |  | V(1) |  |  |  |  | K(1) |  |  |

| AA13 | AA14 | AA15 | AA16 | AA17 | AA18 | AA19 | AA20 | AA21 | AA22 |
|---|---|---|---|---|---|---|---|---|---|
| F(2) | V(3) | K(4) | K(5) | I(3) | I(4) | E(3) | K(6) | I(3) | L(6) |
| I(1) | L(2) | Q(2) | R(1) | V(3) | V(2) | Q(3) |  | F(1) |  |
| M(1) | I(1) |  |  |  |  |  |  | K(1) |  |
| R(1) |  |  |  |  |  |  |  | M(1) |  |
| W(1) |  |  |  |  |  |  |  |  |  |

Figure 43:
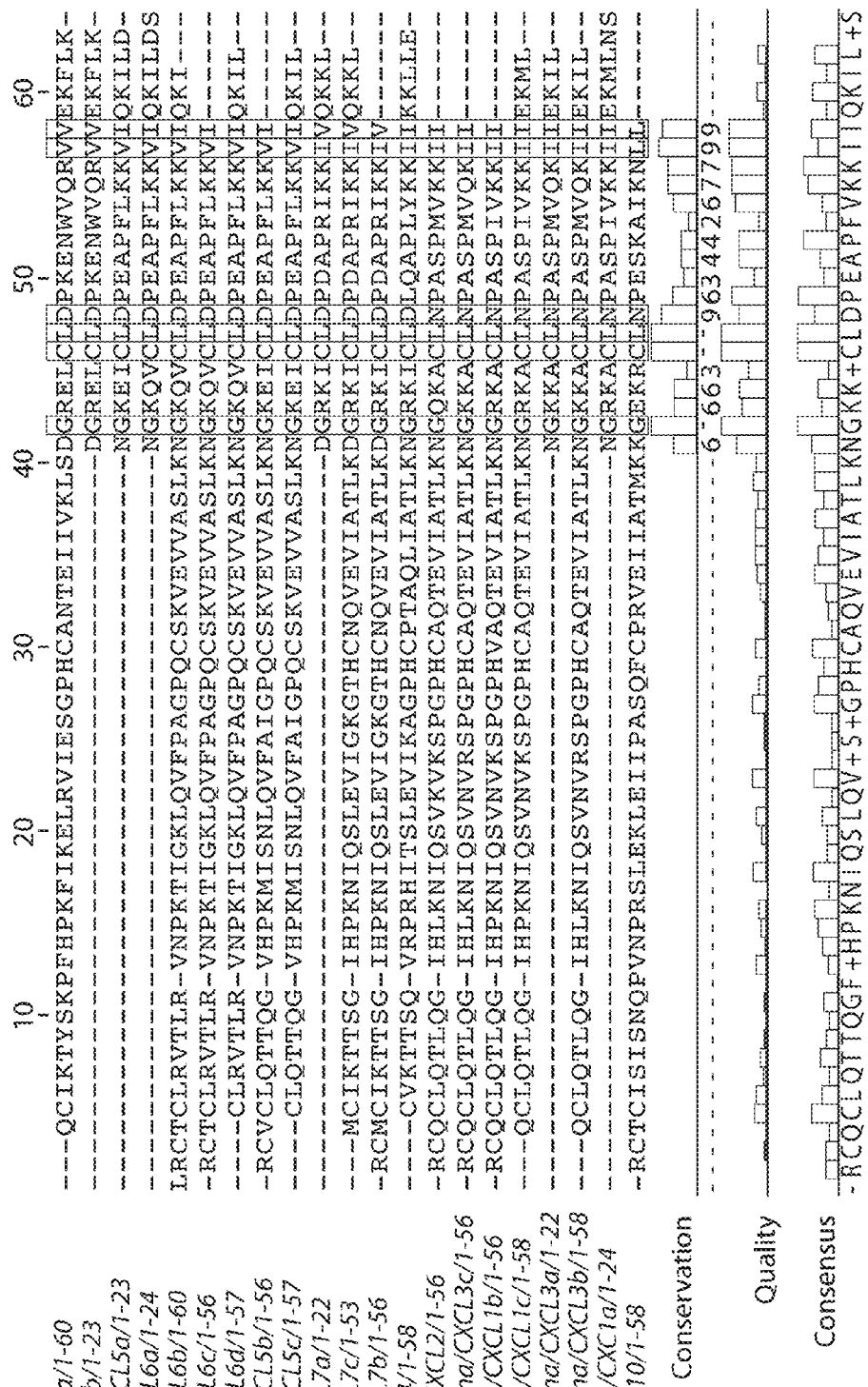
FIG. 43 shows the common motif in all the theoretically predicted anti-angiogenic C-X-C containing proteins. (SEQ ID NOS 109, 110, 95, 98-101, 96, 97, 114, 116, 115, 113, 105, 108, 103, 104, 106, 107, 102 & 111 are disclosed respectively in order of appearance.)

The calculations were repeated using all of the theoretically predicted C-X-C chemokines. These calculations also identified the X-G-X3-C-L-X-P-X10-K-X-L (SEQ ID NO: 188) motif as predicted by the experimentally tested short fragments with minimal alterations (FIG. 43).

All the theoretically predicted C-X-C chemokines include a generic 22-mer that can be described as follows:

(SEQ ID NO: 172)
(N/D/K)-G-X3-C-L-(D/N)-(P/L)-X5-(K/Q)-(K/R/N)-(I/V/L)-(UV/L)-X6.

This analysis indicates that the anti-angiogenic activity of the longer predicted fragments is localized to the sites where the above-identified motif resides.

Collagen Derived Peptides

Figure 44C:
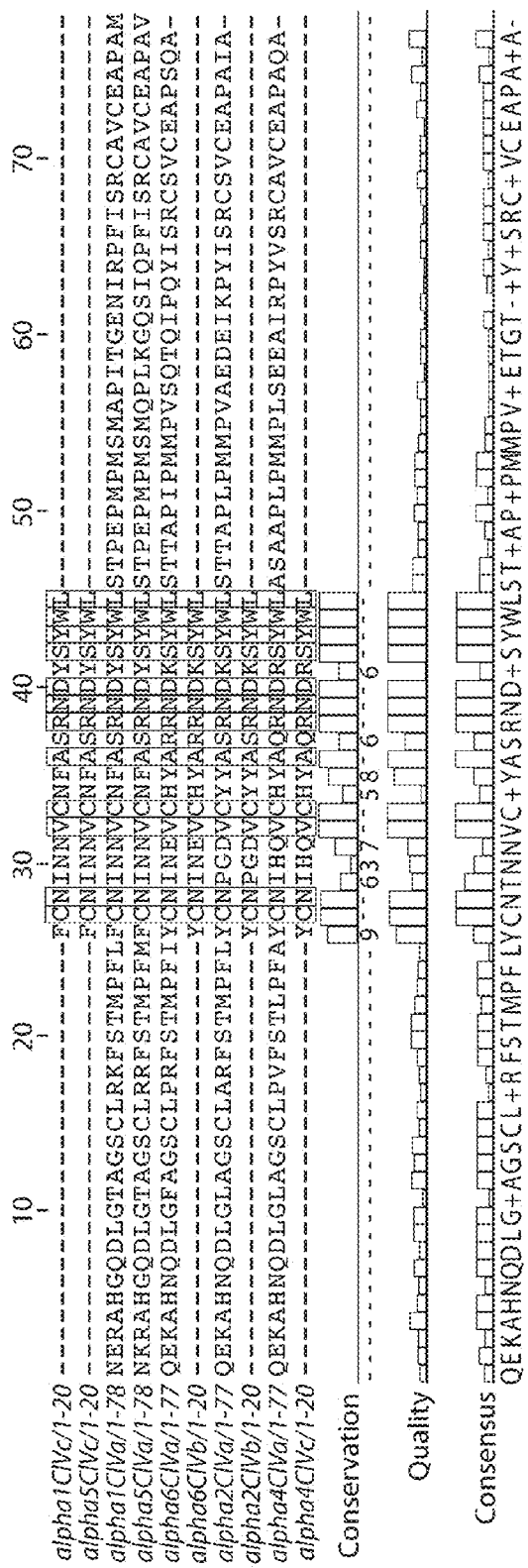

The same procedure used to identify anti-angiogenic motifs in the C-X-C chemokines can be used to identify anti-angiogenic motifs present in collagen related fragments. All the theoretically predicted fragments were used to identify two predominant anti-angiogenic motifs. The most abundant and best characterized includes a conserved 4-amino acid repeat: C-N-X3-V-C (SEQ ID NO: 174) (FIG. 44A). A set of two more motifs is shown in FIGS. 44B and 44C. The Example 5

Results of Migration Experiments

An important constituent of the anti-angiogenic activity of an agent is its ability to reduce endothelial cell migration towards an attractant that is present, such as a growth factor.

Endothelial cell motility or migration can be assessed using the modified Boyden chamber technique (Auerbach et al., *Cancer Metastasis Rev*, 19:167-72, 2000; Auerbach et al., *Clin Chem*, 49:32-40, 2003; Taraboletti and Giavazzi, *Eur J Cancer*, 40:881-9, 2004).

In the current example, a modified Boyden chamber assay was used to test endothelial cell migration from one side of the chamber in the presence of an activator. In brief, the lower compartment of the Boyden chamber was separated from the upper (containing the endothelial cells) by a laminin-coated polycarbonate filter with pores small enough to allow only the active passage of the cells (3 μm pore size). The cells were applied to the upper compartment of the chamber. The cell seeding density is 300,000 cells/ml. Typically, a cell population of 25,000-30,000 cells was applied to each well. Activators include but are not limited to growth factors, such as vascular endothelial growth factor and fibroblast growth factor-2 or conditioned medium (e.g. from tumor cells or NIH-3T3 fibroblasts). In the current example VEGF was used as an activator and was applied to a growth factor and serum free medium. The concentration of the activator applied to the lower chamber is 20 ng/ml. The activator was applied alone as a positive control. The tested anti-angiogenic peptides were applied to the lower chamber at 30 µg/ml concentration along with 20 ng/ml of activator in the serum free medium. As negative control only the serum free and growth factor free medium were applied. Typically within 4-20 hours a sufficient number of cells migrated through the filter to allow measurements to be taken. In this example, the cells were allowed to migrate for 16 hours.

Figure 47:
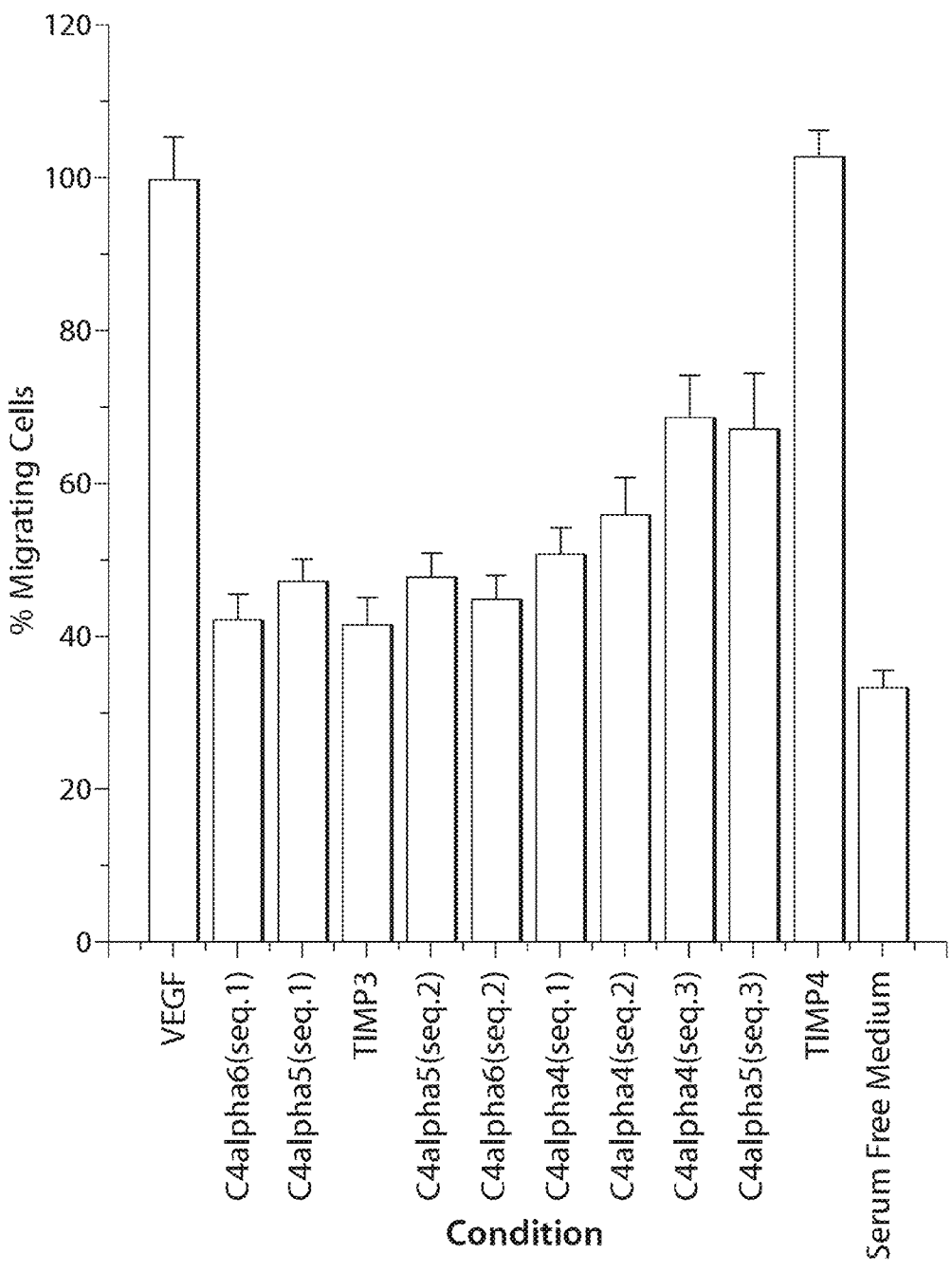
FIG. 47 shows the effect of applied peptides on the migration of HUVECs using a modified Boyden chamber. The cells were allowed to migrate for 16 hours. The peptides applied were C4α6(seq.1): YCNINEVCHYARRNDKSYWL (SEQ ID NO: 93), C4α5(seq.1): LRRFSTMPFMFCNINNVCNF (SEQ ID NO: 89), TIMP3: ECLWTDMLSNF-GYPGYQSKHYACI (SEQ ID NO: 155) C4α5(seq.2): FCNINNVCNFASRNDYSYWL (SEQ ID NO: 90), C4α6 (seq.2): ATPFIECSGARGTCHYFAN (SEQ ID NO: 94), C4α4(seq.1): AAPFLECQGRQGTCHFFAN (SEQ ID NO: 87), C4α4(seq.2): LPVFSTLPFAYCNIHQVCHY (SEQ ID NO: 85), C4α4(seq.3): YCNIHQVCHYAQRNDRSYWL (SEQ ID NO: 86), C4α5(seq.3): SAPFIECHGRGTCNYY-ANS (SEQ ID NO: 91), TIMP4: ECLWTDWLLERK-LYGYQAQHYVCM (SEQ ID NO: 156).

The number of migrating cells was quantified using a cell-permeable fluorescent dye. A fluorescence plate reader was used to quantify the migrating cells by measuring the amount of fluorescence and directly correlating it to cell number. A decrease in cell migration identifies a peptide that inhibits angiogenesis. In the current example the cells were stained with Calcein dye, 90 minutes prior the termination of the experiment. Calcein is internalized by endothelial cells and the cells that migrated towards the lower chamber were counted by measuring the fluorescence at 485 nm excitation and 510 nm emission using a fluorescence plate reader (Victor 3V, Perkin Elmer). The wells were fluorescent impermeable thus the fluorescence emission only from the cells that migrated towards the lower chamber was measured. The intensity of the signal was directly proportional to the number of endothelial cells that were present in the lower chamber. The results were scaled so that 100% represents the mean of the positive control, where the cells are migrating in the presence of VEGF (FIG. 47). Most of the tested peptides significantly reduced the migration of the endothelial cells in the presence of 20 ng/ml VEGF. The peptides applied were C4α6 (YCNINEVCHYARRNDKSYWL) (SEQ ID NO: 93), C4α5 (LRRFSTMPFMFCNINNVCNF) (SEQ ID NO: 89), TIMP3 (ECLWTDMLSNFGYPGYQSKHYACI) (SEQ ID NO: 155), C4α5 (FCNINNVCNFASRNDYSYWL) (SEQ ID NO: 90), C4α6 (ATPFIECSGARGTCHYFAN) (SEQ ID NO: 94), C4α4 (AAPFLECQGRQGTCHFFAN) (SEQ ID NO: 87), C4α4 (LPVFSTLPFAYCNIHQVCHY) (SEQ ID NO: 85), C4α4 (YCNIHQVCHYAQRNDRSYWL) (SEQ ID NO: 86), C4α5 (SAPFIECHGRGTCNYYANS) (SEQ ID NO: 91), TIMP4 (ECLWTDWLLERKLYGYQAQHYVCM) (SEQ ID NO: 156).

Analysis of Long Peptides

Apart from the predicted short peptide fragments that are produced using the aforementioned solid phase synthesis technique, there is a population of predicted anti-angiogenic fragments with lengths spanning from 55 to 134 amino acids. Based on the properties of known anti-angiogenic peptides, short domains of approximately 25 amino acids having anti-angiogenic activity are expected to reside within these longer sequences. In order to identify the domain, where the anti-angiogenic activity is localized, a "shotgun" methodology similar to the one used in proteomics approaches is used to localize the activity within a shorter domain of the initially predicted long fragment. According to this shotgun approach each of the longer sequences is partitioned into multiple sequential shorter fragments of approximately 25 amino acids length. In order to account for the possibility that the active domain resides between these fragments, the sequential peptides are overlapping with a common sequence of length 10-15 amino acids. Thus, one can effectively cover the whole sequence of the predicted long fragments with shorter peptides. However, this methodology is time-consuming and costly.

A more systematic approach to identify and localize the active domains of the longer fragments is achieved by combining the physico-chemical characteristics of the peptides and the results of screening the shorter fragments. The cryptic fragments by definition are comprised of sequences that are hidden in the three-dimensional structure of the protein away from the rest of the protein environment. The parts of the sequence of a protein that are not exposed to an aqueous environment are hydrophobic. Presumably the cryptic fragments that are hidden from aqueous environments are hydrophobic or partially hydrophobic. Thus, the active domains of the cryptic fragments, which are evolutionary hidden from the surrounding environment, are likely to be mostly hydrophobic. Based on this hypothesis, the locations of the active domains within the sequences of the larger predicted fragments are identified by calculating the hydrophobicity of these large fragments. It is highly probable that the active domains are localized at locations where the sequence is hydrophobic. Using these methods, sequences having anti-angiogenic activity are localized within the larger sequences of predicted fragments.

In addition to the information on the hydrophobicity, information from sequences of the short peptides that have been tested to be active and that contain or are parts of a specific conserved domain, in order to identify the active domains of longer fragments that contain the same conserved domain. By performing multiple sequence alignments to the sequences of the long predicted peptides with the sequences of the shorter fragments that are shown to be active, one can investigate the conservation of specific motifs that are common within the two populations of the peptides. If such motifs exist and are common between those two populations then one can directly associate the location of the common motif in the longer fragments with the location of the active domains. From there on one can investigate in the long fragments the sequences surrounding the common motif and identify the location of the active domain.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. An isolated peptide or analog thereof consisting of a sequence having at least 85% amino acid sequence identity to:

Properdin:
    (SEQ ID NO: 49)
    GPWEPCSVTCSKGTRTRRR;
    or

Fibulin-6:
    (SEQ ID NO: 44)
    QPWGTCSESCGKGTQTRAR, wherein the peptide comprises at least one modification.

2. A peptide conjugate comprising the peptide of claim 1 conjugated to an agent that specifically binds a tumor marker or endothelial cell marker.

3. A pharmaceutical composition comprising an effective amount of an isolated peptide of claim 1 in a pharmacologically acceptable excipient.

4. A pharmaceutical composition comprising i) an isolated polypeptide having an amino acid sequence set forth in SEQ ID NO: 49 or SEQ ID NO: 44, and ii) one or more peptides of SEQ ID Nos. 1-43, 45-48, and 50-156.

5. An isolated peptide or analog thereof consisting of a sequence having at least 85% amino acid sequence identity to:

Properdin: GPWEPCSVTCSKGTRTRRR(SEQ ID NO: 49);

Or

Fibulin-6: QPWGTCSESCGKGTQTRAR (SEQ ID NO: 44), wherein the peptide is conjugated to an agent that specifically binds a tumor marker or endothelial cell marker.

6. The isolated peptide or analog there of claim 1, wherein the modification is a sequence alteration or post-translational modification that increases protease resistance, biodistribution, or therapeutic efficacy.

7. A method of reducing blood vessel formation in a tissue or organ the method comprising:
   (a) contacting the tissue, or organ with a vector encoding the polypeptide of claim 1; and
   (b) expressing the polypeptide in a cell of the tissue or organ, thereby reducing blood vessel formation in the tissue or organ.

8. A method for decreasing blood vessel formation in a subject in need thereof, the method comprising administering an effective amount of the peptide of claim 1 to the subject, thereby decreasing blood vessel formation.

* * * * *